United States Patent
Crespo et al.

(10) Patent No.: US 8,933,113 B2
(45) Date of Patent: Jan. 13, 2015

(54) MINERALOCORTICOID RECEPTOR ANTAGONISTS

(75) Inventors: Alejandro Crespo, Edison, NJ (US); Ping Lan, Dayton, NJ (US); Rudrajit Mal, Edison, NJ (US); Anthony Ogawa, Mountainside, NJ (US); Hong Shen, West Windsor, NJ (US); Peter J. Sinclair, Scotch Plains, NJ (US); Zhongxiang Sun, Edison, NJ (US); Ellen K. Vande Bunte, Colts Neck, NJ (US); Zhicai Wu, Montvale, NJ (US); Kun Liu, Shanghai (CN); Robert J. DeVita, Westfield, NJ (US); Dong-Ming Shen, Edison, NJ (US); Min Shu, Greenbrook, NJ (US); John Qiang Tan, Westfield, NJ (US); Changhe Qi, Shanghai (CN); Yuguang Wang, Shanghai (CN); Richard Beresis, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/979,875

(22) PCT Filed: Jan. 19, 2012

(86) PCT No.: PCT/CN2012/070597
§ 371 (c)(1),
(2), (4) Date: Jul. 16, 2013

(87) PCT Pub. No.: WO2012/097744
PCT Pub. Date: Jul. 26, 2012

(65) Prior Publication Data
US 2013/0331419 A1  Dec. 12, 2013

Related U.S. Application Data

(60) Provisional application No. 61/434,543, filed on Jan. 20, 2011.

(51) Int. Cl.
| | | |
|---|---|---|
| A61K 31/416 | (2006.01) | |
| C07D 231/56 | (2006.01) | |
| A61K 31/405 | (2006.01) | |
| A61K 31/404 | (2006.01) | |
| C07D 403/06 | (2006.01) | |
| C07D 209/08 | (2006.01) | |
| C07D 209/10 | (2006.01) | |
| A61K 31/4196 | (2006.01) | |
| A61K 31/422 | (2006.01) | |
| A61K 31/4245 | (2006.01) | |
| A61K 45/06 | (2006.01) | |
| C07D 413/06 | (2006.01) | |

(52) U.S. Cl.
CPC ............ *A61K 31/405* (2013.01); *A61K 31/404* (2013.01); *A61K 31/416* (2013.01); *C07D 231/56* (2013.01); *C07D 403/06* (2013.01); *C07D 209/08* (2013.01); *C07D 209/10* (2013.01); *A61K 31/4196* (2013.01); *A61K 31/422* (2013.01); *A61K 31/4245* (2013.01); *A61K 45/06* (2013.01); *C07D 413/06* (2013.01)
USPC ........................................ 514/406; 548/362.5

(58) Field of Classification Search
USPC ........................................ 514/406; 548/362.5
See application file for complete search history.

(56) References Cited

U.S. PATENT DOCUMENTS

| | | | |
|---|---|---|---|
| 4,342,767 A | 8/1982 | Albers-Schonberg et al. | |
| 4,346,227 A | 8/1982 | Terahara et al. | |
| 4,444,784 A | 4/1984 | Hoffman et al. | |
| 4,845,079 A | 7/1989 | Luly et al. | |
| 4,885,292 A | 12/1989 | Ryono et al. | |
| 4,894,437 A | 1/1990 | TenBrink | |
| 4,980,283 A | 12/1990 | Huang et al. | |
| 5,034,512 A | 7/1991 | Hudspeth et al. | |
| 5,036,053 A | 7/1991 | Himmelsbach et al. | |
| 5,036,054 A | 7/1991 | Kaltenbronn et al. | |
| 5,055,466 A | 10/1991 | Weller, III et al. | |

(Continued)

FOREIGN PATENT DOCUMENTS

| | | |
|---|---|---|
| CN | 1950365 | 4/2007 |
| CN | 1960973 | 5/2007 |

(Continued)

OTHER PUBLICATIONS

International Search Report dated May 3, 2012.

(Continued)

*Primary Examiner* — Samantha Shterengarts
(74) *Attorney, Agent, or Firm* — Dianne Pecoraro; Catherine D. Fitch

(57) ABSTRACT

Disclosed are the compounds of the Formula (I) as well as pharmaceutically acceptable salts thereof, which are useful for treating aldosterone-mediated diseases. The processes for preparing compounds of the Formula (I), the use for the therapy and prophylaxis of the abovementioned diseases and for preparing pharmaceuticals for this purpose, and the pharmaceutical compositions which comprise compounds of the formula (I) are disclosed too.

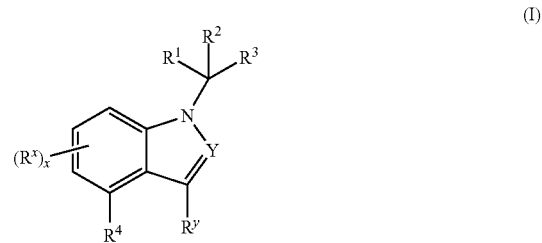

(I)

17 Claims, No Drawings

(56) References Cited

U.S. PATENT DOCUMENTS

| | | | |
|---|---|---|---|
| 5,063,207 | A | 11/1991 | Doherty et al. |
| 5,063,208 | A | 11/1991 | Rosenberg et al. |
| 5,064,965 | A | 11/1991 | Ocain et al. |
| 5,066,643 | A | 11/1991 | Abeles et al. |
| 5,071,837 | A | 12/1991 | Doherty et al. |
| 5,075,451 | A | 12/1991 | Ocain et al. |
| 5,089,471 | A | 2/1992 | Hanson et al. |
| 5,095,119 | A | 3/1992 | Ocain et al. |
| 5,098,924 | A | 3/1992 | Poss |
| 5,104,869 | A | 4/1992 | Albright et al. |
| 5,106,835 | A | 4/1992 | Albright et al. |
| 5,114,937 | A | 5/1992 | Hamby et al. |
| 5,116,835 | A | 5/1992 | Rüger et al. |
| 5,260,440 | A | 11/1993 | Hirai et al. |
| 5,354,772 | A | 10/1994 | Kathawala |
| 2005/0222142 | A1 | 10/2005 | Vu et al. |
| 2005/0222148 | A1 | 10/2005 | Kim et al. |
| 2005/0245515 | A1 | 11/2005 | Dehmlow et al. |
| 2006/0025467 | A1 | 2/2006 | Greenhouse et al. |
| 2007/0072897 | A1 | 3/2007 | Mahaney et al. |

FOREIGN PATENT DOCUMENTS

| | | |
|---|---|---|
| CN | 1960980 | 5/2007 |
| CN | 1993321 | 7/2007 |
| CN | 101309904 | 11/2008 |
| EP | 0775694 | 5/1997 |
| GB | 705652 | 3/1954 |
| JP | 200977744 | 3/1997 |
| WO | 97/23200 | 7/1997 |
| WO | 97/28149 | 8/1997 |
| WO | 0037472 | 6/2000 |
| WO | 02/08188 | 1/2002 |
| WO | 02/17895 | 3/2002 |
| WO | 02060438 | 8/2002 |
| WO | 2004/020408 | 3/2004 |
| WO | 2004/020409 | 3/2004 |
| WO | 2010124114 | 10/2010 |

OTHER PUBLICATIONS

Juss et al., J. of Neuroendocrinology, No. 5, vol. 3 (1993) pp. 461-466.
Pitt et al., N. Engl. J. Med., vol. 348 (14) (2003) pp. 1309-1321.
Funder J. W., Hypertens. Res. vol. 33 (2010) vol. 6, pp. 539-540.
Calhoun et al., J. Am. Soc. Hypertens. vol. 2(6) (2008) pp. 462-468.
Huang et al., Am. J. Physiol. Heart. Circ. Physiol. vol. 2 (2010) pp. H422-H430.
The Rales Investigators, Am. J. Cardiol (1996) vol. 78 pp. 902-907.
Pitt et al., Circulation (2008) vol. 118 (16) pp. 1643-1650.
Williams J. S., Nat. Rev. Endocrinol. (2010) vol. 6(5) pp. 248-250.
Nishizaka et al., Curr. Hypertens. Rep. (2005) vol. 7(5) pp. 343-347.
Gaddam et al., Hypertension (2010) vol. 55(5) pp. 1137-1142.
Zannad et al., Eur. J. Heart Fail (2010) vol. 12 (6) pp. 617-622.
Takai et al., Hypertension (2005) vol. 46 (5) pp. 1135-1139.
Tirosh et al., Curr. Hypertens. Rep. (2010) vol. 12(4) pp. 252-257.
Brilla et al., Journal of Molecular & Cellular Cardiology vol. 25(5) (1993) pp. 563-575.
Suzuki A., Pure Appl. Chem. (1991) vol. 63 pp. 419-422.
Littke et al., J. Am. Chem. Soc. (2000) vol. 122 pp. 4020-4028.
Bayindir et al., Synlett (2010) No. 10, pp. 1455-1458.
Heffernan et al., Bioorganic & Medicinal Chemistry (2009) vol. 17, No. 22, pp. 7802-7815.
Stanley et al., Angewandte Chemie, International Edition (2009) vol. 48, No. 42, pp. 7841-7844.
Mahaney et al., Bioorganic & Medicinal Chemistry Letters (2009) vol. 19 No. 19, pp. 5807-5810.
Cui et al., Angewandte Chemie, International Edition (2009), vol. 48, No. 31, pp. 5737-5740.
Abid et al., Adv. Synth. Catal. (2006) vol. 348 pp. 2919-2196.
Schirok, H., Synthesis (2008) No. 9 pp. 1404-1414.
Matsuda et al., Organic Letters (2008) vol. 10, No. 1 pp. 125-128.
English language Abstract corresponding to CN101309904.
Mahaney et al., Bioorganic & Medicinal Chemistry (2006) vol. 14 No. 24 pp. 8455-8466.
English language Abstract corresponding to CN1993321.
English language Abstract corresponding to CN1950365.
English language Abstract corresponding to CN1960973.
English language Abstract corresponding to CN1960980.
Siebeneicher et al., Angewandte Chemie, International Edition (2003) vol. 42 pp. 3042-3044.
Nilsson et al., Acta Chemica Scandinavian Section B: Organic Chemistry and Biochemistry (1987) vol. B41, No. 4, pp. 261-266.
Nilsson et al., Acta Chemica Scandinavian Section B: Organic Chemistry and Biochemistry (1986) vol. B40, No. 8 pp. 625-651.
Nilsson et al., Acta Chemica Scandinavian Section B: Organic Chemistry and Biochemistry (1985) vol. B39, No. 7 pp. 531-547.
Fujiwara et al., J. Am. Chem. Soc. (1983) vol. 105, pp. 7177-7179.
Wolinsky et al., Tetrahedron (1970) vol. 26, No. 23 pp. 5427-5435.
Pitt et al., N. Engl. J. Med. vol. 341, (1999) pp. 709-717.
Hadley M. E., Endocrinology 2nd Edition (1988) pp. 366-381.
Bomback et al., Clin. Nephrol. (2009) vol. 72(6) pp. 449-456.
Database CAplus [Online]. Columbus, Ohio, US; Chemical Abstracts Service [cited 2008]. Available from: STN International, Columbus, USA. AN: 2008:1383564, RN 1071174-25-8.
Database CAplus [Online]. Columbus, Ohio, US; Chemical Abstracts Service [cited 2008]. Available from: STN International, Columbus, USA. AN: 2008:735721, RN 1033010-14-8.
Database CAplus [Online]. Columbus, Ohio, US; Chemical Abstracts Service [cited 2009]. Available from: STN International, Columbus, USA AN: 2009:1237584.
Database CAplus [Online]. Columbus, Ohio, US; Chemical Abstracts Service [cited 2009]. Available from: STN International, Columbus, USA AN: 2009:877844.
English language translation of JP-09-77744—Mar. 25, 1997—Kyowa Hakko Kogyo Co., Ltd.
International Preliminary Report on Patentability—Aug. 1, 2013.

MINERALOCORTICOID RECEPTOR ANTAGONISTS

BACKGROUND OF THE INVENTION

The Mineralocorticoid Receptor (MR) is a nuclear hormone receptor that is activated by aldosterone and regulates the expression of many genes involved in electrolyte homeostasis and cardiovascular disease. Increased circulating aldosterone increases blood pressure through its effects on natriuresis, with potentially additional effects on the brain, heart and vasculature. In addition, hyperaldosteronism have been linked to many pathophysiological processes resulting in renal and cardiovascular disease. While hyperaldosteronism is commonly caused by aldosterone-producing adenomas, resistant hypertensive patients frequently suffer from increased aldosterone levels often termed as "Aldosterone Breakthrough" as a result of increases in serum potassium or residual AT1R activity. Hyperaldosteronism and aldosterone breakthrough typically results in increased MR activity and MR antagonists have been shown to be effective as antihypertensive agents and also in the treatment of heart failure and primary hyperaldosteronism.

In addition, in visceral tissues, such as the kidney and the gut, MR regulates sodium retention, potassium excretion and water balance in response to aldosterone. MR expression in the brain also appears to play a role in the control of neuronal excitability, in the negative feedback regulation of the hypothalamic-pituitary-adrenal axis, and in the cognitive aspects of behavioral performance (Castren et al., J. of Neuroendocrinology, 3, 461-66 (1993)).

Eplerenone and spironolactone are two MR antagonists that have been shown to be efficacious in treating cardiovascular disease, particularly hypertension and heart failure (RALES Investigators (1999) The effect of spironolactone on morbidity and mortality in patients with severe heart failure, N. Engl. J. Med., 1999, 341(10):709-717; Pitt B, et al., EPHESUS investigator (2003) Eplerenone, a selective aldosterone blocker, in patients with left ventricular dysfunction after myocardial infarction, N. Engl. J. Med., 348(14):1309-1321; Funder J W., (2010) Eplerenone in chronic renal disease: the EVALUATE trial, Hypertens. Res., 33(6):539-40.) Moreover, multiple studies have shown that treatment with spironolactone or eplerenone significantly lower systolic blood pressure in mild-moderate, obese, systolic, PHA, and resistant hypertensive patients (Calhoun D A, et al., (2008) Effectiveness of the selective aldosterone blocker, eplerenone, in patients with resistant hypertension, J. Am. Soc. Hypertens., 2008 November-December; 2(6):462-8; Huang B S, et al., (2010) Central neuronal activation and pressor responses induced by circulating ANG II: role of the brain aldosterone-"ouabain" pathway, Am. J. Physiol. Heart. Circ. Physiol., (2):H422-30; The RALES Investigators. (1996) Effectiveness of spironolactone added to an angiotensin-converting enzyme inhibitor and a loop diuretic for severe chronic congestive heart failure, (The Randomized Aldactone Evaluation Study [RALES]), Am. J. Cardiol., 1996; 78:902-907; Pitt B, et al., EPHESUS Investigators, Serum potassium and clinical outcomes in the Eplerenone Post-Acute Myocardial Infarction Heart Failure Efficacy and Survival Study (EPHESUS), Circulation, 2008 Oct. 14; 118(16):1643-50; Bomback A S et al., (2009), Low-dose spironolactone, added to long-term ACE inhibitor therapy, reduces blood pressure and urinary albumin excretion in obese patients with hypertensive target organ damage, Clin. Nephrol., 72(6):449-56; Williams J S, Hypertension: spironolactone and resistant hypertension, Nat. Rev. Endocrinol., 2010 May; 6(5):248-50; Nishizaka M K, et al., The role of aldosterone antagonists in the management of resistant hypertension. Curr Hypertens Rep. 2005 October; 7(5):343-7. Review; Gaddam K, et al., (2010) Rapid reversal of left ventricular hypertrophy and intracardiac volume overload in patients with resistant hypertension and hyperaldosteronism: a prospective clinical study, Hypertension, 55(5):1137-42; Zannad F, et al., (2010) Rationale and design of the Eplerenone in Mild Patients Hospitalization And Survlval Study in Heart Failure (EMPHASIS-HF), Eur. J. Heart Fail., 12(6):617-22).

Evidence in preclinical models also suggest that MR antagonists would be efficacious in treating the metabolic syndrome and atherosclerosis (Takai, S. et al, (2005) Eplerenone inhibits atherosclerosis in nonhuman primates. Hypertension. 46(5):1135-9; Tirosh, A. et al., G K. (2010) Mineralocorticoid receptor antagonists and the metabolic syndrome. Curr Hypertens Rep. 2010 August; 12(4):252-7).

Also, published PCT application WO 2002/17895 disclosed that aldosterone antagonists are useful in the treatment of subjects suffering from one or more cognitive dysfunctions including, but not limited to psychoses, cognitive disorders (such as memory disturbances), mood disorders (such as depression and bipolar disorder), anxiety disorders and personality disorders.

Elevation in aldosterone levels, or excess stimulation of mineralocorticoid receptors, is linked to several physiological disorders or pathologic disease states, including Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels. (Hadley, M. E., ENDOCRINOLOGY, $2^{nd}$ Ed., pp. 366-81, (1988); and Brilla et al., Journal of Molecular and Cellular Cardiology, 25 (5), pp. 563-75 (1993). Compounds and/or pharmaceutical compositions which act as MR antagonists should be of value in the treatment of any of the above conditions.

Despite significant therapeutic advances in the treatment of hypertension and heart failure, the current standard of care is suboptimal and there is a clear unmet medical need for additional therapeutic/pharmacological interventions. This invention addresses those needs by providing compounds, compositions and methods for the treatment or prevention of hypertension, heart failure, other cardiovascular disorders and other aldosterone disorders.

SUMMARY OF THE INVENTION

The present invention relates to compounds which have Mineralocorticoid Receptor (MR) antagonist activity, which are valuable pharmaceutically active compounds for the therapy and prophylaxis of diseases, for example for treating aldosterone-mediated disorders, including cardiovascular disease. The present invention is directed to compounds of the Formula I

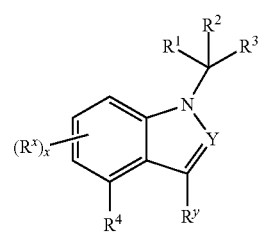

or pharmaceutically acceptable salts thereof. The invention furthermore relates to methods of treating and preventing the above mentioned diseases and to processes for preparing compounds of the Formula I and for pharmaceutical preparations which comprise compounds of Formula I.

DETAILED DESCRIPTION OF THE INVENTION

The invention concerns compounds of Formula I:

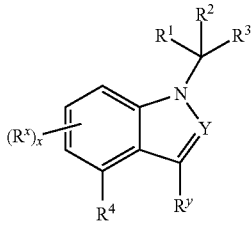

I or pharmaceutically acceptable salts thereof, wherein

Y is N or $CR^y$;

Each $R^y$ is independently H or $C_1$-$C_6$ alkyl, said alkyl is optionally substituted with halo or OH;

Each $R^x$ is independently H, halo, OR, $C_1$-$C_6$ alkyl, $(CR_2)_{0-1}$CN, $C(O)OR^{11}$, $C_3$-$C_{10}$ cycloalkyl, $NR^6COR$, $NR^6SO_2R^8$, or $NH_2$, said alkyl and cycloalkyl are optionally substituted with 1 to 3 substituents selected from halo, OR and $C_1$-$C_6$ alkyl;

Each R is independently H, $CF_3$, $C_1$-$C_6$ alkyl or aryl, said alkyl and aryl are optionally substituted with 1 to 3 substituents selected from halo, aryl and $C_1$-$C_6$ alkyl;

$R^1$ is:
1) 5-membered heteroaryl or heterocyclyl, said heteroaryl or heterocylyl is optionally substituted with one to three $R^5$,
2) $C_1$-$C_6$ alkyl, said alkyl is optionally substituted with one to three $C_1$-$C_6$ alkyl, OR, $NR_2$, $CF_3$, SR, $OS(O)_2R^8$, CN or halo substituents,
3) —$(CR^a{}_2)_nC(O)OR^{11}$,
4) —$(CR^a{}_2)_nC(O)NRR^7$,
5) —CN;
6) $(CR^a{}_2)_{0-4}C(O)R^c$,
7) $C_3$-$C_{10}$ cycloalkyl-$R^5$, or
8) —$(CR^a{}_2)_nOC(O)R^c$;

$R^2$ is:
1) H,
2) $C_1$-$C_6$ alkyl,
3) —$(CR^b{}_2)_m$—$C_3$-$C_6$ cycloalkyl,
4) —$(CR^a{}_2)_m$—$C(O)OR^{11}$,
5) —$(CR^b{}_2)_m$—$C_2$-$C_6$ alkenyl,
6) —$(CR^b{}_2)_m$—$C_2$-$C_6$ alkynyl,
7) —$(CR^b{}_2)_m$-aryl, or
8) —$(CR^b{}_2)_m$-heteroaryl;

Where said alkyl, cycloalkyl, alkenyl, alkynyl, aryl and heteroaryl are optionally substituted with one to three groups selected from $R^{12}$;

optionally, $R^1$ and $R^2$ may be joined to form a cyclic ring, as illustrated:

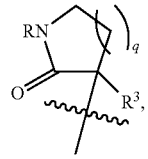

where integer q is 1 or 2;

$R^3$ is aryl, wherein said aryl is optionally substituted with one to three $R^9$;

$R^4$ is
1) H,
2) —$NR^6S(O)_2R^8$,
3) $C_1$-$C_6$ alkyl,
4) $C_3$-$C_6$ cycloalkyl,
5) —$N(O)_2$,
6) —$(CH_2)_{0-1}$—CN,
7) halo,
8) —$C(O)OR^{11}$,
9) —$NH_2$,
10) —OR,
11) —$(CR^a{}_2)_t$—$SO_2R^{10}$,
12) —$NR^6C(O)R^{10}$,
13) —$NR^6C(O)OR^{10}$,
14) —$NR^6{}_2$,
15) aryl,
16) heterocyclyl, or
17) heteroaryl;
where said alkyl, cycloalkyl, aryl, heterocyclyl or heteroaryl may be optionally substituted with one to three halo, OR or $C_1$-$C_6$ alkyl substituents;

Each $R^5$ is independently H, OR, CN, aryl, heteroaryl, $C(O)OR^{11}$, $C(O)NRR^7$, $C_1$-$C_6$ alkyl, $CF_3$, or $C_3$-$C_{10}$ cycloalkyl, where said alkyl, cycloalkyl, aryl or heteroaryl may be optionally substituted with one to three halo, OR or $CF_3$;

Each $R^6$ is independently H, $C_1$-$C_6$ alkyl, $C(O)OR^{11}$, or $S(O)_2R^8$;

Each $R^7$ is independently
1) H,
2) $C_1$-$C_6$ alkyl, optionally substituted with 1 to 3 substituents selected from halo, OR, CN, $CF_3$, aryl and $C_3$-$C_{10}$ cycloalkyl, where said aryl and cycloalkyl are optionally substituted with aryl,
3) $C_3$-$C_{10}$ cycloalkyl, optionally substituted with one to three OR, CN, $CF_3$, aryl or halo substituents,
4) —$(CR^a{}_2)_nC(O)OR^{11}$,
5) —$(CR^a{}_2)_nC(O)R^c$, or
6) —$(CR^a{}_2)_nC(O)NR_2$;

Each $R^8$ is independently $C_1$-$C_6$ alkyl, $C_3$-$C_{10}$ cycloalkyl, $NRR^7$, aryl or $CF_3$, said alkyl, aryl and cycloalkyl are optionally substituted with one to three halo, CN, OR or $NH_2$ substituents;

Each $R^9$ is independently halo, CN, $CF_3$, $OCF_3$, $C_1$-$C_6$ alkyl, OR, $NH_2$, aryl or heteroaryl, where said alkyl, aryl or heteroaryl may be optionally substituted with one to three halo, CN, $OCF_3$, OR, $C_1$-$C_6$ alkyl or $NH_2$ substituents;

Each $R^{10}$ is independently $C_1$-$C_6$ alkyl, aryl, or $CF_3$, said alkyl is optionally substituted with 1-3 halo substituents;

Each $R^{11}$ is independently H, $C_1$-$C_6$ alkyl, or aryl;

Each $R^{12}$ is independently halo, CN, $CF_3$, $OCF_3$, $C(O)OR^{11}$, $C_1$-$C_6$ alkyl, OR, $NH_2$, aryl or heteroaryl, where said alkyl, aryl or heteroaryl may be optionally substituted with one to three halo, CN, $OCF_3$, OR, $C_1$-$C_6$ alkyl or $NH_2$ substituents;

Each $R^a$ is independently H or $C_1$-$C_6$ alkyl, said alkyl is optionally substituted with one to three halo substituents;

Each $R^b$ is independently H, OR, halo, or $C_1$-$C_6$ alkyl, said alkyl is optionally substituted with one to three halo substituents;

$R^c$ is $C_1$-$C_6$ alkyl or heterocyclyl, said alkyl and heterocyclyl are optionally substituted with one to three halo, CN, $OCF_3$, OR, $C_1$-$C_6$ alkyl or $NH_2$ substituents;

m is 0 or 1;

n is 0, 1, 2, 3 or 4;

t is 0, 1, 2 or 3; and x is 0, 1, 2 or 3.

In an embodiment, the invention concerns compounds of Formula I:

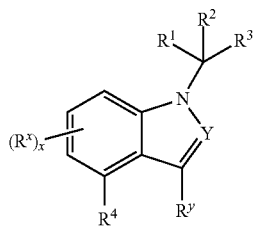

I or pharmaceutically acceptable salts thereof, wherein

Y is N or $CR^y$;

Each $R^y$ is independently H or $C_1$-$C_6$ alkyl, said alkyl is optionally substituted with halo or OH;

Each $R^x$ is independently H, halo, OR, $C_1$-$C_6$ alkyl, $(CR_2)_{0-1}$CN, OR, $C(O)OR^{11}$, $C_3$-$C_{10}$ cycloalkyl, $NR^6COR$, $NR^6SO_2R^8$, or $NH_2$, said alkyl and cycloalkyl are optionally substituted with 1 to 3 substituents selected from halo, OR and $C_1$-$C_6$ alkyl;

Each R is independently H, $CF_3$, $C_1$-$C_6$ alkyl or aryl, said alkyl and aryl are optionally substituted with 1 to 3 substituents selected from halo, aryl and $C_1$-$C_6$ alkyl;

$R^1$ is:
1) 5-membered heteroaryl or heterocyclyl, said heteroaryl or heterocylyl is optionally substituted with one to three $R^5$,
2) $C_1$-$C_6$ alkyl, said alkyl is optionally substituted with one to three OR, CN or halo substituents,
3) $-(CR^a{}_2)_n C(O)OR^{11}$,
4) $-(CR^a{}_2)_n C(O)NRR^7$,
5) $-(CR^a{}_2)_{1-4} C(O)R^c$, or
6) $-CN$;

$R^2$ is:
1) H,
2) $C_1$-$C_6$ alkyl, said alkyl is optionally substituted with one to three OR, CN or halo substituents,
3) $-(CR^b{}_2)_m-C_3$-$C_6$ cycloalkyl, said cycloalkyl is optionally substituted with 1 to 3 substituents selected from OR, halo or $NH_2$,
4) $-(CR^a{}_2)_m-C(O)OR^{11}$,
5) $-(CR^b{}_2)_m-C_2$-$C_6$ alkenyl,
6) $-(CR^b{}_2)_m-C_2$-$C_6$ alkynyl,
7) $-(CR^b{}_2)_m$-aryl, or
8) $-(CR^b{}_2)_m$-heteroaryl;

optionally, $R^1$ and $R^2$ may be joined to form a cyclic ring, as illustrated:

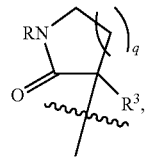

where integer q is 1 or 2;

$R^3$ is aryl, wherein said aryl is optionally substituted with one to three $R^9$;

$R^4$ is
1) H,
2) $-NR^6S(O)_2R^8$,
3) $C_1$-$C_6$ alkyl,
4) $C_3$-$C_6$ cycloalkyl,
5) $-N(O)_2$,
6) $-(CH_2)_{0-1}-CN$,
7) halo,
8) $-C(O)OR^{11}$,
9) $-NH_2$,
10) $-OR$,
11) $-(CR^a{}_2)_t-SO_2R^{10}$,
12) $-NR^6C(O)R^{10}$,
13) aryl,
14) heterocyclyl, or
15) heteroaryl;
  where said alkyl, cycloalkyl, aryl, heterocyclyl or heteroaryl may be optionally substituted with one to three halo, OR or $C_1$-$C_6$ alkyl substituents;

Each $R^5$ is independently H, aryl, heteroaryl, $C(O)NRR^7$, $C_1$-$C_6$ alkyl, $CF_3$, or $C_3$-$C_{10}$ cycloalkyl, where said alkyl, cycloalkyl, aryl or heteroaryl may be optionally substituted with one to three halo, OR or $CF_3$;

Each $R^6$ is independently H, $C_1$-$C_6$ alkyl, or $S(O)_2R^8$;

Each $R^7$ is independently
1) H,
2) $C_1$-$C_6$ alkyl, optionally substituted with 1 to 3 substituents selected from halo, OR, CN, $CF_3$, aryl and $C_3$-$C_{10}$ cycloalkyl, where said aryl and cycloalkyl are optionally substituted with aryl,
3) $C_3$-$C_{10}$ cycloalkyl, optionally substituted with one to three OR, CN, $CF_3$, aryl or halo substituents,
4) $-(CR^a{}_2)_n C(O)OR^{11}$,
5) $-(CR^a{}_2)_n C(O)R^c$, or
6) $-(CR^a{}_2)_n C(O)NR_2$;

Each $R^8$ is independently $C_1$-$C_6$ alkyl, $C_3$-$C_{10}$ cycloalkyl, aryl or $CF_3$, said alkyl, aryl and cycloalkyl are optionally substituted with one to three halo, CN, OR or $NH_2$ substituents;

Each $R^9$ is independently halo, CN, $OCF_3$, $C_1$-$C_6$ alkyl, OR, $NH_2$, aryl or heteroaryl, where said alkyl, aryl or heteoaryl may be optionally substituted with one to three halo, CN, $OCF_3$, OR, $C_1$-$C_6$ alkyl or $NH_2$ substituents;

Each $R^{10}$ is independently $C_1$-$C_6$ alkyl, aryl, or $CF_3$, said alkyl is optionally substituted with 1-3 halo substituents;

Each $R^{11}$ is independently H, $C_1$-$C_6$ alkyl, or aryl;

Each $R^a$ is independently H or $C_1$-$C_6$ alkyl, said alkyl is optionally substituted with one to three halo substituents;

Each $R^b$ is independently H, halo, or $C_1$-$C_6$ alkyl, said alkyl is optionally substituted with one to three halo substituents;

$R^c$ is heterocyclyl;

m is 0 or 1;

n is 0, 1 or 2;

t is 0 or 1; and x is 0, 1, 2 or 3.

In one embodiment of Formula I, $R^y$ is H and all other variables are as previously defined in Formula I.

In another embodiment, the instant invention is related to a compound of Formula I, as illustrated by Formula II:

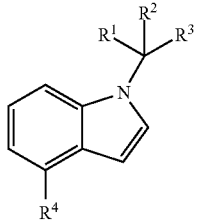

II or a pharmaceutically acceptable salt thereof, wherein:
$R^2$ is:
1) H,
2) $C_1$-$C_6$ alkyl, said alkyl is optionally substituted with one to three OR, CN or halo substituents, or
3) —$(CR^b_2)_m$—$C_3$-$C_6$ cycloalkyl, said cycloalkyl is optionally substituted with one to three OR, halo or $NH_2$ substituents;

$R^3$ is phenyl, wherein said phenyl is optionally substituted with one to three $R^9$;
$R^4$ is:
1) —$NR^6S(O)_2R^8$,
2) —$(CR^a_2)_t$—$SO_2R^{10}$, or
3) —$NR^6C(O)R^{10}$;
Each $R^9$ is independently halo or OR;
and all other variables are as previously defined in Formula I.

In another embodiment, the instant invention is related to a compound of Formula I, as illustrated by Formula III:

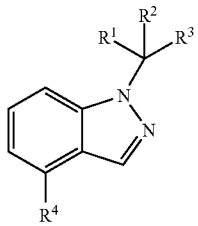

III or a pharmaceutically acceptable salt thereof, wherein:
$R^2$ is:
1) H,
2) $C_1$-$C_6$ alkyl, said alkyl is optionally substituted with one to three OR, CN or halo substituents, or
3) —$(CR^b_2)_m$—$C_3$-$C_6$ cycloalkyl, said cycloalkyl is optionally substituted with one to three OR, halo or $NH_2$ substituents;

$R^3$ is phenyl, wherein said phenyl is optionally substituted with one to three $R^9$;
$R^4$ is:
1) —$NR^6S(O)_2R^8$,
2) —$(CR^a_2)_t$—$SO_2R^{10}$, or
3) —$NR^6C(O)R^{10}$;
Each $R^9$ is independently halo or OR;
and all other variables are as previously defined in Formula I.

In another embodiment, the instant invention is related to a compound of Formula I, as illustrated by Formula IV:

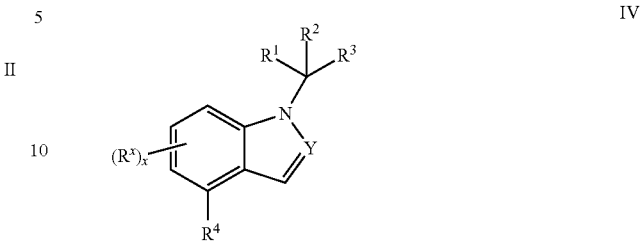

IV or a pharmaceutically acceptable salt thereof, wherein:
Y is N or $CR^y$;
Each $R^y$ is independently H or $C_1$-$C_6$ alkyl, said alkyl is optionally substituted with halo or OH;
Each $R^x$ is independently H, halo, OR, or $C_1$-$C_6$ alkyl, said alkyl is optionally substituted with 1 to 3 substituents selected from halo, OR and $C_1$-$C_6$ alkyl;
Each R is independently H, $CF_3$, $C_1$-$C_6$ alkyl or aryl, said alkyl and aryl are optionally substituted with 1 to 3 substituents selected from halo, aryl and $C_1$-$C_6$ alkyl;
$R^1$ is:
1) 5-membered heteroaryl or heterocyclyl, said heteroaryl or heterocylyl is optionally substituted with one to three $R^5$,
2) $C_1$-$C_6$ alkyl, said alkyl is optionally substituted with one to three $C_1$-$C_6$ alkyl, OR, $NR_2$, $CF_3$, SR, $OS(O)_2R^8$, CN or halo substituents,
3) —$(CR^a_2)_nC(O)OR^{11}$,
4) $(CR^a_2)_{0-4}C(O)R^c$,
5) $C_3$-$C_{10}$ cycloalkyl-$R^5$, or
6) —$(CR^a_2)_nOC(O)R^c$;
$R^2$ is
1) $C_1$-$C_6$ alkyl,
2) —$(CR^b_2)_m$—$C_3$-$C_6$ cycloalkyl,
3) —$(CR^a_2)_mC(O)OR^{11}$,
4) —$(CR^b_2)_m$—$C_2$-$C_6$ alkenyl, or
5) —$(CR^b_2)_m$—$C_2$-$C_6$ alkynyl,
Where said alkyl, cycloalkyl, alkenyl and alkynyl is optionally substituted with one to three groups selected from $R^{12}$;
$R^3$ is phenyl, wherein said phenyl is optionally substituted with one to three $R^9$;
$R^4$ is
1) —$NR^6S(O)_2R^8$,
2) $C_1$-$C_6$ alkyl,
3) halo,
4) —$C(O)OR^{11}$,
5) —$NH_2$,
6) —OR, or
7) —$(CR^a_2)_t$—$SO_2R^{10}$,
where said alkyl may be optionally substituted with one to three halo, OR or $C_1$-$C_6$ alkyl substituents;
Each $R^5$ is independently H, OR, CN, $C(O)OR^{11}$, $C(O)NRR^7$, $C_1$-$C_6$ alkyl, $CF_3$, or $C_3$-$C_{10}$ cycloalkyl, where said alkyl, cycloalkyl, aryl and heteroaryl may be optionally substituted with one to three halo, OR or $CF_3$;
Each $R^6$ is independently H, $C_1$-$C_6$ alkyl, $C(O)OR^{11}$, or $S(O)_2R^8$;
Each $R^7$ is independently
1) H,
2) $C_1$-$C_6$ alkyl, optionally substituted with 1 to 3 substituents selected from halo, OR, CN, $CF_3$, aryl and $C_3$-$C_{10}$ cycloalkyl, where said aryl and cycloalkyl are optionally substituted with aryl,
3) $C_3$-$C_{10}$ cycloalkyl, optionally substituted with one to three OR, CN, $CF_3$, aryl or halo substituents, 4) —(CR$^a_2$)$_n$C(O)OR$^{11}$, 5) —(CR$^a_2$)$_n$C(O)R$^c$, or 6) —(CR$^a_2$)$_n$C(O)NR$_2$;

Each R$^8$ is independently C$_1$-C$_6$ alkyl, C$_3$-C$_{10}$ cycloalkyl, NRR$^7$ or CF$_3$, said alkyl, aryl and cycloalkyl are optionally substituted with one to three halo, CN, OR or NH$_2$ substituents;

Each R$^9$ is independently halo, CN, CF$_3$, OCF$_3$, C$_1$-C$_6$ alkyl, OR, or NH$_2$, where said alkyl may be optionally substituted with one to three halo, CN, OCF$_3$, OR, C$_1$-C$_6$ alkyl or NH$_2$ substituents;

Each R$^{10}$ is independently C$_1$-C$_6$ alkyl, aryl, or CF$_3$, said alkyl is optionally substituted with 1-3 halo substituents;

Each R$^{11}$ is independently H or C$_1$-C$_6$ alkyl;

Each R$^{12}$ is independently halo, CN, CF$_3$, OCF$_3$, C(O)OR$^{11}$, C$_1$-C$_6$ alkyl, OR, NH$_2$, where said alkyl may be optionally substituted with one to three halo, CN, OCF$_3$, OR, C$_1$-C$_6$ alkyl or NH$_2$ substituents;

Each R$^a$ is independently H or C$_1$-C$_6$ alkyl, said alkyl is optionally substituted with one to three halo substituents;

Each R$^b$ is independently H, OR, halo, or C$_1$-C$_6$ alkyl, said alkyl is optionally substituted with one to three halo substituents;

R$^C$ is C$_1$-C$_6$ alkyl or heterocyclyl, said alkyl and heterocyclyl are optionally substituted with one to three halo, CN, OCF$_3$, OR, C$_1$-C$_6$ alkyl or NH$_2$ substituents;

m is 0 or 1;

n is 0, 1, 2, 3 or 4;

t is 0, 1 or 2; and x is 0 or 1.

In an embodiment, the invention is a compound which is

| IUPAC Name |
| --- |
| methyl (4-chlorophenyl)(4-nitro-1H-indol-1-yl)acetate |
| methyl (2-chloro-4-fluorophenyl)(4-nitro-1H-indol-1-yl)acetate |
| methyl (2,4-dichlorophenyl)(4-nitro-1H-indol-1-yl)acetate |
| methyl (3-bromophenyl)(4-nitro-1H-indol-1-yl)acetate |
| methyl (4-methoxyphenyl)(4-nitro-1H-indol-1-yl)acetate |
| methyl (2-chloro-4-fluorophenyl)(1H-indol-1-yl)acetate |
| methyl (2-chloro-4-fluorophenyl)(4-cyano-1H-indol-1-yl)acetate |
| ethyl 1-[1-(2-chloro-4-fluorophenyl)-2-methoxy-2-oxoethyl]-1H-indole-4-carboxylate |
| methyl (2-chloro-4-fluorophenyl)(4-chloro-1H-indol-1-yl)acetate |
| methyl (2-chloro-4-fluorophenyl)(4-fluoro-1H-indol-1-yl)acetate |
| methyl (2-chloro-4-fluorophenyl)(5-cyano-1H-indol-1-yl)acetate |
| methyl (2-chloro-4-fluorophenyl)(5-chloro-1H-indol-1-yl)acetate |
| methyl (2-chloro-4-fluorophenyl)(5-fluoro-1H-indol-1-yl)acetate |
| methyl (2-chloro-4-fluorophenyl)(6-chloro-1H-indol-1-yl)acetate |
| methyl (2-chloro-4-fluorophenyl)(7-fluoro-1H-indol-1-yl)acetate |
| methyl [7-(benzyloxy)-1H-indol-1-yl](2-chloro-4-fluorophenyl)acetate |
| methyl (4-chlorophenyl){4-[(methylsulfonyl)amino]-1H-indol-1-yl}acetate |
| tert-butyl (4-chlorophenyl){4-[(methylsulfonyl)amino]-1H-indol-1-yl}acetate |
| methyl (4-chlorophenyl){4-[(methylsulfonyl)amino]-1H-indazol-1-yl}acetate |
| methyl (2-chloro-4-fluorophenyl)(4-{[(trifluoromethyl)sulfonyl]amino}-1H-indol-1-yl)acetate |
| methyl {4-[(methylsulfonyl)amino]-1H-indol-1-yl}(phenyl)acetate |
| methyl (2-chloro-4-fluorophenyl){4-[(methylsulfonyl)amino]-1H-indol-1-yl}acetate |
| methyl (2,4-dichlorophenyl){4-[(methylsulfonyl)amino]-1H-indol-1-yl}acetate |
| methyl (4-bromophenyl){4-[(methylsulfonyl)amino]-1H-indol-1-yl}acetate |
| methyl 2-(4-chlorophenyl)-2-{4-[(methylsulfonyl)amino]-1H-indol-1-yl}butanoate |
| (R)-methyl 2-(4-chlorophenyl)-2-{4-[(methylsulfonyl)amino]-1H-indol-1-yl}butanoate |
| (S)-methyl 2-(4-chlorophenyl)-2-{4-[(methylsulfonyl)amino]-1H-indol-1-yl}butanoate |
| tert-Butyl 2-(4-chlorophenyl)-2-{4-[(methylsulfonyl)amino]-1H-indol-1-yl}butanoate. |
| tert-Butyl 2-(4-chlorophenyl)-3-cyano-2-{4-[(methylsulfonyl)amino]-1H-indol-1-yl}propanoate |
| Methyl 2-(4-chlorophenyl)-2-{4-[(methylsulfonyl)amino]-1H-indol-1-yl}propanoate |
| Methyl 2-(2,4-dichlorophenyl)-2-{4-[(methylsulfonyl)amino]-1H-indol-1-yl}propanoate |
| Methyl 2-(2,4-dichlorophenyl)-2-{4-[(methylsulfonyl)amino]-1H-indol-1-yl}butanoate |
| Methyl 2-(2-chloro-4-fluorophenyl)-2-{4-[(methylsulfonyl)amino]-1H-indol-1-yl}butanoate |
| Methyl 2-(4-chlorophenyl)-2-{4-[(methylsulfonyl)amino]-1H-indazol-1-yl}butanoate |
| Methyl 2-(4-chlorophenyl)-2-{4-[(methylsulfonyl)amino]-1H-indol-1-yl}pent-4-enoate |
| Methyl 2-(4-chlorophenyl)-2-{4-[(methylsulfonyl)amino]-1H-indol-1-yl}-3-phenylpropanoate |
| Dimethyl 2-(4-chlorophenyl)-2-{4-[(methylsulfonyl)amino]-1H-indol-1-yl}butanedioate |
| Methyl 2-(4-chlorophenyl)-3-cyano-2-{4-[(methylsulfonyl)amino]-1H-indol-1-yl}propanoate |
| Methyl 2-(4-chlorophenyl)-3-methoxy-2-{4-[(methylsulfonyl)amino]-1H-indol-1-yl}propanoate |
| Methyl 2-(4-chlorophenyl)-3-cyclopropyl-2-{4-[(methylsulfonyl)amino]-1H-indol-1-yl}propanoate |
| (R)-2-(4-chlorophenyl)-N-methyl-2-{4-[(methylsulfonyl)amino]-1H-indol-1-yl}butanamide |
| (R)-2-(4-chlorophenyl)-2-{4-[(methylsulfonyl)amino]-1H-indol-1-yl}butanamide |
| (R)-2-(4-chlorophenyl)-N-cyclopropyl-2-{4-[(methylsulfonyl)amino]-1H-indol-1-yl}butanamide |
| 2-(4-chlorophenyl)-N-(2-methoxyethyl)-2-(4-[(methylsulfonyl)amino]-1H-indol-1-yl}butanamide |
| (R)-N-benzyl-2-(4-chlorophenyl)-2-{4-[(methylsulfonyl)amino]-1H-indol-1-yl}butanamide |
| (R)-2-(4-chlorophenyl)-N-(1-methylethyl)-2-{4-[(methylsulfonyl)amino]-1H-indol-1-yl}butanamide |

| IUPAC Name |
| --- |
| (R)-N-tert-butyl-2-(4-chlorophenyl)-2-{4-[(methylsulfonyl)amino]-1H-indol-1-yl}butanamide. |
| 2-(4-chlorophenyl)-N-ethyl-2-{4-[(methylsulfonyl)amino]-1H-indol-1-yl}butanamide |
| (R)-2-(4-chlorophenyl)-2-{4-[(methylsulfonyl)amino]-1H-indol-1-yl}-N-(2,2,2-trifluoroethyl)butanamide |
| 2-(4-chlorophenyl)-N-(2-cyanoethyl)-2-{4-[(methylsulfonyl)amino]-1H-indol-1-yl}butanamide |
| 2-(4-chlorophenyl)-N-(2-fluoroethyl)-2-(4-[(methylsulfonyl)amino]-1H-indol-1-yl}butanamide |
| 2-(4-chlorophenyl)-2-{4-[(methylsulfonyl)amino]-1H-indol-1-yl}-N-(2-phenylethyl)butanamide |
| (R)-2-(4-chlorophenyl)-N-(cyanomethyl)-2-{4-[(methylsulfonyl)amino]-1H-indol-1-yl}butanamide |
| methyl N-[2-(4-chlorophenyl)-2-{4-[(methylsulfonyl)amino]-1H-indol-1-yl}butanoyl]glycinate |
| 2-(4-chlorophenyl)-3-cyano-N-methyl-2-{4-[(methylsulfonyl)amino]-1H-indol-1-yl}propanamide |
| N-benzyl-2-(4-chlorophenyl)-3-cyano-2-{4-[(methylsulfonyl)amino]-1H-indol-1-yl}propanamide |
| 2-(4-chlorophenyl)-3-cyano-2-(4-[(methylsulfonyl)amino]-1H-indol-1-yl}-N-(2,2,2-trifluoroethyl)propanamide |
| 2-(4-chlorophenyl)-3-cyclopropyl-N-methyl-2-{4-[(methylsulfonyl)amino]-1H-indol-1-yl}propanamide |
| (R)-methyl N-{1-[1-(4-chlorophenyl)-1-(5-methyl-1,2,4-oxadiazol-3-yl)propyl]-1H-indol-4-yl}methanesulfonamide |
| (R)-N-{1-[1-(4-chlorophenyl)-1-(5-phenyl-1,2,4-oxadiazol-3-yl)propyl]-1H-indol-4-yl} methanesulfonamide |
| (R)-N-(1-{1-(4-chlorophenyl)-1-[5-(4-fluorophenyl)-1,2,4-oxadiazol-3-yl]propyl}-1H-indol-4-yl)methanesulfonamide |
| (R)-N-(1-{1-(4-chlorophenyl)-1-[5-(4-chlorophenyl)-1,2,4-oxadiazol-3-yl]propyl}-1H-indol-4-yl)methanesulfonamide |
| (R)-N-(1-{1-(4-chlorophenyl)-1-[5-(4-methoxyphenyl)-1,2,4-oxadiazol-3-yl]propyl}-1H-indol-4-yl)methanesulfonamide |
| (R)-N-{1-[1-(4-chlorophenyl)-1-(5-cyclopropyl-1,2,4-oxadiazol-3-yl)propyl]-1H-indol-4-yl}methanesulfonamide |
| N-{1-[(4-chlorophenyl)(3-phenyl-1,2,4-oxadiazol-5-yl)methyl]-1H-indol-4-yl}methanesulfonamide |
| (R)-N-{1-[1-(4-chlorophenyl)-1-(3-phenyl-1H-1,2,4-triazol-5-yl)propyl]-1H-indol-4-yl}methanesulfonamide |
| (R)-N-{1-[1-(4-chlorophenyl)-1-(5-methyl-4H-1,2,4-triazol-3-yl)propyl]-1H-indol-4-yl}methanesulfonamide |
| (R)-N-(1-{1-(4-chlorophenyl)-1-[5-(trifluoromethyl)-4H-1,2,4-triazol-3-yl]propyl}-1H-indol-4-yl)methanesulfonamide |
| (R)-N-{1-[1-(4-chlorophenyl)-1-(5-cyclopropyl-1,3,4-oxadiazol-2-yl)propyl]-1H-indol-4-yl}methanesulfonamide |
| N-{1-[1-(4-chlorophenyl)-1-(5-methyl-1,3,4-oxadiazol-2-yl)propyl]-1H-indol-4-yl}methanesulfonamide |
| N-(1-{1-(4-chlorophenyl)-1-[5-(trifluoromethyl)-1,3,4-oxadiazol-2-yl]propyl}-1H-indol-4-yl)methanesulfonamide |
| (R)-N-{1-[1-(4-chlorophenyl)-1-(5-phenyl-1,3,4-oxadiazol-2-yl)propyl]-1H-indol-4-yl} methanesulfonamide |
| (R)-N-(1-{1-(4-chlorophenyl)-1-[5-(4-chlorophenyl)-1,3,4-oxadiazol-2-yl]propyl}-1H-indol-4-yl)methanesulfonamide |
| (R)-N-(1-{1-(4-chlorophenyl)-1-[5-(4-fluorophenyl)-1,3,4-oxadiazol-2-yl]propyl}-1H-indol-4-yl)methanesulfonamide |
| (R)-N-{1-[1-(4-chlorophenyl)-1-{5-[4-(trifluoromethyl)phenyl]-1,3,4-oxadiazol-2-yl}propyl]-1H-indol-4-yl}methanesulfonamide |
| (R)-N-(1-{1-(4-chlorophenyl)-1-[5-(4-methoxyphenyl)-1,3,4-oxadiazol-2-yl]propyl}-1H-indol-4-yl)methanesulfonamide |
| (R)-N-(1-{1-(4-chlorophenyl)-1-[5-(3,5-difluorophenyl)-1,3,4-oxadiazol-2-yl]propyl}-1H-indol-4-yl)methanesulfonamide |
| N-{1-[1-(4-chlorophenyl)-2-cyano-1-(5-phenyl-1,3,4-oxadiazol-2-yl)ethyl]-1H-indol-4-yl}methanesulfonamide |
| N-{1-[1-(4-chlorophenyl)-1-(4-phenyl-1,3-oxazol-2-yl)propyl]-1H-indol-4-yl}methanesulfonamide |
| methyl 2-(3'-methoxybiphenyl-3-yl)-2-{4-[(methylsulfonyl)amino]-1H-indol-1-yl}butanoate |
| Methyl (2'-chlorobiphenyl-3-yl){4-[(methylsulfonyl)amino]-1H-indol-1-yl}acetate |
| Methyl {4-[(methylsulfonyl)amino]-1H-indol-1-yl}[2'-(trifluoromethoxy) biphenyl-3-yl]acetate |
| Methyl {4-[(methylsulfonyl)amino]-1H-indol-1-yl}[4'-(trifluoromethoxy)biphenyl-3-yl]acetate |
| N-{1-[(2R)-2-(4-chlorophenyl)-1-hydroxybutan-2-yl]-1H-indol-4-yl}methanesulfonamide |
| N-{1-[(2S)-2-(4-chlorophenyl)-1-hydroxybutan-2-yl]-1H-indol-4-yl}methanesulfonamide |
| methyl 2-(4-chlorophenyl)-3-cyano-2-{4-[(methylsulfonyl)amino]-1H-indol-1-yl}propanoate |
| N-{1-[3-(4-chlorophenyl)-2-oxopyrrolidin-3-yl]-1H-indol-4-yl}methanesulfonamide |

| IUPAC Name |
| --- |
| N-(1-(2-(4-chlorophenyl)-1-hydroxybutan-2-yl)-6-fluoro-1H-indol-4-yl)methanesulfonamide |
| N-(1-(2-(2,4-dichlorophenyl)-1-hydroxybutan-2-yl)-1H-indol-4-yl)methanesulfonamide; |
| N-(1-(2-(4-chlorophenyl)-1-hydroxybutan-2-yl)-1H-indazol-4-yl)methanesulfonamide; |
| N-(1-(1-hydroxy-2-(4-(trifluoromethyl)phenyl)butan-2-yl)-1H-indazol-4-yl)methanesulfonamide; |
| N-(1-(3-(4-chlorophenyl)-2-hydroxy-2-methylpentan-3-yl)-6-fluoro-1H-indol-4-yl)methane sulfonamide; |
| N-(1-(3-(4-chlorophenyl)-2-hydroxy-2-methylpentan-3-yl)-1H-indazol-4-yl)methanesulfonamide; |
| N-(1-(2-hydroxy-2-methyl-3-(4-(trifluoromethyl)phenyl)pentan-3-yl)-1H-indazol-4-yl)methanesulfonamide; |
| 1-(1-(3-(4-chlorophenyl)-2-hydroxy-2-methylpentan-3-yl)-1H-indazol-4-yl)-3-methyl-sulfonylurea; |
| 1-(1-(3-(4-chlorophenyl)-2-hydroxy-2-methylpentan-3-yl)-1H-indazol-4-yl)-3,3-dimethyl-sulfonylurea; |
| N-(1-(2-(4-chlorophenyl)-1-methoxybutan-2-yl)-1H-indol-4-yl)methanesulfonamide; |
| N-(1-(2-(4-chlorophenyl)-1-methoxybutan-2-yl)-1H-indazol-4-yl)methanesulfonamide; |
| N-(1-(3-(4-chlorophenyl)-2-oxopentan-3-yl)-6-fluoro-1H-indol-4-yl)methanesulfonamide; |
| N-(1-(3-(4-chlorophenyl)-2-oxopentan-3-yl)-1H-indol-4-yl)methanesulfonamide; |
| N-(1-(3-(4-chlorophenyl)-2-oxopentan-3-yl)-1H-indazol-4-yl)methanesulfonamide; |
| N-(1-(3-(4-chlorophenyl)-2-oxopentan-3-yl)-1H-indazol-4-yl)methanesulfonamide; |
| N-(1-(2-oxo-3-(4-(trifluoromethyl)phenyl)pentan-3-yl)-1H-indol-4-yl)methanesulfonamide; |
| N-(1-(2-oxo-3-(4-(trifluoromethyl)phenyl)pentan-3-yl)-1H-indazol-4-yl)methanesulfonamide; |
| 1-(1-(3-(4-chlorophenyl)-2-oxopentan-3-yl)-1H-indazol-4-yl)-3-methyl-sulfonylurea; |
| N-{1-[3-(4-chlorophenyl)-2-hydroxypentan-3-yl]-1H-indazol-4-ylmethanesulfonamide; |
| N-{1-[3-(4-chlorophenyl)-2-hydroxypentan-3-yl]-1H-indazol-4-ylmethanesulfonamide |
| N-(1-(3-(4-chlorophenyl)-2-hydroxypentan-3-yl)-1H-indol-4-yl)methanesulfonamide; |
| N-(1-(3-(4-chlorophenyl)-2-hydroxypentan-3-yl)-1H-indol-4-yl)methanesulfonamide |
| N-(1-(3-(2,4-dichlorophenyl)-2-hydroxypentan-3-yl)-1H-indol-4-yl)methanesulfonamide; |
| N-(1-(3-(4-chlorophenyl)-2-hydroxypentan-3-yl)-6-fluoro-1H-indol-4-yl)methanesulfonamide; |
| N-(6-fluoro-1-(2-hydroxy-3-(4-(trifluoromethyl)phenyl)pentan-3-yl)-1H-indazol-4-yl)methanesulfonamide; |
| N-(1-(2-hydroxy-3-(4-(trifluoromethyl)phenyl)pentan-3-yl)-1H-indol-4-yl)methanesulfonamide; |
| N-(1-(2-hydroxy-3-(4-(trifluoromethyl)phenyl)pentan-3-yl)-1H-indazol-4-yl)methanesulfonamide |
| N-(1-(2-hydroxy-3-(4-(trifluoromethyl)phenyl)pentan-3-yl)-1H-indazol-4-yl)methanesulfonamide |
| 1-(1-(3-(4-chlorophenyl)-2-hydroxypentan-3-yl)-1H-indazol-4-yl)-3-methyl-sulfonylurea; |
| 3-(1-(3-(4-chlorophenyl)-2-hydroxypentan-3-yl)-1H-indazol-4-yl)-1,1-dimethyl-sulfonylurea; |
| N-(3-(3-(4-chlorophenyl)-2-hydroxypentan-3-yl)-1H-indazol-7-yl)methanesulfonamide; |
| N-(1-(1-(4-chlorophenyl)-1-(2-cyanocyclopropyl)propyl)-1H-indazol-4-yl)methanesulfonamide; |
| N-(1-(2-(4-chlorophenyl)-1-cyanobutan-2-yl)-1H-indol-4-yl)methanesulfonamide; |
| N-(1-(2-(4-chlorophenyl)-1-cyanobutan-2-yl)-1H-indazol-4-yl)methanesulfonamide; |
| N-(1-(2-(4-chlorophenyl)-1-cyanobutan-2-yl)-6-fluoro-1H-indol-4-yl)methanesulfonamide; |
| N-(1-(2-(4-chlorophenyl)-1-cyanobutan-2-yl)-6-fluoro-1H-indol-4-yl)methanesulfonamide; |
| N-(1-(1-cyano-2-(4-(trifluoromethyl)phenyl)butan-2-yl)-1H-indol-4-yl)methanesulfonamide; |
| (E)-N-(1-(3-(4-chlorophenyl)-1-cyanopent-1-en-3-yl)-1H-indol-4-yl)methanesulfonamide; |
| (E)-N-(1-(1-cyano-3-(4-methoxyphenyl)pent-1-en-3-yl)-1H-indol-4-yl)methanesulfonamide; |
| (E)-N-(1-(3-(4-chlorophenyl)-1-cyanopent-1-en-3-yl)-1H-indazol-4-yl)methanesulfonamide; |
| (E)-N-(1-(3-(4-chlorophenyl)-1-cyanopent-1-en-3-yl)-6-fluoro-1H-indazol-4-yl)methanesulfonamide; |
| N-(1-(3-(4-chlorophenyl)-5-cyanohex-4-en-3-yl)-1H-indol-4-yl)methanesulfonamide; |
| N-(1-(3-(4-Chlorophenyl)-1-cyano-2-methylpent-1-en-3-yl)-1H-indol-4-yl)methanesulfonamide; |
| (E)-4-(4-amino-1H-indazol-1-yl)-4-(4-chlorophenyl)hex-2-enenitrile; |
| (E)-4-(4-amino-6-fluoro-1H-indazol-1-yl)-4-(4-chlorophenyl)hex-2-enenitrile; |
| N-(1-(2-(4-chlorophenyl)-1-hydroxybutan-2-yl)-1H-indazol-4-yl)-N-((2-(trimethylsilyl)ethoxy)methyl)methanesulfonamide; |
| (E)-N-(1-(3-(4-chlorophenyl)-1-cyanopent-1-en-3-yl)-6-fluoro-1H-indazol-4-yl)-N-(methylsulfonyl)methanesulfonamide; |
| N-(1-(3-(4-chlorophenyl)-1-cyanopentan-3-yl)-1H-indazol-4-yl)methanesulfonamide; |
| N-(1-(3-(4-chlorophenyl)-1-cyanopentan-3-yl)-1H-indazol-4-yl)methanesulfonamide |
| N-(1-(1-cyano-3-(4-methoxyphenyl)pentan-3-yl)-1H-indol-4-yl)methanesulfonamide; |
| N-(1-(3-(4-chlorophenyl)-1-cyanopentan-3-yl)-1H-indol-4-yl)methanesulfonamide |

| IUPAC Name |
| --- |
| N-(1-(1-cyano-3-(4-(trifluoromethyl)phenyl)pentan-3-yl)-1H-indazol-4-yl)methanesulfonamide |
| N-(1-(3-(4-chlorophenyl)-1-cyanopentan-3-yl)-6-fluoro-1H-indol-4-yl)methanesulfonamide; |
| N-(1-(3-(4-chlorophenyl)-1-cyanopentan-3-yl)-6-fluoro-1H-indol-4-yl)methanesulfonamide |
| N-(1-(1-cyano-3-phenylpentan-3-yl)-6-fluoro-1H-indazol-4-yl)methanesulfonamide; |
| N-(1-(3-(4-chlorophenyl)-1-cyanopentan-3-yl)-6-fluoro-1H-indazol-4-yl)methanesulfonamide; |
| N-(1-(3-(4-Chlorophenyl)-1-cyano-2-oxopentan-3-yl)-1H-indol-4-yl)methanesulfonamide; |
| N-(1-(1-(4-Chlorophenyl)-1-(3-cyano-4,5-dihydrofuran-2-yl)propyl)-1H-indol-4-yl)methanesulfonamide; |
| N-(2-chloroethyl)-2-(4-chlorophenyl)-2-(4-(methylsulfonamido)-1H-indol-1-yl)butanamide |
| 2-(4-chlorophenyl)-N-(cyanomethyl)-2-(4-(methylsulfonamido)-1H-indol-1-yl)butanamide; |
| N-(1-(1-(4-chlorophenyl)-1-(3-ethyl-1,2,4-oxadiazol-5-yl)propyl)-1H-indol-4-yl)methanesulfonamide; |
| N-(1-(1-(4-chlorophenyl)-1-(3-ethyl-1,2,4-oxadiazol-5-yl)propyl)-1H-indol-4-yl)methanesulfonamide |
| N-(1-(1-(4-chlorophenyl)-1-(2-ethyl-2H-1,2,3-triazol-4-yl)propyl)-1H-indol-4-yl)methanesulfonamide; |
| Methyl 2-(4-chlorophenyl)-2-(4-(2-(methylsulfonyl)ethyl)-1H-indol-1-yl)butanoate; |
| N-(1-(1-(4-chlorophenyl)-1-(1-hydroxycyclopropyl)propyl)-1H-indol-4-yl)methanesulfonamide; |
| methyl 2-(4-chlorophenyl)-4-fluoro-2-(4-(methylsulfonamido)-1H-indol-1-yl)butanoate; |
| 5-(1-(4-chlorophenyl)-1-(4-(methylsulfonamido)-1H-indazol-1-yl)propyl)-1,2,4-oxadiazole-3-carboxamide; |
| N-(1-(1-(4-chlorophenyl)-1-(3-cyano-1,2,4-oxadiazol-5-yl)propyl)-1H-indazol-4-yl)methanesulfonamide; |
| N-(1-(3-(4-chlorophenyl)-1,1,1-trifluoropentan-3-yl)-1H-indazol-4-yl)methanesulfonamide; |
| N-(1-(3-(4-Chlorophenyl)-1-hydroxypentan-3-yl)-1H-indol-4-yl)methanesulfonamide; |
| N-(1-(3-(4-Chlorophenyl)-1-hydroxypentan-3-yl)-1H-indol-4-yl)methanesulfonamide |
| N-(1-(3-(4-Chlorophenyl)-1-fluoropentan-3-yl)-1H-indol-4-yl)methanesulfonamide; |
| N-(1-(3-(4-Chlorophenyl)-1-fluoropentan-3-yl)-1H-indol-4-yl)methanesulfonamide |
| 3-(4-Chlorophenyl)-3-(4-(methylsulfonamido)-1H-indol-1-yl)pentyl methanesulfonate; |
| N-(1-(3-(4-Chlorophenyl)-1-methoxypentan-3-yl)-1H-indol-4-yl)methanesulfonamide; |
| N-(1-(3-(4-Chlorophenyl)-1-(methylthio)pentan-3-yl)-1H-indol-4-yl)methanesulfonamide; |
| methyl 4-(4-amino-1H-indol-1-yl)-4-(4-chlorophenyl)hexanoate; |
| methyl 4-(4-chlorophenyl)-4-(4-(methylsulfonamido)-1H-indazol-1-yl)hexanoate; |
| N-(1-(3-(4-chlorophenyl)-6-hydroxyhexan-3-yl)-1H-indol-4-yl)methanesulfonamide; |
| N-(1-(3-(4-chlorophenyl)-6-fluorohexan-3-yl)-1H-indol-4-yl)methanesulfonamide; |
| (E)-methyl 4-(4-chlorophenyl)-4-(4-(methylsulfonamido)-1H-indazol-1-yl)hex-2-enoate; |
| N-(1-(3-(4-chlorophenyl)-6-oxoheptan-3-yl)-1H-indazol-4-yl)methanesulfonamide; |
| N-(1-(3-(4-chlorophenyl)-2-hydroxy-1-methoxypentan-3-yl)-1H-indol-4-yl)methanesulfonamide; |
| N-(1-(3-(4-chlorophenyl)pentan-3-yl)-1H-indol-4-yl)methanesulfonamide; |
| N-(1-(3-(4-chlorophenyl)pent-1-en-3-yl)-1H-indol-4-yl)methanesulfonamide; |
| N-(1-(2-amino-3-(4-chlorophenyl)pentan-3-yl)-1H-indol-4-yl)methanesulfonamide |
| N-(1-(1-amino-2-(4-chlorophenyl)butan-2-yl)-1H-indol-4-yl)methanesulfonamide |
| N-(1-(1-(4-chlorophenyl)-1-cyanopropyl)-1H-indol-4-yl)ethanesulfonamide |
| N-(1-(1-(4-chlorophenyl)-1-(2-ethyl-2H-tetrazol-5-yl)propyl)-1H-indol-4-yl)methanesulfonamide |
| N-(1-(3-(4-chlorophenyl)-6,6,6-trifluorohexan-3-yl)-1H-indol-4-yl)methanesulfonamide; |
| N-(1-(3-(4-chlorophenyl)-1-cyanopent-1-yn-3-yl)-1H-indol-4-yl)methanesulfonamide; | or a pharmaceutically acceptable salt thereof.

In another embodiment, the invention is a compound which is:

(R)—N-{1-[(2R)-2-(4-chlorophenyl)-1-hydroxybutan-2-yl]-1H-indol-4-yl}methanesulfonamide;

N-(1-(1-(4-chlorophenyl)-1-(2-cyanocyclopropyl)propyl)-1H-indazol-4-yl)methanesulfonamide;

N-(1-(1-(4-chlorophenyl)-1-(3-ethyl-1,2,4-oxadiazol-5-yl)propyl)-1H-indol-4-yl)methanesulfonamide;

N-(1-(2-(4-chlorophenyl)-1-hydroxybutan-2-yl)-1H-indazol-4-yl)methanesulfonamide;

N-(1-(1-(4-chlorophenyl)-1-(1-hydroxycyclopropyl)propyl)-1H-indol-4-yl)methanesulfonamide;

N-(1-(3-(4-chlorophenyl)-2-hydroxypentan-3-yl)-6-fluoro-1H-indol-4-yl)methanesulfonamide;

N-(1-(2-(4-chlorophenyl)-1-hydroxybutan-2-yl)indolin-4-yl)methanesulfonamide;

N-{1-[3-(4-chlorophenyl)-2-hydroxypentan-3-yl]-1H-indazol-4-ylmethanesulfonamide;

N-(1-(2-amino-3-(4-chlorophenyl)pentan-3-yl)-1H-indol-4-yl)methanesulfonamide;

1-(1-(3-(4-chlorophenyl)-2-hydroxy-2-methylpentan-3-yl)-1H-indazol-4-yl)-3-methyl-sulfonylurea;

methyl {4-[(methylsulfonyl)amino]-1H-indol-1-yl}(phenyl)acetate;

N-(1-(3-(4-chlorophenyl)-2-hydroxy-2-methylpentan-3-yl)-6-fluoro-1H-indol-4-yl)methane sulfonamide;

N-(1-(3-(4-chlorophenyl)-2-hydroxy-2-methylpentan-3-yl)-1H-indol-4-yl)methanesulfonamide;

N-(1-(3-(4-chlorophenyl)-2-hydroxy-2-methylpentan-3-yl)-1H-indazol-4-yl)methanesulfonamide;

N-(1-(2-hydroxy-2-methyl-3-(4-(trifluoromethyl)phenyl)pentan-3-yl)-1H-indazol-4-yl)methanesulfonamide;

N-(1-(2-(4-chlorophenyl)-1-methoxybutan-2-yl)-1H-indol-4-yl)methanesulfonamide;
N-(1-(3-(4-chlorophenyl)-2-oxopentan-3-yl)-1H-indazol-4-yl)methanesulfonamide;
N-(1-(2-hydroxy-3-(4-(trifluoromethyl)phenyl)pentan-3-yl)-1H-indazol-4-yl)methanesulfonamide;
(E)-N-(1-(3-(4-chlorophenyl)-1-cyanopent-1-en-3-yl)-6-fluoro-1H-indazol-4-yl)methanesulfonamide;
N-(1-(3-(4-chlorophenyl)-1-cyanopentan-3-yl)-1H-indazol-4-yl)methanesulfonamide;
N-(1-(1-cyano-3-(4-methoxyphenyl)pentan-3-yl)-1H-indol-4-yl)methanesulfonamide;
N-(1-(3-(4-chlorophenyl)-1-cyanopentan-3-yl)-1H-indol-4-yl)methanesulfonamide;
N-(1-(1-cyano-3-(4-(trifluoromethyl)phenyl)pentan-3-yl)-1H-indazol-4-yl)methanesulfonamide;
N-(1-(3-(4-chlorophenyl)-1-cyanopentan-3-yl)-6-fluoro-1H-indol-4-yl)methanesulfonamide;
N-(1-(1-cyano-3-phenylpentan-3-yl)-6-fluoro-1H-indazol-4-yl)methanesulfonamide;
N-(1-(3-(4-Chlorophenyl)-1-hydroxypentan-3-yl)-1H-indol-4-yl)methanesulfonamide;
N-(1-(3-(4-chlorophenyl)-6-hydroxyhexan-3-yl)-1H-indol-4-yl)methanesulfonamide;
N-(1-(3-(4-chlorophenyl)pentan-3-yl)-1H-indol-4-yl)methanesulfonamide;
or a pharmaceutically acceptable salt thereof.

In a further embodiment, the invention is a compound which is:
(R)—N-{1-[(2R)-2-(4-chlorophenyl)-1-hydroxybutan-2-yl]-1H-indol-4-yl}methanesulfonamide;
N-(1-(1-(4-chlorophenyl)-1-(2-cyanocyclopropyl)propyl)-1H-indazol-4-yl)methanesulfonamide;
N-(1-(1-(4-chlorophenyl)-1-(3-ethyl-1,2,4-oxadiazol-5-yl)propyl)-1H-indol-4-yl)methanesulfonamide;
N-(1-(2-(4-chlorophenyl)-1-hydroxybutan-2-yl)-1H-indazol-4-yl)methanesulfonamide;
N-(1-(1-(4-chlorophenyl)-1-(1-hydroxycyclopropyl)propyl)-1H-indol-4-yl)methanesulfonamide;
N-(1-(3-(4-chlorophenyl)-2-hydroxypentan-3-yl)-6-fluoro-1H-indol-4-yl)methanesulfonamide;
N-(1-(2-(4-chlorophenyl)-1-hydroxybutan-2-yl)indolin-4-yl)methanesulfonamide;
N-{1-[3-(4-chlorophenyl)-2-hydroxypentan-3-yl]-1H-indazol-4-ylmethanesulfonamide;
N-(1-(2-amino-3-(4-chlorophenyl)pentan-3-yl)-1H-indol-4-yl)methanesulfonamide;
1-(1-(3-(4-chlorophenyl)-2-hydroxy-2-methylpentan-3-yl)-1H-indazol-4-yl)-3-methyl-sulfonylurea;
or a pharmaceutically acceptable salt thereof.

As used herein except where noted, "alkyl" is intended to include both branched- and straight-chain saturated aliphatic hydrocarbon groups having the specified number of carbon atoms. The term "cycloalkyl" means carbocycles containing no heteroatoms. Examples of cycloalkyl include cyclopropyl, cyclobutyl, cyclopentyl, cyclohexyl, cycloheptyl, decahydronaphthyl and the like. Commonly used abbreviations for alkyl groups are used throughout the specification, e.g. methyl may be represented by conventional abbreviations including "Me" or CH₃ or a symbol that is an extended bond without defined terminal group, e.g. "⌇—", ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-6}$ alkyl" (or "C$_1$-C$_6$ alkyl") for example, means linear or branched chain alkyl groups, including all isomers, having the specified number of carbon atoms. C$_{1-6}$ alkyl includes all of the hexyl alkyl and pentyl alkyl isomers as well as n-, iso-, sec- and t-butyl, n- and isopropyl, ethyl and methyl. "C$_{1-4}$ alkyl" means n-, iso-, sec- and t-butyl, n- and isopropyl, ethyl and methyl. If no number is specified, 1-10 carbon atoms are intended for linear or branched alkyl groups. The phrase "C$_1$-C$_6$ alkyl, said alkyl is optionally substituted with one to three" groups refers to alkyl groups having 0, 1, 2 or 3 substituents attached to one or more carbon atoms. For example, a substituted butyl group (C$_4$ alkyl) could have 1, 2 or 3 substituents on one, two, three or four of the carbon atoms of the butyl group. Also, the group "CF$_3$", for example, is a methyl group having three fluorine atoms attached the same carbon atom.

"Alkenyl" unless otherwise indicated, means carbon chains which contain at least one carbon-carbon double bond, and which may be linear or branched or combinations thereof. Examples of alkenyl include, but are not limited to, vinyl, allyl, isopropenyl, pentenyl, hexenyl, heptenyl, 1-propenyl, 2-butenyl, 2-methyl-2-butenyl, and the like. The term "cycloalkenyl" means carbocycles containing no heteroatoms having at least one carbon-carbon double bond.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "C$_2$-C$_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

"Aryl" unless otherwise indicated, means mono- and bicyclic aromatic rings containing 6-12 carbon atoms. Examples of aryl include, but are not limited to, phenyl, naphthyl, indenyl and the like. "Aryl" also includes monocyclic rings fused to an aryl group. Examples include tetrahydronaphthyl, indanyl and the like. The preferred aryl is phenyl.

"Heteroaryl" unless otherwise indicated, means a mono- or bicyclic aromatic ring or ring system having 5 to 10 atoms and containing at least one heteroatom selected from O, S and N. Examples include, but are not limited to, pyrrolyl, isoxazolyl, isothiazolyl, pyrazolyl, pyridyl, pyridinyl, oxazolyl, oxadiazolyl, thiadiazolyl, thiazolyl, imidazolyl, triazolyl, tetrazolyl, furanyl, triazinyl, thienyl, pyrimidyl, pyrimidinyl, pyridazinyl, pyrazinyl, and the like. Heteroaryl also includes aromatic heterocyclic groups fused to heterocycles that are non-aromatic or partially aromatic, and aromatic heterocyclic groups fused to cycloalkyl rings. Additional examples of heteroaryls include, but are not limited to, dihydrofuranyl, indazolyl, thienopyrazolyl, imidazopyridazinyl, pyrazolopyrazolyl, pyrazolopyridinyl, imidazopyridinyl and imidazothiazolyl. Heteroaryl also includes such groups in charged form, e.g., pyridinium.

"Heterocyclyl", unless otherwise indicated, means a 4-, 5- or 6-membered monocyclic saturated ring containing at least one heteroatom selected from N, S and O, in which the point of attachment may be carbon or nitrogen. Examples of "heterocyclyl" include, but are not limited to, azetidinyl, pyrrolidinyl, piperidinyl, piperazinyl, morpholinyl, imidazolidinyl, 2,3-dihydrofuro(2,3-b)pyridyl, benzoxazinyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). Heterocyclyl moreover includes such moieties in charged form, e.g., piperidinium.

"Halogen (or halo)" unless otherwise indicated, includes fluorine (fluoro), chlorine (chloro), bromine (bromo) and iodine (iodo). In one embodiment, halo is fluorine or chlorine.

By "oxo" is meant the functional group "=O" which is an oxygen atom connected to the molecule via a double bond, such as, for example, (1) "C=(O)", that is a carbonyl group; (2) "S=(O)", that is, a sulfoxide group; and (3) "N=(O)", that is, an N-oxide group, such as pyridyl-N-oxide.

Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

Reference to the compounds of structural Formula I includes the compounds of other generic structural Formulae that fall within the scope of Formula I, including but not limited to Formula II, Formula III and/or Formula IV.

When any variable (e.g., R, $R^a$, $R^x$, etc.) occurs more than one time in any constituent or in Formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

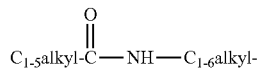

In choosing compounds of the present invention, one of ordinary skill in the art will recognize that the various substituents, i.e. $R^a$, $R^b$, $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Where a substituent or variable has multiple definitions, it is understood that the substituent or variable is defined as being selected from the group consisting of the indicated definitions.

Optical Isomers—Diastereoisomers—Geometric Isomers—Tautomers—Atropisomers:

Compounds of structural Formula I may contain one or more asymmetric centers and can thus occur as racemates and racemic mixtures, single enantiomers, diastereoisomeric mixtures and individual diastereoisomers. The present invention is meant to comprehend all such isomeric forms of the compounds of structural Formula I.

Compounds of structural Formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer or isomers of a compound of the general structural Formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

For compounds described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds of structural Formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural Formula I. For example, different isotopic forms of hydrogen (H) include protium ($^1$H) and deuterium ($^2$H, also denoted as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural Formula I, can be prepared without undue experimentation by conventional techniques well known to those skilled in the art or by processes analogous to those described in the Schemes and Examples herein using appropriate isotopically-enriched reagents and/or intermediates.

The present invention includes all stereoisomeric forms of the compounds of the Formula I. Centers of asymmetry that are present in the compounds of Formula I can all independently of one another have S configuration or R configuration. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the Formula I or at the stage of an intermediate during the synthesis. The present invention also includes all tautomeric forms of the compounds of Formula I.

The present invention includes all atropisomer forms of the compounds of Formula I. Atropisomers are stereoisomers resulting from hindered rotation about single bonds where the steric strain barrier to rotation is high enough to allow for the isolation of the conformers. Atropisomers display axial chirality. Separation of atropisomers is possibly by chiral resolution methods such as selective crystallization.

Salts:

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, including but not limited to the ethyl acetate solvate, and in particular, the hydrates of the compounds of structural Formula I are included in the present invention as well.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts. The terms "physiologically acceptable salt(s)" and "pharmaceutically acceptable salt(s)" are intended to have the same meaning and are used interchangeably herein.

As appropriate, the following embodiments may apply to structural Formulae I, II, III and/or IV.

In an embodiment, each $R^x$ is independently H, halo, OR, $C_1$-$C_6$ alkyl, $(CR_2)_{0-1}CN$, $NR^6COR$, $NR^6SO_2R^8$ or $NH_2$. In another embodiment, each $R^x$ is independently H, halo, OR, $C_1$-$C_6$ alkyl, or $(CR_2)_{0-1}CN$. In further embodiment, each $R^x$ is independently H or halo.

In an embodiment, each $R^y$ is independently H or $C_1$-$C_6$ alkyl. In another embodiment, each $R^y$ is H.

In an embodiment, $R^1$ is
1) 5-membered heteroaryl or heterocyclyl, said heteroaryl or heterocylyl is optionally substituted with one to three $R^5$,
2) $C_1$-$C_6$ alkyl, said alkyl is optionally substituted with one to three $C_1$-$C_6$ alkyl, OR, $NR_2$, $CF_3$, SR, $OS(O)_2R^8$, CN or halo substituents,
3) —$(CR^a_2)_nC(O)OR^{11}$,
4) —$(CR^a_2)_nC(O)NRR^7$,
5) —CN;
6) $(CR^a_2)_{0-4}C(O)R^c$,
7) $C_3$-$C_{10}$ cycloalkyl-$R^5$, or
8) —$(CR^a_2)_nOC(O)R^c$.

In a further embodiment, $R^1$ is
1) 5-membered heteroaryl or heterocyclyl, said heteroaryl or heterocylyl is optionally substituted with one to three $R^5$,
2) $C_1$-$C_6$ alkyl, said alkyl is optionally substituted with one to three $C_1$-$C_6$ alkyl, OR, $NR_2$, $CF_3$, SR, $OS(O)_2R^8$, CN or halo substituents,
3) —$(CR^a_2)_nC(O)OR^{11}$,
4) $(CR^a_2)_{0-4}C(O)R^c$,
5) $C_3$-$C_{10}$ cycloalkyl-$R^5$, or
6) —$(CR^a_2)_nOC(O)R^c$.

In another embodiment, $R^1$ is
1) 5-membered heteroaryl, said heteroaryl is optionally substituted with one to three $R^5$, 2) $C_1$-$C_6$ alkyl, said alkyl is optionally substituted with one to three $C_1$-$C_6$ alkyl, OR, $NR_2$, $CF_3$, SR, $OS(O)_2R^8$, CN or halo substituents,
3) —$(CR^a{}_2)_nC(O)OR^{11}$,
4) $(CR^a{}_2)_{0-4}C(O)R^c$, or
5) $C_3$-$C_{10}$ cycloalkyl-$R^5$.

In an embodiment, $R^2$ is
1) $C_1$-$C_6$ alkyl,
2) —$(CR^b{}_2)_m$—$C_3$-$C_6$ cycloalkyl,
3) —$(CR^a{}_2)_m$—$C(O)OR^{11}$,
4) —$(CR^b{}_2)_m$—$C_2$-$C_6$ alkenyl,
5) —$(CR^b{}_2)_m$—$C_2$-$C_6$ alkynyl,
6) —$(CR^b{}_2)_m$-aryl, or
7) —$(CR^b{}_2)_m$-heteroaryl;

Where said alkyl, cycloalkyl, alkenyl, alkynyl, aryl and heteroaryl are optionally substituted with one to three groups selected from $R^{12}$.

In another embodiment, $R^2$ is 1) $C_1$-$C_6$ alkyl, 2) —$(CR^b{}_2)_m$—$C_3$-$C_6$ cycloalkyl, 3) —$(CR^a{}_2)_mC(O)OR^{11}$, 4) —$(CR^b{}_2)_m$—$C_2$-$C_6$ alkenyl, or 5) —$(CR^b{}_2)_m$—$C_2$-$C_6$ alkynyl, where said alkyl, cycloalkyl, alkenyl, or alkynyl are optionally substituted with one to three groups selected from $R^{12}$. In a further embodiment, $R^2$ is 1) $C_1$-$C_6$ alkyl, 2) —$(CR^b{}_2)_m$—$C_3$-$C_6$ cycloalkyl, 3) —$(CR^b{}_2)_m$—$C_2$-$C_6$ alkenyl or 4) —$(CR^b{}_2)_m$—$C_2$-$C_6$ alkynyl, where said alkyl, cycloalkyl, alkenyl, or alkynyl are optionally substituted with one to three groups selected from $R^{12}$. In another embodiment, $R^2$ is $C_1$-$C_6$ alkyl.

In an embodiment, $R^3$ is phenyl, optionally substituted with one to three $R^9$ groups. In a further embodiment, $R^3$ is phenyl, optionally substituted with one to three halo, OR, $CF_3$, or $C_1$-$C_6$ alkyl groups.

In an embodiment, $R^4$ is
1) —$NR^6S(O)_2R^8$,
2) $C_1$-$C_6$ alkyl,
3) $C_3$-$C_6$ cycloalkyl,
4) —$N(O)_2$,
5) —$(CH_2)_{0-1}$—CN,
6) halo,
7) —$C(O)OR^{11}$,
8) —$NH_2$,
9) —OR,
10) —$(CR^a{}_2)_t$—$SO_2R^{10}$,
11) —$NR^6C(O)R^{10}$,
12) —$NR^6C(O)OR^{10}$,
13) —$NR^6{}_2$,
   where said alkyl and cycloalkyl may be optionally substituted with one to three halo, OR or $C_1$-$C_6$ alkyl substituents.

In another embodiment, $R^4$ is 1) —$NR^6S(O)_2R^8$, 2) $C_1$-$C_6$ alkyl, 3) $C_3$-$C_6$ cycloalkyl, 4) —$C(O)OR^{11}$, 5) —$(CR^a{}_2)_t$—$SO_2R^{10}$, 6) —$NR^6C(O)R^{10}$, 7) —$NR^6C(O)OR^{10}$, or 8) —$NR^6{}_2$, where said alkyl and cycloalkyl may be optionally substituted with one to three halo, OR or $C_1$-$C_6$ alkyl substituents. In a further embodiment, $R^4$ is 1) —$NR^6S(O)_2R^8$, 2) —$(CR^a{}_2)_t$—$SO_2R^{10}$, or 3) —$NR^6{}_2$. In another embodiment, $R^4$ is —$NR^6S(O)_2R^8$.

In an embodiment, t is 0, 1, 2 or 3. In another embodiment, t is 0, 1 or 2.

In an embodiment, x is 0, 1, 2 or 3. In another embodiment, x is 0, 1 or 2. In a further embodiment, x is 0 or 1.

The present invention also relates to processes for the preparation of the compounds of the Formula I which are described in the following and by which the compounds of the invention are obtainable.

The compounds of the Formula I according to the invention competitively antagonize the mineralocortoid receptor (MR) and they are therefore useful agents for the therapy and prophylaxis of disorders related to increased aldosterone levels. The ability for the compounds of the Formula I to antagonize MR can be examined, for example, in the activity assay described below.

One aspect of the invention that is of interest relates to a compound in accordance with formula I or a pharmaceutically acceptable salt thereof for use in a method of treatment of the human or animal body by therapy.

Another aspect of the invention that is of interest relates to a compound in accordance with formula I or a pharmaceutically acceptable salt thereof for use as an anti-hypertensive agent in a human or animal.

Another aspect of the invention that is of interest is a method of treating cardiovascular disease, heart failure, hypertension, atherosclerosis, primary hyperaldosternoism or a related condition in a human patient in need of such treatment comprising administering a therapeutically effective amount of a compound of formula I or a pharmaceutically acceptable salt thereof.

Another aspect of the invention that is of interest relates to a method of treating metabolic syndrome in a mammal in need of such treatment, comprising administering a therapeutically effective amount of a compound of formula I or a pharmaceutically acceptable salt thereof.

Another aspect of the invention that is of interest relates to a method of treating a physiological or pathologic disease, selected from including Conn's Syndrome, primary and secondary hyperaldosternism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, and disorders associated with excess catecholamine levels in a human patient in need of such treatment comprising administering to the patient a therapeutically effective amount of a compound of formula I or a pharmaceutically acceptable salt thereof.

Another aspect of the invention that is of interest is a method of treating renal failure in a human patient in need of such treatment comprising administering a therapeutically effective amount of a compound of formula I or a pharmaceutically acceptable salt thereof.

Another aspect of the invention that is of interest is a method of treating hypertension, including, but not limited to, essential hypertension, resistant hypertension, systolic hypertension, pulmonary arterial hypertension, and the like.

Additionally, another aspect of the invention is a method of treating hypertension in an obese animal or human.

Additionally, another aspect of the invention is a method of treating hypertension in a diabetic animal or human.

The compounds of the Formula I and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

A subject of the present invention therefore also are the compounds of the Formula I and their pharmaceutically acceptable salts for use as pharmaceuticals, their use for antagonizing mineralocorticoid receptors and in particular their use in the therapy and prophylaxis of the abovementioned syndromes as well as their use for preparing medicaments for these purposes.

The terms "therapeutically effective (or efficacious) amount" and similar descriptions such as "an amount efficacious for treatment" are intended to mean that amount of a pharmaceutical drug that will elicit the biological or medical response of a tissue, a system, animal or human that is being sought by a researcher, veterinarian, medical doctor or other clinician. The terms "prophylactically effective (or efficacious) amount" and similar descriptions such as "an amount efficacious for prevention" are intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hypertension, and a prophylactically effective amount, e.g., for prevention of myocardial infarction.

Furthermore, a subject of the present invention are pharmaceutical preparations (or pharmaceutical compositions) which comprise as active component an effective dose of at least one compound of the Formula I and/or a pharmaceutically acceptable salt thereof and a customary pharmaceutically acceptable carrier, i.e., one or more pharmaceutically acceptable carrier substances and/or additives.

Thus, a subject of the invention are, for example, said compound and its physiologically or pharmaceutically acceptable salts for use as a pharmaceutical, pharmaceutical preparations which comprise as active component an effective dose of said compound and/or a physiologically (or pharmaceutically) acceptable salt thereof and a customary pharmaceutically acceptable carrier, and the uses of said compound and/or a physiologically (or pharmaceutically) acceptable salt thereof in the therapy or prophylaxis of the abovementioned syndromes as well as their use for preparing medicaments for these purposes.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of active compound of the Formula I and/or its physiologically (or pharmaceutically) acceptable salts in the pharmaceutical preparations normally is from 0.2 to 700 mg, preferably from 1 to 500 mg, per dose, but depending on the type of the pharmaceutical preparation it can also be higher. The pharmaceutical preparations usually comprise 0.5 to 90 percent by weight of the compounds of the Formula I and/or their physiologically (or pharmaceutically) acceptable salts. The preparation of the pharmaceutical preparations can be carried out in a manner known per se. For this purpose, one or more compounds of the Formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the Formula I and their physiologically (or pharmaceutically) acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of the Formula I to be administered and/or of a pharmaceutically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the Formula I. In general, a daily dose of approximately 0.01 to 100 mg/kg, preferably 0.01 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds of the Formula I bind to the mineralocorticoid receptor and antagonize the biological effects of aldosterone and cortisol. On account of this property, apart from use as pharmaceutically active compounds in human medicine and veterinary medicine, they can also be employed as a scientific tool or as aid for biochemical investigations in which such an effect on the mineralocorticoid receptor is intended, and also for diagnostic purposes, for example in the in vitro diagnosis of cell samples or tissue samples. The compounds of the Formula I and salts thereof can furthermore be employed, as already mentioned above, as intermediates for the preparation of other pharmaceutically active compounds.

One or more additional pharmacologically active agents may be administered in combination with a compound of Formula I. An additional active agent (or agents) is intended to mean a pharmaceutically active agent (or agents) different from the compound of Formula I. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents).

The above-mentioned compounds are also of use in combination with other pharmacologically active compounds. Additional active compounds that may be used in combination with the compounds of the instant invention, either co-administered or in a fixed combination, include, but are not limited to, angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan, valsartan, candesartan, olmesartan, telmesartan) neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075, 451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4 (S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide, chlorthalidone, furosemide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., niacin, HMG Co-A reductase inhibitors), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. troglitazone, pioglitazone, englitazone, MCC-555, rosiglitazone, balaglitazone, netoglitazone, T-131, LY-300512, LY-818, and compounds disclosed in WO02/08188, WO2004/020408, and WO2004/020409.

(b) biguanides, such as metformin and phenformin;

(c) protein tyrosine phosphatase-1B (PTP-1B) inhibitors;

(d) dipeptidyl peptidase-IV (DPP-4) inhibitors, such as sitagliptin, saxagliptin, vildagliptin, and alogliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARα agonists, such as fenofibric acid derivatives (gemfibrozil, clofibrate, fenofibrate and bezafibrate), (v) cholesterol absorption inhibitors, such as ezetimibe, (vi) acyl CoA:cholesterol acyltransferase (ACAT) inhibitors, such as avasimibe, (vii) CETP inhibitors, such as torcetrapib, and (viii) phenolic antioxidants, such as probucol;

(i) PPARα/γ dual agonists, such as muraglitazar, tesaglitazar, farglitazar, and JT-501;

(j) PPARδ agonists, such as those disclosed in WO97/28149;

(k) anti-obesity compounds, such as fenfluramine, dexfenfluramine, phentiramine, subitramine, orlistat, neuropeptide Y Y5 inhibitors, MC4R agonists, cannabinoid receptor 1 (CB-1) antagonists/inverse agonists (e.g., rimonabant and taranabant), and $\beta_3$ adrenergic receptor agonists;

(l) ileal bile acid transporter inhibitors;

(m) agents intended for use in inflammatory conditions, such as aspirin, non-steroidal anti-inflammatory drugs, glucocorticoids, azulfidine, and cyclooxygenase-2 (Cox-2) selective inhibitors;

(n) glucagon receptor antagonists;

(O) GLP-1;

(p) GIP-1;

(q) GLP-1 analogs and derivatives, such as exendins, (e.g., exenatide and liruglatide), and (r) 11β-hydroxysteroid dehydrogenase-1 (HSD-1) inhibitors.

One or more additional active agents may be administered with the compounds described herein. The additional active agent or agents can be lipid modifying compounds or agents having other pharmaceutical activities, or agents that have both lipid-modifying effects and other pharmaceutical activities. Examples of additional active agents which may be employed include but are not limited to HMG-CoA reductase inhibitors, which include statins in their lactonized or dihydroxy open acid forms and pharmaceutically acceptable salts and esters thereof, including but not limited to lovastatin (see U.S. Pat. No. 4,342,767), simvastatin (see U.S. Pat. No. 4,444,784), dihydroxy open-acid simvastatin, particularly the ammonium or calcium salts thereof, pravastatin, particularly the sodium salt thereof (see U.S. Pat. No. 4,346,227), fluvastatin particularly the sodium salt thereof (see U.S. Pat. No. 5,354,772), atorvastatin, particularly the calcium salt thereof (see U.S. Pat. No. 5,273,995), pitavastatin also referred to as NK-104 (see PCT international publication number WO 97/23200) and rosuvastatin, also known as CRESTOR®; see U.S. Pat. No. 5,260,440); HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; endothelial lipase inhibitors; bile acid sequestrants; LDL receptor inducers; platelet aggregation inhibitors, for example glycoprotein IIb/IIIa fibrinogen receptor antagonists and aspirin; human peroxisome proliferator activated receptor gamma (PPAR-gamma) agonists including the compounds commonly referred to as glitazones for example pioglitazone and rosiglitazone and, including those compounds included within the structural class known as thiazolidine diones as well as those PPAR-gamma agonists outside the thiazolidine dione structural class; PPAR-alpha agonists such as clofibrate, fenofibrate including micronized fenofibrate, and gemfibrozil; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; diuretics (e.g., chlorthalidone, hydrochlorothiazide), sympatholitics, endothelin antagonists; agents that enhance ABCA1 gene expression; cholesteryl ester transfer protein (CETP) inhibiting compounds, 5-lipoxygenase activating protein (FLAP) inhibiting compounds, 5-lipoxygenase (5-LO) inhibiting compounds, farnesoid X receptor (FXR) ligands including both antagonists and agonists; Liver X Receptor (LXR)-alpha ligands, LXR-beta ligands, bisphosphonate compounds such as alendronate sodium; cyclooxygenase-2 inhibitors such as rofecoxib and celecoxib; and compounds that attenuate vascular inflammation.

The compounds of Formula I can be synthesized in accordance with the general schemes provided below where $R^1$, $R^2$, and $R^9$ are defined as above (unless otherwise indicated), taking into account the specific examples that are provided. Throughout the synthetic schemes and examples, abbreviations are used with the following meanings unless otherwise indicated:

ABCA1=adenosyltriphosphate-binding cassette-family A1
Ac=acetate, acetyl
AIBN is 2,2'-azobis(2-methylpropionitrile);
aq. is aqueous;
Ar is Aryl;
Bn is benzyl;
Boc is tertbutylcarbamoyl;
br is broad;
Bu is butyl;
$^t$Bu is tert-butyl;
CDI is carbonyl diimidazole;
celite is Celite® diatomaceous earth;
CHO is Chinese hamster ovary
cpm is counts per minute;
° C. is degrees Celsius;
δ is chemical shift;
$^c$Pr is cyclopropyl;
DAST is diethylaminosulfur trifluoride;
DBU is 1,8-diazabicyclo[5.4.0]undec-7-ene;
DCM is dichloromethane;
d is doublet;
DEA is diethyl amine;
DEAD is diethylazodicarboxylate;
DIAD is diisopropylazodicarboxylate;
DIBAL-H is diisobutylaluminum hydride;
DIPEA is diisopropylethylamine;
DMAP is 4-dimethylaminopyridine;
DME is 1,2-dimethoxyethane;
DMF is N,N-dimethylformamide;
dppf is 1,1'-bis(diphenylphosphino)ferrocene;
DMSO is dimethyl sulfoxide;
EA is ethyl acetate;
EDC is N-(3-dimethylaminopropyl)-N'-ethylcarbodiimide hydrochloride;
EDCI is 1-ethyl-3-(3-dimethylaminopropyl)carbodiimide hydrochloride;
EDTA is ethylendiamine tetraacetic acid;
ES-MS is electrospray ion-mass spectroscopy;
Et is ethyl;
$Et_2O$ is diethyl ether;
EtOH is ethanol,
EtOAc is ethyl acetate;
FBS is fetal bovine serum
FXR is farnesoid X receptor;
halo is a halogen (preferably fluorine or chlorine),
HATU is O-(7-azabenzotriazol-1-yl)-N,N,N',N'-tetramethyluronium hexafluorophosphate;
HetAr or HAR is Heteroaryl;
HMG-CoA is 3-hydroxy-3-methyl-glutaryl coenzyme A;
HMPA is hexamethylphosphoric acid triamide;
$^1$HNMR is proton nuclear magnetic resonance;
HOAt is 1-hydroxy-7-azabenzotriazole;
HOBt is 1-hydroxybenzotriazole;
HPLC is high performance liquid chromatography;
Hz is hertz;
i is Iso;
$^i$Pr is isopropyl;
IP is the inflection point for a given dose-response titration curve;
J is internuclear coupling constant;
kg is kilogram;
LiHMDS is lithium bis(trimethylsilyl)amide;
LG is leaving group;
$LTB_4$ is leukotriene $B_4$;
LXR is liver X receptor;
m is multiplet;
M is molar;
Me is methyl;
μg is microgram;
MeCN is acetonitrile;
MeOH is methanol;
MHz is megahertz;
mm is millimeter;
μL is microliter;
mM is milimolar;
μM is micromolar;
mmol is milimoles;
Ms is methanesulfonyl;
MS is mass spectrum, and a mass spectrum obtained by ES-MS may be denoted herein by "ES";

MsCl is methanesulfonyl chloride;
m/z is mass to charge ratio;
n is normal;
NBS is N-bromosuccinimide
nm is nanometer;
NMM is N-methylmorpholine;
NMO is N-methylmorpholine-N-oxide;
NMP is N-methylpyrrolidin-2-one;
nPr is n-propyl;
p is pentet;
p is para;
Pd/C is palladium carbon;
PE is petroleum ether;
PEG is polyethylene glycol;
Ph is phenyl;
Phen.H$_2$O is 1,10-phenanthroline monohydrate;
Phth is phthalimidoyl;
PPARα is peroxisome proliferator activated receptor alpha;
Pr is propyl;
iPr is isopropyl;
Pre-HPLC is preparative high performance liquid chromatography;
Pt/C is platinum carbon;
PtO$_2$ is platinum (IV) oxide;
PyBOP is benzotriazole-1-yl-oxy-tris-pyrrolidino-phosphonium hexafluorophosphate;
q is quartet;
rt or RT is room temperature;
s is singlet; sec is secondary;
(s) is solid
SEC is size exclusion chromatography;
SEM is 2-(trimethylsilyl)ethoxymethyl;
SFC is supercritical-fluid chromatography;
t is triplet;
t-Bu is t-butyl;
$^t$BuOH is tert-butanol;
tert is tertiary;
Tf is trifluoromethanesulfonyl;
TEA is triethyl amine;
TFA is trifluoroacetic acid;
TFAA is trifluoroacetic anhydride;
THF is tetrahydrofuran;
TLC is thin layer chromatography;
TMS is trimethylsilyl;
Ts is tosyl;
U is units
UV is ultraviolet;
× g is times gravity
% wt/wt is weight percentage of a given solid reagent

SCHEMES

Reaction schemes A-N illustrate the methods employed in the synthesis of the compounds of Formula I. All abbreviations are as defined above unless indicated otherwise. In the Schemes, all substituents are as defined above in Formula I unless indicated otherwise.

Reaction scheme A illustrates a method of synthesis of compounds of type 2. In this method, a phenylacetic acid derivative of type 1 is treated with a bromine source, such as N-bromosuccinimide or the like, in the presence of a suitable initiator, such as AIBN, to afford an α-bromophenylacetate of type 2. The reaction is run in an inert solvent, such as carbon tetrachloride or benzene, at elevated temperatures between 70° C. and the boiling temperature of the solvent.

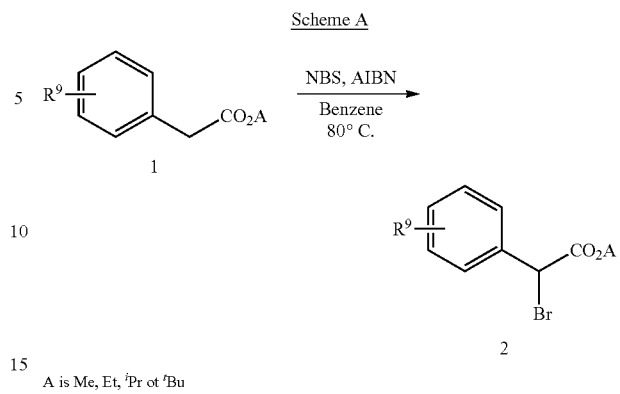

Scheme A

A is Me, Et, $^i$Pr ot $^t$Bu

Reaction scheme B illustrates a method of synthesis of compounds of type 4. In this method, a substituted indole or indazole of type 3 is treated with a suitable base, such as sodium hydride in examples involving substituted indoles or cesium carbonate in examples involving substituted indazoles, followed by reaction with electrophiles, such as α-bromophenylacetates of type 2, to afford compounds of type 4. The reaction is performed in a polar aprotic solvent, such as DMF or DMSO, at temperatures between 0° C. and room temperature. The product is a compound of type 4, which can be elaborated to compounds of the present invention (I) as described in the subsequent schemes.

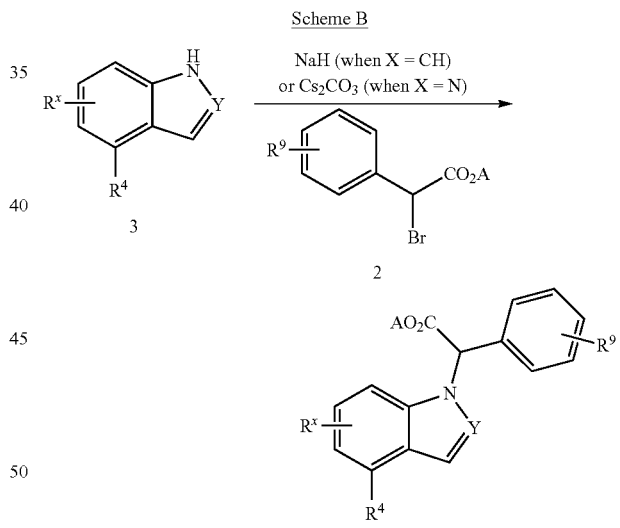

Scheme B

A is Me, Et, $^i$Pr or $^t$Bu

Reaction scheme C illustrates a method for preparing a compound of type 6, by treating compounds of type 4a, wherein R$^4$=NO$_2$. In this method, compound 4a is treated with a suitable catalyst, such as Pt/C (Pd/C can be utilized when compound 4a does not contain additional reactive functionality such as halogen substitution), under a hydrogen atmosphere (balloon pressure) in a suitable solvent, such as ethyl acetate or the like, to afford an aminoindole of type 5. Alternatively, the nitro group can be reduced by treating compounds of type 4a with tin(II)chloride in the presence of strong acid, such as concentrated HCl or sulfuric acid, in a protic solvent, such as ethanol or the like, at elevated temperatures between 50° C. and the boiling temperature of the solvent. The products of type 5 can be treated with ditertbutyl dicarbonate under basic conditions, such as reaction conditions known as Schotten-Baumen conditions. The product is a compound of type 6, which can be elaborated to compounds of the present invention (I) as described in the subsequent schemes.

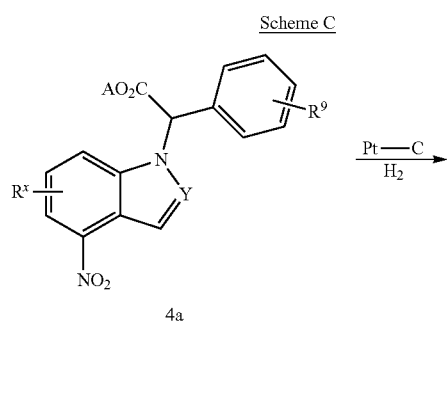

Scheme C

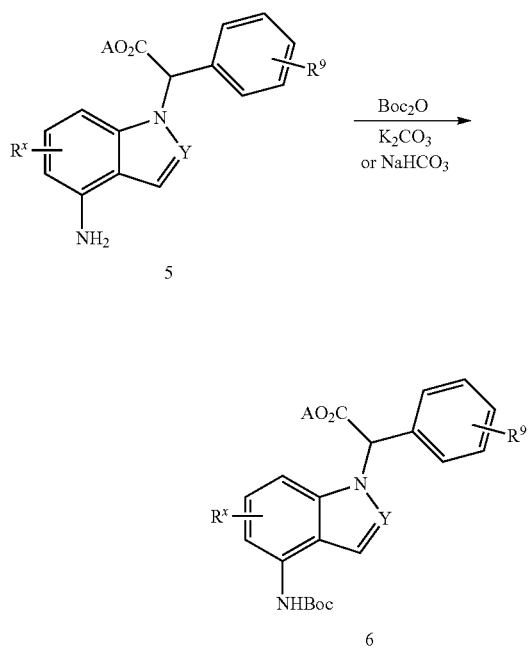

A is Me, Et, $^i$Pr or $^t$Bu

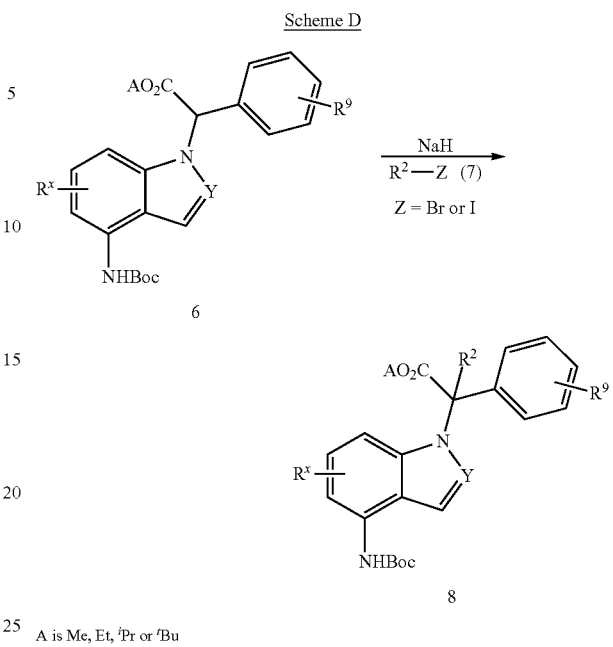

Scheme D

A is Me, Et, $^i$Pr or $^t$Bu

Reaction scheme E illustrates a method of synthesis of compounds of type 9. In this method, compounds of type 8 are first treated under strongly acidic conditions, such as trifluoroacetic acid or concentrated HCl, to yield aminoindoles or aminoindazoles of type 5a, which are subsequently reacted with a suitable electrophile source, such as a sulfonyl chloride or an acyl halide or acyl anhydride, in the presence of a suitable base, such as 4-methylmorpholine or diisopropylethylamine or the like. The product of the reaction is a compound of type 9, which can be elaborated to compounds of the present invention (I) as described in the subsequent schemes.

Scheme E

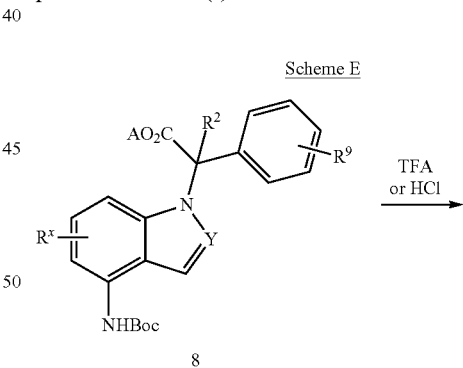

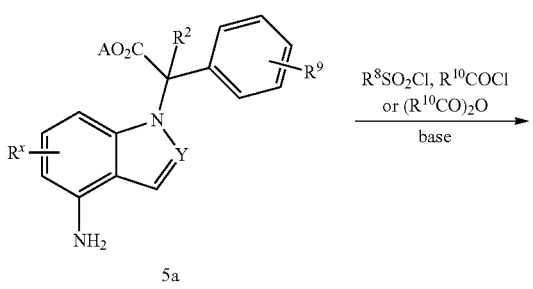

Reaction scheme D illustrates a method of synthesis of compounds of type 8. In this method, substrates of type 6 are treated with a suitable base, such as sodium hydride, followed by reaction of the corresponding anion with electrophiles of type 7 to afford the desired product. Most conditions involve slow addition of solutions of 6 to a mixture containing the base prior to addition of the electrophile (7). The reaction is run in a polar aprotic solvent, such as DMF or the like, at temperatures between −20° C. and 0° C., and the product of the reaction is a compound of type 8, which can be elaborated to compounds of the present invention (I) as described in the subsequent schemes.

-continued

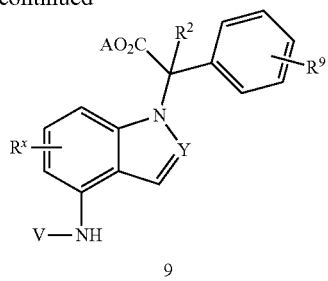

9

A is Me, Et, $^i$Pr or $^t$Bu
V is —COR$^{10}$ or —SO$_2$R$^8$, as defined for R$^4$ for the present invention (I)

Reaction scheme F illustrates a method of synthesis of compounds of structural formula 12 via an organotransition metal catalyzed cross-coupling reaction commonly referred to as the Suzuki reaction. In this method, an aryl- or heteroaryl-compound of type 10, is reacted with a boronic acid (11) or boronate (12) coupling partner in the presence of a suitable palladium catalyst, such as [1,1'-bis(diphenylphosphino)ferrocene]dichloropalladium(II) or tetrakistriphenylphosphinepalladium(0) or the like, and a base such as aqueous sodium carbonate or aqueous tribasic sodium phosphate or the like (*Pure Appl. Chem.* 1991, 63, 419-422). The reaction is performed in an inert organic solvent such as a toluene-EtOH mixture or dioxane, at temperatures above rt, for a period of 3-24 h. Recent advancements in the Suzuki reaction have allowed this type of transformation to be conducted in many cases at rt (for example, see: *J. Am. Chem. Soc.* 2000, 122, 4020-4028 and references cited therein). The product of the reaction is a compound of type 13, which can be elaborated to furnish other compounds of the present invention (I) as described in subsequent schemes.

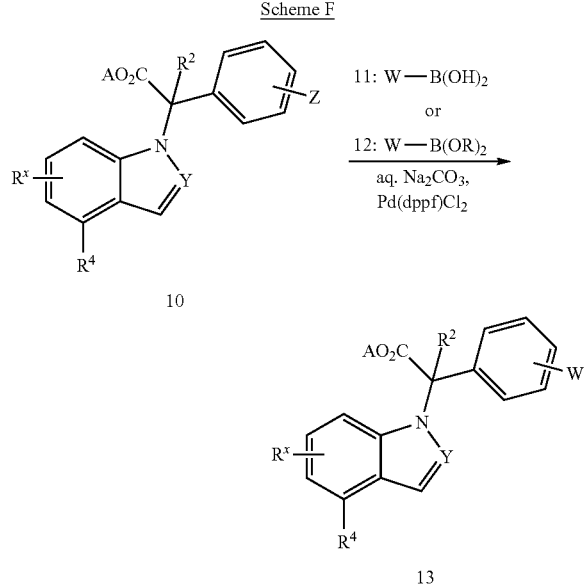

A is Me, Et, $^i$Pr or $^t$Bu
Z = a suitable leaving group, such as OTf, Br or I
W = aryl or heteroaryl group as defined for R$^9$ in formula I or a group that can be converted to any aryl or heteroaryl group as defined for R$^9$ in formula I Reaction scheme G illustrates a method of synthesis of compounds of structural formula 15 following methods similar to those previously described in Scheme F. Compounds of type 15 that are derived from inputs of type 14 that contain additional functional groups can be elaborated to furnish other compounds of the present invention (I).

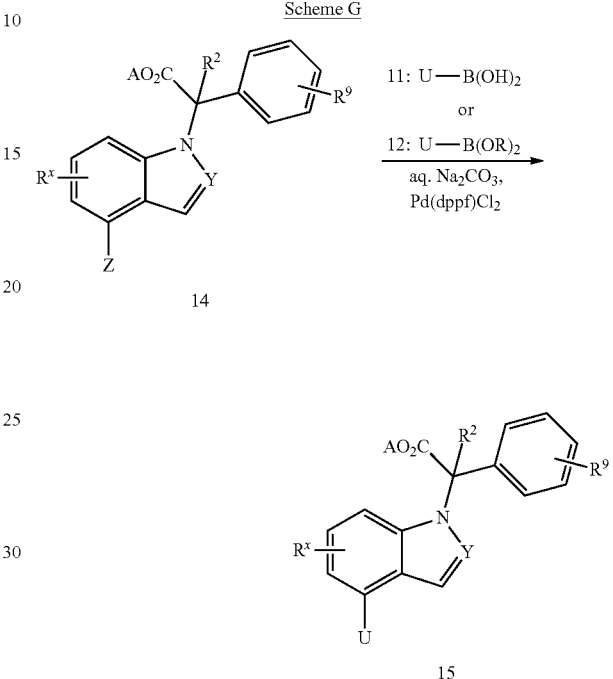

A is Me, Et, $^i$Pr or $^t$Bu
Z = a suitable leaving group, such as OTf, Br or I
U = aryl or heteroaryl group as defined for R$^4$ in formula I or a group that can be converted to any aryl or heteroaryl group as defined for R$^4$ in formula I Reaction scheme H illustrates a method of synthesis of compounds of structural formula 17. In this method, compounds of type 16 can be hydrolyzed to carboxylic acids of type 17 using a variety of methods known to those skilled in organic synthesis. The product carboxylic acid of structural formula 17 can be used in a variety of methods known in organic synthesis to afford compounds of the present invention (I).

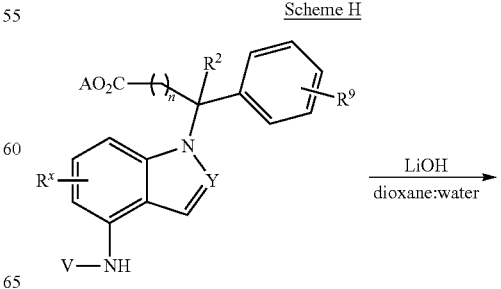

16

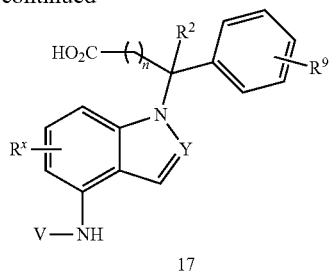

n = 0, 1, or 2
Y is Me, Et, ⁱPr or ᵗBu
V is ——COR¹⁰ or ——SO₂R⁸, as defined for R⁴ in formula (I)

Reaction scheme I illustrates the method of synthesis of compounds of structural formula 20. In the most general case, compounds of type 18 are treated with an amine of type 19 to afford an amide of type 20. The amide bond coupling reaction illustrated in reaction scheme I is conducted in an appropriate inert solvent such as DMF, DCM or the like and may be performed with a variety of reagents suitable for amide coupling reactions such as HATU, EDC or PyBOP. Conditions for the amide bond coupling reaction shown in reaction Scheme I are known to those skilled in organic synthesis. Such modifications may include, but are not limited to, the use of basic reagents such as triethylamine, DIPEA, or NMM, or the addition of an additive such as HOAt or HOBt. Alternatively, 19 may be treated with an activated ester or acid chloride derivative of 18, which also affords 20. The amide bond coupling shown in reaction Scheme I is usually conducted at a temperatures between 0° C. and room temperature, occasionally at elevated temperatures, and the coupling reaction is conducted for periods of 1 to 24 hours. The product of the reaction is a compound of type 20, which can be elaborated to furnish other compounds of the present invention (I) as described in subsequent schemes.

Scheme I

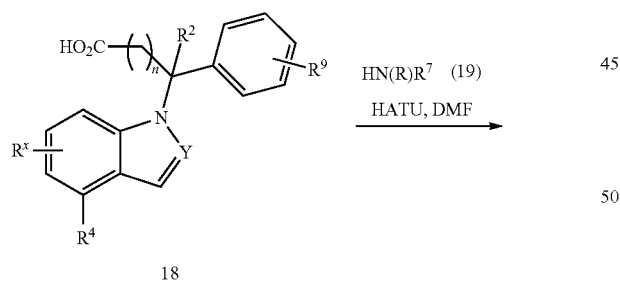

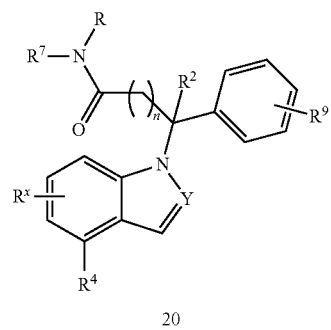

Reaction scheme J illustrates a method for the synthesis of compounds of type 22. In this method, a primary amide of type 21 is treated with a dehydrating reagent, such as cyanuric chloride or the like, to generate a nitrile of type 22. The reaction is performed in an inert solvent, such as DCM or DMF, between 0° C. and room temperature. The product of the reaction is a compound of type 22, which can be elaborated to furnish other compounds of the present invention (I) as described in subsequent schemes.

Scheme J

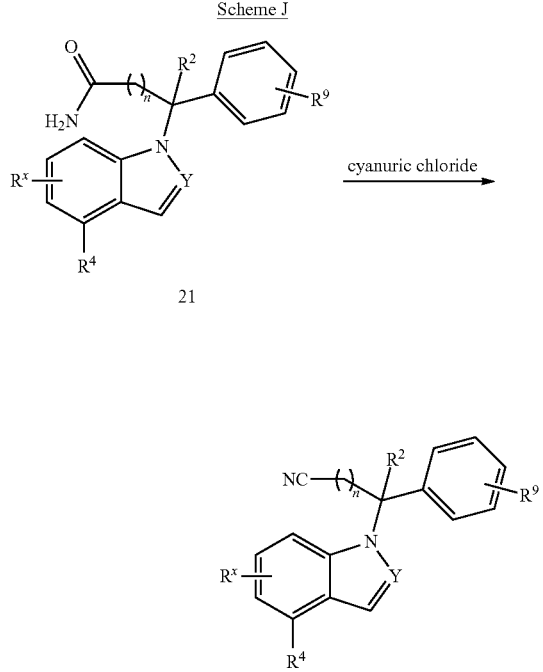

Scheme K illustrates in the most generalized manner how compounds of type 23 can be elaborated to a variety of heterocyclic derivatives of structural formula 24 using known methods in organic synthesis. Specific examples of such transformations are shown in the Examples section.

Such transformations are described in 1) Joule, J. A; Mills, K. and Smith, G. F. Heterocyclic Chemistry, Chapman & Hall, 1995, 3rd Edn., and references cited therein; 2) Katritzky, A. R.; Rees, C. W. (Eds), Comprehensive Heterocyclic Chemistry: The Structure, Reactions, Synthesis, and Uses of Heterocyclic Compounds, Pergamon Press, Oxford, 1984, 8v, and references cited therein; and 3) Comprehensive Heterocyclic Chemistry II: Review of the Literature 1982-1995: The Structure, Reactions, Synthesis and Uses of Heterocyclic Compounds, Pergamon Press, New York, 2nd Edn., 1996, 11v, and references cited therein. (Comprehensive Heterocyclic Chemistry, vol. 4-6 Pergamon Press, New York, 1984, and references therein).

Scheme K

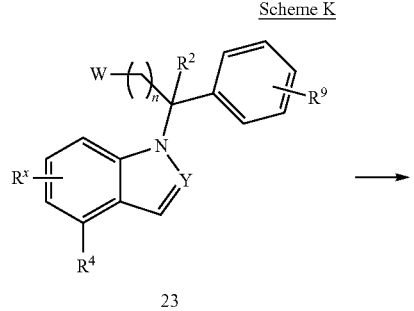

23

24 n = 0, 1, or 2
W = CO₂H, CO₂Me, CN

Scheme L illustrates a method for the synthesis of compounds of type 26. In this method, an ester of type 25 is treated with a strong reducing agent, such as lithium borohydride or lithium aluminum hydride or the like, in an etheral solvent, such as THF or diethyl ether, between 0° C. and room temperature. The product of the reaction is an alcohol of type 26 that can be elaborated to furnish other compounds of the present invention (I) as described in subsequent schemes.

Scheme L

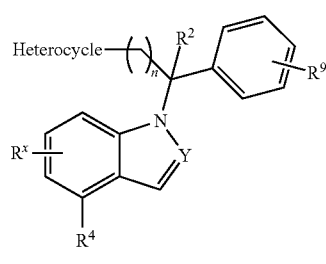

25

-continued

26 n = 0, 1, or 2
A = Me or Et

Scheme M illustrates a method for the synthesis of compounds of type 28. In this method, a cyanoester of type 27 is treated with an excess of reducing agent, such as sodium borohydride, in the presence of an inorganic accelerating agent, such as cobalt(II)chloride, to afford an amine intermediate (not shown) that undergoes intramolecular cyclization onto the ester moiety to yield a lactam of type 28. This product can be elaborated to furnish other compounds of the present invention (I) as described in subsequent schemes.

Scheme M

27

28 n = 0 or 1
A = Me or Et

Scheme N illustrates the method for the resolution of a racemic compound of structural formula 29 in which the asterisked carbon is a center of chirality. Generally, the latter, or intermediates en route to their preparation, may be resolved to afford enantiomerically pure compounds such as 30 and 31 by chiral stationary phase liquid chromatography techniques or other suitable methods known in organic synthesis.

Scheme N

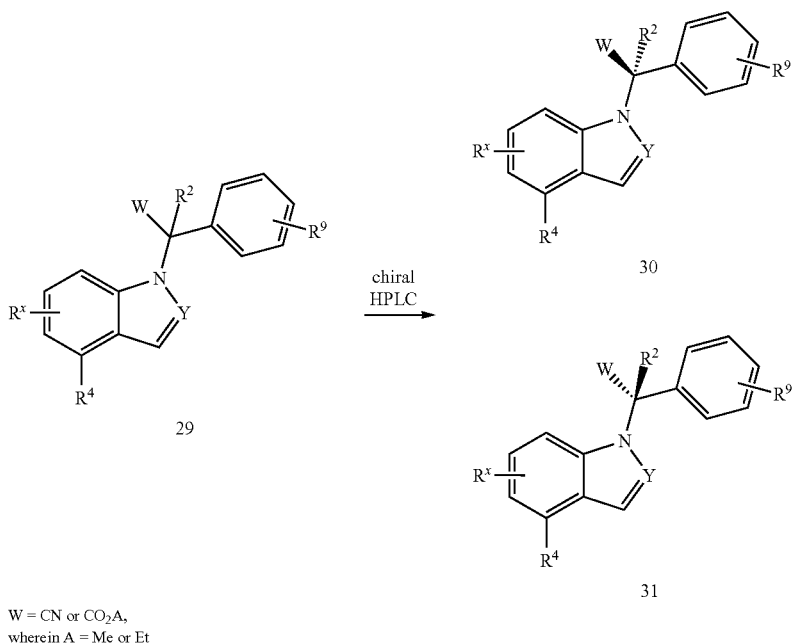

W = CN or CO$_2$A,
wherein A = Me or Et

The following examples are provided so that the invention might be more fully understood. Unless otherwise indicated, the starting materials are commercially available. They should not be construed as limiting the invention in any way.

REPRESENTATIVE EXAMPLES

The following examples are provided to more fully illustrate the present invention, and shall not be construed as limiting the scope in any manner. Unless stated otherwise:
1) All operations were carried out at room or ambient temperature (rt), that is, at a temperature in the range 18-25° C.;
2) Reactions are generally done using commercially available anhydrous solvents under an inert atmosphere, either nitrogen or argon;
3) Microwave reactions were done using a Biotage Initiator™ or CEM Explorer® system;
4) Evaporation of solvent was carried out using a rotary evaporator under reduced pressure (4.5-30 mmHg) with a bath temperature of up to 50° C.;
5) The course of reactions was followed by thin layer chromatography (TLC) and/or tandem high performance liquid chromatography (HPLC) followed by electron spray mass spectroscopy (MS), herein termed LCMS, and any reaction times are given for illustration only;
6) The structure of all final compounds was assured by at least one of the following techniques: MS or proton nuclear magnetic resonance (1H NMR) spectrometry, and the purity was assured by at least one of the following techniques: TLC or HPLC;
7) $^1$H NMR spectra were recorded on either a Varian Unity or a Varian Inova instrument at 400, 500 or 600 MHz using the indicated solvent; when line-listed, NMR data is in the form of delta values for major diagnostic protons, given in parts per million (ppm) relative to residual solvent peaks (multiplicity and number of hydrogens); conventional abbreviations used for signal shape are: s. singlet; d. doublet (apparent); t. triplet (apparent); m. multiplet; br. broad; etc.;
8) MS data were recorded on a Waters Micromass unit, interfaced with a Hewlett-Packard (Agilent 1100) HPLC instrument, and operating on MassLynx/OpenLynx software; electrospray ionization was used with positive (ES+) or negative ion (ES−) detection; and diode array detection.
9) Purification of compounds by preparative reverse phase HPLC was performed on a Gilson system using a YMC-Pack Pro C18 column (150×20 mm i.d.) eluting at 20 mL/min with a water/acetonitrile (0.1% TFA) gradient (5% acetonitrile to 95% acetonitrile) or on a Shimadzu system using a Sunfire Prep C18 OBD 5 μM column (100×30 mm i.d.) eluting at 50 mL/min with a water/acetonitrile (0.1% TFA) gradient;
10) Purification of compounds by preparative thin layer chromatography (PTLC) was conducted on 20×20 cm glass plates coated with silica gel, commercially available from Analtech; or E. Merck.
11) Flash column chromatography was carried out on a glass silica gel column using Kieselgel 60, 0.063-0.200 mm (SiO$_2$), or on a Biotage SiO$_2$ cartridge system using the Biotage Horizon and Biotage SP-1 systems; or a Teledyne Isco SiO$_2$ cartridge using the CombiFlashRf system;
12) Chemical symbols have their usual meanings, and the following abbreviations have also been used: h (hours), min (minutes), v (volume), w (weight), b.p. (boiling point), m.p. (melting point), L (liter(s)), mL (milliliters), g (gram(s)), mg (milligrams(s)), mol (moles), mmol (millimoles), eq or equiv (equivalent(s)), IC50 (molar concentration which results in 50% of maximum possible inhibition), EC50 (molar concentration which results in 50% of maximum possible efficacy), uM (micromolar), nM (nanomolar).

Intermediates

Intermediates used in the synthesis of compounds of this invention can be prepared using the following procedures. In the Tables associated with the following Schemes, compounds having mass spectral data were synthetically prepared.

Example I-1A

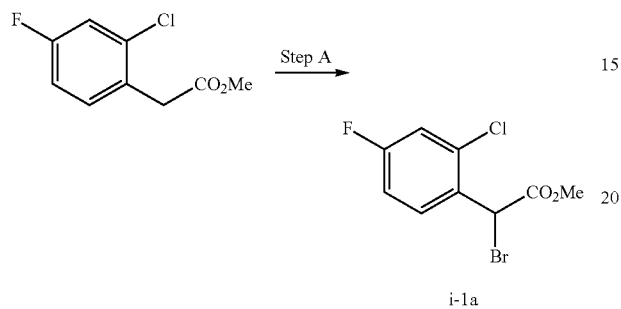

i-1a

Step A: Preparation of Methyl bromo(2-chloro-4-fluorophenyl)acetate (i-1a)

Methyl 2-chloro-4-fluorophenylacetate (3.15 g, 15.6 mmol), N-bromosuccinimide (2.77 g, 15.6 mmol) and AIBN (255 mg, 1.56 mmol) were suspended in benzene (50.0 mL) and degassed via $N_2$ stream. The resulting mixture was heated to 80° C. for 12 h. After cooling to rt, the mixture was partially concentrated in vacuo and partitioned between ether and water. The layers were separated, and the organic layer was washed with water and brine. The organics were dried ($MgSO_4$), filtered and concentrated in vacuo. The resulting crude oil was purified by flash chromatography on silica gel (gradient elution; 0%-20% EtOAc/hexanes as eluent) to afford the title compound i-1a. $^1$HNMR (500 MHz, $CDCl_3$): δ 7.82 (dd, 1H, J=6.0, 8.8 Hz), 7.17 (dd, 1H, J=2.6, 8.3 Hz), 7.08 (m, 1H), 5.88 (s, 1H), 3.84 (s, 3H).

Following procedures similar to those described in Scheme i-1, the following additional compounds represented in Table i-1 can be prepared:

TABLE i-1

$^1$H NMR and parent Ion m/z $(MH)^+$ data for compounds.

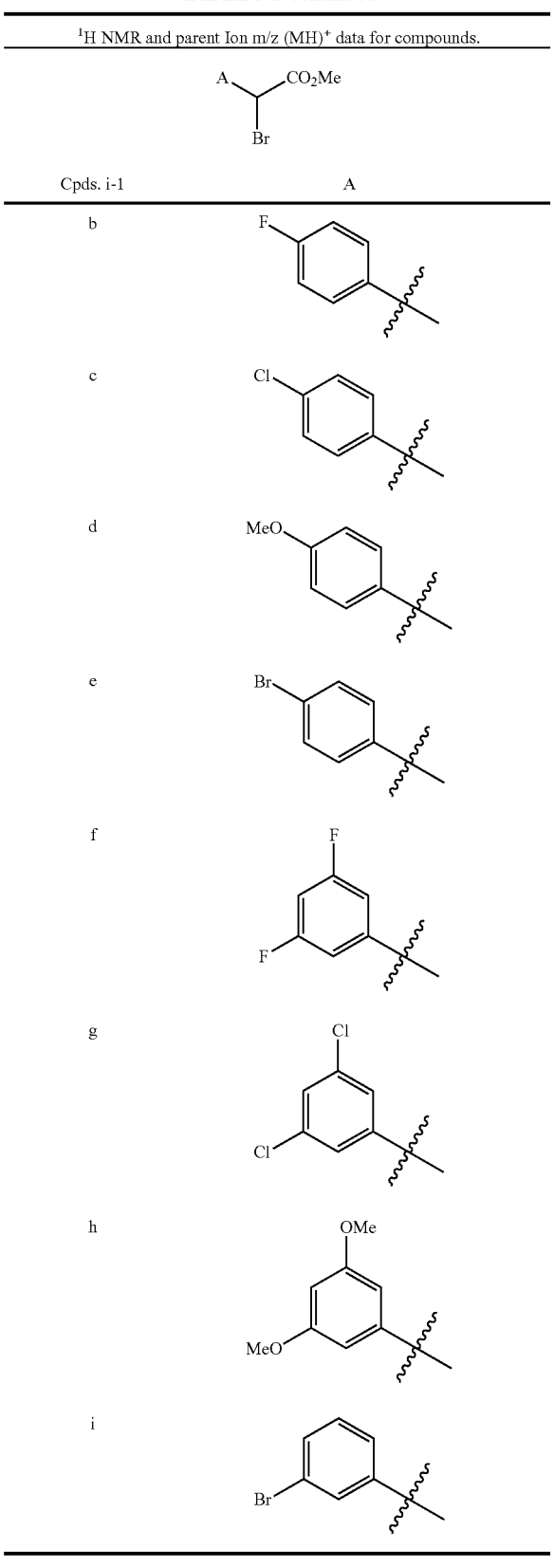

| Cpds. i-1 | A |
|---|---|
| a | 2,4-dichlorophenyl |
| b | 4-fluorophenyl |
| c | 4-chlorophenyl |
| d | 4-methoxyphenyl |
| e | 4-bromophenyl |
| f | 3,5-difluorophenyl |
| g | 3,5-dichlorophenyl |
| h | 3,5-dimethoxyphenyl |
| i | 3-bromophenyl |

For i-1a: Methyl bromo(2,4-dichlorophenyl)acetate: $^1$HNMR (500 MHz, $CDCl_3$): δ 7.75 (d, 1H, J=8.6 Hz), 7.42 (s, 1H), 7.33 (d, 1H, J=8.5 Hz), 5.86 (s, 1H), 3.83 (s, 3H).

For i-1b: Methyl bromo(4-fluorophenyl)acetate: $^1$HNMR (500 MHz, CDCl$_3$): δ 7.58 (m, 2H), 7.08 (m, 2H), 5.38 (s, 1H), 3.82 (s, 3H).

For i-1c: Methyl bromo(4-chlorophenyl)acetate: $^1$HNMR (500 MHz, CDCl$_3$): δ 7.51 (d, 2H, J=8.5 Hz), 7.37 (d, 2H, J=8.5 Hz), 5.35 (s, 1H), 3.82 (s, 3H).

For i-1d: Methyl bromo(4-methoxyphenyl)acetate: $^1$HNMR (500 MHz, CDCl$_3$): δ 7.49 (d, 2H, J=9.0 Hz), 6.88 (d, 2H, J=9.0 Hz), 5.40 (s, 1H), 3.76 (s, 3H), 3.75 (s, 3H).

For i-1e: Methyl bromo(4-bromophenyl)acetate: $^1$HNMR (500 MHz, CDCl$_3$): δ 7.53 (d, 2H, J=8.6 Hz), 7.45 (d, 2H, J=8.5 Hz), 5.33 (s, 1H), 3.82 (s, 3H).

For i-1f: Methyl bromo(3,5-difluorophenyl)acetate: $^1$HNMR (500 MHz, CDCl$_3$): δ 7.13 (m, 2H), 6.84 (m, 1H), 5.30 (s, 1H), 3.84 (s, 3H).

For i-1 g: Methyl bromo(3,5-dichlorophenyl)acetate: $^1$HNMR (500 MHz, CDCl$_3$): δ 7.46 (m, 1H), 7.20 (m, 2H), 5.26 (s, 1H), 3.84 (s, 3H).

For i-1i: Methyl bromo(3-bromophenyl)acetate: m/z (ES) 307 (MH)$^+$.

In the Tables in the following Examples, compounds having mass spectral data were synthetically prepared.

Example 1

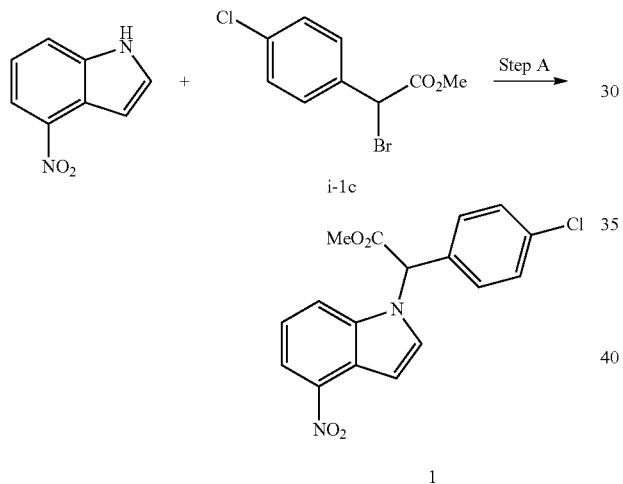

Step A: Preparation of methyl (4-chlorophenyl)(4-nitro-1H-indol-1-yl)acetate (1)

A solution of 4-nitroindole (6.89 g, 42.5 mmol) in DMF (20 mL) was added dropwise to a stirred suspension of sodium hydride (1.70 g of a 60% wt/wt dispersion in mineral oil, 42.5 mmol) in DMF (100 mL) at 0° C. After 10 min, a solution of i-1c (11.2 g, 42.5 mmol) in DMF (20 mL) was added slowly dropwise, and the resulting mixture was stirred at 0° C. for 3 h. The reaction was quenched by addition of saturated aqueous ammonium chloride and extracted with ether. The combined organics were washed with water and brine, dried (MgSO$_4$), filtered and concentrated in vacuo. The resulting crude oil was purified by flash chromatography on silica gel (gradient elution; 0%-20% EtOAc/hexanes as eluent) to afford the title compound 1. m/z (ES) 345 (MH)$^+$; IP=C rating.

Following procedures similar to those described in Example 1, the following additional compounds represented in Tables 1 and 1A were prepared:

TABLE 1

Parent Ion m/z (MH)$^+$ and Primary Assay IP data for compounds.

| Compound # | R$^3$ |
|---|---|
| 2 | 2-chloro-4-fluorophenyl |
| 3 | 2,4-dichlorophenyl |
| 4 | 3-bromophenyl |
| 5 | 4-methoxyphenyl |

2: methyl (2-chloro-4-fluorophenyl)(4-nitro-1H-indol-1-yl)acetate: m/z (ES) 363 (MH)$^+$; IP=B rating.

3: methyl (2,4-dichlorophenyl)(4-nitro-1H-indol-1-yl)acetate: $^1$HNMR (500 MHz, CDCl$_3$): δ 8.20 (dd, 1H, J=4.6, 7.9 Hz), 7.72 (d, 1H, J=8.2 Hz), 7.53 (m, 1H), 7.36 (m, 4H), 7.22 (m, 1H), 6.64 (s, 1H), 3.88 (s, 3H). IP=B rating.

4: methyl (3-bromophenyl)(4-nitro-1H-indol-1-yl)acetate: $^1$HNMR (500 MHz, CDCl$_3$): δ 8.21 (d, 1H, J=8.0 Hz), 7.66 (d, 1H, J=8.3 Hz), 7.60 (d, 1H, J=8.0 Hz), 7.52 (s, 1H), 7.46 (d, 1H, J=3.3 Hz), 7.35 (m, 3H), 7.27 (d, 1H, J=7.9 Hz), 6.29 (s, 1H), 3.88 (s, 3H). IP=C rating.

5: methyl (4-methoxyphenyl)(4-nitro-1H-indol-1-yl)acetate: $^1$HNMR (500 MHz, CDCl$_3$): δ 8.18 (d, 1H, J=8.3 Hz), 7.68 (d, 1H, J=8.1 Hz), 7.36 (d, 1H, J=3.4 Hz), 7.32 (d, 2H, J=8.4 Hz), 7.30 (m, 1H), 7.28 (d, 1H, J=3.3 Hz), 6.98 (d, 2H, J=8.7 Hz), 6.26 (s, 1H), 3.86 (s, 3H), 3.85 (s, 3H). IP=C rating.

TABLE 1A

Parent Ion m/z (MH)$^+$ and Primary Assay IP data for compounds

1A

| compound # | R$^p$ |
|---|---|
| 6 | H |
| 7 | 4-CN |
| 8 | 4-CO$_2$Et |
| 9 | 4-Cl |
| 10 | 4-F |
| 11 | 5-CN |
| 12 | 5-Cl |
| 13 | 5-F |
| 14 | 6-Cl |
| 15 | 7-F |
| 16 | 7-OBn |

6: methyl (2-chloro-4-fluorophenyl)(1H-indol-1-yl)acetate: m/z (ES) 318 (MH)$^+$; IP=C rating.

7: methyl (2-chloro-4-fluorophenyl)(4-cyano-1H-indol-1-yl)acetate: m/z (ES) 343 (MH)$^+$; IP=B rating.

8: ethyl 1-[1-(2-chloro-4-fluorophenyl)-2-methoxy-2-oxoethyl]-1H-indole-4-carboxylate: m/z (ES) 390 (MH)$^+$; IP=C rating.
9: methyl (2-chloro-4-fluorophenyl)(4-chloro-1H-indol-1-yl)acetate: m/z (ES) 352 (MH)$^+$; IP=C rating.
10: methyl (2-chloro-4-fluorophenyl)(4-fluoro-1H-indol-1-yl)acetate: m/z (ES) 336 (MH)$^+$; IP=C rating.
11: methyl (2-chloro-4-fluorophenyl)(5-cyano-1H-indol-1-yl)acetate: m/z (ES) 343 (MH)$^+$; IP=C rating.
12: methyl (2-chloro-4-fluorophenyl)(5-chloro-1H-indol-1-yl)acetate: m/z (ES) 352 (MH)$^+$; IP=C rating.
13: methyl (2-chloro-4-fluorophenyl)(5-fluoro-1H-indol-1-yl)acetate: m/z (ES) 336 (MH)$^+$; IP=C rating.
14: methyl (2-chloro-4-fluorophenyl)(6-chloro-1H-indol-1-yl)acetate: m/z (ES) 352 (MH)$^+$; IP=C rating.
15: methyl (2-chloro-4-fluorophenyl)(7-fluoro-1H-indol-1-yl)acetate: m/z (ES) 336 (MH)$^+$; IP=C rating.
16: methyl [7-(benzyloxy)-1H-indol-1-yl](2-chloro-4-fluorophenyl)acetate: m/z (ES) 424 (MH)$^+$; IP=C rating.

Example 2

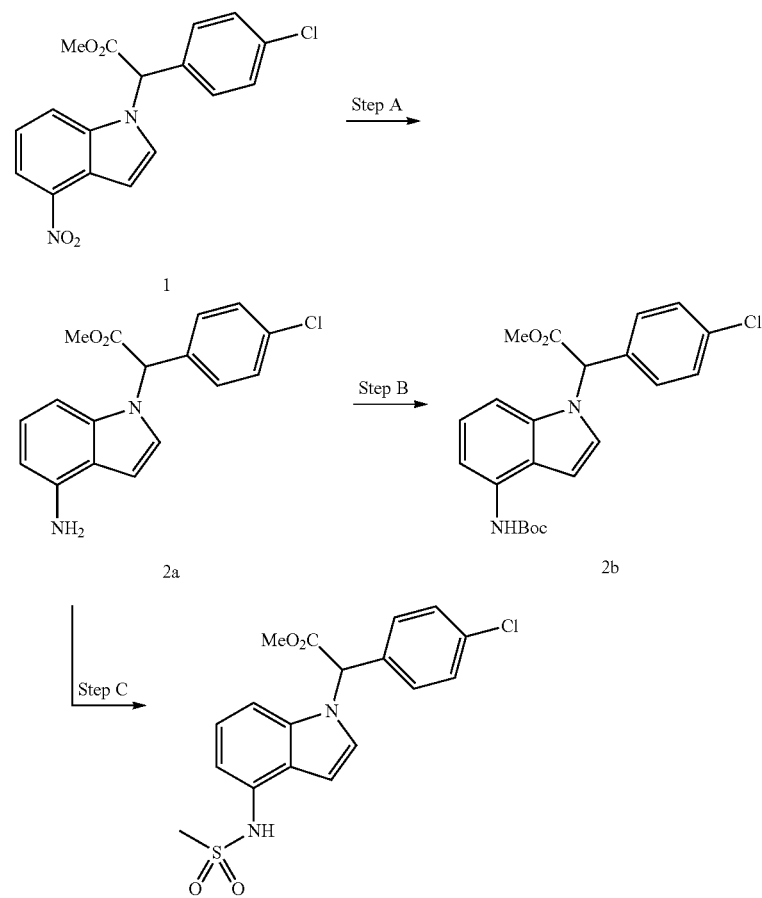

Step A: Preparation of methyl (4-amino-1H-indol-1-yl)(4-chlorophenyl)acetate (2a)

A solution of 1 (8.28 g, 24.0 mmol) in ethyl acetate (240 mL) was degassed, at which point platinum on carbon (1.41 g of a 10% wt/wt mixture, 0.721 mmol) was added, and the resulting suspension was stirred under a hydrogen atmosphere (balloon). After 3 h, the reaction mixture was filtered through a short column of CELITE® eluting with EtOAc. The combined organics were concentrated in vacuo to afford the title compound 2a. m/z (ES) 315 (MH)$^+$.

Step B: Preparation of methyl {4-[(tert-butoxycarbonyl)amino]-1H-indol-1-yl}(4-chlorophenyl)acetate (2b)

Di-tert-butyl dicarbonate 5.24 g, 24.0 mmol) was added to a stirred solution of 2a (7.56 g, 24.0 mmol) in dioxane (60 mL) and saturated aqueous sodium bicarbonate (15 mL). The resulting mixture was stirred at rt overnight, at which point, the reaction was partially concentrated in vacuo. The resulting mixture was partitioned between ethyl acetate and saturated aqueous ammonium chloride. The layers were separated, and the aqueous layer was extracted with ethyl acetate. The combined organics were dried (Na$_2$SO$_4$), filtered and concentrated in vacuo. The resulting crude oil was purified by flash chromatography on silica gel (gradient elution; 0%-20% EtOAc/hexanes as eluent) to afford the title compound 2b m/z (ES) 437 (MNa)$^+$.

Step C: Preparation of methyl (4-chlorophenyl){4-[(methylsulfonyl)amino]-1H-indol-1-yl}acetate (17)

Methanesulfonyl chloride (159 μL, 2.04 mmol) was added to a stirred solution of 2b (320 mg, 1.02 mmol) and triethylamine (213 μL, 1.53 mmol) in DCM (3 mL) at rt. After 1 h, the reaction mixture was poured into water and extracted with DCM. The combined organics were washed with brine, dried ($Na_2SO_4$), filtered and concentrated in vacuo. The crude residue was purified by preparative reversed phase HPLC on YMC Pack Pro C18 stationary phase ($CH_3CN/H_2O$ as eluent, 0.05% TFA as modifier), followed by lyophilization of the purified fractions to afford the title compound 17. m/z (ES) 393 $(MH)^+$ IP=C rating.

Following procedures similar to those described above in Example 2, the following compound were prepared:

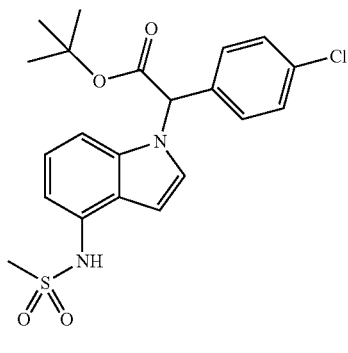

18

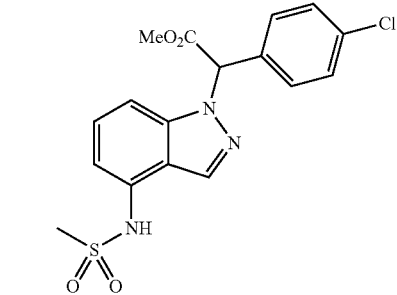

19

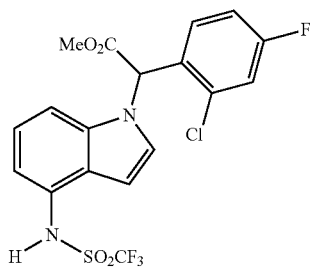

20

18: tert-butyl (4-chlorophenyl){4-[(methylsulfonyl)amino]-1H-indol-1-yl}acetate: m/z (ES) 435 $(MH)^+$; IP=C rating.
19: methyl (4-chlorophenyl){4-[(methylsulfonyl)amino]-1H-indazol-1-yl}acetate: m/z (ES) 394 $(MH)^+$; IP=C rating.
20: methyl (2-chloro-4-fluorophenyl)(4-{[(trifluoromethyl)sulfonyl]amino}-1H-indol-1-yl)acetate: m/z (ES) 465 $(MH)^+$; IP=C rating.

Following procedures similar to those described in Example 2, the following additional compounds represented in Table 2 were prepared:

TABLE 2

Parent Ion m/z $(MH)^+$ and Primary Assay IP data for compounds.

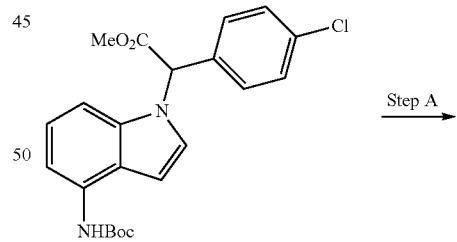

2A

| Compound # | R³ |
|---|---|
| 21 | phenyl |
| 22 | 2-chloro-4-fluorophenyl |
| 23 | 2,4-dichlorophenyl |
| 24 | 4-bromophenyl |

21: methyl {4-[(methylsulfonyl)amino]-1H-indol-1-yl}(phenyl)acetate: m/z (ES) 381 $(MNa)^+$; IP=C rating.
22: methyl (2-chloro-4-fluorophenyl){4-[(methylsulfonyl)amino]-1H-indol-1-yl}acetate: m/z (ES) 411 $(MH)^+$; IP=B rating.
23: methyl (2,4-dichlorophenyl){4-[(methylsulfonyl)amino]-1H-indol-1-yl}acetate: m/z (ES) 427 $(MH)^+$; IP=A rating.
24: methyl (4-bromophenyl){4-[(methylsulfonyl)amino]-1H-indol-1-yl}acetate: m/z (ES) 437 $(MH)^+$; IP=C rating.

Example 3

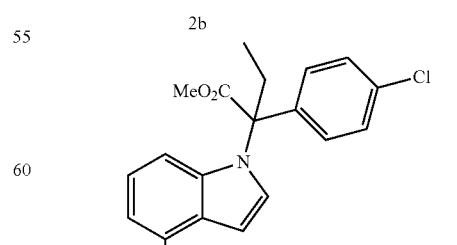

2b

3a

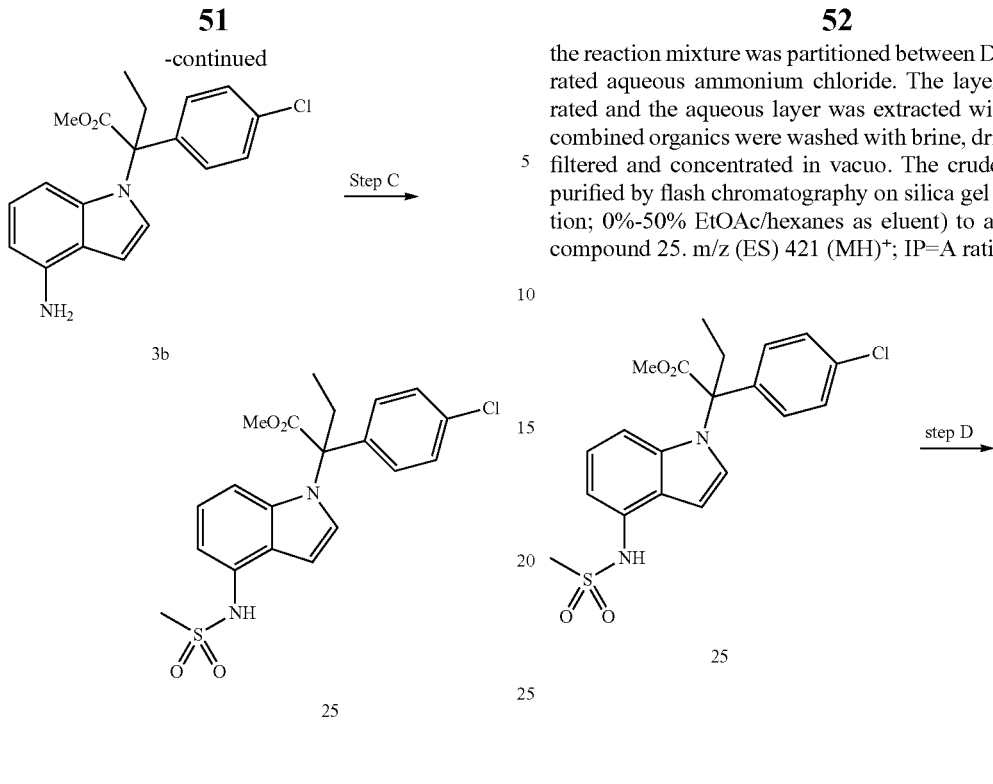

Step A: Preparation of methyl 2-{4-[(tert-butoxycarbonyl)amino]-1H-indol-1-yl}-2-(4-chlorophenyl)butanoate (3a)

A solution of 2b (10.0 g, 24.1 mmol) in DMF (20 mL) was added via syringe pump (1.6 mL/min) to a stirred suspension of sodium hydride (964 mg of a 60% wt/wt dispersion in mineral oil, 24.1 mmol) in DMF (60 mL) at 0° C. After 15 min, iodoethane (2.34 mL, 28.9 mmol) was added rapidly dropwise, and the resulting mixture was stirred at 0° C. for 2 h. The reaction was quenched by addition of saturated aqueous ammonium chloride and extracted with ether. The combined organics were washed with water and brine, dried (MgSO$_4$), filtered and concentrated in vacuo. The resulting crude oil was purified by flash chromatography on silica gel (gradient elution; 0%-20% EtOAc/hexanes as eluent) to afford the title compound 3a. m/z (ES) 465 (MNa)$^+$.

Step B: Preparation of methyl 2-(4-amino-1H-indol-1-yl)-2-(4-chlorophenyl)butanoate (3b)

Trifluoroacetic acid (37.5 mL, 487 mmol) was added rapidly dropwise to a stirred solution of 3a (8.62 g, 19.5 mmol) in DCM (100 mL) at 0° C. After 1 h, the reaction was quenched by careful addition of saturated aqueous sodium bicarbonate, followed by NaHCO$_3$(s) and extracted with ether. The organics were washed with saturated aqueous sodium bicarbonate, dried (MgSO$_4$), filtered and concentrated in vacuo to afford the title compound 3b. m/z (ES) 343 (MH)$^+$.

Step C: Preparation of methyl 2-(4-chlorophenyl)-2-{4-[(methylsulfonyl)amino]-1H-indol-1-yl}butanoate (25)

Methanesulfonyl chloride (1.59 mL, 20.4 mmol) was added to a stirred solution of 3b (6.67 g, 19.5 mmol) and 4-methylmorpholine (2.78 mL, 25.3 mmol) in DCM (100 mL) at 0° C. After 30 min, an additional portion of methanesulfonyl chloride (0.80 mL, 10.2 mmol) was added. After 1 h, the reaction mixture was partitioned between DCM and saturated aqueous ammonium chloride. The layers were separated and the aqueous layer was extracted with DCM. The combined organics were washed with brine, dried (Na$_2$SO$_4$), filtered and concentrated in vacuo. The crude residue was purified by flash chromatography on silica gel (gradient elution; 0%-50% EtOAc/hexanes as eluent) to afford the title compound 25. m/z (ES) 421 (MH)$^+$; IP=A rating Enantiomers 25a and 25b were separated using preparative normal phase chiral HPLC. A solution of 25 in MeOH/acetonitrile was injected onto a CHIRALCEL® AS-H (available from Chiral Technologies, Inc., Exton, Pa.) semi-preparative (250×30 mm) HPLC column (eluting with 45% [(2:1) MeOH:acetonitrile]/CO$_2$ with a column temperature of 35° C. at 70 mL/min with UV detection at 220 nm). The enantiomers were separated with the faster eluting enantiomer 25a having a retention time of 2.61 min and the slower eluting enantiomer 25b having a retention time of 3.13 min, with the retention times derived from injection onto an analytical CHIRALCEL® AS-H HPLC column (4.6×250 mm, 2.1 mL/min, 40% [(2:1) MeOH:acetonitrile]/CO$_2$, 35° C.). The separated fractions were concentrated to provide the enantiomers 25a and 25b. Under the separation conditions cited above, the faster eluting (R)-enantiomer 25a is preferred for making final products. For 25a: m/z (ES) 421 (MH)$^+$; IP=A rating. For 25b: m/z (ES) 421 (MH)$^+$; IP=B rating Following procedures similar to those described above in Example 3, the following compound were prepared:

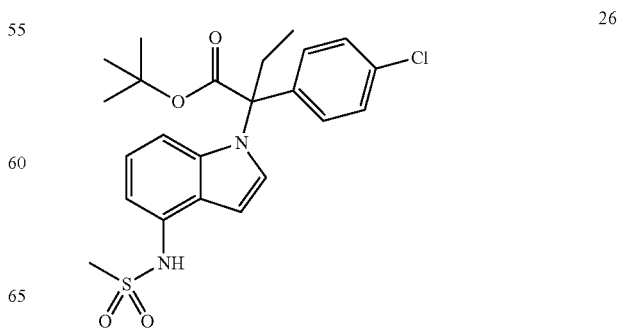

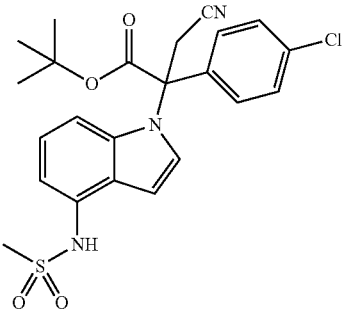

26: tert-Butyl 2-(4-chlorophenyl)-2-{4-[(methylsulfonyl)amino]-1H-indol-1-yl}butanoate: m/z (ES) 463 (MH)+; IP=B rating.

27: tert-Butyl 2-(4-chlorophenyl)-3-cyano-2-{4-[(methylsulfonyl)amino]-1H-indol-1-yl}propanoate: m/z (ES) 496 (MNa)+; IP=B rating.

Following procedures similar to those described above in Example 3, the following additional compounds were prepared:

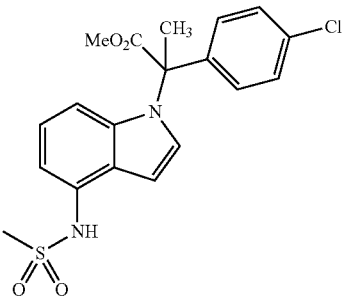

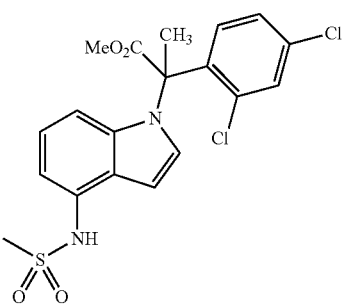

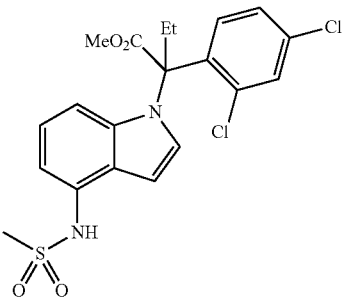

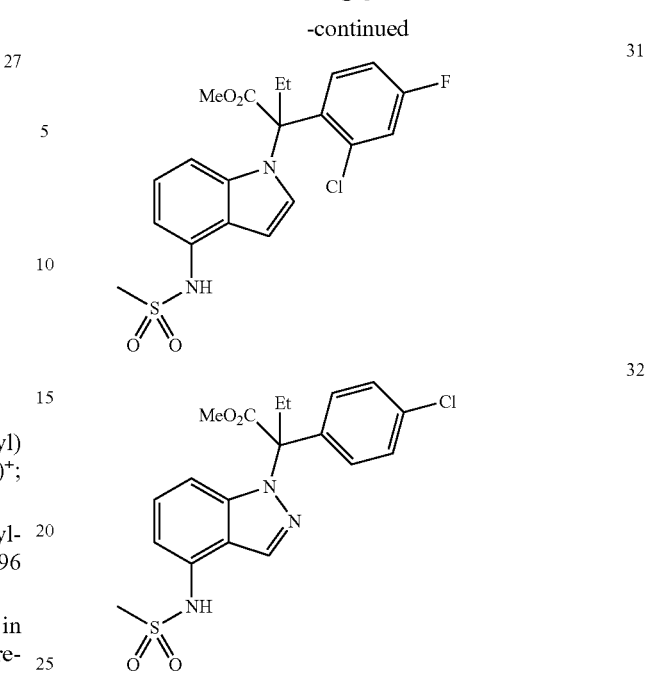

28: Methyl 2-(4-chlorophenyl)-2-{4-[(methylsulfonyl)amino]-1H-indol-1-yl}propanoate: m/z (ES) 407 (MH)+; IP=B rating.

29: Methyl 2-(2,4-dichlorophenyl)-2-{4-[(methylsulfonyl)amino]-1H-indol-1-yl}propanoate: m/z (ES) 441 (MH)+; IP=C rating.

30: Methyl 2-(2,4-dichlorophenyl)-2-{4-[(methylsulfonyl)amino]-1H-indol-1-yl}butanoate: m/z (ES) 455 (MH)+; IP=B rating.

31: Methyl 2-(2-chloro-4-fluorophenyl)-2-{4-[(methylsulfonyl)amino]-1H-indol-1-yl}butanoate: m/z (ES) 439 (MH)+; IP=B rating.

32: Methyl 2-(4-chlorophenyl)-2-{4-[(methylsulfonyl)amino]-1H-indazol-1-yl}butanoate: m/z (ES) 422 (MH)+; IP=B rating.

Additional compounds, as shown in Table 3, were prepared:

TABLE 3

Parent Ion m/z (MH)+ and Primary Assay IP data for compounds.

| Ex. | R² |
|---|---|
| 33 | —CH₂CH=CH₂ |
| 34 | —CH₂Ph |
| 35 | —CH₂CO₂Me |
| 36 | —CH₂CN |
| 37 | —CH₂OMe |

TABLE 3-continued

Parent Ion m/z (MH)+ and Primary Assay IP data for compounds.

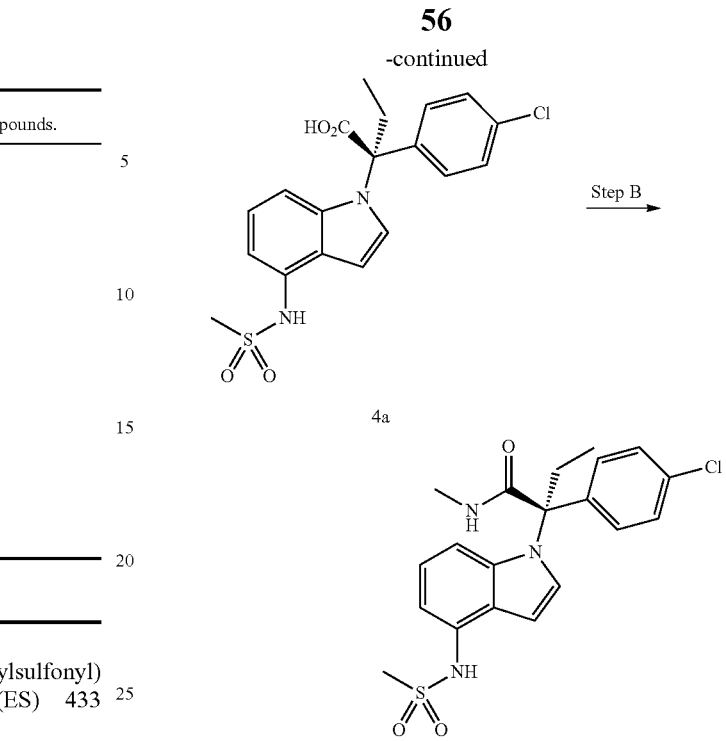

| Ex. | R² |
|---|---|
| 38 | —CH₂cPr |

33: Methyl 2-(4-chlorophenyl)-2-{4-[(methylsulfonyl)amino]-1H-indol-1-yl}pent-4-enoate: m/z (ES) 433 (MH)+; IP=B rating.

34: Methyl 2-(4-chlorophenyl)-2-{4-[(methylsulfonyl)amino]-1H-indol-1-yl}-3-phenylpropanoate: m/z (ES) 483 (MH)+; IP=B rating.

35: Dimethyl 2-(4-chlorophenyl)-2-{4-[(methylsulfonyl)amino]-1H-indol-1-yl}butanedioate: m/z (ES) 487 (MNa)+; IP=A rating.

36: Methyl 2-(4-chlorophenyl)-3-cyano-2-{4-[(methylsulfonyl)amino]-1H-indol-1-yl}propanoate: m/z (ES) 432 (MH)+; IP=A rating.

37: Methyl 2-(4-chlorophenyl)-3-methoxy-2-{4-[(methylsulfonyl)amino]-1H-indol-1-yl}propanoate: m/z (ES) 437 (MH)+; IP=C rating.

38: Methyl 2-(4-chlorophenyl)-3-cyclopropyl-2-{4-[(methylsulfonyl)amino]-1H-indol-1-yl}propanoate: m/z (ES) 469 (MNa)+; IP=A rating.

Example 4

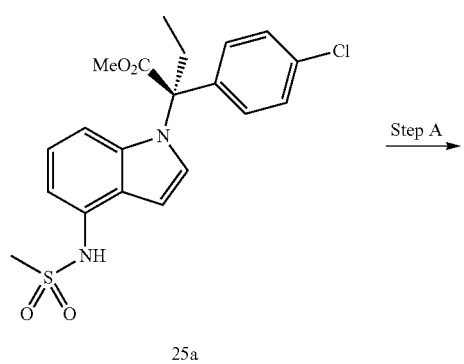

Step A: Preparation of (R)-2-(4-chlorophenyl)-2-{4-[(methylsulfonyl)amino]-1H-indol-1-yl}butanoic acid (4a)

Lithium hydroxide (484 mg, 20.2 mmol) was added to a stirred solution of 325a (850 mg, 2.02 mmol) in dioxane (16 mL) and water (4 mL), and the resulting mixture was heated to 70° C. for 3 h. After cooling to rt, the reaction mixture was poured into 1M HCl and extracted with ethyl acetate. The combined organics were washed with brine, dried (Na₂SO₄), filtered and concentrated in vacuo to afford the title compound 4a. m/z (ES) 407 (MH)+.

Step B: Preparation of (R)-2-(4-chlorophenyl)-N-methyl-2-{4-[(methylsulfonyl)amino]-1H-indol-1-yl}butanamide (39)

O-(7-azabenzotriazol-1-yl)-N,N,N',N'-tetramethyluronium hexafluorophosphate (1.34 g, 3.56 mmol) was added to a stirred solution of 4a (967 mg, 2.38 mmol) and 4-methylmorpholine (523 μL, 4.75 mmol) in DMF (12 mL). After 5 min, methylamine (3.56 mL of a 2.0 M solution in methanol, 7.13 mmol) was added, and the resulting mixture was allowed to stir at rt. After 3 h, the reaction mixture was partitioned between ethyl acetate and water. The layers were separated, and the organics were washed with water and brine, dried (Na₂SO₄), filtered and concentrated in vacuo. The crude residue was purified by flash chromatography on silica gel (gradient elution; 0%-85% EtOAc/hexanes as eluent) to afford the title compound 39. m/z (ES) 420 (MH)+; IP=B rating.

Following procedures similar to those described above in Example 4, the following additional compounds represented in Table 4 were prepared:

TABLE 4

Parent Ion m/z (MH)⁺ and Primary Assay IP data for compounds.

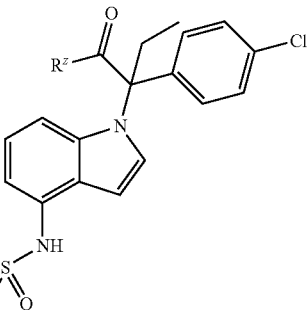

| Ex. #4 | R$^z$ |
|---|---|
| 40 | —NH$_2$ |
| 41 | —NH$^c$Pr |
| 42 | —NH(CH$_2$)$_2$OMe |
| 43 | —NHBn |
| 44 | —NH$^i$Pr |
| 45 | —NH$^t$Bu |
| 46 | —NHEt |
| 47 | —NHCH$_2$CF$_3$ |
| 48 | —NH(CH$_2$)$_2$CN |
| 49 | —NH(CH$_2$)$_2$F |
| 50 | —NH(CH$_2$)$_2$Ph |
| 51 | —NHCH$_2$CN |
| 52 | —NHCH$_2$CO$_2$Me |

40: (R)-2-(4-chlorophenyl)-2-{4-[(methylsulfonyl)amino]-1H-indol-1-yl}butanamide: m/z (ES) 406 (MH)⁺; IP=B rating.

41: (R)-2-(4-chlorophenyl)-N-cyclopropyl-2-{4-[(methylsulfonyl)amino]-1H-indol-1-yl}butanamide: m/z (ES) 446 (MH)⁺; IP=B rating.

42: 2-(4-chlorophenyl)-N-(2-methoxyethyl)-2-{4-[(methylsulfonyl)amino]-1H-indol-1-yl}butanamide: m/z (ES) 464 (MH)⁺; IP=C rating.

43: (R)—N-benzyl-2-(4-chlorophenyl)-2-{4-[(methylsulfonyl)amino]-1H-indol-1-yl}butanamide: m/z (ES) 496 (MH)⁺; IP=C rating.

44: (R)-2-(4-chlorophenyl)-N-(1-methylethyl)-2-{4-[(methylsulfonyl)amino]-1H-indol-1-yl}butanamide: m/z (ES) 448 (MH)⁺; IP=B rating.

45: (R)—N-tert-butyl-2-(4-chlorophenyl)-2-{4-[(methylsulfonyl)amino]-1H-indol-1-yl}butanamide: m/z (ES) 462 (MH)⁺; IP=C rating.

46: 2-(4-chlorophenyl)-N-ethyl-2-{4-[(methylsulfonyl)amino]-1H-indol-1-yl}butanamide: m/z (ES) 434 (MH)⁺; IP=B rating.

47: (R)-2-(4-chlorophenyl)-2-{4-[(methylsulfonyl)amino]-1H-indol-1-yl}-N-(2,2,2-trifluoroethyl)butanamide: m/z (ES) 488 (MH)⁺; IP=A rating.

48: 2-(4-chlorophenyl)-N-(2-cyanoethyl)-2-{4-[(methylsulfonyl)amino]-1H-indol-1-yl}butanamide: m/z (ES) 459 (MH)⁺; IP=C rating.

49: 2-(4-chlorophenyl)-N-(2-fluoroethyl)-2-{4-[(methylsulfonyl)amino]-1H-indol-1-yl}butanamide: m/z (ES) 474 (MNa)⁺; IP=B rating.

50: 2-(4-chlorophenyl)-2-{4-[(methylsulfonyl)amino]-1H-indol-1-yl}-N-(2-phenylethyl)butanamide: m/z (ES) 532 (MNa)⁺; IP=C rating.

51: 2-(4-chlorophenyl)-N-(cyanomethyl)-2-{4-[(methylsulfonyl)amino]-1H-indol-1-yl}butanamide: m/z (ES) 467 (MNa)⁺; IP=A rating.

52: methyl N-[2-(4-chlorophenyl)-2-{4-[(methylsulfonyl)amino]-1H-indol-1-yl}butanoyl]glycinate: m/z (ES) 478 (MH)⁺; IP=B rating.

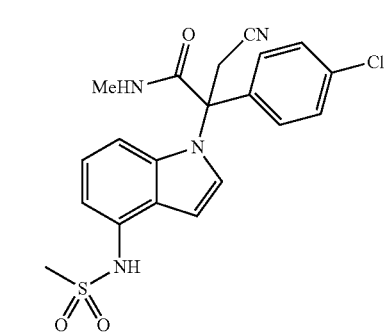

53

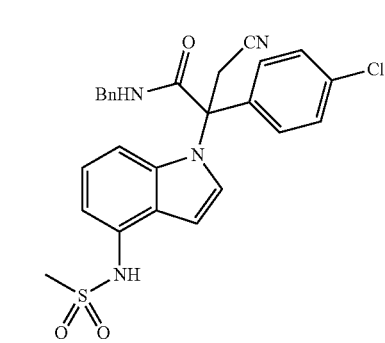

54

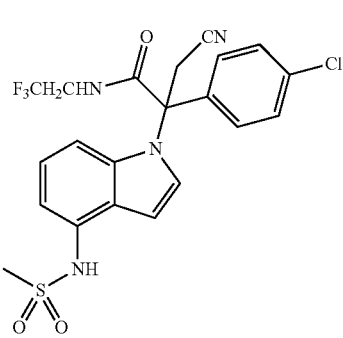

55

53: 2-(4-chlorophenyl)-3-cyano-N-methyl-2-{4-[(methylsulfonyl)amino]-1H-indol-1-yl}propanamide: m/z (ES) 431 (MH)⁺; IP=B rating.

54: N-benzyl-2-(4-chlorophenyl)-3-cyano-2-{4-[(methylsulfonyl)amino]-1H-indol-1-yl}propanamide: m/z (ES) 507 (MH)⁺; IP=B rating.

55: 2-(4-chlorophenyl)-3-cyano-2-{4-[(methylsulfonyl)amino]-1H-indol-1-yl}-N-(2,2,2-trifluoroethyl)propanamide: m/z (ES) 499 (MH)⁺; IP=B rating.

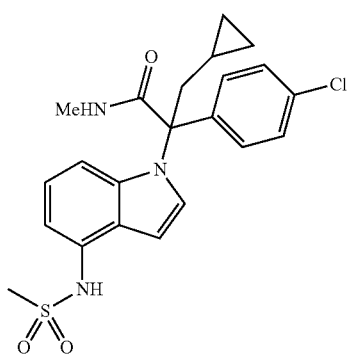

56: 2-(4-chlorophenyl)-3-cyclopropyl-N-methyl-2-{4-[(methylsulfonyl)amino]-1H-indol-1-yl}propanamide: m/z (ES) 468 (MNa)$^+$; IP=B rating.

Example 5

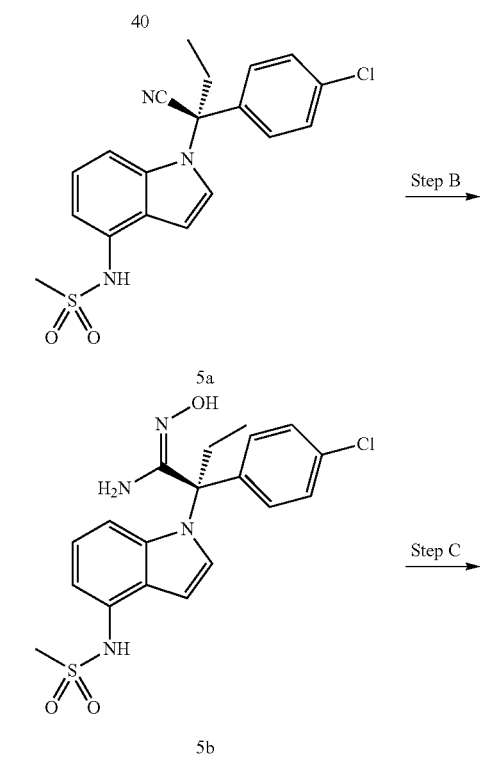

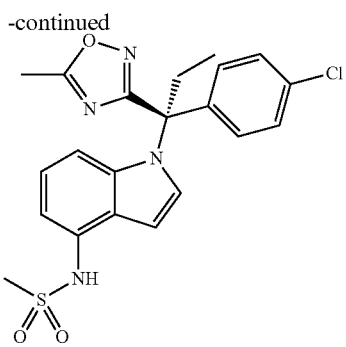

Step A: Preparation of (R)—N-{1-[1-(4-chlorophenyl)-1-cyanopropyl]-1H-indol-4-yl}methanesulfonamide (5a)

Cyanuric chloride (17.3 mg, 0.094 mmol) was added to a stirred solution of 40 (38.0 mg, 0.094 mmol) in DMF (0.50 mL), and the reaction mixture was allowed to stir at rt for 3 h. The reaction mixture was poured into brine and the resulting mixture was extracted with ethyl acetate. The organics were dried (Na$_2$SO$_4$), filtered and concentrated in vacuo. The crude residue was purified by flash chromatography on silica gel (gradient elution; 0%-50% EtOAc/hexanes as eluent) to afford the title compound 5a. m/z (ES) 361 (M-CN)$^+$; IP=A rating.

Step B: Preparation of (R)-(1E)-2-(4-chlorophenyl)-N-hydroxy-2-{4-[(methylsulfonyl)amino]-1H-indol-1-yl}butanimidamide (5b)

A mixture of 5a (30.0 mg, 0.077 mmol), hydroxylamine (156 μL of a 50% wt/wt aqueous solution, 2.55 mmol) and potassium carbonate (1.1 mg, 7.7 μmol) in ethanol (1.2 mL) was heated in a microwave reactor at 120° C. for 10 min. After cooling to rt, the reaction mixture was concentrated in vacuo, and the resulting crude residue was partitioned between ethyl acetate and water. The layers were separated, and the organics were washed with brine, dried (Na$_2$SO$_4$), filtered and concentrated in vacuo to afford the title compound 5b. m/z (ES) 421 (MH)$^+$.

Step C: Preparation of (R)-methyl N-{1-[1-(4-chlorophenyl)-1-(5-methyl-1,2,4-oxadiazol-3-yl)propyl]-1H-indol-4-yl}methanesulfonamide (57)

(Benzyltriazol-1-yloxy)tris(dimethylamino)phosphonium hexafluorophosphate (37 mg, 0.083 mmol) was added to a mixture of 5b (35 mg, 0.083 mmol), acetic acid (4.8 μL, 0.083 mmol) and N,N-diisopropylethylamine (29 μL, 0.166 mmol) in acetonitrile (1.50 mL). The resulting mixture was stirred at rt for 30 sec, then heated in a microwave reactor at 150° C. for 20 min. After cooling to rt, the reaction mixture was diluted with water, and the mixture was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 57. m/z (ES) 445 (MH)$^+$; IP=A rating Following procedures similar to those described above in Example 5, the following additional compounds represented in Table 5 were be prepared:

TABLE 5

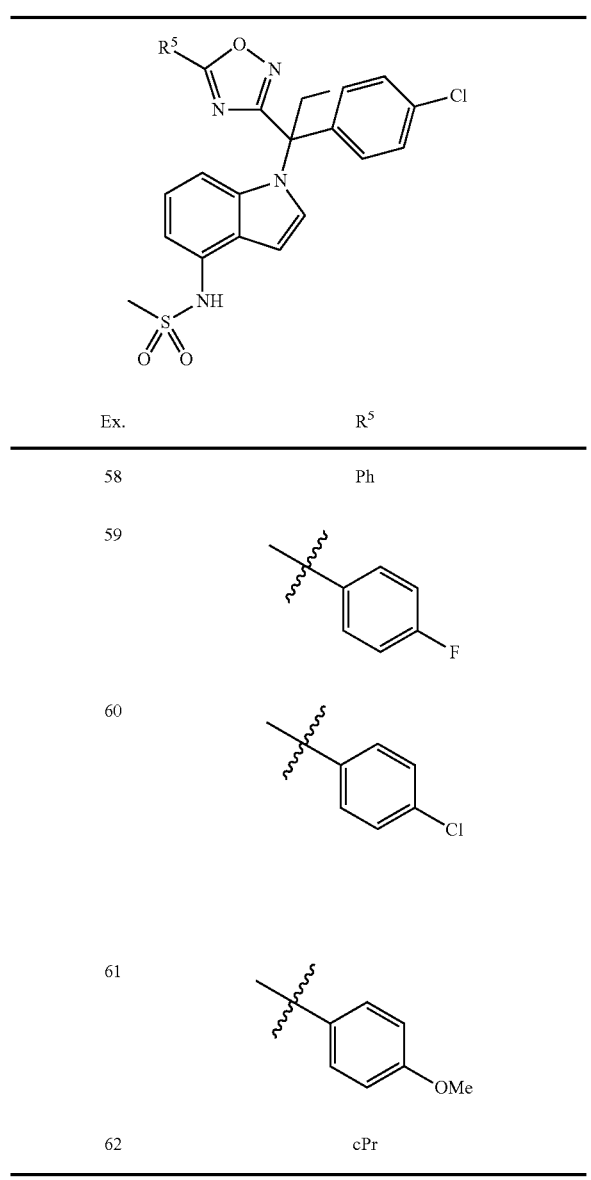

| Ex. | R⁵ |
|---|---|
| 58 | Ph |
| 59 | 4-fluorophenyl |
| 60 | 4-chlorophenyl |
| 61 | 4-methoxyphenyl |
| 62 | cPr |

Table 5. Parent Ion m/z (MH)⁺ and Primary Assay IP data for compounds.

58: (R)—N-{1-[1-(4-chlorophenyl)-1-(5-phenyl-1,2,4-oxadiazol-3-yl)propyl]-1H-indol-4-yl}methanesulfonamide: m/z (ES) 507 (MH)⁺; IP=C rating.

59: N-(1-{1-(4-chlorophenyl)-1-[5-(4-fluorophenyl)-1,2,4-oxadiazol-3-yl]propyl}-1H-indol-4-yl)methanesulfonamide: m/z (ES) 525 (MH)⁺; IP=A rating.

60: N-(1-{1-(4-chlorophenyl)-1-[5-(4-chlorophenyl)-1,2,4-oxadiazol-3-yl]propyl}-1H-indol-4-yl)methanesulfonamide: m/z (ES) 541 (MH)⁺; IP=A rating.

61: (R)—N-(1-{1-(4-chlorophenyl)-1-[5-(4-methoxyphenyl)-1,2,4-oxadiazol-3-yl]propyl}-1H-indol-4-yl)methanesulfonamide: m/z (ES) 537 (MH)⁺; IP=A rating.

62: (R)—N-{1-[1-(4-chlorophenyl)-1-(5-cyclopropyl-1,2,4-oxadiazol-3-yl)propyl]-1H-indol-4-yl}methanesulfonamide: m/z (ES) 471 (MH)⁺; IP=A rating.

Example 6

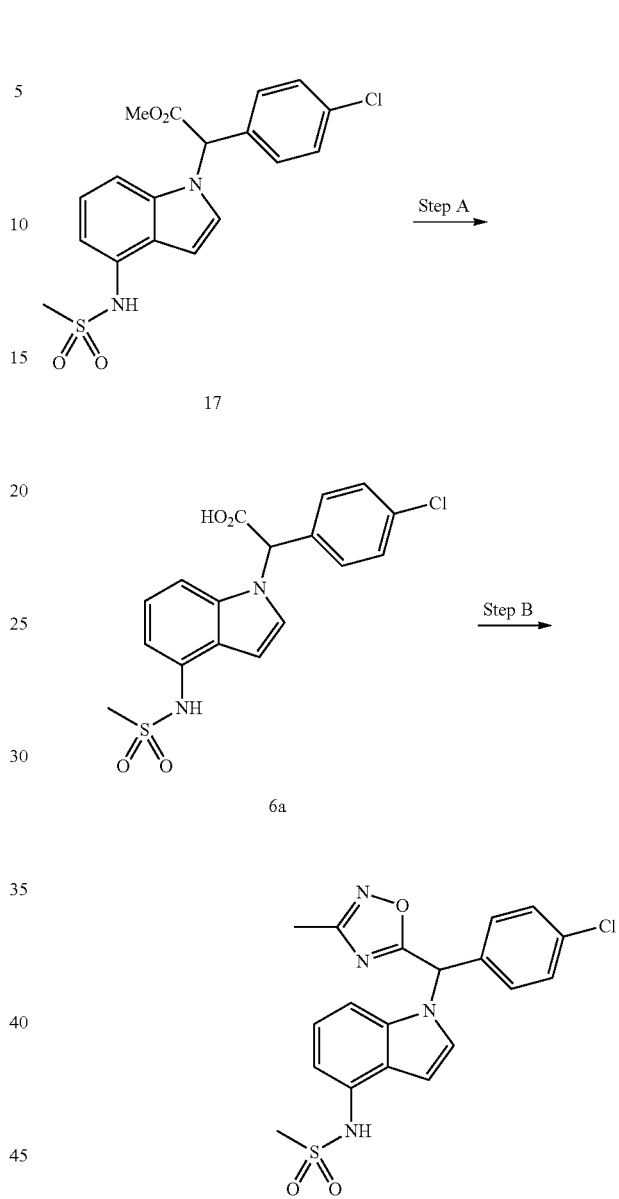

Step A: Preparation of (4-chlorophenyl){4-[(methylsulfonyl)amino]-1H-indol-1-yl}acetic acid 6a)

Compound 6a was prepared from compound 17 following procedures similar to those previously described in Example 4, step A.

Step B: Preparation of N-{1-[(4-chlorophenyl)(3-phenyl-1,2,4-oxadiazol-5-yl)methyl]-1H-indol-4-yl}methanesulfonamide (63)

N'-Hydroxybenzenecarboximidamide (49 mg, 0.36 mmol) was added to a stirred solution of compound 6a (90 mg, 0.24 mmol), N-(3-dimethylaminopropyl)-N'-ethylcarbodiimide hydrochloride (91 mg, 0.48 mmol), 1-hydroxybenzotriazole (44 mg, 0.29 mmol) and N,N,-diisopropylethylamine (50 μL, 0.29 mmol) in DMF (2.4 mL). The reaction was allowed to stir at rt for 2 h, at which time, the reaction was partitioned between ethyl acetate and water. The layers were separated, and the organic layer was washed with water and brine, dried over MgSO$_4$, filtered and concentrated to a crude oil that was dissolved in toluene (2.0 mL). The resulting mixture was heated to 100° C. for 1 h, at which time, the reaction was concentrated in vacuo, and the resulting crude residue was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 63. m/z (ES) 479 (MH)$^+$; IP=C rating.

Example 7

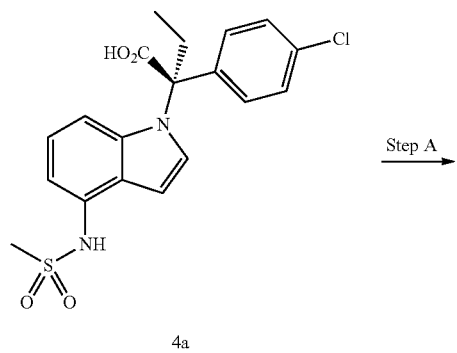

4a

Step A: Preparation of (R)—N-{1-[1-(4-chlorophenyl)-1-(3-phenyl-1H-1,2,4-triazol-5-yl)propyl]-1H-indol-4-yl}methanesulfonamide (64)

Compound 64 was synthesized from compound 4a following procedures similar to those presented in Example 6, substituting [imino(phenyl)methyl]hydrazinium iodide for N'-hydrozybenzenecaroximidamide. m/z (ES) 506 (MH)$^+$; IP=C rating.

Following procedures similar to those described above in Example 7, the following additional compounds represented in Table 7 were prepared:

TABLE 7

| Ex. | R$^5$ |
|---|---|
| 65 | Me |
| 66 | CF$_3$ |

Table 7. Parent Ion m/z (MH)$^+$ and Primary Assay IP data for compounds.

65: (R)—N-{1-[1-(4-chlorophenyl)-1-(5-methyl-4H-1,2,4-triazol-3-yl)propyl]-1H-indol-4-yl}methanesulfonamide: m/z (ES) 444 (MH)$^+$; IP=B rating.

66: (R)—N-(1-{1-(4-chlorophenyl)-1-[5-(trifluoromethyl)-4H-1,2,4-triazol-3-yl]propyl}-1H-indol-4-yl)methanesulfonamide: m/z (ES) 428 (M-CF$_3$)$^+$; IP=B rating.

Example 8

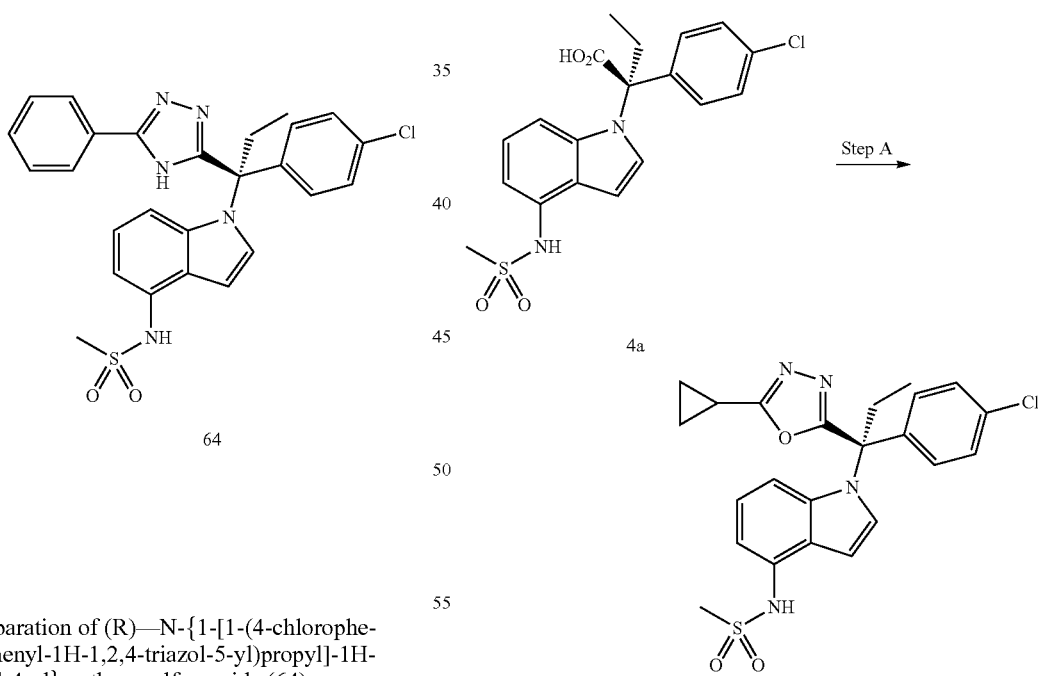

Step A: Preparation of (R)—N-{1-[1-(4-chlorophenyl)-1-(5-cyclopropyl-1,3,4-oxadiazol-2-yl)propyl]-1H-indol-4-yl}methanesulfonamide (67)

A solution of 4a (60 mg, 0.147 mmol), cyclopropylcarboxylic acid hydrazide (15.5 mg, 0.155 mmol), O-(7-azabenzotriazol-1-yl)-N,N,N',N'-tetramethyluronium hexafluorophosphate (84 mg, 0.221 mmol) and N,N-diisopropylethylamine (77 μL, 0.442 mmol) in DMF (1 mL) was stirred at rt for 1.5 h. The reaction mixture was partitioned between ethyl acetate and water. The layers were separated, and the organics were washed with water and brine, dried (Na$_2$SO$_4$), filtered and concentrated in vacuo to afford crude residue that was dissolved in THF (2 mL).

(Methoxycarbonylsulfamoyl)triethylammonium hydroxide (105 mg, 0.442 mmol) was added, and the resulting mixture was heated at 60° C. for 2 h. After cooling to rt, the reaction mixture was concentrated in vacuo, and the resulting crude residue was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 67. m/z (ES) 471 (MH)$^+$; IP=B rating.

Following procedures similar to those described above in Example 8, the following additional compounds represented in Table 8 were prepared:

TABLE 8

| Ex. #8 | R$^5$ |
|---|---|
| 68 | Me |
| 69 | CF$_3$ |
| 70 | Ph |
| 71 | 4-chlorophenyl |
| 72 | 4-fluorophenyl |
| 73 | 4-trifluoromethylphenyl |

TABLE 8-continued

| Ex. #8 | R$^5$ |
|---|---|
| 74 | 4-methoxyphenyl |
| 75 | 3,5-difluorophenyl |

Table 8. Parent Ion m/z (MH)$^+$ and Primary Assay IP data for compounds.

68: N-{1-[1-(4-chlorophenyl)-1-(5-methyl-1,3,4-oxadiazol-2-yl)propyl]-1H-indol-4-yl}methanesulfonamide: m/z (ES) 467 (MNa)$^+$; IP=B rating.

69: N-(1-{1-(4-chlorophenyl)-1-[5-(trifluoromethyl)-1,3,4-oxadiazol-2-yl]propyl}-1H-indol-4-yl)methanesulfonamide: m/z (ES) 499 (MNa)$^+$; IP=B rating.

70: N-{1-[1-(4-chlorophenyl)-1-(5-phenyl-1,3,4-oxadiazol-2-yl)propyl]-1H-indol-4-yl}methanesulfonamide: m/z (ES) 529 (MNa)$^+$; IP=C rating.

71: N-(1-{1-(4-chlorophenyl)-1-[5-(4-chlorophenyl)-1,3,4-oxadiazol-2-yl]propyl}-1H-indol-4-yl)methanesulfonamide: m/z (ES) 563 (MNa)$^+$; IP=A rating.

72: N-(1-{1-(4-chlorophenyl)-1-[5-(4-fluorophenyl)-1,3,4-oxadiazol-2-yl]propyl}-1H-indol-4-yl)methanesulfonamide: m/z (ES) 547 (MNa)$^+$; IP=B rating.

73: N-{1-[1-(4-chlorophenyl)-1-{5-[4-(trifluoromethyl)phenyl]-1,3,4-oxadiazol-2-yl}propyl]-1H-indol-4-yl}methanesulfonamide: m/z (ES) 597(MNa)$^+$; IP=B rating.

74: N-(1-{1-(4-chlorophenyl)-1-[5-(4-methoxyphenyl)-1,3,4-oxadiazol-2-yl]propyl}-1H-indol-4-yl)methanesulfonamide: m/z (ES) 537 (MH)$^+$; IP=B rating.

75: N-(1-{1-(4-chlorophenyl)-1-[5-(3,5-difluorophenyl)-1,3,4-oxadiazol-2-yl]propyl}-1H-indol-4-yl)methanesulfonamide: m/z (ES) 565 (MNa)$^+$; IP=C rating.

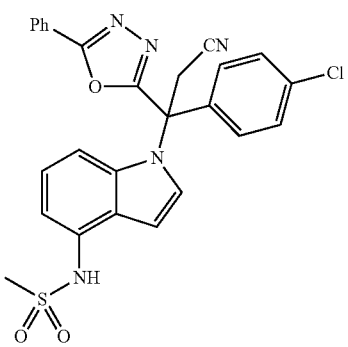

76: N-{1-[1-(4-chlorophenyl)-2-cyano-1-(5-phenyl-1,3,4-oxadiazol-2-yl)ethyl]-1H-indol-4-yl}methanesulfonamide: m/z (ES) 540 (MNa)⁺; IP=B rating.

Example 9

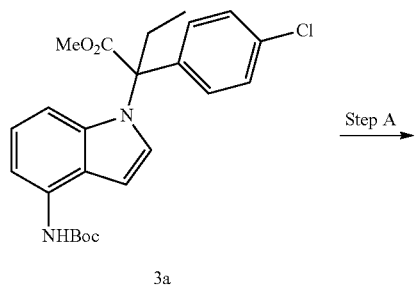

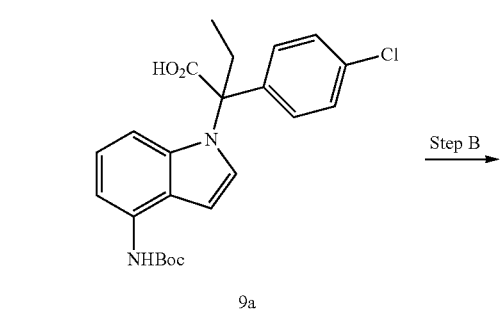

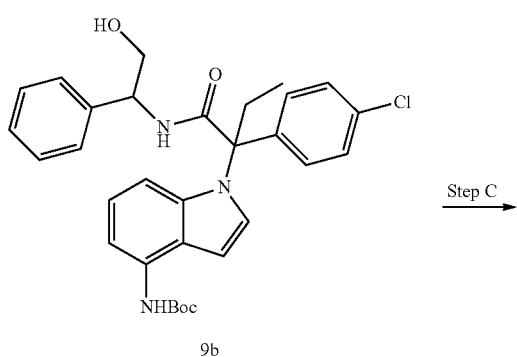

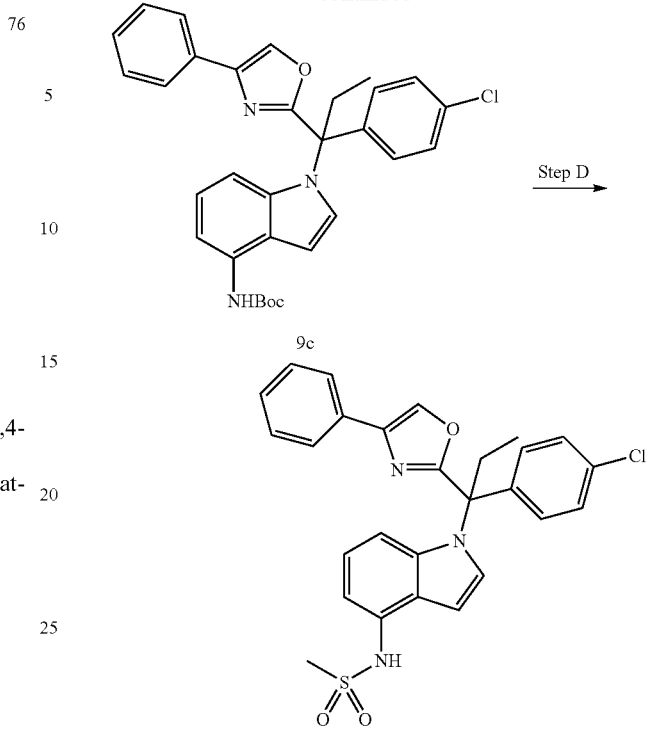

Step A: Preparation of 2-{4-[(tert-butoxycarbonyl)amino]-1H-indol-1-yl}-2-(4-chlorophenyl)butanoic acid (9a)

Compound 9a was prepared from compound 3a following procedures similar to those described in Example 4, step A, substituting compound 3a for compound 3c. m/z (ES) 429 (MH)⁺.

Step B: Preparation of tert-butyl (1-{2-(4-chlorophenyl)-1-[(2-hydroxy-1-phenylethyl)amino]-1-oxobutan-2-yl}-1H-indol-4-yl)carbamate (9b)

Compound 9b was prepared from compound 9a following procedures similar to those described in Example 4, step B, substituting compound 9a for compound 4a. m/z (ES) 548 (MH)⁺.

Step C: Preparation of tert-butyl {1-[1-(4-chlorophenyl)-1-(4-phenyl-1,3-oxazol-2-yl)propyl]-1H-indol-4-yl}carbamate (9c)

Dess-Martin periodinane (46 mg, 0.109 mmol) was added to a stirred solution of 9b (40 mg, 0.073 mmol) in DCM (0.73 mL) at 0° C. After 2 h, the reaction was quenched by addition of saturated aqueous sodium thiosulfate and extracted with DCM. The combined organics were washed with water and brine, dried (Na₂SO₄), filtered and concentrated in vacuo to afford crude residue that was dissolved in DCM (1 mL) and added dropwise to a stirred solution in which triphenylphosphine (172 mg, 0.657 mmol), followed by triethylamine (31 µL, 0.220 mmol), had been added to iodine (28 mg, 0.110 mmol) in DCM (1 mL) at 0° C. The resulting mixture was warmed to rt, and after 1 h, quenched with saturated aqueous sodium thiosulfate. The mixture was extracted with ethyl acetate, and the combined organics were washed with water and brine, dried (Na$_2$SO$_4$), filtered and concentrated in vacuo to afford crude residue that was purified by flash chromatography on silica gel (gradient elution; 0%-50% EtOAc/hexanes as eluent) to afford the title compound 9c. m/z (ES) 528 (MH)$^+$.

Step D: Preparation of N-{1-[1-(4-chlorophenyl)-1-(4-phenyl-1,3-oxazol-2-yl)propyl]-1H-indol-4-yl}methanesulfonamide (77)

Compound 77 was prepared from compound 9c in two steps following procedures described in Example 3, step B, substituting compound 9c for compound 3a, the product of which being converted to compound 77 following procedures described in Example 3, step C. m/z (ES) 528 (MNa)$^+$; IP=C rating.

Example 10

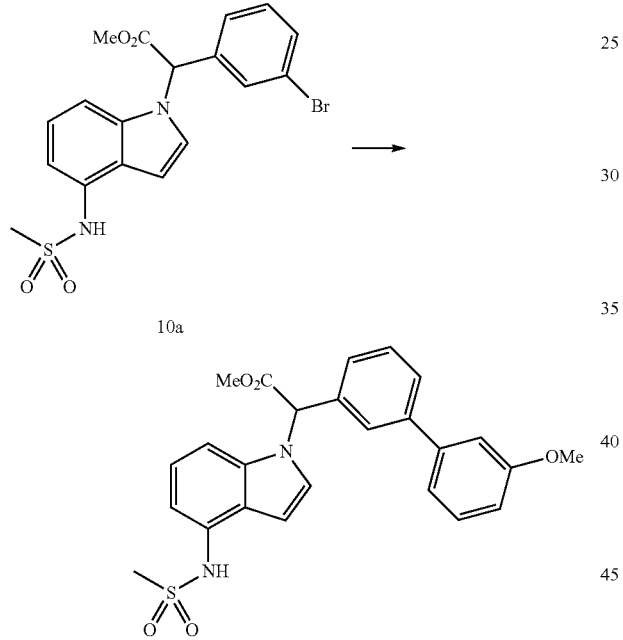

10a

78

Step A: Preparation of methyl (3-bromophenyl){4-[(methylsulfonyl)amino]-1H-indol-1-yl}acetate (10a)

Compound 10a was prepared by initially reacting i-1i with 4-nitroindole following procedures as described in Example 1. The product of the reaction was reacted under conditions described in Example 2, step A, followed by Example 2, step C to afford the title compound 10a. m/z (ES) 437 (MH)$^+$.

Step B: Preparation of methyl 2-(3'-methoxybiphenyl-3-yl)-2-{4-[(methylsulfonyl)amino]-1H-indol-1-yl}butanoate (78)

[1,1'-Bis(diphenylphosphino)ferrocene]dichloropalladium(II) (17 mg, 0.24 mmol) was added to a stirred solution of 10a (50 mg, 0.114 mmol) and 3-methoxyphenylboronic acid (21 mg, 0.140 mmol) in dioxane (0.6 mL) and saturated aqueous sodium bicarbonate (0.125 mL) at rt. The resulting solution was irradiated in a microwave reactor at 120° C. for 10 min. After cooling to rt, the reaction mixture was filtered through a short column of CELITE® eluting with EtOAc. The resulting crude oil was purified by preparative reversed phase HPLC on YMC Pack Pro C18 stationary phase (CH$_3$CN/H$_2$O as eluent, 0.05% TFA as modifier), followed by lyophilization of the purified fractions to afford the title compound 78. m/z (ES) 465 (MH)$^+$; IP=C rating.

Following procedures similar to those described above in Example 10, the following additional compounds represented in Table 10 were prepared:

TABLE 10

| Compound # | R$^9$ |
|---|---|
| 79 | 2-chlorophenyl |
| 80 | 2-(trifluoromethoxy)phenyl |
| 81 | 4-(trifluoromethoxy)phenyl |

Table 10. Parent Ion m/z (MH)$^+$ and Primary Assay IP data for compounds.

79: Methyl (2'-chlorobiphenyl-3-yl){4-[(methylsulfonyl)amino]-1H-indol-1-yl}acetate: m/z (ES) 469 (MH)$^+$; IP=C rating.

80: Methyl {4-[(methylsulfonyl)amino]-1H-indol-1-yl}[2'-(trifluoromethoxy)biphenyl-3-yl]acetate: m/z (ES) 519 (MH)$^+$; IP=C rating.

81: Methyl {4-[(methylsulfonyl)amino]-1H-indol-1-yl}[4'-(trifluoromethoxy)biphenyl-3-yl]acetate: m/z (ES) 519 (MH)⁺; IP=C rating.

Example 11

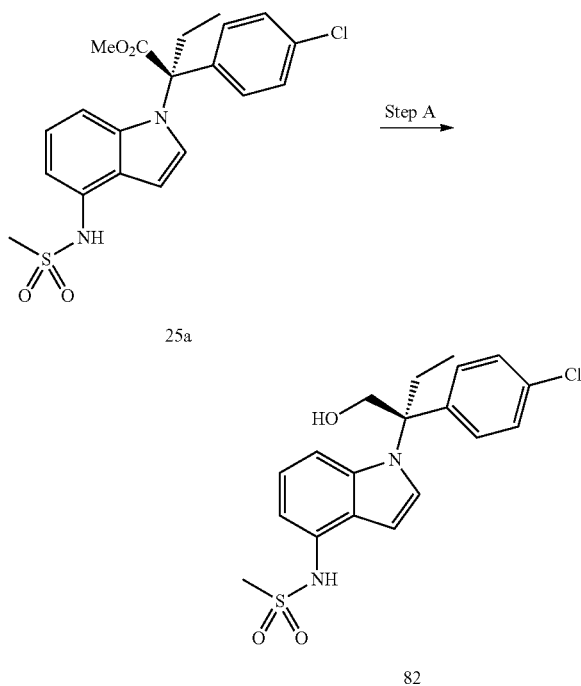

Step A: Preparation of (R)—N-{1-[(2R)-2-(4-chlorophenyl)-1-hydroxybutan-2-yl]-1H-indol-4-yl}methanesulfonamide (82)

Lithium borohydride (15 mg, 0.713 mmol) was added to a stirred solution of 25a (200 mg, 0.475 mmol) in THF (2.4 mL) at 0° C., and the reaction mixture was allowed to warm to rt overnight. The excess lithium borohydride was quenched by careful addition of 1M HCl, and the resulting mixture was partitioned between ethyl acetate and brine. The layers were separated, and the organic layer was dried (Na₂SO₄), filtered and concentrated in vacuo. The resulting crude residue was purified by flash chromatography on silica gel (gradient elution; 0%-60% EtOAc/hexanes as eluent) to afford the title compound 82. m/z (ES) 393 (MH)⁺; IP=A rating Following procedures similar to those described above in Example 11, compound 83 was prepared by substituting compound 25b for compound 25a. m/z (ES) 393 (MH)⁺; IP=B rating.

Example 12

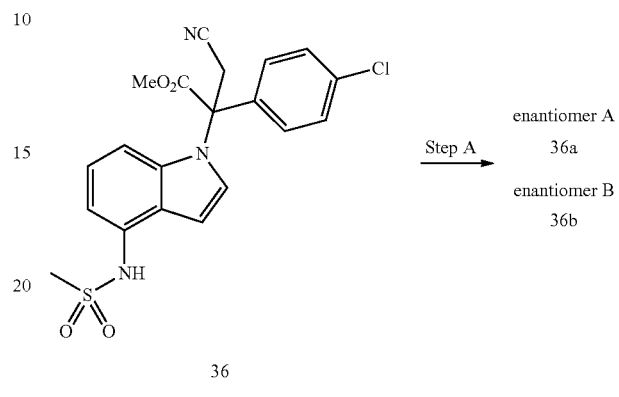

Enantiomers 36a and 36b were separated using preparative normal phase chiral HPLC. A solution of 36 in DCM/MeOH/acetonitrile was injected onto a CHIRALCEL® OD-H (available from Chiral Technologies, Inc., Exton, Pa.) semi-preparative (250×30 mm) HPLC column (eluting with 40% [(2:1) MeOH:acetonitrile]/CO₂ with a column temperature of 35° C. at 70 mL/min with UV detection at 230 nm). The enantiomers were separated with the faster eluting enantiomer 36a having a retention time of 2.33 min and the slower eluting enantiomer 36b having a retention time of 2.93 min, with the retention times derived from injection onto an analytical CHIRALCEL® OD-H HPLC column (4.6×250 mm, 2.4 mL/min, 40% [(2:1) MeOH:acetonitrile]/CO₂, 35° C.). The separated fractions were concentrated to provide the enantiomers 36a and 36b. Under the separation conditions cited above, the slower eluting enantiomer 36b is preferred for making final products. For 36a: m/z (ES) 432 (MH)⁺; IP=C rating For 36b: m/z (ES) 432 (MH)⁺; IP=A rating.

Example 13

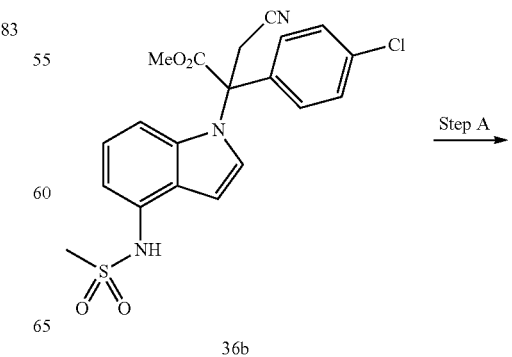

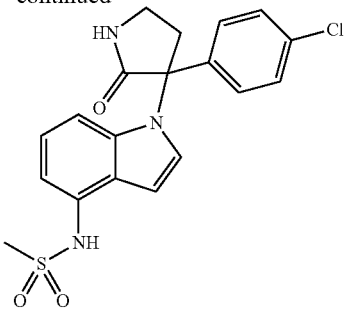

84

Step A: Preparation of N-{1-[3-(4-chlorophenyl)-2-oxopyrrolidin-3-yl]-1H-indol-4-yl}methanesulfonamide (84)

Sodium borohydride (13 mg, 0.347 mmol) was added in several portions to a stirred solution of 36b (30 mg, 0.069 mmol) and cobalt (II) chloride hexahydrate (8.3 mg, 0.035 mmol) in methanol (0.35 mL), and the reaction mixture was stirred at rt overnight. The reaction was quenched by careful addition of 1M HCl, and diluted with acetonitrile. The resulting solution was purified directly by preparative reversed phase HPLC on YMC Pack Pro C18 stationary phase ($CH_3CN/H_2O$ as eluent, 0.05% TFA as modifier), followed by lyophilization of the purified fractions to afford the title compound 84. m/z (ES) 404 $(MH)^+$. IP=B rating Example 14

N-(1-(2-(4-chlorophenyl)-1-hydroxybutan-2-yl)-6-fluoro-1H-indol-4-yl)methanesulfonamide (Compound 85)

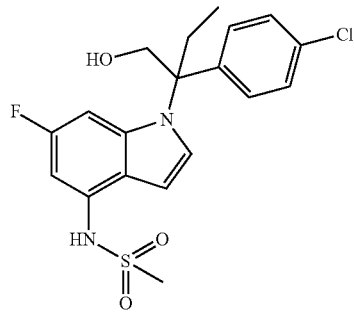 [SMILES: CCC(CO)(c1ccc(Cl)cc1)n1ccc2c(NS(C)(=O)=O)cc(F)cc21]

Step A: 5-fluoro-2-methyl-1,3-dinitrobenzene

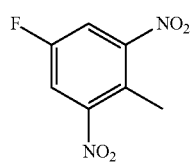

Fuming sulphuric acid (105 mL) was added dropwise to 4-fluoro-1-methyl-2-nitrobenzene (30 g, 0.194 mol) at −5° C.~0° C. and a mixture of fuming sulphuric acid (54 mL) and fuming nitric acid (18 mL) was added dropwise to it at −5° C.~0° C. over the period of 3 h. After complete addition, the reaction mixture was stirred for 3 hours at ambient temperature. TLC showed complete conversion of starting material to the product. The reaction mixture was poured into ice and extracted with dichloromethane. The combined organic layers was washed with water (600 mL), sat. sodium bicarbonate (600 mL) and brine (600 mL). It was dried over anhydrous magnesium sulfate and concentrated under reduced pressure to give the crude product, which was purified by silica gel column chromatography (PE:EA=20:1) to afford the title compound.

Step B: 2-(4-fluoro-2,6-dinitrophenyl)-N,N-dimethylethenamine

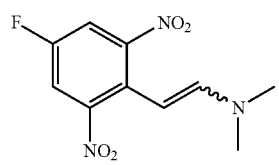

To a solution of 5-fluoro-2-methyl-1,3-dinitrobenzene (15 g, 0.075 mol) in N,N-dimethylformamide (300 mL) was added dimethylformamide dimethylacetal (89 g, 0.75 mol). The bright red reaction mixture was heated at 120° C. for 5 h, then concentrated in vacuo to provide 18 g crude product, which was used in the next step without further purification. LC/MS m/z=256.2 $[M+H]^+$.

Step C: 6-fluoro-1H-indol-4-amine

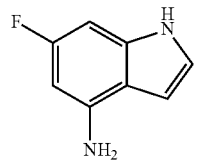

2-(4-fluoro-2,6-dinitrophenyl)-N,N-dimethylethenamine (18 g, 0.071 mol) was dissolved in ethanol (1000 mL), and charged with 10% palladium on carbon (2.0 g). The mixture was hydrogenated at room temperature overnight. The mixture was filtrated through celite and washed with ethanol. The filtrate was combined and evaporated in vacuo. The residue was purified by silica gel flash chromatography (PE:EA=2:1) to afford the title compound. LC/MS m/z=151.2 $[M+H]^+$.

Step D: 1-(4-chlorobenzyl)-6-fluoro-1H-indol-4-amine

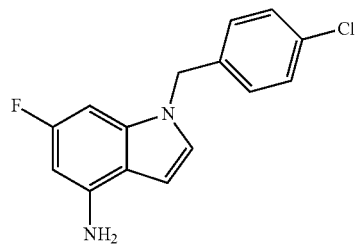 [SMILES: Nc1cc(F)cc2c1ccn2Cc1ccc(Cl)cc1]

A mixture of 6-fluoro-1H-indol-4-amine (5 g, 0.033 mol), 4-chlorobenzyl chloride (5.55 g, 0.035 mol) and sodium hydroxide (1.32 g, 0.033 mol) was heated at 60° C. for 3 h. The solvent was evaporated and the residue was dissolved in EA (150 mL) and water (70 mL). The aqueous layer was extracted with EA and washed with brine (100 mL), dried over sodium sulfate and concentrated in vacuo. The residue was purified by silica gel flash chromatography (PE:EA=8:1) to afford the title compound. LC/MS m/z=275.1 [M+H]$^+$.

Step E: tert-butyl 1-(4-chlorobenzyl)-6-fluoro-1H-indol-4-ylcarbamate

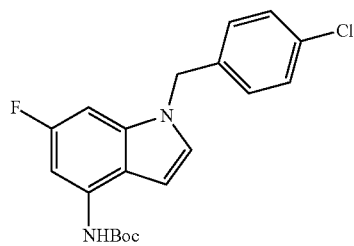 [SMILES: CC(C)(C)OC(=O)Nc1cc(F)cc2c1ccn2Cc1ccc(Cl)cc1]

The mixture of 1-(4-chlorobenzyl)-6-fluoro-1H-indol-4-amine (7 g, 0.026 mol) and di-tert-butyl dicarbonate (11 g, 0.051 mol) in t-butyl alcohol (100 mL) was heated at 50° C. for 16 h. The solvent was evaporated and the solid was filtrated and washed with PE to afford the title compound. LC/MS m/z=375.1 [M+H]$^+$.

Step F: 2-(4-(tert-butoxycarbonylamino)-6-fluoro-1H-indol-1-yl)-2-(4-chlorophenyl)acetic acid

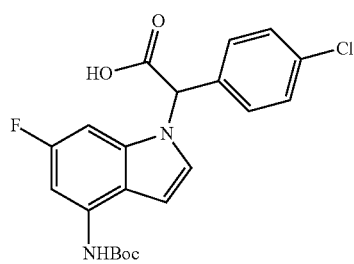 [SMILES: CC(C)(C)OC(=O)Nc1cc(F)cc2c1ccn2C(C(=O)O)c1ccc(Cl)cc1]

To the mixture of tert-butyl 1-(4-chlorobenzyl)-6-fluoro-1H-indol-4-ylcarbamate (8 g, 0.021 mol) in THF (300 mL) was added dropwise BuLi (2.5 M, 34 mL, 0.084 mol) at −78° C. and the mixture was stirred for another 30 min at −78° C. An excess of dry ice was added and the solution was warmed slowly to room temperature. The resulting mixture was partitioned between ethyl acetate and saturated aqueous ammonium chloride. The aqueous layer was extracted with EA and washed with brine (100 mL), dried over sodium sulfate and concentrated in vacuo to afford the title compound (8 g, yield 89%). LC/MS m/z=363.1 [M-$^t$Bu+H]$^+$.

Step G: methyl 2-(4-amino-6-fluoro-1H-indol-1-yl)-2-(4-chlorophenyl)acetate

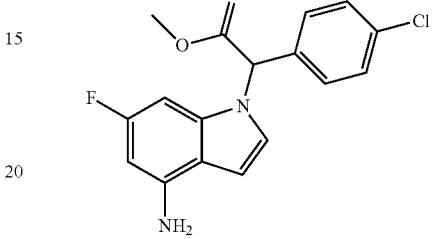

To a solution of 2-(4-(tert-butoxycarbonylamino)-6-fluoro-1H-indol-1-yl)-2-(4-chlorophenyl)acetic acid (8 g, 0.019 mol) in methanol (100 mL) was added sulfuric acid (1 mL) and the mixture was stirred for 2 h at 50° C. The resulting mixture was partitioned between ethyl acetate and saturated aqueous sodium bicarbonate. The aqueous layer was extracted with EA and washed with brine (100 mL), dried over sodium sulfate and concentrated in vacuo to afford crude title compound (5.7 g), which was used in the next step without further purification. LC/MS m/z=333.1 [M+H]$^+$.

Step H: methyl 2-(4-(tert-butoxycarbonylamino)-6-fluoro-1H-indol-1-yl)-2-(4-chlorophenyl) acetate

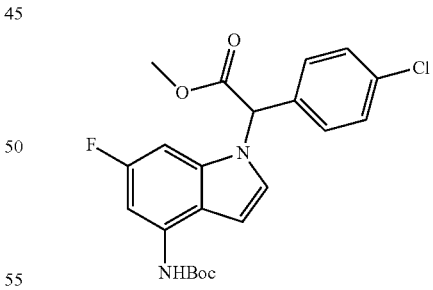

The mixture of methyl 2-(4-amino-6-fluoro-1H-indol-1-yl)-2-(4-chlorophenyl)acetate (5.7 g, 0.017 mol) and di-tert-butyl dicarbonate (7.4 g, 0.034 mol) in t-butyl alcohol (80 mL) was heated at 50° C. for 10 h. The solvent was evaporated and the residue was purified by silica gel flash chromatography (PE:EA=8:1) to afford the title compound. LC/MS m/z=377.1 [M-$^t$Bu+H]$^+$.

Step I: methyl 2-(4-(tert-butoxycarbonylamino)-6-fluoro-1H-indol-1-yl)-2-(4-chlorophenyl)butanoate

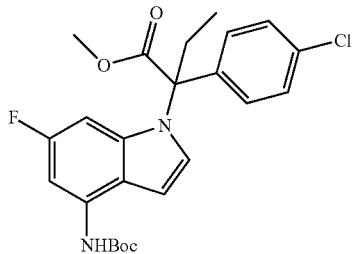 [SMILES: CCC(C(=O)OC)(c1ccc(Cl)cc1)n1ccc2c(NC(=O)OC(C)(C)C)cc(F)cc21]

LiHMDS (20 mL, 0.020 mol) was added dropwise to a stirred solution of methyl 2-(4-(tert-butoxycarbonylamino)-6-fluoro-1H-indol-1-yl)-2-(4-chlorophenyl)acetate (4.32 g, 0.010 mol) in THF (80 mL) and HMPA (20 mL) at −78° C. The resulting mixture was stirred for another 1 h at −78° C. Iodoethane (2.3 g, 0.015 mol) was added to the above solution. The reaction mixture was warmed to −20° C. and stirred for 20 min. The mixture was quenched with sat. ammonium chloride and extracted with EA, washed with brine and dried over sodium sulfate and concentrated in vacuo. The residue was purified by silica gel flash chromatography (PE:EA=8:1) to afford the title compound. LC/MS m/z=405.1 [M-$^t$Bu+H]$^+$.

Step J: methyl 2-(4-amino-6-fluoro-1H-indol-1-yl)-2-(4-chlorophenyl)butanoate

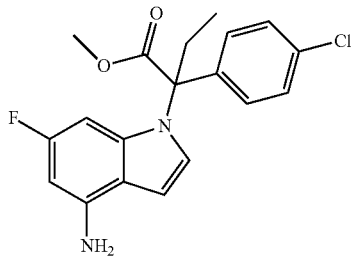 [SMILES: CCC(C(=O)OC)(c1ccc(Cl)cc1)n1ccc2c(N)cc(F)cc21]

Trifluoroacetic acid (4 mL) was added rapidly dropwise to a stirred solution of methyl 2-(4-(tert-butoxycarbonylamino)-6-fluoro-1H-indol-1-yl)-2-(4-chlorophenyl)butanoate (0.92 g, 2 mmol) in DCM (10 mL) at 0° C. After 1 h, the reaction was quenched by careful addition of saturated aqueous sodium bicarbonate, followed by extraction with ether. The organic layers were washed with saturated aqueous sodium bicarbonate, dried over sodium sulfate, filtered and concentrated in vacuo to afford the title compound. LC/MS m/z=361.1 [M+H]$^+$.

Step K: methyl 2-(4-chlorophenyl)-2-(6-fluoro-4-(methylsulfonamido)-1H-indol-1-yl)butanoate

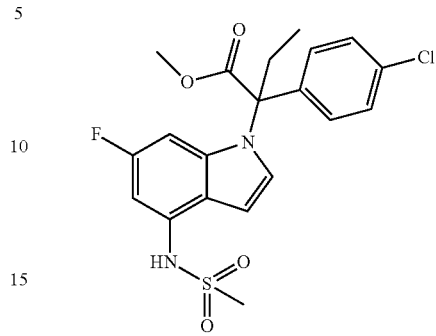

Methanesulfonyl chloride (0.23 g, 2 mmol) was added to a stirred solution of methyl 2-(4-amino-6-fluoro-1H-indol-1-yl)-2-(4-chlorophenyl)butanoate (0.6 g, 1.7 mmol) and 4-methylmorpholine (0.25 g, 2.5 mmol) in DCM (8 mL) at 0° C. After 30 min, an additional portion of methanesulfonyl chloride (0.1 g, 1 mmol) was added. After 1 h, the reaction mixture was partitioned between DCM and saturated aqueous ammonium chloride. The layers were separated and the aqueous layer was extracted with DCM. The combined organic layers were washed with brine, dried over sodium sulfate, filtered and concentrated in vacuo. The residue was purified by silica gel flash chromatography (PE:EA=2:1) to afford the title compound. LC/MS m/z=439.1 [M+H]$^+$.

Step L: N-(1-(2-(4-chlorophenyl)-1-hydroxybutan-2-yl)-6-fluoro-1H-indol-4-yl)methanesulfonamide (Compound 85)

To a solution of methyl 2-(4-chlorophenyl)-2-(6-fluoro-4-(methylsulfonamido)-1H-indol-1-yl)butanoate (0.5 g, 1.14 mmol) in THF (5 mL) was added dropwise lithium aluminum hydride solution (1.4 mL, 1 M in THF) at −78° C. The reaction mixture was stirred for 0.5 hours at −78° C. TLC and LCMS monitored the reaction was over, then 3M HCl solution was added carefully into the reaction to adjust pH=2~3 in ice bath. The organic layer was separated and the aqueous layer was extracted with EA. The combined organic layer was washed with brine and dried over anhydrous sodium sulfate. The resulting mixture was filtered and concentrated in vacuo. The residue was purified by silica gel flash chromatography (PE:EA=2:1) to afford the title compound. LC/MS m/z=411.1 [M+H]$^+$.

Using the procedure described in Example 14, but in step J replacing 2-(4-(tert-butoxycarbonylamino)-6-fluoro-1H-indol-1-yl)-2-(4-chlorophenyl)butanoate with methyl 2-(4-(tert-butoxycarbonylamino)-1H-indol-1-yl)-2-(4-chlorophenyl)butanoate, methyl 2-(4-(tert-butoxycarbonylamino)-1H-indol-1-yl)-2-(2,4-dichlorophenyl)butanoate, methyl 2-(4-(tert-butoxycarbonylamino)-1H-indazol-1-yl)-2-(4-chlorophenyl)butanoate, methyl 2-(4-(tert-butoxycarbonylamino)-1H-indazol-1-yl)-2-(4-(trifluoromethyl)phenyl)butanoate, compounds 86-89 of Table 11 were prepared respectively.

Compound 86 was obtained using enantiomer A in Example 3 step D as starting material.
Compound 88 was obtained by the below chiral separation conditions:
Column: AS-H
Mobile phase: A: Hexane, B: EtOH (0.1% DEA), A:B=70:30 at 1.0 mL/min
Column Temp: 40.2° C.

TABLE 11

| Compound Number | IP Rating | Structure | IUPAC Name | LCMS m/z [M + H]+ |
|---|---|---|---|---|
| 85 | B | 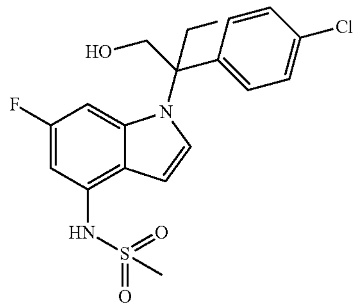 [SMILES: CCC(CO)(c1ccc(Cl)cc1)n1ccc2c(NS(C)(=O)=O)cc(F)cc21] | N-(1-(2-(4-chlorophenyl)-1-hydroxybutan-2-yl)-6-fluoro-1H-indol-4-yl)methanesulfonamide | 411.1 |
| 86 | A | 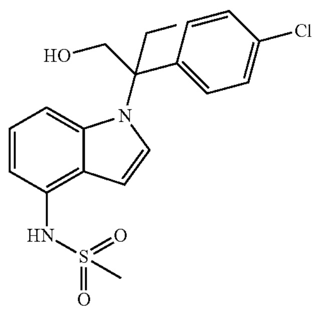 [SMILES: CCC(CO)(c1ccc(Cl)cc1)n1ccc2c(NS(C)(=O)=O)cccc21] | N-(1-(2-(4-chlorophenyl)-1-hydroxybutan-2-yl)-1H-indol-4-yl)methanesulfonamide (enantiomer) | 393.1 |
| 87 | B | 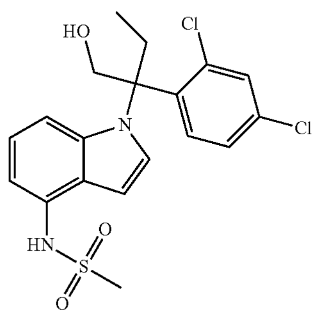 [SMILES: CCC(CO)(c1ccc(Cl)cc1Cl)n1ccc2c(NS(C)(=O)=O)cccc21] | N-(1-(2-(2,4-dichlorophenyl)-1-hydroxybutan-2-yl)-1H-indol-4-yl)methanesulfonamide | 427.1 |
| 88 | A | 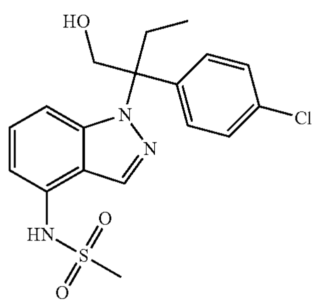 [SMILES: CCC(CO)(c1ccc(Cl)cc1)n1ncc2c(NS(C)(=O)=O)cccc21] | N-(1-(2-(4-chlorophenyl)-1-hydroxybutan-2-yl)-1H-indazol-4-yl)methanesulfonamide (enantiomer A, r.t. = 9.17 min) | 394.1 |
| 89 | B | 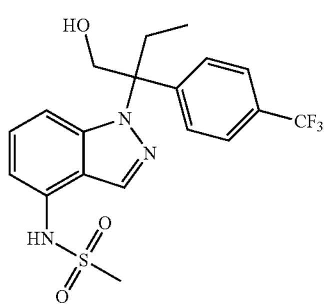 [SMILES: CCC(CO)(c1ccc(C(F)(F)F)cc1)n1ncc2c(NS(C)(=O)=O)cccc21] | N-(1-(1-hydroxy-2-(4-(trifluoromethyl)phenyl)butan-2-yl)-1H-indazol-4-yl)methanesulfonamide | 428.1 |

Example 15

N-(1-(3-(4-chlorophenyl)-2-hydroxy-2-methylpentan-3-yl)-6-fluoro-1H-indol-4-yl)methane sulfonamide (Compound 90)

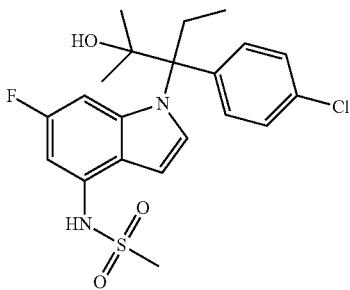 [SMILES: CCC(c1ccc(Cl)cc1)(n1ccc2c(NS(C)(=O)=O)cc(F)cc21)C(C)(C)O]

Step A: tert-butyl 1-(3-(4-chlorophenyl)-2-hydroxy-2-methylpentan-3-yl)-6-fluoro-1H-indol-4-ylcarbamate

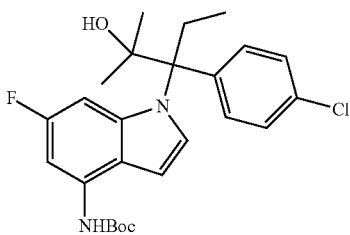 [SMILES: CCC(c1ccc(Cl)cc1)(n1ccc2c(NC(=O)OC(C)(C)C)cc(F)cc21)C(C)(C)O]

To a solution of methyl 2-(4-(tert-butoxycarbonylamino)-6-fluoro-1H-indol-1-yl)-2-(4-chlorophenyl)butanoate (1.0 g, 2.17 mmol), as described in Example 14 Step I, in ether (5 mL) was added CH$_3$Li (7.2 mL, 21.7 mmol, 3.0 M in ether) dropwise at 0° C. and stirred for 30 min. The mixture was quenched with saturated ammonium chloride solution, and extracted with ethyl acetate. The organic layers was washed with brine, dried over sodium sulfate, filtered and evaporated. The residue was purified by Prep-TLC (eluent: ethyl acetate/petroleum ether=4:1) to obtain the title compound. LC/MS m/z=461.2 [M+H]$^+$.

Step B: 3-(4-amino-6-fluoro-1H-indol-1-yl)-3-(4-chlorophenyl)-2-methylpentan-2-ol

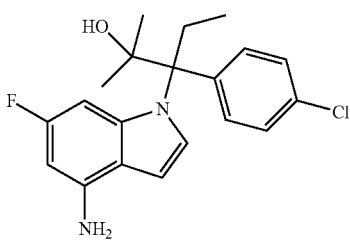 [SMILES: CCC(c1ccc(Cl)cc1)(n1ccc2c(N)cc(F)cc21)C(C)(C)O]

A mixture of tert-butyl 1-(3-(4-chlorophenyl)-2-hydroxy-2-methylpentan-3-yl)-6-fluoro-1H-indol-4-ylcarbamate (250 mg, 0.543 mmol) and TFA/DCM (V/V=¼, 10 mL) was stirred at room temperature for 2 h. After removing the solvent, the residue was dissolved in ethyl acetate (20 mL), pH value adjusted to 9~10 with a saturated sodium bicarbonate solution, dried over sodium sulfate, then filtered. After removing the organic solvent, a crude compound was obtained without purification. LC/MS m/z=361.2 [M+H]$^+$.

Step C: N-(1-(3-(4-chlorophenyl)-2-hydroxy-2-methylpentan-3-yl)-6-fluoro-1H-indol-4-yl)methanesulfonamide (Compound 90)

To a mixture of compound 3-(4-amino-6-fluoro-1H-indol-1-yl)-3-(4-chlorophenyl)-2-methylpentan-2-ol (176 mg, 0.489 mmol) and NMM (145 mg, 1.467 mmol) in DCM (10.0 mL) was added methanesulfonyl chloride (112 mg, 0.978 mmol) dropwise. Then the mixture was stirred at room temperature overnight. The reaction was quenched with saturated ammonium chloride solution, and extracted with ethyl acetate (50 mL). The organic layers was washed with brine, dried over dry sodium sulfate, filtered and evaporated. The residue was purified by Prep-TLC (eluent: ethyl acetate/petroleum=4:1) to obtain the title compound. LC/MS m/z=438.9 [M+H]$^+$. $^1$H NMR (400 MHz, MeOD) δ 8.02 (s, 1H), 7.57-7.25 (m, 4H), 6.86 (dd, J=10.9, 2.1 Hz, 1H), 6.74 (d, J=3.6 Hz, 1H), 5.85 (d, J=11.1 Hz, 1H), 3.00 (s, 3H), 2.84-2.73 (m, 1H), 2.61-2.47 (m, 1H), 1.31 (s, 3H), 1.27 (s, 3H), 0.64 (t, J=7.3 Hz, 3H).

Using the procedure described in Example 15, but in step A replacing 2-(4-(tert-butoxycarbonylamino)-6-fluoro-1H-indol-1-yl)-2-(4-chlorophenyl)butanoate with methyl 2-(4-(tert-butoxycarbonylamino)-1H-indol-1-yl)-2-(4-chlorophenyl)butanoate, methyl 2-(4-(tert-butoxycarbonylamino)-1H-indazol-1-yl)-2-(4-chlorophenyl)butanoate, methyl 2-(4-(tert-butoxycarbonylamino)-1H-indazol-1-yl)-2-(4-(trifluoromethyl)phenyl) butanoate, compounds 91-93 of Table 12 were prepared respectively. Also using the procedure described in Example 15, but in step C replacing methanesulfonyl chloride with methylsulfamoyl chloride, dimethylsulfamoyl chloride, compounds 94 and 95 of Table 12 were prepared respectively.

Compound 90 was obtained by the below chiral separation conditions:
Column: AS-H
Mobile phase: A: CO$_2$, B: MeOH (0.1% DEA), A:B=70:30 at 3.0 mL/min
Column Temp: 40° C.
Compound 91 was obtained by the below chiral separation conditions:
Column: OJ-H
Mobile phase: A: n-Hexane, B: EtOH (0.1% DEA), A:B=70:30 at 1.0 mL/min
Column Temp: 40° C.
Compound 92 was obtained by the below chiral separation conditions:
Column: OJ-H
Mobile phase: A: n-Hexane, B: MeOH (0.1% DEA), A:B=70:30 at 3.0 mL/min
Column Temp: 37.7° C.
Compound 93 was obtained by the below chiral separation conditions:
Column: AS-H
Mobile phase: A: CO$_2$, B: MeOH, A:B=70:30 at 3.0 mL/min
Column Temp: 38.1° C.
Compound 94 and 95 were obtained using enantiomer A intermediate (example 18 step D) as starting material.

TABLE 12

| Compound Number | IP Rating | Structure | IUPAC Name | LCMS m/z [M + H]+ |
|---|---|---|---|---|
| 90 | A | 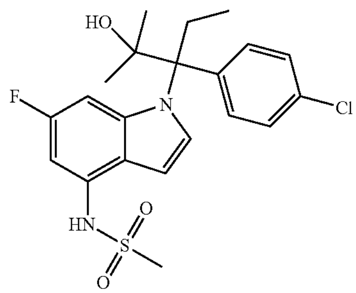 [SMILES: CCC(c1ccc(Cl)cc1)(n1ccc2c(NS(C)(=O)=O)cc(F)cc21)C(C)(C)O] | N-(1-(3-(4-chlorophenyl)-2-hydroxy-2-methylpentan-3-yl)-6-fluoro-1H-indol-4-yl)methanesulfonamide (enantiomer B, r.t. = 3.11 min) | 438.9 |
| 91 | A | 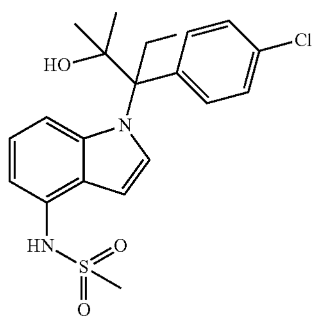 [SMILES: CCC(c1ccc(Cl)cc1)(n1ccc2c(NS(C)(=O)=O)cccc21)C(C)(C)O] | N-(1-(3-(4-chlorophenyl)-2-hydroxy-2-methylpentan-3-yl)-1H-indol-4-yl)methane sulfonamide (enantiomer A, r.t. = 9.61 min) | 421.1 |
| 92 | A | 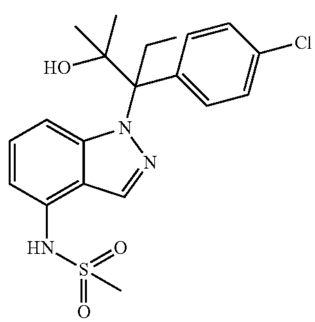 [SMILES: CCC(c1ccc(Cl)cc1)(n1ncc2c(NS(C)(=O)=O)cccc21)C(C)(C)O] | N-(1-(3-(4-chlorophenyl)-2-hydroxy-2-methylpentan-3-yl)-1H-indazol-4-yl)methane sulfonamide (enantiomer A, r.t. = 2.2 min) | 422.1 |
| 93 | A | 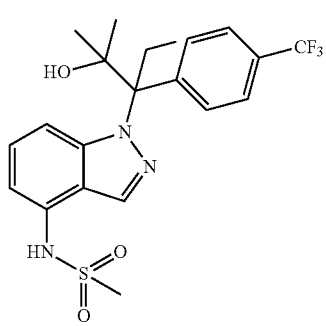 [SMILES: CCC(c1ccc(C(F)(F)F)cc1)(n1ncc2c(NS(C)(=O)=O)cccc21)C(C)(C)O] | N-(1-(2-hydroxy-2-methyl-3-(4-(trifluoromethyl)phenyl)pentan-3-yl)-1H-indazol-4-yl)methane sulfonamide (enantiomer A, r.t. = 1.87 min) | 456.1 |

TABLE 12-continued

| Compound Number | IP Rating | Structure | IUPAC Name | LCMS m/z [M + H]+ |
|---|---|---|---|---|
| 94 | A | 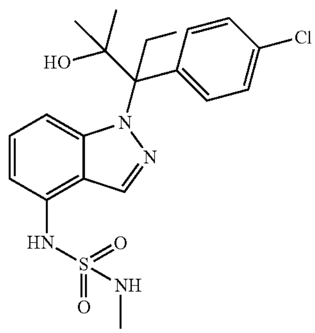 [SMILES: CCC(c1ccc(Cl)cc1)(n1ncc2c(NS(=O)(=O)NC)cccc21)C(C)(C)O] | 1-(1-(3-(4-chlorophenyl)-2-hydroxy-2-methylpentan-3-yl)-1H-indazol-4-yl)-3-methyl-sulfonylurea (enantiomer) | 437.1 |
| 95 | B | 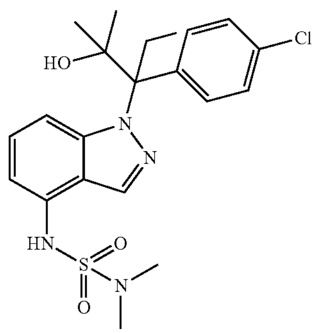 [SMILES: CCC(c1ccc(Cl)cc1)(n1ncc2c(NS(=O)(=O)N(C)C)cccc21)C(C)(C)O] | 3-(1-(3-(4-chlorophenyl)-2-hydroxy-2-methylpentan-3-yl)-1H-indazol-4-yl)-1,1-dimethyl-sulfonylurea (enantiomer) | 451.1 |

Example 16

N-(1-(2-(4-chlorophenyl)-1-methoxybutan-2-yl)-1H-indol-4-yl)methanesulfonamide

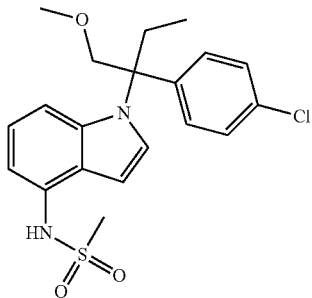

Step A: Methyl 2-(4-amino-1H-indol-1-yl)-2-(4-chlorophenyl)butanoate

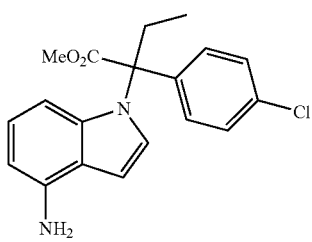 [SMILES: CCC(C(=O)OC)(c1ccc(Cl)cc1)n1ccc2c(N)cccc21]

A mixture of methyl 2-(4-(tert-butoxycarbonylamino)-1H-indol-1-yl)-2-(4-chlorophenyl)butanoate (500 mg), as described in Example 3 Step A, in 10 mL of 4 N HCl/MeOH was stirred at room temperature for 1 h. Then the solvent was removed. The residue was dissolved in EA (30 mL) and pH value was adjusted to 9~10 with saturated aq. NaHCO$_3$. The organic layers was washed with water (10 mL), brine, dried over sodium sulfate and concentrated to give the title product as a pale brown solid. LC/MS m/z=343.2 [M+H]+.

Step B: Methyl 2-(4-chlorophenyl)-2-(4-(2,5-dimethyl-1H-pyrrol-1-yl)-1H-indol-1-yl)butanoate

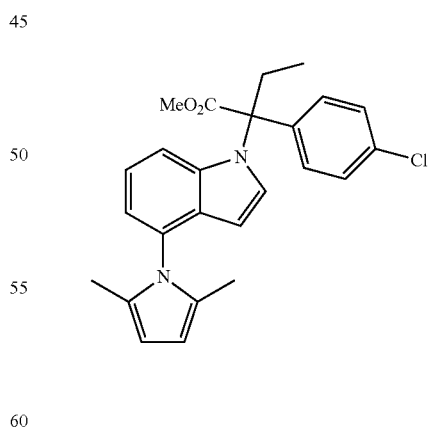

A mixture of methyl 2-(4-amino-1H-indol-1-yl)-2-(4-chlorophenyl)butanoate (140 mg), hexane-2,5-dione (166 mg) and 4-methylbenzenesulfonic acid (3 mg) in toluene (5 mL) was stirred under reflux for 30 min. Concentrated, the residue was purified by chromatography on silica gel column (5-15% ethyl acetate in hexanes) to give the title compound as a yellow solid. LC/MS m/z=421.2 [M+H]+.

Step C: 2-(4-Chlorophenyl)-2-(4-(2,5-dimethyl-1H-pyrrol-1-yl)-1H-indol-1-yl)butan-1-ol

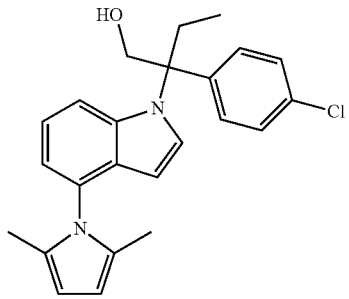 [SMILES: CCC(CO)(c1ccc(Cl)cc1)n1ccc2c(-n3c(C)ccc3C)cccc21]

To a suspension of LiBH4 (22 mg) in THF (3 mL) was added MeOH (32 mg, 5.43 mmol) and a solution of methyl 2-(4-chlorophenyl)-2-(4-(2,5-dimethyl-1H-pyrrol-1-yl)-1H-indol-1-yl)butanoate (105 mg) in THF (3 mL). The mixture was stirred at room temperature for 2 h. The solution was quenched with saturated ammonium chloride solution, and extracted with ethyl acetate (20 mL). The organic layer was washed with brine, dried over sodium sulfate, and evaporated. The residue was purified by chromatography on silica gel (25-35% ethyl acetate in hexanes) to afford the title compound as a pale yellow solid. LC/MS m/z=393.2 [M+H]+.

Step D: 1-(2-(4-Chlorophenyl)-1-methoxybutan-2-yl)-4-(2,5-dimethyl-1H-pyrrol-1-yl)-1H-indole

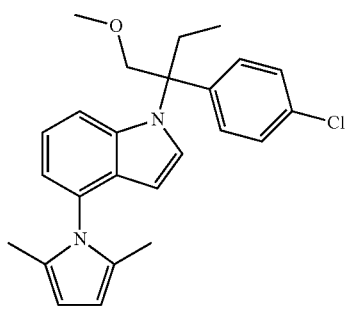 [SMILES: CCC(COC)(c1ccc(Cl)cc1)n1ccc2c(-n3c(C)ccc3C)cccc21]

A solution of 2-(4-chlorophenyl)-2-(4-(2,5-dimethyl-1H-pyrrol-1-yl)-1H-indol-1-yl)butan-1-ol (89 mg) in dry DMF (3 mL) was treated by NaH (60% in oil, 18 mg) at 0° C. for 30 min, then was added iodomethane (97 mg). The mixture was stirred at room temperature for 2 h. The solution was quenched with saturated ammonium chloride solution, and extracted with ethyl acetate (25 mL). The organic layers was washed with brine, dried over sodium sulfate, and evaporated to afford the title compound as a white solid. LC/MS m/z=407.1 [M+H]+.

Step E: 1-(2-(4-Chlorophenyl)-1-methoxybutan-2-yl)-1H-indol-4-amine

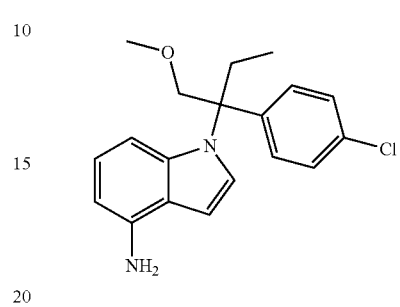

To the mixture of 1-(2-(4-chlorophenyl)-1-methoxybutan-2-yl)-4-(2,5-dimethyl-1H-pyrrol-1-yl)-1H-indole (70 mg) in ethanol/H2O (3 mL/1 mL) was added NH2OH—HCl (178 mg) and triethylamine (87 mg) and the reaction mixture was refluxed for 18 h in an oil bath, cooled to room temperature, concentrated, and extracted with ethyl acetate (30 mL). The organic layers were combined, dried over anhydrous sodium sulfate, and concentrated under vacuum. The residue was purified using a silica gel column (20-40% ethyl acetate in hexane) to afford the title compound as a brown solid. LC/MS m/z=329.1 [M+H]+.

Step F: N-(1-(2-(4-chlorophenyl)-1-methoxybutan-2-yl)-1H-indol-4-yl)methanesulfonamide To a mixture of 1-(2-(4-chlorophenyl)-1-methoxybutan-2-yl)-1H-indol-4-amine (30 mg) and 4-methylmorpholine (46 mg) in DCM (3 mL) was added methanesulfonyl chloride (16 mg) dropwise. Then the mixture was stirred at room temperature overnight. The solution was quenched with saturated ammonium chloride solution, and extracted with ethyl acetate (20 mL). The organic layer was washed with brine, dried over sodium sulfate, and evaporated. The residue was purified by chromatography on silica gel (20-30% ethyl acetate in hexane) to afford the title compound as a white solid. LC/MS m/z=407.1 [M+H]+.

Using the procedure described in Example 13, but in step A replacing methyl 2-(4-(tert-butoxycarbonylamino)-1H-indol-1-yl)-2-(4-chlorophenyl)butanoate with methyl 2-(4-(tert-butoxycarbonylamino)-1H-indazol-1-yl)-2-(4-chlorophenyl)butanoate compound 97 of Table 13 was prepared. Compound 96 and compound 97 were obtained by the below chiral separation conditions:

Column: OZ—H

Mobile phase: A: CO2, B: MeOH (0.1% DEA), A:B=70:30 at 3.0 mL/min

Column Temp: 40.2° C.

TABLE 13

| Compound Number | IP Rating | Structure | IUPAC Name | LCMS m/z [M + H]+ |
|---|---|---|---|---|
| 96 | A | 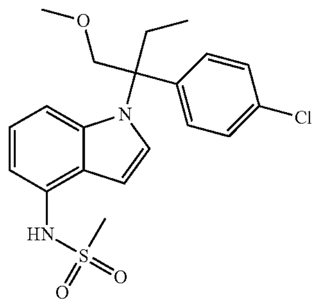 [SMILES: CCC(COC)(c1ccc(Cl)cc1)n1ccc2c(NS(C)(=O)=O)cccc21] | N-(1-(2-(4-chlorophenyl)-1-methoxybutan-2-yl)-1H-indol-4-yl)methanesulfonamide (enantiomer A, r.t. = 2.36 min) | 407.1 |
| 97 | A | 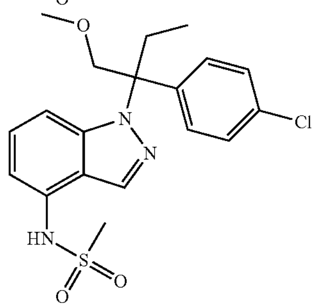 | N-(1-(2-(4-chlorophenyl)-1-methoxybutan-2-yl)-1H-indazol-4-yl)methanesulfonamide (enantiomer A, r.t. = 3.24 min) | 408.1 |

Example 17

N-(1-(3-(4-chlorophenyl)-2-oxopentan-3-yl)-6-fluoro-1H-indol-4-yl)methanesulfonamide (Compound 98)

Step A: tert-butyl 1-(3-(4-chlorophenyl)-2-oxopentan-3-yl)-6-fluoro-1H-indol-4-ylcarbamate

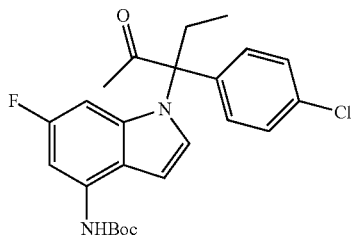 [SMILES: CCC(C(C)=O)(c1ccc(Cl)cc1)n1ccc2c(NC(=O)OC(C)(C)C)cc(F)cc21]

Both products tert-butyl 1-(3-(4-chlorophenyl)-2-oxopentan-3-yl)-6-fluoro-1H-indol-4-ylcarbamate and tert-butyl 1-(3-(4-chlorophenyl)-2-hydroxy-2-methylpentan-3-yl)-6-fluoro-1H-indol-4-ylcarbamate were obtained in Example 15 step A.

Step B: 3-(4-amino-6-fluoro-1H-indol-1-yl)-3-(4-chlorophenyl)pentan-2-one

Using the same procedure described for the preparation of Example 15, step B but replacing the tert-butyl 1-(3-(4-chlorophenyl)-2-hydroxy-2-methylpentan-3-yl)-6-fluoro-1H-indol-4-ylcarbamate with tert-butyl 1-(3-(4-chlorophenyl)-2-oxopentan-3-yl)-6-fluoro-1H-indol-4-ylcarbamate gave the title compound. LC/MS m/z=345.2 [M+H]+.

Step C: N-(1-(3-(4-chlorophenyl)-2-oxopentan-3-yl)-6-fluoro-1H-indol-4-1)methanesulfonamide (Compound 98)

Using the same procedure described for the preparation of Example 15, step C but replacing 3-(4-amino-6-fluoro-1H-indol-1-yl)-3-(4-chlorophenyl)-2-methylpentan-2-ol with 3-(4-amino-6-fluoro-1H-indol-1-yl)-3-(4-chlorophenyl)pentan-2-one gave the title compound. LC/MS m/z=423.2 [M+H]+.

Using the procedure described in Example 17, but in step A replacing 2-(4-(tert-butoxycarbonylamino)-6-fluoro-1H-indol-1-yl)-2-(4-chlorophenyl)butanoate with methyl 2-(4-(tert-butoxycarbonylamino)-1H-indol-1-yl)-2-(4-chlorophenyl)butanoate, methyl 2-(4-(tert-butoxycarbonylamino)-1H-indazol-1-yl)-2-(4-chlorophenyl)butanoate, methyl 2-(4-(tert-butoxycarbonylamino)-1H-indol-1-yl)-2-(4-(trifluoromethyl)phenyl)butanoate, methyl 2-(4-(tert-butoxycarbonylamino)-1H-indazol-1-yl)-2-(4-(trifluoromethyl)phenyl)butanoate, compounds 99-104 of Table 14 were prepared respectively. Also using the procedure described in Example 17, but in step C replacing methanesulfonyl chloride with methylsulfamoyl chloride, compounds 105 of Table 14 was prepared.

Compound 100 and compound 101 were obtained by the below chiral separation conditions:
Column: OJ-H
Mobile phase: A: Hexane, B: MeOH, A:B=60:40 at 3.0 mL/min
Column Temp: 40.7° C.

Compound 102 and compound 103 were obtained by the below chiral separation conditions:

Column: AD-H
Mobile phase: A: $CO_2$, B: MeOH, A:B=85:15 at 3.0 mL/min
Column Temp: 41.3° C.

Compound 104 was obtained by the below chiral separation conditions:
Column: OJ-H
Mobile phase: A: $CO_2$, B: MeOH (0.1% DEA), A:B=70:30 at 3.0 mL/min
Column Temp: 39.9° C.
Compound 105 was obtained using enantiomer A in Example 18 step D as starting material.

TABLE 14

| Compound Number | IP Rating | Structure | IUPAC Name | LCMS m/z $[M + H]^+$ |
|---|---|---|---|---|
| 98 | A | 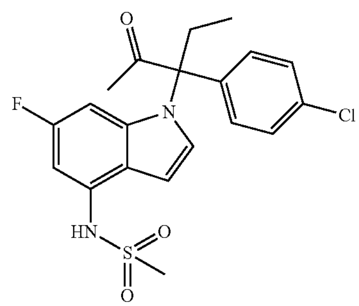 [SMILES: CCC(C(C)=O)(c1ccc(Cl)cc1)n1ccc2c(NS(C)(=O)=O)cc(F)cc21] | N-(1-(3-(4-chlorophenyl)-2-oxopentan-3-yl)-6-fluoro-1H-indol-4-1)methanesulfonamide | 423.1 |
| 99 | A | 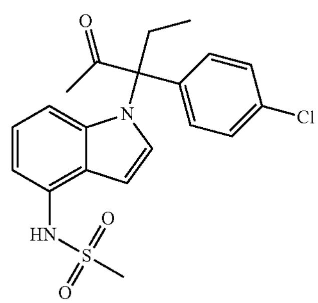 [SMILES: CCC(C(C)=O)(c1ccc(Cl)cc1)n1ccc2c(NS(C)(=O)=O)cccc21] | N-(1-(3-(4-chlorophenyl)-2-oxopentan-3-yl)-1H-indol-4-yl)methanesulfonamide | 405.1 |
| 100 | A | 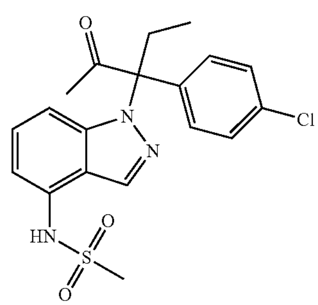 [SMILES: CCC(C(C)=O)(c1ccc(Cl)cc1)n1ncc2c(NS(C)(=O)=O)cccc21] | N-(1-(3-(4-chlorophenyl)-2-oxopentan-3-yl)-1H-indazol-4-yl)methanesulfonamide (enantiomer A, r.t. = 2.85 min) | 406.1 |
| 101 | B | 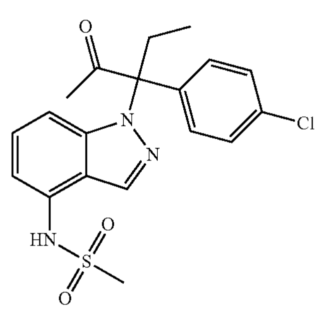 [SMILES: CCC(C(C)=O)(c1ccc(Cl)cc1)n1ncc2c(NS(C)(=O)=O)cccc21] | N-(1-(3-(4-chlorophenyl)-2-oxopentan-3-yl)-1H-indazol-4-yl)methanesulfonamide (enantiomer B, r.t. = 3.79 min) | 406.1 |

TABLE 14-continued

| Compound Number | IP Rating | Structure | IUPAC Name | LCMS m/z [M + H]+ |
|---|---|---|---|---|
| 102 | B | 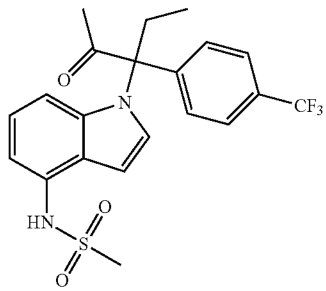 [SMILES: CCC(C(C)=O)(c1ccc(C(F)(F)F)cc1)n1ccc2c(NS(C)(=O)=O)cccc21] | N-(1-(2-oxo-3-(4-(trifluoromethyl)phenyl)pentan-3-yl)-1H-indol-4-yl)methanesulfonamide (enantiomer A, r.t. = 3.74 min) | 439.1 |
| 103 | B | 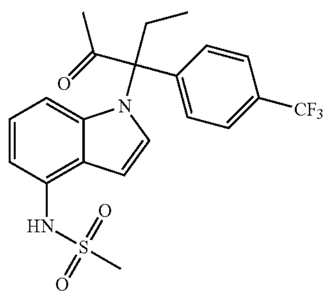 [SMILES: CCC(C(C)=O)(c1ccc(C(F)(F)F)cc1)n1ccc2c(NS(C)(=O)=O)cccc21] | N-(1-(2-oxo-3-(4-(trifluoromethyl)phenyl)pentan-3-yl)-1H-indol-4-yl)methanesulfonamide (enantiomer B, r.t. = 4.69 min) | 439.1 |
| 104 | B | 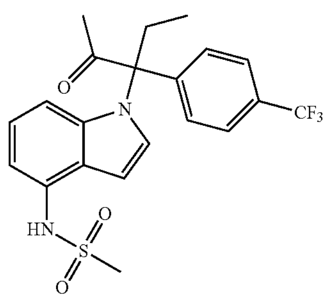 [SMILES: CCC(C(C)=O)(c1ccc(C(F)(F)F)cc1)n1ccc2c(NS(C)(=O)=O)cccc21] | N-(1-(2-oxo-3-(4-(trifluoromethyl)phenyl)pentan-3-yl)-1H-indazol-4-yl)methanesulfonamide (enantiomer A, r.t. = 1.81 min) | 440.1 |
| 105 | A | 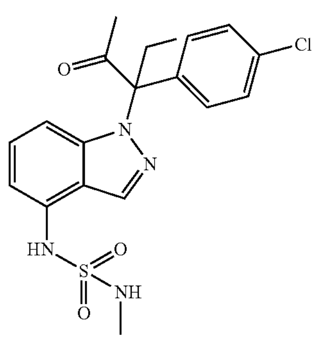 [SMILES: CCC(C(C)=O)(c1ccc(Cl)cc1)n1ncc2c(NS(=O)(=O)NC)cccc21] | 1-(1-(3-(4-chlorophenyl)-2-oxopentan-3-yl)-1H-indazol-4-yl)-3-methyl-sulfonylurea (enantiomer) | 421.1 |

Example 18

N-{1-[3-(4-chlorophenyl)-2-hydroxypentan-3-yl]-1H-indazol-4-yl}methanesulfonamide (Compound 106)

Step A: the mixture of methyl 2-(4-chlorophenyl)-2-(4-nitro-1H-indazol-1-yl)acetate and methyl 2-(4-chlorophenyl)-2-(4-nitro-2H-indazol-2-yl)acetate

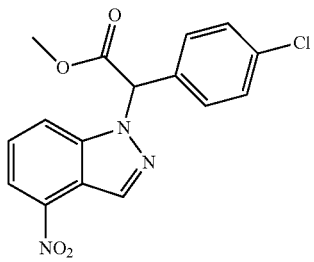

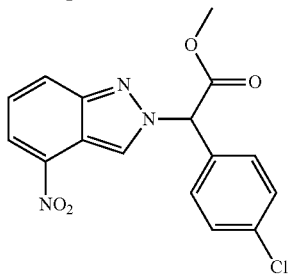

A bottle flask was charged with K₂CO₃ (85 g, 613 mmol) in CH₃CN (500 mL) and then a solution of 4-nitro-1H-indazole (50 g, 307 mmol) in CH₃CN (500 mL) was added. After the solution was stirred for 30 min, a solution of methyl 2-bromo-2-(4-chlorophenyl)acetate (100 g, 379 mmol), as described in Example 1 Step A, in CH₃CN (250 mL) was added dropwise at room temperature. The mixture was stirred overnight and then was filtered through a celite pad. The filtrate was concentrated and the residue (black oil) was freezed to give a solid. Ether (150 mL) was added and the mixture was stirred for 15 min. Then it was filtered and the solid was washed with PE (100 mL). The crude title compound (39 g, 37%) was used directly in the next step.

Step B: methyl 2-(4-amino-1H-indazol-1-yl)-2-(4-chlorophenyl)acetate

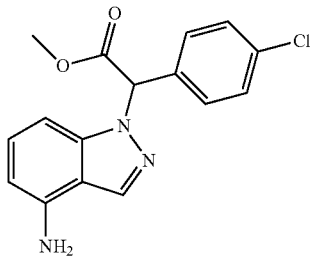 [SMILES: COC(=O)C(c1ccc(Cl)cc1)n1ncc2c(N)cccc21]

The mixture of the product from Step A (39 g, 113 mmol) was dissolved in ethanol (400 mL), and charged with 10% platinum on carbon (4.0 g). The mixture was hydrogenated at room temperature 2 days. The mixture was filtrated through celite and washed with ethanol. The filtrate was combined and evaporated in vacuo. The crude product (22 g, 62%) was used directly in the next step. LC/MS m/z=316.1 [M+H]⁺.

Step C: methyl 2-(4-(tert-butoxycarbonylamino)-1H-indazol-1-yl)-2-(4-chlorophenyl)acetate

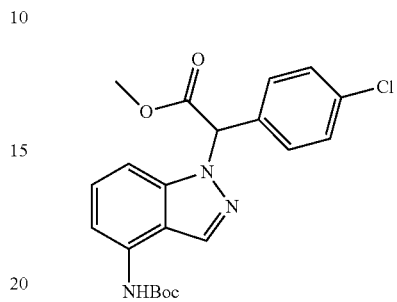

The compound from step B (22 g, 70 mml) and (Boc)₂O (30 g, 140 mmol) were dissolved in dioxane (260 mL). Then sat. Na₂CO₃ aq (50 mL) was added to the mixture at 0° C. The mixture was stirred at room temperate for 2 days. Then the solvent was removed under reduced pressure, and the residue was dissolved in EtOAc (500 mL), washed with H₂O (100 mL), brine (100 mL). The organic layer was dried over anhydrous Na₂SO₄, concentrated and the residue was purified by silica gel column (PE:EA=20:1 to 8:1) to give the title compound (23 g, 80%) LC/MS m/z=416.1[M+H]⁺.

Step D: methyl 2-(4-(tert-butoxycarbonylamino)-1H-indazol-1-yl)-2-(4-chlorophenyl)butanoate

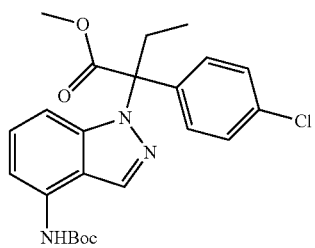 [SMILES: CCC(C(=O)OC)(c1ccc(Cl)cc1)n1ncc2c(NC(=O)OC(C)(C)C)cccc21]

The compound from step C (1 g, 2.4 mml) and EtI (42 mg, 2.6 mmol) were dissolved in anhydrous DMF (10 mL) Then NaH (144 mg, 3.6 mmol, 60%) was added to the mixture slowly at 0° C. After 30 minutes, the reaction mixture was quenched by saturate NH₄Cl (10 mL), extracted with EA, dried over anhydrous Na₂SO₄, filtered and the filtrate was concentrated under reduced pressure. The residue was purified by silica gel column (PE:EA=20:1 to 5:1 to give the title compound (0.608 g, 57%). LC/MS m/z=444.1[M+H]⁺. The two enantiomers were separated by SFC chiral separation.

Enantiomer A and enantiomer B were obtained by the below chiral separation conditions:

Column: AD-H

Mobile phase: A: CO₂, B: MeOH, A:B=80:20 at 1.0 mL/min

Column Temp: 38.3° C.

enantiomer A, r.t.=3.71 min, enantiomer B, r.t.=4.73 min

Step E: tert-butyl 1-(2-(4-chlorophenyl)-1-hydroxybutan-2-yl)-1H-indazol-4-ylcarbamate

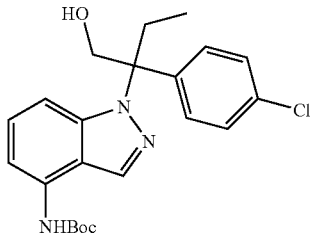 [SMILES: CCC(CO)(c1ccc(Cl)cc1)n1ncc2c(NC(=O)OC(C)(C)C)cccc21]

To a solution of methyl 2-[4-(tert-butoxycarbonylamino)-1H-indazol-1-yl]-2-(4-chlorophenyl)butanoate (3.5 g, 7.90 mmol), in THF (140 mL) at 0° C. was added LiBH$_4$ (0.7 g, 31.6 mmol). The mixture was allowed to stir overnight at RT. Then it was quenched with saturated NH$_4$Cl (200 mL) carefully, and extracted with CH$_2$Cl$_2$. The combined organic layers were washed with brine (80 mL), dried over anhydrous sodium sulfate, filtered and the solvent was removed in vacuo to afford the desired product. LC/MS m/z=416.3 [M+H]$^+$.

Step F: tert-butyl 1-[2-(4-chlorophenyl)-1-oxobutan-2-yl]-1H-indazol-4-ylcarbamate

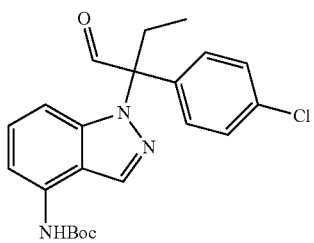 [SMILES: CCC(C=O)(c1ccc(Cl)cc1)n1ncc2c(NC(=O)OC(C)(C)C)cccc21]

To a solution of Dess-Martin periodinane (8.12 g, 19.15 mmol) in DCM (90 mL) at 0° C. was added a solution of tert-butyl 1-[2-(4-chlorophenyl)-1-hydroxybutan-2-yl]-1H-indazol-4-ylcarbamate (3.18 g, 7.67 mmol) in DCM (20 mL). The mixture was allowed to stir at rt for 2 hours. Then it was filtered and the filtrate was concentrated in vacuo to afford the crude product. The product was purified via column chromatography (0-10% EtOAc/hexanes) to provide the desired product.

Step G: tert-butyl 1-[3-(4-chlorophenyl)-2-hydroxypentan-3-yl]-1H-indazol-4-ylcarbamate

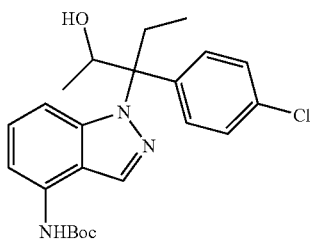 [SMILES: CCC(c1ccc(Cl)cc1)(C(C)O)n1ncc2c(NC(=O)OC(C)(C)C)cccc21]

To a solution of tert-butyl 1-[2-(4-chlorophenyl)-1-oxobutan-2-yl]-1H-indazol-4-ylcarbamate (2.50 g, 6.05 mmol) in anhydrous THF (50 mL) was added methylmagnesium bromide (2.5 M in ether, 7.3 mL, 18.15 mmol) at 0° C. The mixture was stirred for anther 30 min at 0° C., then saturated NH$_4$Cl (100 mL) was added and the mixture was extracted with EA. The combined organic layers were washed with brine (50 mL), dried over anhydrous sodium sulfate, filtered and the solvent was removed in vacuo to provide the desired product.

Step H: 3-(4-amino-1H-indazol-1-yl)-3-(4-chlorophenyl)pentan-2-ol

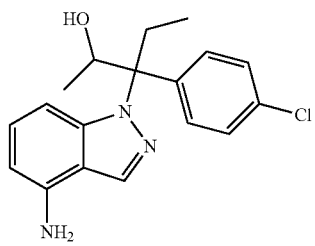 [SMILES: CCC(c1ccc(Cl)cc1)(C(C)O)n1ncc2c(N)cccc21]

Using the same procedure described for the preparation of Example 15, step B but replacing the tert-butyl 1-(3-(4-chlorophenyl)-2-hydroxy-2-methylpentan-3-yl)-6-fluoro-1H-indol-4-ylcarbamate with tert-butyl 1-[2-(4-chlorophenyl)-1-oxobutan-2-yl]-1H-indazol-4-ylcarbamate gave the title compound.

Step I: N-(1-(3-(4-chlorophenyl)-2-hydroxypentan-3-yl)-1H-indazol-4-yl)methane-sulfonamide Using the same procedure described for the preparation of Example 15, but in step C replacing the 3-(4-amino-6-fluoro-1H-indol-1-yl)-3-(4-chlorophenyl)-2-methylpentan-2-ol with 3-(4-amino-1H-indazol-1-yl)-3-(4-chlorophenyl)pentan-2-ol gave the title compound. LC/MS m/z=408.2 [M+H]$^+$.

Using the procedure described in Example 18, but in step E replacing methyl 2-[4-(tert-butoxycarbonylamino)-1H-indazol-1-yl]-2-(4-chlorophenyl)butanoate with methyl 2-(4-(tert-butoxycarbonylamino)-1H-indol-1-yl)-2-(4-chlorophenyl)butanoate, methyl 2-(4-(tert-butoxycarbonylamino)-1H-indol-1-yl)-2-(2,4-dichlorophenyl)butanoate, methyl 2-(4-(tert-butoxycarbonylamino)-6-fluoro-1H-indol-1-yl)-2-(2,4-dichlorophenyl)butanoate, methyl 2-(4-(tert-butoxycarbonylamino)-6-fluoro-1H-indazol-1-yl)-2-(4-(trifluoromethyl)phenyl)butanoate, methyl 2-(4-(tert-butoxycarbonylamino)-1H-indol-1-yl)-2-(4-(trifluoromethyl)phenyl)butanoate, methyl 2-(4-(tert-butoxycarbonylamino)-1H-indazol-1-yl)-2-(4-(trifluoromethyl)phenyl) butanoate, compounds 108-117 of Table 15 were prepared respectively. Also using the procedure described in Example 18, but in step E replacing methanesulfonyl chloride with methylsulfamoyl chloride and dimethylsulfamoyl chloride, compound 118 and compound 119 of Table 15 were prepared respectively.

Compound 106 and compound 107 were obtained by the below chiral separation conditions:
Column: IC
Mobile phase: A: Hexane, B: EtOH (0.1% DEA), A:B=70:30 at 1.0 mL/min
Column Temp: 40° C.

Compound 108 and compound 109 were obtained by the below chiral separation conditions:
Column: IA
Mobile phase: A: Hexane, B: EtOH (0.1% DEA), A:B=70:30 at 1.0 mL/min
Column Temp: 30° C.
Compound III was obtained by following the chiral separation conditions:
Column: IA
Mobile phase: A: Hexane, B: EtOH (0.1% DEA), A:B=70:30 at 1.0 mL/min
Column Temp: 30° C.

Compound 113 and compound 114 were obtained by the below chiral separation conditions:
Column: AD-H
Mobile phase: A: $CO_2$, B: MeOH (0.1% DEA), A:B=50:50 at 3.0 mL/min
Column Temp: 38.4° C.
Compound 115, 116 and compound 117 were obtained by the below chiral separation conditions:
Column: AS-H
Mobile phase: A: $CO_2$, B: MeOH (0.1% DEA), A:B=93:7 at 3.0 mL/min
Column Temp: 41.3° C.

TABLE 15

| Compound Number | IP Rating | Structure | IUPAC Name | LCMS m/z [M + H]+ |
|---|---|---|---|---|
| 106 | A | 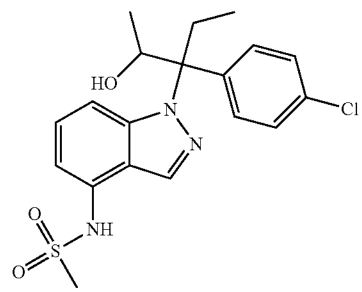 [SMILES: CCC(c1ccc(Cl)cc1)(C(C)O)n1ncc2c(NS(C)(=O)=O)cccc21] | N-{1-[3-(4-chlorophenyl)-2-hydroxypentan-3-yl]-1H-indazol-4-yl}methanesulfonamide (diastereoisomer A, r.t. = 6.39 min) | 408.2 |
| 107 | A | 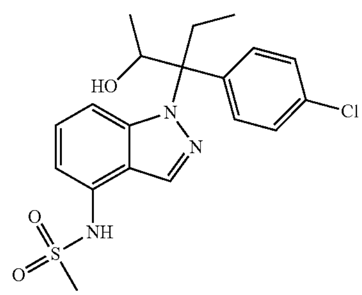 [SMILES: CCC(c1ccc(Cl)cc1)(C(C)O)n1ncc2c(NS(C)(=O)=O)cccc21] | N-{1-[3-(4-chlorophenyl)-2-hydroxypentan-3-yl]-1H-indazol-4-yl}methanesulfonamide (diastereoisomer B, .t. = 11.71 min) | 408.2 |
| 108 | A | 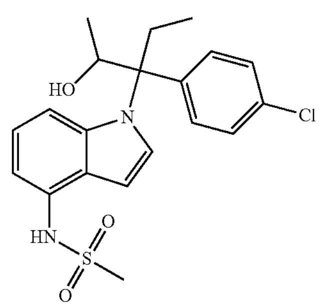 [SMILES: CCC(c1ccc(Cl)cc1)(C(C)O)n1ccc2c(NS(C)(=O)=O)cccc21] | N-(1-(3-(4-chlorophenyl)-2-hydroxypentan-3-yl)-1H-indol-4-yl)methanesulfonamide (diastereoisomer A, r.t. = 8.27 min) | 407.1 |
| 109 | A | 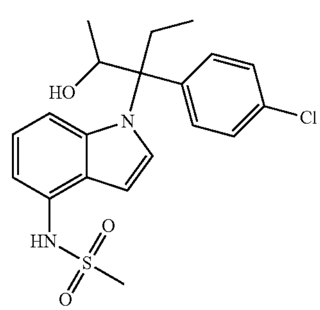 [SMILES: CCC(c1ccc(Cl)cc1)(C(C)O)n1ccc2c(NS(C)(=O)=O)cccc21] | N-(1-(3-(4-chlorophenyl)-2-hydroxypentan-3-yl)-1H-indol-4-yl)methanesulfonamide (diastereoisomer B, r.t. = 21.59 min) | 407.1 |

TABLE 15-continued

| Compound Number | IP Rating | Structure | IUPAC Name | LCMS m/z [M + H]+ |
|---|---|---|---|---|
| 110 | A | 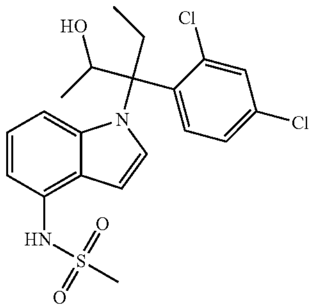 [SMILES: CCC(c1ccc(Cl)cc1Cl)(C(C)O)n1ccc2c(NS(C)(=O)=O)cccc21] | N-(1-(3-(2,4-dichlorophenyl)-2-hydroxypentan-3-yl)-1H-indol-4-yl)methanesulfonamide | 441.1 |
| 111 | A | 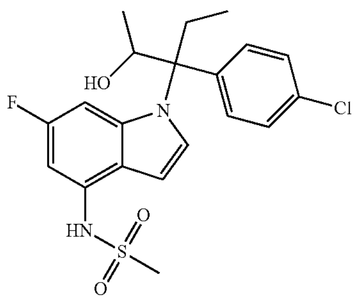 [SMILES: CCC(c1ccc(Cl)cc1)(C(C)O)n1ccc2c(NS(C)(=O)=O)cc(F)cc21] | N-(1-(3-(4-chlorophenyl)-2-hydroxypentan-3-yl)-6-fluoro-1H-indol-4-yl)methanesulfonamide (diastereoisomer A, r.t. = 1.97 min) | 425.1 |
| 112 | A | 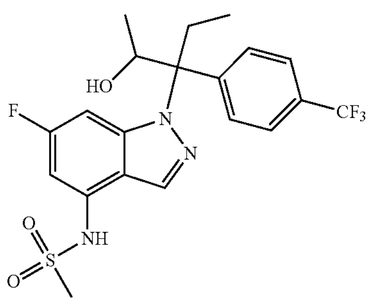 [SMILES: CCC(c1ccc(C(F)(F)F)cc1)(C(C)O)n1ncc2c(NS(C)(=O)=O)cc(F)cc21] | N-(6-fluoro-1-(2-hydroxy-3-(4-(trifluoromethyl)phenyl)pentan-3-yl)-1H-indazol-4-yl)methanesulfonamide | 425.1 |
| 113 | A | 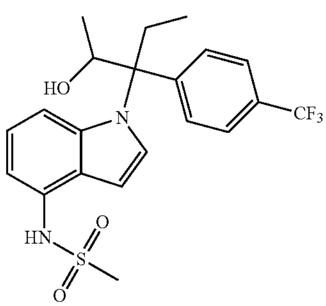 [SMILES: CCC(c1ccc(C(F)(F)F)cc1)(C(C)O)n1ccc2c(NS(C)(=O)=O)cccc21] | N-(1-(2-hydroxy-3-(4-(trifluoromethyl)phenyl)pentan-3-yl)-1H-indol-4-yl)methanesulfonamide (diastereoisomer A, r.t. = 1.44 min) | 441.1 |
| 114 | A | 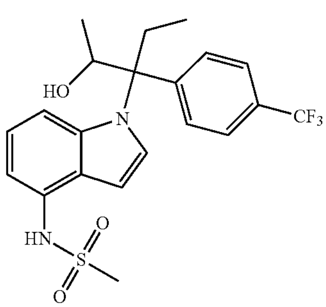 [SMILES: CCC(c1ccc(C(F)(F)F)cc1)(C(C)O)n1ccc2c(NS(C)(=O)=O)cccc21] | N-(1-(2-hydroxy-3-(4-(trifluoromethyl)phenyl)pentan-3-yl)-1H-indol-4-yl)methanesulfonamide (diastereoisomer B, r.t. = 2.52 min) | 441.1 |

TABLE 15-continued

| Compound Number | IP Rating | Structure | IUPAC Name | LCMS m/z [M + H]+ |
|---|---|---|---|---|
| 115 | A | 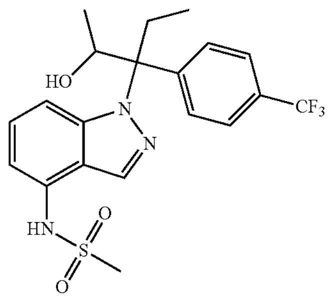 | N-(1-(2-hydroxy-3-(4-(trifluoromethyl)phenyl)pentan-3-yl)-1H-indazol-4-yl)methanesulfonamide (diastereoisomer A, r.t. = 4.91 min) | 442.1 |
| 116 | A | 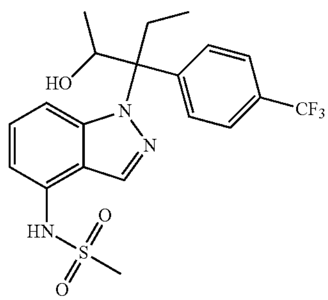 [SMILES: CCC(c1ccc(C(F)(F)F)cc1)(C(C)O)n1ncc2c(NS(C)(=O)=O)cccc21] | N-(1-(2-hydroxy-3-(4-(trifluoromethyl)phenyl)pentan-3-yl)-1H-indazol-4-yl)methanesulfonamide (diastereoisomer C, r.t. = 5.35 min) | 442.1 |
| 117 | A | 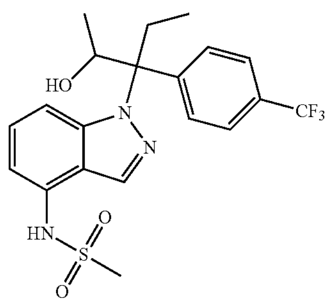 [SMILES: CCC(c1ccc(C(F)(F)F)cc1)(C(C)O)n1ncc2c(NS(C)(=O)=O)cccc21] | N-(1-(2-hydroxy-3-(4-(trifluoromethyl)phenyl)pentan-3-yl)-1H-indazol-4-yl)methanesulfonamide (diastereoisomer D, r.t. = 6.05 min) | 442.1 |
| 118 | A | 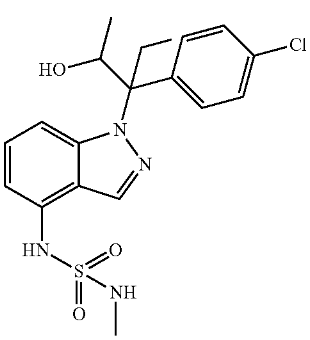 [SMILES: CCC(c1ccc(Cl)cc1)(C(C)O)n1ncc2c(NS(=O)(=O)NC)cccc21] | 1-(1-(3-(4-chlorophenyl)-2-hydroxypentan-3-yl)-1H-indazol-4-yl)-3-methyl-sulfonylurea | 423.1 |
| 119 | A | 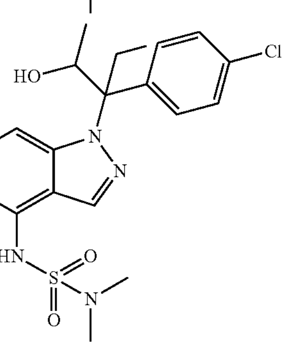 | 3-(1-(3-(4-chlorophenyl)-2-hydroxypentan-3-yl)-1H-indazol-4-yl)-1,1-dimethyl-sulfonylurea | 437.1 |

Example 20

N-(1-(1-(4-chlorophenyl)-1-(2-cyanocyclopropyl)propyl)-1H-indazol-4-yl)methanesulfonamide (Compound 120)

Step A: methyl 2-(4-amino-1H-indazol-1-yl)-2-(4-chlorophenyl)butanoate

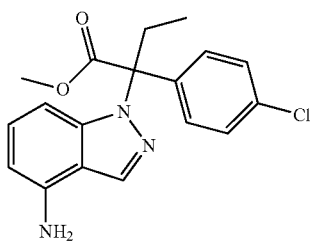 [SMILES: CCC(C(=O)OC)(c1ccc(Cl)cc1)n1ncc2c(N)cccc21]

A mixture of methyl 2-(4-(tert-butoxycarbonylamino)-1H-indazol-1-yl)-2-(4-chlorophenyl)butanoate (3.0 g, 6.8 mmol), as described in Example 18 Step D, in 4 N HCl/MeOH (20 mL) was stirred at room temperature for 2 h. After removing the solvent, the residue was dissolved in ethyl acetate (80 mL), pH value adjusted to 9-10 with saturated sodium bicarbonate solution, dried over sodium sulfate, then filtered. After removing the organic solvent, the residue was used for the next step without purification. LC/MS m/z=344.1 [M+H]+.

Step B: methyl 2-(4-chlorophenyl)-2-(4-(methylsulfonamido)-1H-indazol-1-yl)butanoate

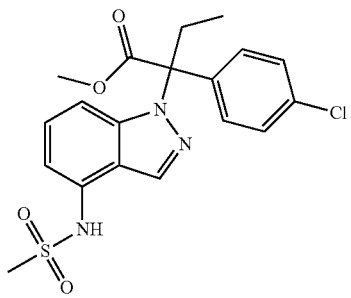 [SMILES: CCC(C(=O)OC)(c1ccc(Cl)cc1)n1ncc2c(NS(C)(=O)=O)cccc21]

To a mixture of methyl 2-(4-amino-1H-indazol-1-yl)-2-(4-chlorophenyl)butanoate (1.0 g, 2.9 mmol) and NMM (0.9 g, 8.7 mmol) in DCM (10 mL) was added MsCl (0.4 g, 3.2 mmol) dropwise, Then the mixture was stirred at room temperature overnight. The solution was quenched with saturated NH₄Cl solution, and extracted with ethyl acetate (50 mL). The organic layer was washed with brine, dried over sodium sulfate, filtered and evaporated. The residue was purified by silica gel chromatography (eluent: PE/EA=4/1) to afford the title compound as a yellow solid. LC/MS m/z=422.1 [M+H]+.

Step C: methyl 2-(4-chlorophenyl)-2-(4-(N-((2-(trimethylsilyl)ethoxy)methyl)methyl sulfon amido)-1H-indazol-1-yl)butanoate

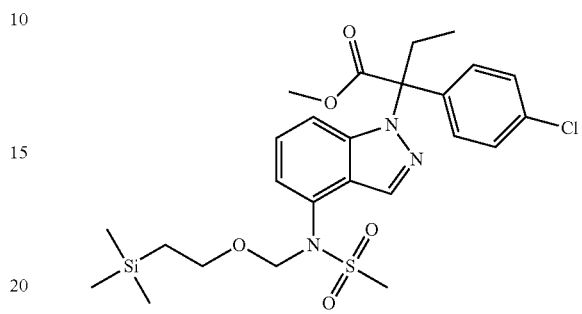

A solution of methyl 2-(4-chlorophenyl)-2-(4-(methylsulfonamido)-1H-indazol-1-yl)butanoate (500 mg, 1.19 mmol) in dry THF (8 mL) was treated by NaH (95 mg, 2.38 mmol, 60% in oil) at 0° C. for 30 min, then was added (2-(chloromethoxy)ethyl)trimethylsilane (295 mg, 1.78 mmol) dropwise. The mixture was stirred at room temperature for 2 h. The solution was quenched with saturated NH₄Cl solution, and extracted with ethyl acetate (30 mL). The organic layer was washed with brine, dried over dry sodium sulfate, filtered and evaporated. The residue was purified by silica gel chromatography (PE/EA=6/1) to afford the title compound as a pale yellow solid. LC/MS m/z=551.8 [M+H]+.

Step D: N-(1-(2-(4-chlorophenyl)-1-hydroxybutan-2-yl)-1H-indazol-4-yl)-N-((2-(trimethylsilyl) ethoxy)methyl)methanesulfonamide

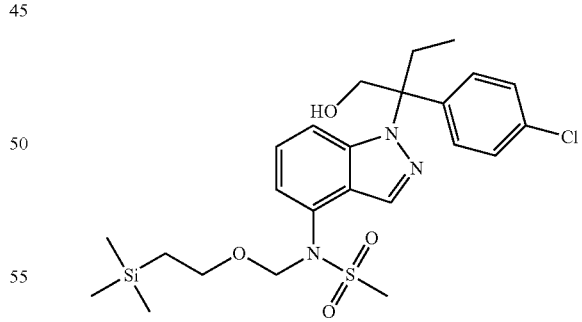

To a suspension of LiBH₄ (120 mg, 5.43 mmol) in THF (5 mL) was added MeOH (174 mg, 5.43 mmol) and a solution of methyl 2-(4-chlorophenyl)-2-(4-(N-((2-(trimethylsilyl)ethoxy)methyl)methylsulfonamido)-1H-indazol-1-yl)butanoate (600 mg, 1.09 mmol) in THF (8 mL) followed. The mixture was stirred at room temperature for 2 h. The solution was quenched with saturated NH₄Cl solution, and extracted with ethyl acetate (30 mL). The organic layer was washed with brine, dried over sodium sulfate, filtered and evaporated.

The residue was purified by silica gel chromatography (PE/EA=3/1) to afford the title compound as a pale yellow solid. LC/MS m/z=524.2 [M+H]⁺.

Step E: N-(1-(2-(4-chlorophenyl)-1-oxobutan-2-yl)-1H-indazol-4-yl)-N-((2-(trimethylsilyl) ethoxy)methyl)methanesulfonamide

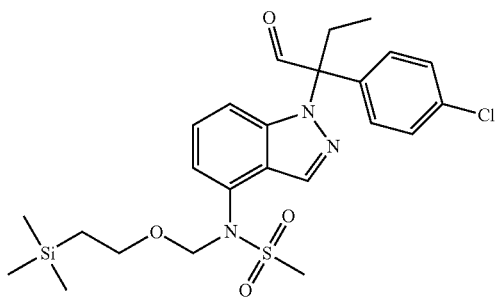 [SMILES: CCC(C=O)(c1ccc(Cl)cc1)n1ncc2c(N(COCC[Si](C)(C)C)S(C)(=O)=O)cccc21]

A solution of N-(1-(2-(4-chlorophenyl)-1-hydroxybutan-2-yl)-1H-indazol-4-yl)-N-((2-(trimethylsilyl)ethoxy)methyl)methanesulfonamide (560 mg, 1.07 mmol) in DCM (10 mL) was added to Dess-Martin periodinane (590 mg, 1.39 mmol) in portion at 0° C. and stirred for 1.5 h. The mixture was diluted with water, and extracted with ethyl acetate. The organic layer was washed with brine, dried over sodium sulfate, filtered and evaporated. The residue was purified by silica gel chromatography (PE/EA=8/1) to afford the title compound as a yellow solid. LC/MS m/z=522.1 [M+H]⁺.

Step F: (E)-N-(1-(3-(4-chlorophenyl)-1-cyanopent-1-en-3-yl)-1H-indazol-4-yl)-N-((2-(trimethylsilyl) ethoxy)methyl)methanesulfonamide

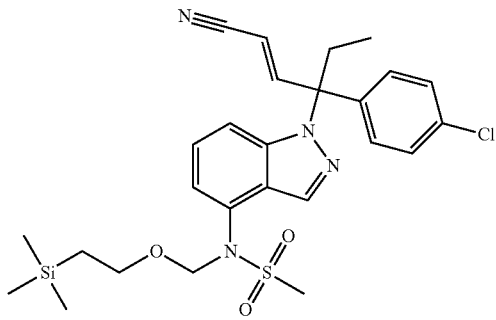 [SMILES: CCC(/C=C/C#N)(c1ccc(Cl)cc1)n1ncc2c(N(COCC[Si](C)(C)C)S(C)(=O)=O)cccc21]

To a mixture of diethyl cyanomethylphosphonate (20 mg, 0.12 mmol), LiCl (5 mg, 0.12 mmol) and DBU (18 mg, 0.12 mmol) in MeCN (2 mL) was added a solution of N-(1-(2-(4-chlorophenyl)-1-oxobutan-2-yl)-1H-indazol-4-yl)-N-((2-(trimethylsilyl)ethoxy)methyl) methane sulfonamide (50 mg, 0.10 mmol) in MeCN (1 mL). The mixture was stirred at room temperature for 2 h and evaporated. The residue was purified by silica gel chromatography (PE/EA=6/1) to afford the title compound as a white solid. LC/MS m/z=545.2 [M+H]⁺.

Step G: N-(1-(1-(4-chlorophenyl)-1-(2-cyanocyclopropyl)propyl)-1H-indazol-4-yl)-N-((2-(trimethylsilyl)ethoxy)methyl)methanesulfonamide

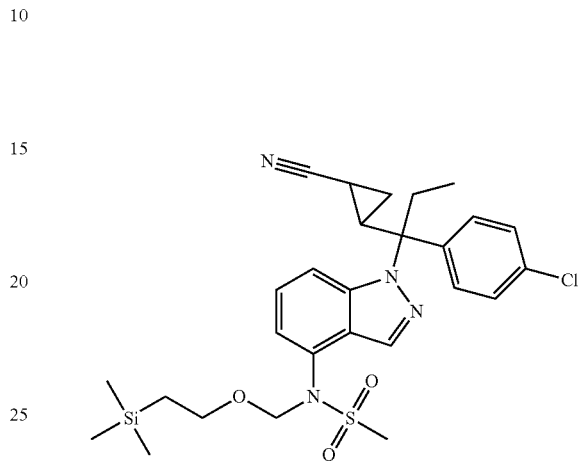

A suspension of NaH (22 mg) in anhydrous DMSO (0.9 mL) was added trimethylsulfoxonium iodide (128 mg) at 0° C. and the mixture was stirred at rt for 3 h until the solution became clear. Then was added the solution of (E)-N-(1-(3-(4-chlorophenyl)-1-cyanopent-1-en-3-yl)-1H-indazol-4-yl)-N-((2-(trimethylsilyl)ethoxy)methyl) methanesulfonamide (42 mg) in anhydrous DMSO (0.1 mL) and the reaction mixture was stirred at 70° C. for 16 h. The solution was quenched with saturated NH₄Cl solution, extracted with ethyl acetate (15 mL). The organic layer was washed with brine, dried over dry sodium sulfate, filtered and evaporated. The residue was purified by silica gel chromatography (PE/EA=4/1) to afford the title compound as a white solid. LC/MS m/z=559.2 [M+H]⁺.

Step H: N-(1-(1-(4-chlorophenyl)-1-(2-cyanocyclopropyl)propyl)-1H-indazol-4-yl)methane sulfonamide (Compound 120)

A mixture of N-(1-(1-(4-chlorophenyl)-1-(2-cyanocyclopropyl)propyl)-1H-indazol-4-yl)-N-((2-(trimethylsilyl)ethoxy)methyl)methanesulfonamide (14 mg) in 2 N HCl/EtOH (1 mL/1 mL) was stirred at 50° C. for 3 h, cooled to room temperature, concentrated, and extracted with ethyl acetate (10 mL). The organic layers were combined, dried over anhydrous sodium sulfate, and concentrated in vacuo. The residue was purified using a silica gel column (PE/EA=3/1) to afford the title compound as a brown solid. LC/MS m/z=429.1 [M+H]⁺.

TABLE 17

| Compound Number | IP Rating | Structure | IUPAC Name | LCMS m/z [M + H]+ |
|---|---|---|---|---|
| 120 | A | 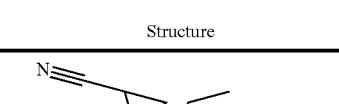 | N-(1-(1-(4-chlorophenyl)-1-(2-cyanocyclopropyl)propyl)-1H-indazol-4-yl)methanesulfonamide | 429.1 |

Example 21

N-(1-(2-(4-chlorophenyl)-1-cyanobutan-2-yl)-1H-indol-4-yl)methanesulfonamide Step A: tert-Butyl 1-(2-(4-chlorophenyl)-1-hydroxybutan-2-yl)-1H-indol-4-ylcarbamate

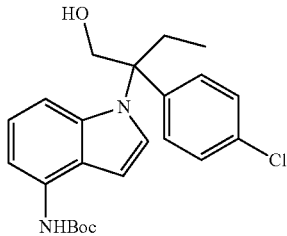 [SMILES: CCC(CO)(c1ccc(Cl)cc1)n1ccc2c(NC(=O)OC(C)(C)C)cccc21]

To a solution of methyl 2-(4-(tert-butoxycarbonylamino)-1H-indol-1-yl)-2-(4-chlorophenyl)butanoate (5 g, 11.3 mmol), as described in Example 3 Step A, in tetrahydrofuran (50 mL) was added lithium aluminium hydride (644 mg, 16.95 mmol) at 0° C. The mixture was gradually warmed to room temperature and stirred for 4 h. Water (10 mL) was carefully added to the reaction mixture, then extracted with ethyl acetate. The combined organic layers were washed with brine (30 mL), dried over anhydrous sodium sulfate, filtered and concentrated. The crude product was purified by silica gel chromatography eluting with PE/EA (30/1 to 10/1, v/v) to give the title compound as a colorless amorphous solid. LC/MS m/z=359.9 [M-$^t$Bu+H]+.

Step B: tert-Butyl 1-(2-(4-chlorophenyl)-1-oxobutan-2-yl)-1H-indol-4-ylcarbamate

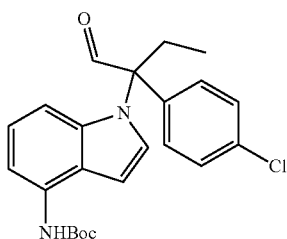 [SMILES: CCC(C=O)(c1ccc(Cl)cc1)n1ccc2c(NC(=O)OC(C)(C)C)cccc21]

To the product from Step A (2 g, 4.82 mmol) in dichloromethane (30 mL) was added Dess-Martin periodinane (3.06 g, 7.23 mmol) at 0° C. The mixture was stirred for 2 h. The solvent was removed under reduced pressure. The crude product was purified by silica gel chromatography eluting with PE/EA (30/1 to 15/1, v/v) to afford the title compound as a colorless amorphous solid. LC/MS m/z=357.9 [M-$^t$Bu+H]+.

Step C: tert-butyl 1-(2-(4-chlorophenyl'-1-cyanobutan-2-yl)-1H-indol-4-ylcarbamate

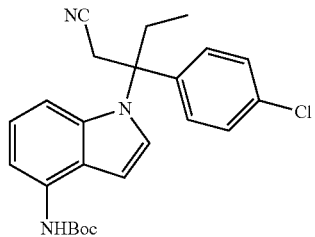 [SMILES: CCC(CC#N)(c1ccc(Cl)cc1)n1ccc2c(NC(=O)OC(C)(C)C)cccc21]

To a suspension of t-BuOK (683 mg, 6.10 mmol) in THF (30 mL) was added a solution of tosylmethyl isocyanide (239 mg, 1.22 mmol) in THF (5 mL) at −78° C. The mixture was stirred for 15 minutes, then treated with a solution of the product from Step B (419 mg, 1.02 mmol) in THF (10 mL) dropwise, and continued to stir for 1.5 hours at −78° C. To the cooled reaction mixture was added methanol (100 mL). The mixture was filtered via a short silica gel column and evaporated. The residue was dissolved in MeOH (40 mL), and then t-BuOK (137 mg, 1.22 mmol) was added. The resulting mixture was refluxed for 30 minutes. After removing the solvent, the residue was dissolved in water (50 mL), and extracted with EtOAc. The combined organic layers were washed with brine (10 mL), dried over Na$_2$SO$_4$, filtered and evaporated under reduced pressure. The crude product was purified by silica gel column chromatography eluting with PE/EA (20/1 to 5/1, v/v) to give the title compound as a white solid. LC/MS m/z=446.1 [M+Na]+.

Step D: 3-(4-amino-1H-indol-1-yl)-3-(4-chlorophenyl)pentanenitrile

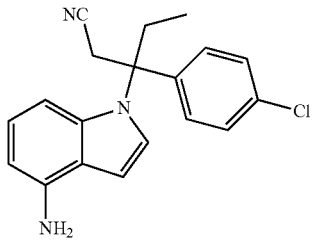 [SMILES: CCC(CC#N)(c1ccc(Cl)cc1)n1ccc2c(N)cccc21]

The mixture of the product from Step C (250 mg, 0.59 mmol) and 4 N HCl/MeOH (10 mL) was stirred at room temperature for 2 h. After solvent was removed in vacuo, the residue was dissolved in ethyl acetate (20 mL), pH value adjusted to 9~10 with a saturated sodium bicarbonate solution, dried over sodium sulfate, then filtered. After removing the organic solvent, the title compound as a colorless oil was obtained. LC/MS m/z=324.1 [M+H]$^+$.

Step E: N-(1-(2-(4-chlorophenyl)-1-cyanobutan-2-yl)-1H-indol-4-yl)methanesulfonamide To a solution of the product from Step D (170 mg, 0.52 mmol) and N-methylmorpholine (105 mg, 1.04 mmol) in dichloromethane (15 mL) was added methanesulfonyl chloride (89 mg, 0.79 mmol) at room temperature. The mixture was stirred for 2 h, then diluted with water (15 mL) and extracted with ethyl acetate. The combined organic layers were washed with brine (10 mL), dried over Na$_2$SO$_4$, filtered and concentrated. The crude product was purified by PREP-TLC eluting with PE/EA (3/1, v/v) to give the title compound as a colorless amorphous solid. LC/MS m/z=402.1 [M+H]$^+$.

Using the procedure described in Example 21, but in step A replacing 2-(4-(tert-butoxycarbonylamino)-1H-indol-1-yl)-2-(4-chlorophenyl)butanoate with methyl 2-(4-(tert-butoxycarbonylamino)-1H-indazol-1-yl)-2-(4-chlorophenyl)butanoate, methyl 2-(4-(tert-butoxycarbonylamino)-6-fluoro-1H-indol-1-yl)-2-(4-chlorophenyl)butanoate, methyl 2-(4-(tert-butoxycarbonylamino)-1H-indol-1-yl)-2-(4-(trifluoromethyl)phenyl)butanoate, compounds 123-126 of Table 18 were prepared respectively.

Compound 121 and compound 122 were obtained by the below chiral separation conditions:
Column: RegisCell-OD
Mobile phase: A: CO$_2$, B: MeOH, A:B=60:40 at 1.0 mL/min
Column Temp: 39.9° C.

Compound 123 was obtained by the below chiral separation conditions:
Column: AD-H
Mobile phase: A: CO$_2$, B: MeOH (0.1% DEA), A:B=55:45 at 3.0 mL/min
Column Temp: 39.7° C.

Compound 124 and compound 126 were obtained by the below chiral separation conditions:
Column: OJ-H
Mobile phase: A: n-Hexane, B: EtOH, A:B=70:30 at 1.0 mL/min
Column Temp: 40° C.

TABLE 18

| Compound Number | IP Rating | Structure | IUPAC Name | LCMS m/z [M + H]$^+$ |
|---|---|---|---|---|
| 121 | A | 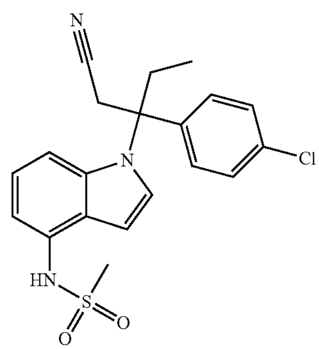 [SMILES: CCC(CC#N)(c1ccc(Cl)cc1)n1ccc2c(NS(C)(=O)=O)cccc21] | N-(1-(2-(4-chlorophenyl)-1-cyanobutan-2-yl)-1H-indol-4-yl)methanesulfonamide (enantiomer A, r.t. = 2.23 min) | 402.1 |
| 122 | A | 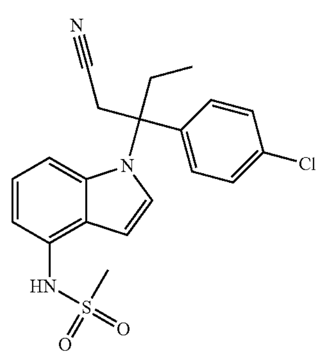 [SMILES: CCC(CC#N)(c1ccc(Cl)cc1)n1ccc2c(NS(C)(=O)=O)cccc21] | N-(1-(2-(4-chlorophenyl)-1-cyanobutan-2-yl)-1H-indol-4-yl)methanesulfonamide (enantiomer B, r.t. = 3.32 min) | 402.1 |

TABLE 18-continued

| Compound Number | IP Rating | Structure | IUPAC Name | LCMS m/z [M + H]+ |
|---|---|---|---|---|
| 123 | A | 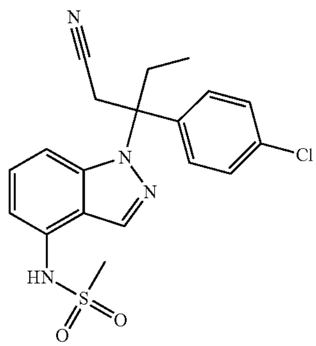 [SMILES: CCC(CC#N)(c1ccc(Cl)cc1)n1ncc2c(NS(C)(=O)=O)cccc21] | N-(1-(2-(4-chlorophenyl)-1-cyanobutan-2-yl)-1H-indazol-4-yl)methanesulfonamide (enantiomer A, r.t. = 3.28 min) | 403.1 |
| 124 | B | 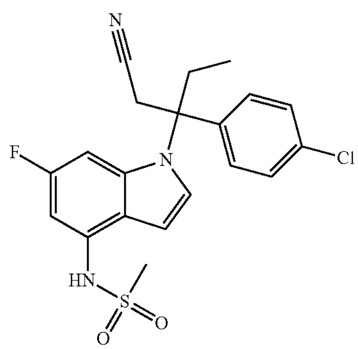 [SMILES: CCC(CC#N)(c1ccc(Cl)cc1)n1ccc2c(NS(C)(=O)=O)cc(F)cc21] | N-(1-(2-(4-chlorophenyl)-1-cyanobutan-2-yl)-6-fluoro-1H-indol-4-yl)methanesulfonamide (enantiomer A, r.t. = 4.77 min) | 420.1 |
| 125 | A | 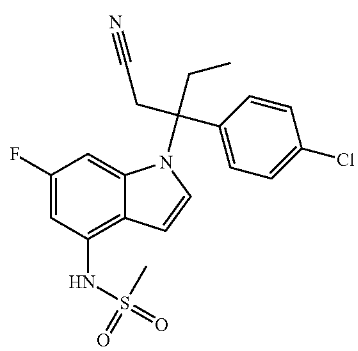 [SMILES: CCC(CC#N)(c1ccc(Cl)cc1)n1ccc2c(NS(C)(=O)=O)cc(F)cc21] | N-(1-(2-(4-chlorophenyl)-1-cyanobutan-2-yl)-6-fluoro-1H-indol-4-yl)methanesulfonamide (enantiomer B, r.t. = 9.89 min) | 420.1 |
| 126 | A | 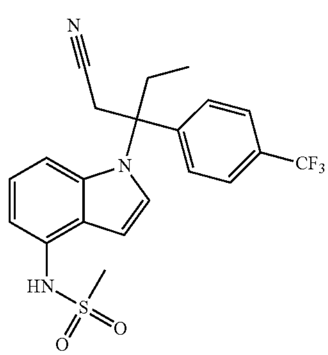 [SMILES: CCC(CC#N)(c1ccc(C(F)(F)F)cc1)n1ccc2c(NS(C)(=O)=O)cccc21] | N-(1-(1-cyano-2-(4-(trifluoromethyl)phenyl)butan-2-yl)-1H-indol-4-yl)methanesulfonamide | 436.1 |

Example 22

(E)-N-(1-(3-(4-chlorophenyl)-1-cyanopent-1-en-3-yl)-1H-indol-4-yl)methanesulfonamide (Compound 127)

Step A: (E)-tert-butyl 1-(3-(4-chlorophenyl)-1-cyanopent-1-en-3-yl)-1H-indol-4-ylcarbamate

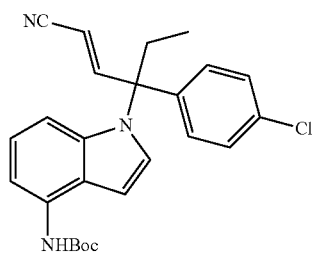 [SMILES: CCC(/C=C/C#N)(c1ccc(Cl)cc1)n1ccc2c(NC(=O)OC(C)(C)C)cccc21]

To a mixture of diethyl cyanomethylphosphonate (145 mg, 0.76 mmol), LiCl (43 mg, 1.01 mmol) and DBU (255 mg, 1.01 mmol) in acetonitrile (15 mL) was added a solution of tert-butyl 1-(2-(4-chlorophenyl)-1-oxobutan-2-yl)-1H-indol-4-ylcarbamate (210 mg, 1.02 mmol), as described in Example 21 Step B, in acetonitrile (3 mL). The mixture was stirred at room temperature for 2 h and the volatile was evaporated. The residue was purified by silica gel chromatography eluting with PE/EA (10/1 to 3/1, v/v) to afford the title compound as a white solid. LC/MS m/z=458.1 [M+Na]$^+$.

Step B: (E)-4-(4-amino-1H-indol-1-yl)-4-(4-chlorophenyl)hex-2-enenitrile

A mixture of the product from Step A (177 mg, 0.406 mmol) and 4 N HCl/MeOH (10 mL) was stirred at room temperature for 2 h. After removing the solvent, the residue was dried in vacuo to afford the title compound as a white solid. LC/MS m/z=336.1 [M+H]$^+$.

Step C: (E)-N-(1-(3-(4-chlorophenyl)-1-cyanopent-1-en-3-yl)-1H-indol-4-yl)methanesulfonamide To a mixture of compound from step B (123 mg, 0.367 mmol) and NMM (74 mg, 0.734 mmol) in DCM (15 mL) was added methanesulfonyl chloride (62 mg, 0.550 mmol) dropwise. Then the mixture was stirred at room temperature overnight. The reaction was quenched with saturated ammonium chloride solution, and extracted with ethyl acetate (20 mL). The organic layer was washed with brine, dried over sodium sulfate, filtered and evaporated. The residue was purified by silica gel chromatography eluting with PE/EA (10/1 to 3/1, v/v) to afford the title compound as a white solid. LC/MS m/z=436.1 [M+Na]$^+$.

Using the procedure described in Example 22, but in step A replacing tert-butyl 1-(2-(4-chlorophenyl)-1-oxobutan-2-yl)-1H-indol-4-ylcarbamate with tert-butyl 1-(2-(4-methoxyphenyl)-1-oxobutan-2-yl)-1H-indol-4-ylcarbamate• •tert-butyl 1-(2-(4-chlorophenyl)-1-oxobutan-2-yl)-1H-indazol-4-ylcarbamate• •tert-butyl 1-(2-(4-chlorophenyl)-1-oxobutan-2-yl)-6-fluoro-1H-indazol-4-ylcarbamate• •compound 128-130 of Table 19 were prepared respectively. Using the procedure described in Example 22, but in step A replacing diethyl cyanomethylphosphonate with diethyl 1-cyanoethylphosphonate, compound 131 was prepared.

TABLE 19

| Compound Number | IP Rating | Structure | IUPAC Name | LCMS m/z [M + H]$^+$ |
|---|---|---|---|---|
| 127 | A | 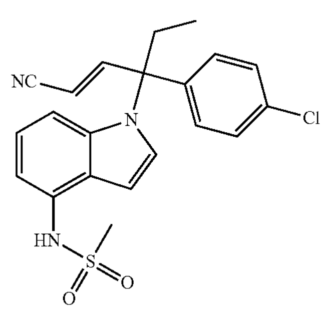 [SMILES: CCC(/C=C/C#N)(c1ccc(Cl)cc1)n1ccc2c(NS(C)(=O)=O)cccc21] | (E)-N-(1-(3-(4-chlorophenyl)-1-cyanopent-1-en-3-yl)-1H-indol-4-yl)methanesulfonamide | 414.1 |

TABLE 19-continued

| Compound Number | IP Rating | Structure | IUPAC Name | LCMS m/z [M + H]+ |
|---|---|---|---|---|
| 128 | A | 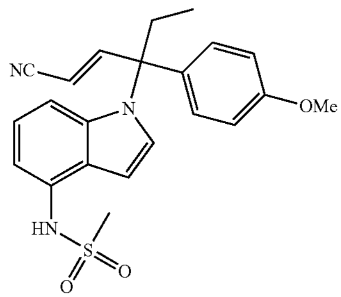 [SMILES: CCC(/C=C/C#N)(c1ccc(OC)cc1)n1ccc2c(NS(C)(=O)=O)cccc21] | (E)-N-(1-(1-cyano-3-(4-methoxyphenyl)pent-1-en-3-yl)-1H-indol-4-yl)methanesulfonamide | 410.1 |
| 129 | A | 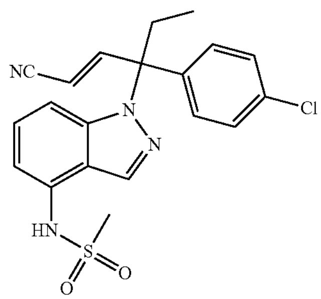 [SMILES: CCC(/C=C/C#N)(c1ccc(Cl)cc1)n1ncc2c(NS(C)(=O)=O)cccc21] | (E)-N-(1-(3-(4-chlorophenyl)-1-cyanopent-1-en-3-yl)-1H-indazol-4-yl)methanesulfonamide | 415.1 |
| 130 | A | 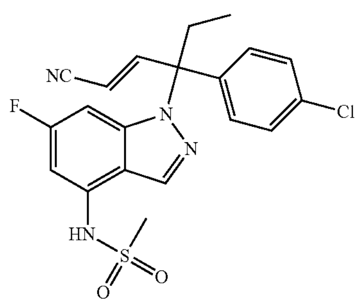 [SMILES: CCC(/C=C/C#N)(c1ccc(Cl)cc1)n1ncc2c(NS(C)(=O)=O)cc(F)cc21] | (E)-N-(1-(3-(4-chlorophenyl)-1-cyanopent-1-en-3-yl)-6-fluoro-1H-indazol-4-yl)methanesulfonamide | 433.1 |
| 131 | A | 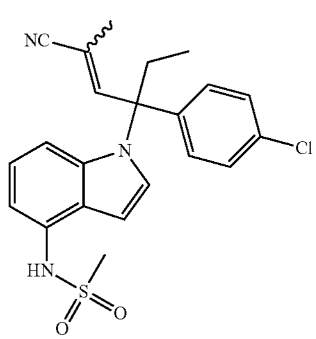 | N-(1-(3-(4-chlorophenyl)-5-cyanohex-4-en-3-yl)-1H-indol-4-yl)methanesulfonamide (Z and E) | 428.1 |

Example 23

N-(1-(3-(4-Chlorophenyl)-1-cyano-2-methylpent-1-en-3-yl)-1H-indol-4-yl)methanesulfonamide (Compound 132)

Step A: N-(1-(3-(4-chlorophenyl)-2-oxopentan-3-yl)-1H-indol-4-yl)methanesulfonamide

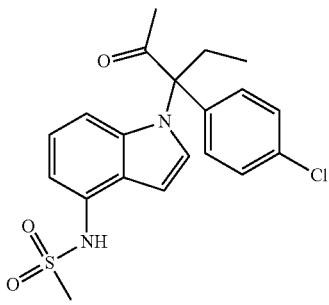 [SMILES: CCC(C(C)=O)(c1ccc(Cl)cc1)n1ccc2c(NS(C)(=O)=O)cccc21]

To a solution of methyl 2-(4-chlorophenyl)-2-(4-(methylsulfonamido)-1H-indol-1-yl)butanoate (1 g, 2.38 mmol), as described in Example 3 Step C, in THF (30 mL) was added CH$_3$Li (3.2 mL, 4.76 mmol, 1.5 M in ether) dropwise at 0° C. and stirred for 0.5 h. The mixture was quenched with saturated ammonium chloride solution, and extracted with ethyl acetate. The organic layer was washed with brine, dried over sodium sulfate, filtered and evaporated. The residue was purified by silica gel chromatography eluting with PE/EA (15/1 to 6/1, v/v) to afford the title compound as a colorless amorphous solid. LC/MS m/z=427.1 [M+Na]$^+$.

Step B: N-(1-(3-(4-chlorophenyl)-1-cyano-2-hydroxy-2-methylpentan-3-yl)-1H-indol-4-yl)methanesulfonamide To a solution of acetonitrile (244 mg, 5.94 mmol) in THF (20 mL) was added n-BuLi (2.6 mL, 6.5 mmol, 2.5 M in hexane) dropwise at −78° C. After stirring for 0.5 h, a solution of the product from Step A (480 mg, 1.19 mmol) in THF (5 mL) was added to the mixture at −78° C. The resulting mixture was stirred at −78° C. for 0.5 h, and then quenched with saturated ammonium chloride solution, extracted with ethyl acetate. The organic layer was washed with brine, dried over sodium sulfate, filtered and evaporated. The residue was purified by silica gel chromatography eluting with PE/EA (15/1 to 4/1, v/v) to afford the title compound as a colorless amorphous solid. LC/MS m/z=468.0 [M+Na]$^+$.

Step C: N-(1-(3-(4-Chlorophenyl)-1-cyano-2-methylpent-1-en-3-yl)-1H-indol-4-yl)methane sulfonamide (Compound 132)

A mixture of the product from Step B (200 mg, 0.449 mmol), TFAA (283 mg, 1.35 mmol), triethylamine (136 mg, 1.35 mmol) and DMAP (165 mg, 1.35 mmol) in dichloromethane (20 mL) was stirred at room temperature for 2 h. The solvent was evaporated and the residue was purified by PREP-TLC eluting with PE/EA (3/1, v/v) to give the title compound as a colorless amorphous solid. LC/MS m/z=450.0 [M+Na]$^+$.

TABLE 20

| Compound Number | IP Rating | Structure | IUPAC Name | LCMS m/z [M + Na]$^+$ |
|---|---|---|---|---|
| 132 | A | 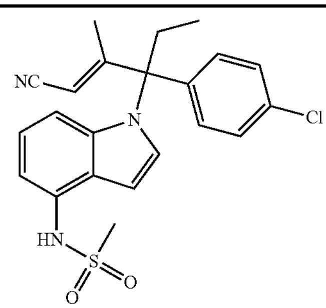 | N-(1-(3-(4-Chlorophenyl)-1-cyano-2-methylpent-1-en-3-yl)-1H-indol-4-yl)methane sulfonamide (E) | 450.0 |

Example 24

(E)-4-(4-amino-1H-indazol-1-yl)-4-(4-chlorophenyl)hex-2-enenitrile (Compound 133)

Using the same procedure described for the preparation of Example 22, but in step A replacing the tert-butyl 1-(2-(4-chlorophenyl)-1-oxobutan-2-yl)-1H-indol-4-ylcarbamate with tert-butyl 1-(2-(4-chlorophenyl)-1-oxobutan-2-yl)-1H-indazol-4-ylcarbamate, tert-butyl 1-(2-(4-chlorophenyl)-1-oxobutan-2-yl)-6-fluoro-1H-indazol-4-ylcarbamate gave the compound 133 and compound 134.

TABLE 21

| Compound Number | IP Rating | Structure | IUPAC Name | LCMS m/z [M + H]+ |
|---|---|---|---|---|
| 133 | B | ![structure] | (E)-4-(4-amino-1H-indazol-1-yl)-4-(4-chlorophenyl)hex-2-enenitrile | 337.1 |
| 134 | B | ![structure] | (E)-4-(4-amino-6-fluoro-1H-indazol-1-yl)-4-(4-chlorophenyl)hex-2-enenitrile | 355.1 |

Example 25

(E)-tert-butyl 1-(3-(4-chlorophenyl)-1-cyanopent-1-en-3-yl)-1H-indazol-4-yl(methylsulfonyl) carbamate (Compound 135)

Step A: (E)-tert-butyl 1-(3-(4-chlorophenyl)-1-cyanopent-1-en-3-yl)-1H-indazol-4-ylcarbamate

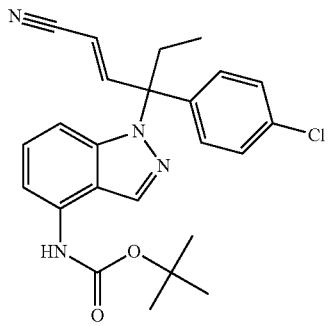 [SMILES: CCC(/C=C/C#N)(c1ccc(Cl)cc1)n1ncc2c(NC(=O)OC(C)(C)C)cccc21]

To a mixture of diethyl cyanomethylphosphonate (305 mg), LiCl (74 mg) and DBU (327 mg) in MeCN (15 mL) was added a solution of (E)-tert-butyl 1-(3-(4-chlorophenyl)-1-cyanopent-1-en-3-yl)-1H-indazol-4-ylcarbamate (600 mg), as described in Example 18 Step F, in MeCN (5 mL). The mixture was stirred at room temperature for 2 h and evaporated. The residue was purified by silica gel chromatography (PE/EA=6/1) to afford the title compound as a white solid. LC/MS m/z=437.1 [M+H]+.

Step B: N-(1-(2-(4-chlorophenyl)-1-hydroxybutan-2-yl)-1H-indazol-4-yl)-N-((2-(trimethylsilyl) ethoxy) methyl)methanesulfonamide

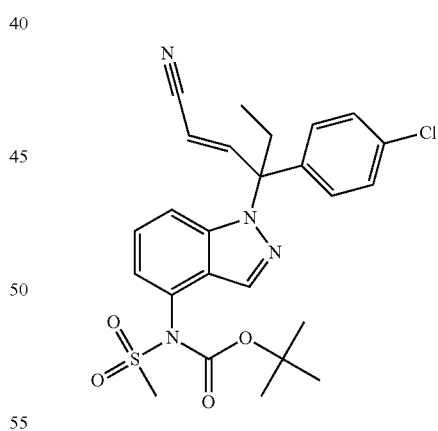

A solution of (E)-tert-butyl 1-(3-(4-chlorophenyl)-1-cyanopent-1-en-3-yl)-1H-indazol-4-ylcarbamate (50 mg, 1.19 mmol) in anhydrous DMF (2 mL) was treated by NaH (9 mg, 60% in oil) at 0° C. for 30 min, then was added methanesulfonyl chloride (50 mg). The mixture was stirred at room temperature for 1 h. The solution was quenched with saturated NH₄Cl solution, extracted with ethyl acetate (15 mL). The organic layer was washed with water, brine, dried over sodium sulfate, filtered and evaporated. The residue was purified by silica gel chromatography (PE/EA=6/1) to afford the title compound as a white solid. LC/MS m/z=515.2 [M+H]+.

TABLE 22

| Compound Number | IP Rating | Structure | IUPAC Name | LCMS m/z [M + H]+ |
|---|---|---|---|---|
| 135 | A | 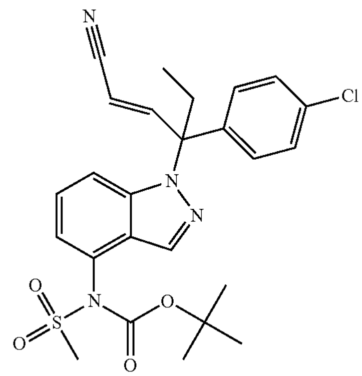 [SMILES: CCC(/C=C/C#N)(c1ccc(Cl)cc1)n1ncc2c(N(C(=O)OC(C)(C)C)S(C)(=O)=O)cccc21] | N-(1-(2-(4-chlorophenyl)-1-hydroxybutan-2-yl)-1H-indazol-4-yl)-N-((2-(trimethylsilyl)ethoxy)methyl)methanesulfonamide (E) | 515.2 |

Example 26
(E)-N-(1-(3-(4-chlorophenyl)-1-cyanopent-1-en-3-yl)-6-fluoro-1H-indazol-4-yl)-N-(methylsulfonyl)methanesulfonamide (Compound 136)

Using the same procedure described for the preparation of Example 22, step C but replacing the (E)-4-(4-amino-1H-indol-1-yl)-4-(4-chlorophenyl)hex-2-enenitrile with (E)-4-(4-amino-6-fluoro-1H-indazol-1-yl)-4-(4-chlorophenyl)hex-2-enenitrile gave the compound 136.

A mixture of methyl (E)-tert-butyl 1-(3-(4-chlorophenyl)-1-cyanopent-1-en-3-yl)-1H-indazol-4-ylcarbamate (500 mg), as described in Example 25 Step A, in 15 mL of 4 N HCl/MeOH was stirred at room temperature for 1 h. Then the solvent was removed. The residue was dissolved in EA (30 mL) and pH value was adjusted to 9-10 with saturated aq. NaHCO₃. The organic layer was washed with water (10 mL), brine, dried (Na₂SO₄) and concentrated. The residue was purified on revered—phase HPLC (0.05% NH₄HCO₃ in H₂O-MeCN) to give the title product as a pale brown solid. LC/MS m/z=337.2 [M+H]+.

TABLE 23

| Compound Number | IP Rating | Structure | IUPAC Name | LCMS m/z [M + H]+ |
|---|---|---|---|---|
| 136 | A | 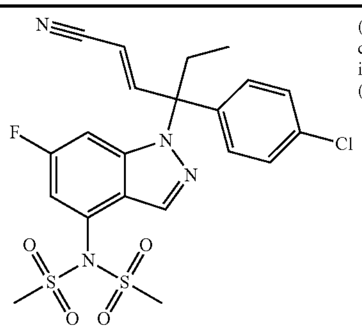 | (E)-N-(1-(3-(4-chlorophenyl)-1-cyanopent-1-en-3-yl)-6-fluoro-1H-indazol-4-yl)-N-(methylsulfonyl)methanesulfonamide | 511.1 |

Example 27
N-(1-(3-(4-chlorophenyl)-1-cyanopentan-3-yl)-1H-indazol-4-yl)methanesulfonamide Step A: (E)-4-(4-amino-1H-indazol-1-yl)-4-(4-chlorophenyl)hex-2-enenitrile

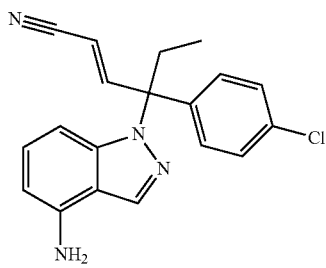 [SMILES: CCC(/C=C/C#N)(c1ccc(Cl)cc1)n1ncc2c(N)cccc21]

Step B: (E)-N-(1-(3-(4-chlorophenyl)-1-cyanopent-1-en-3-yl)-1H-indazol-4-yl)methane sulfonamide

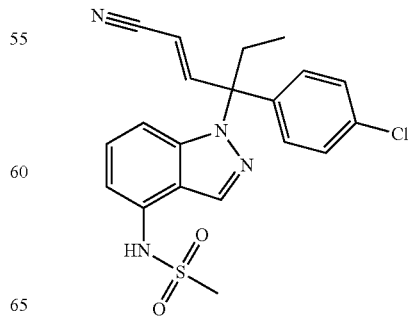

To a mixture of (E)-4-(4-amino-1H-indazol-1-yl)-4-(4-chlorophenyl)hex-2-enenitrile (130 mg) and NMM (117 mg) in DCM (5 mL) was added MsCl (53 mg), Then the mixture was stirred at room temperature for 2 h. The solution was quenched with saturated NH$_4$Cl solution, and extracted with ethyl acetate (30 mL). The organic layer was washed with brine, dried over dry sodium sulfate, filtered and evaporated. The residue was purified by silica gel chromatography (eluent: PE/EA=5/1) to afford the title compound as a pale yellow solid. LC/MS m/z=415.2 [M+H]$^+$.

Step C: N-(1-(3-(4-chlorophenyl)-1-cyanopentan-3-yl)-1H-indazol-4-yl)methanesulfonamide A mixture of (E)-N-(1-(3-(4-chlorophenyl)-1-cyanopent-1-en-3-yl)-1H-indazol-4-yl)methanesulfonamide (60 mg) and 10% Pd/C in EA (4 mL) was stirred at room temperature under H$_2$ atmosphere for 16 h. The mixture was filtered and evaporated to give the title compound as a pale yellow solid. LC/MS m/z=417.2[M+H]$^+$.

Using the procedure described in Example 27, but in step B replacing (E)-4-(4-amino-1H-indazol-1-yl)-4-(4-chlorophenyl)hex-2-enenitrile with (E)-4-(4-amino-1H-indazol-1-yl)-4-(4-methoxyphenyl)hex-2-enenitrile, (E)-4-(4-amino-1H-indol-1-yl)-4-(4-chlorophenyl)hex-2-enenitrile, (E)-4-(4-amino-1H-indazol-1-yl)-4-(4-(trifluoromethyl)phenyl)hex-2-enenitrile, (E)-4-(4-amino-6-fluoro-1H-indol-1-yl)-4-(4-chlorophenyl)hex-2-enenitrile, (E)-4-(4-amino-6-fluoro-1H-indazol-1-yl)-4-phenylhex-2-enenitrile, (E)-4-(4-amino-6-fluoro-1H-indazol-1-yl)-4-(4-chlorophenyl)hex-2-enenitrile, compound 139-145 were prepared respectively. Compound 137 and compound 138 were obtained by the below chiral separation conditions:
Column: AS-H
Mobile phase: A: CO$_2$, B: MeOH, A:B=60:40 at 3.0 mL/min
Column Temp: 38.8° C.
Compound 140 was obtained by the below chiral separation conditions:
Column: AD-H
Mobile phase: A: CO$_2$, B: MeOH, A:B=60:40 at 3.0 mL/min
Column Temp: 38.6° C.
Compound 141 was obtained by the below chiral separation conditions:
Column: AD-H
Mobile phase: A: CO$_2$, B: MeOH (0.1% DEA), A:B=93:7 at 2.97 mL/min
Column Temp: 40.1° C.
Compound 142 and compound 144 were obtained by the below chiral separation conditions:
Column: AS-H
Mobile phase: A: CO$_2$, B: MeOH, A:B=50:50 at 3.0 mL/min
Column Temp: 39.9° C.

TABLE 24

| Compound Number | IP Rating | Structure | IUPAC Name | LCMS m/z [M + H]$^+$ |
|---|---|---|---|---|
| 137 | B | 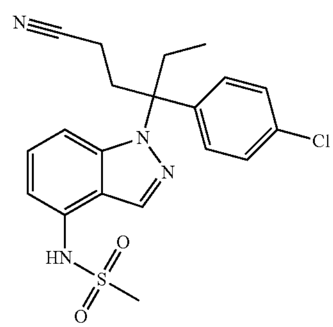 [SMILES: CCC(CCC#N)(c1ccc(Cl)cc1)n1ncc2c(NS(C)(=O)=O)cccc21] | N-(1-(3-(4-chlorophenyl)-1-cyanopentan-3-yl)-1H-indazol-4-yl)methanesulfonamide (enantiomer A, r.t. = 2.4 min) | 417.2 |
| 138 | A | 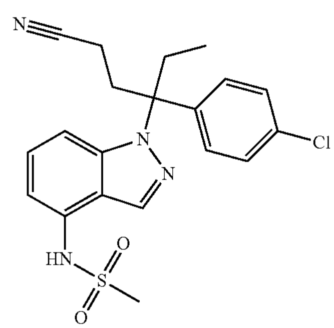 [SMILES: CCC(CCC#N)(c1ccc(Cl)cc1)n1ncc2c(NS(C)(=O)=O)cccc21] | N-(1-(3-(4-chlorophenyl)-1-cyanopentan-3-yl)-1H-indazol-4-yl)methanesulfonamide (enantiomer B, r.t. = 3.94 min) | 417.2 |

TABLE 24-continued

| Compound Number | IP Rating | Structure | IUPAC Name | LCMS m/z [M + H]+ |
|---|---|---|---|---|
| 139 | A | 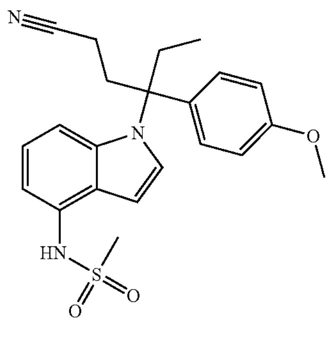 [SMILES: CCC(CCC#N)(c1ccc(OC)cc1)n1ccc2c(NS(C)(=O)=O)cccc21] | N-(1-(1-cyano-3-(4-methoxyphenyl)pentan-3-yl)-1H-indol-4-yl)methanesulfonamide | 412.2 |
| 140 | A | 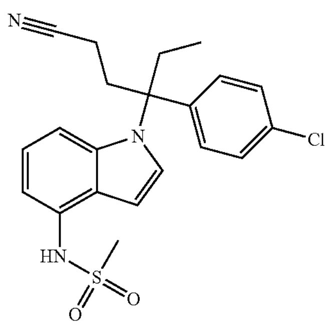 [SMILES: CCC(CCC#N)(c1ccc(Cl)cc1)n1ccc2c(NS(C)(=O)=O)cccc21] | N-(1-(3-(4-chlorophenyl)-1-cyanopentan-3-yl)-1H-indol-4-yl)methanesulfonamide (enantiomer A, r.t. = 3.57 min) | 416.1 |
| 141 | A | 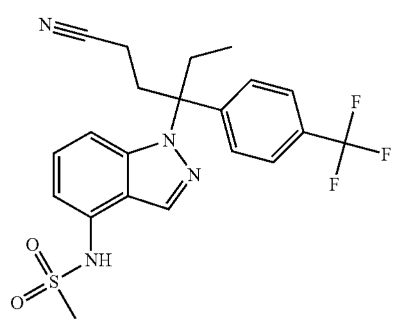 [SMILES: CCC(CCC#N)(c1ccc(C(F)(F)F)cc1)n1ncc2c(NS(C)(=O)=O)cccc21] | N-(1-(1-cyano-3-(4-(trifluoromethyl)phenyl)pentan-3-yl)-1H-indazol-4-yl)methanesulfonamide (enantiomer A, r.t. = 4.91 min) | 451.1 |
| 142 | A | 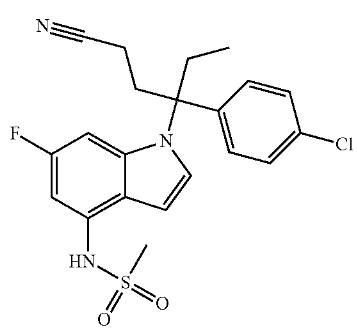 | N-(1-(3-(4-chlorophenyl)-1-cyanopentan-3-yl)-6-fluoro-1H-indol-4-yl)methanesulfonamide (enantiomer A, r.t. = 2.12 min) | 434.1 |

TABLE 24-continued

| Compound Number | IP Rating | Structure | IUPAC Name | LCMS m/z [M + H]+ |
|---|---|---|---|---|
| 143 | A | 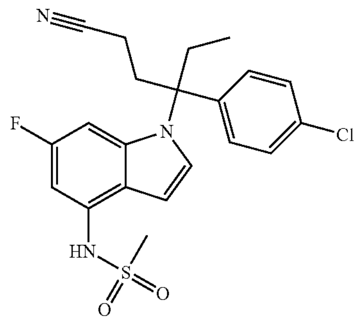 [SMILES: CCC(CCC#N)(c1ccc(Cl)cc1)n1ccc2c(NS(C)(=O)=O)cc(F)cc21] | N-(1-(3-(4-chlorophenyl)-1-cyanopentan-3-yl)-6-fluoro-1H-indol-4-yl)methanesulfonamide (enantiomer B, r.t. = 2.85 min) | 434.1 |
| 144 | A | 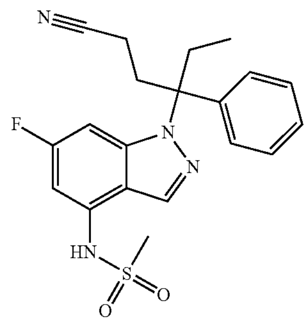 [SMILES: CCC(CCC#N)(c1ccccc1)n1ncc2c(NS(C)(=O)=O)cc(F)cc21] | N-(1-(1-cyano-3-phenylpentan-3-yl)-6-fluoro-1H-indazol-4-yl)methanesulfonamide | 401.1 |
| 145 | A | 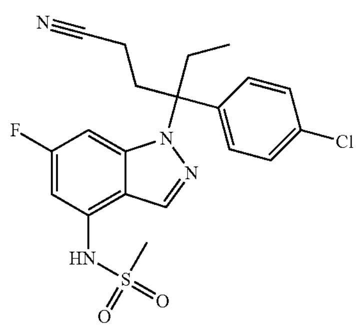 | N-(1-(3-(4-chlorophenyl)-1-cyanopentan-3-yl)-6-fluoro-1H-indazol-4-yl)methanesulfonamide | 435.1 |

Example 28

N-(1-(3-(4-Chlorophenyl)-1-cyano-2-oxopentan-3-yl)-1H-indol-4-yl)methanesulfonamide (Compound 146)

Step A: N-(1-(3-(4-Chlorophenyl)-1-cyano-2-oxopentan-3-yl)-1H-indol-4-yl)methane-sulfonamide To a solution of acetonitrile (180 mg, 4.4 mmol) in tetrahydrofuran (3 mL) was added BuLi (1.9 mL, 4.8 mmol, 2.5 M in hexane) at −78° C. After stirring for 30 min, a solution of methyl 2-(4-chlorophenyl)-2-(4-(methylsulfonamido)-1H-indol-1-yl)butanoate (840 mg, 2.0 mmol, Enantiomer A), as described in Example 3 step D, in tetrahydrofuran (3 mL) was added to the mixture at −78° C. The resulting mixture was stirred at −78° C. for another 1 h, and then quenched with water (15 mL), extracted with ethyl acetate. The combined organics were washed with brine (15 mL), dried over Na$_2$SO$_4$, filtered and concentrated. The crude product was purified by silica gel chromatography eluting with PE/EA (5/1 to 3/1, v/v) to get the title compound as a colorless amorphous solid (Enantiomer A). LC/MS m/z=429.8[M+H]+.

TABLE 25

| Compound Number | IP Rating | Structure | IUPAC Name | LCMS m/z [M + H]+ |
|---|---|---|---|---|
| 146 | A | 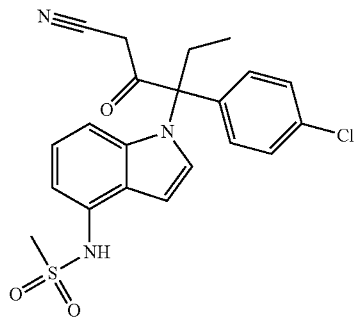 [SMILES: CCC(C(=O)CC#N)(c1ccc(Cl)cc1)n1ccc2c(NS(C)(=O)=O)cccc21] | N-(1-(3-(4-Chlorophenyl)-1-cyano-2-oxopentan-3-yl)-1H-indol-4-yl)methanesulfonamide (enantiomer) | 429.8 |

Example 29

N-(1-(1-(4-Chlorophenyl)-1-(3-cyano-4,5-dihydrofuran-2-yl)propyl)-1H-indol-4-yl)methane-sulfonamide (Compound 147)

To a solution of N-(1-(3-(4-chlorophenyl)-1-cyano-2-oxopentan-3-yl)-1H-indol-4-yl)methanesulfonamide (50 mg, 0.116 mmol, enantiomer A), as described in Example 28 step A, in DMF (2 mL) was added NaH (9 mg, 0348 mmol, 60% in oil) at 0° C. After stirring for 30 min, 1,2-dibromoethane (22 mg, 0.116 mmol) was added to the mixture at 0° C. The resulting mixture was stirred at 0° C. for another 1 h, and then quenched with water (15 mL), extracted with ethyl acetate. The combined organic layers were washed with brine (10 mL), dried over $Na_2SO_4$, filtered and concentrated. The crude product was purified by silica gel chromatography eluting with PE/EA (5/1 to 3/1, v/v) to give the title compound as a colorless amorphous solid. LC/MS m/z=456.1 $[M+H]^+$.

TABLE 26

| Compound Number | IP Rating | Structure | IUPAC Name | LCMS m/z [M + H]+ |
|---|---|---|---|---|
| 147 | B | 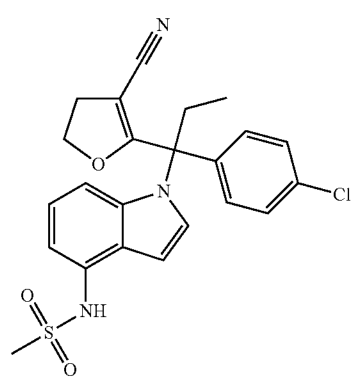 [SMILES: CCC(C1=C(C#N)CCO1)(c1ccc(Cl)cc1)n1ccc2c(NS(C)(=O)=O)cccc21] | N-(1-(1-(4-Chlorophenyl)-1-(3-cyano-4,5-dihydrofuran-2-yl)propyl)-1H-indol-4-yl)methanesulfonamide (enantiomer) | 456.1 |

Example 30

N-(2-chloroethyl)-2-(4-chlorophenyl)-2-(4-(methyl-sulfonamido)-1H-indol-1-yl)butanamide (Compound 148)

Step A: 2-(4-chlorophenyl)-2-(4-(methylsulfona-mido)-1H-indol-1-yl)butanoic acid

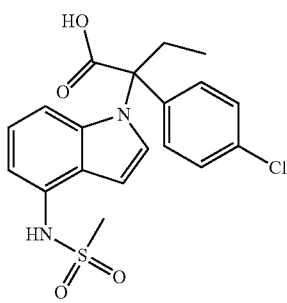 [SMILES: CCC(C(=O)O)(c1ccc(Cl)cc1)n1ccc2c(NS(C)(=O)=O)cccc21]

A mixture of methyl 2-(4-chlorophenyl)-2-(4-(methylsulfonamido)-1H-indol-1-yl)butanoate (840 mg, 2 mmol), as described in Example 3 step C, and 2 M LiOH (5 mL) in methanol (5 mL) was heated to 50° C. for 5 h. The reaction was acidified with 1M HCl and the volatile was removed under reduced pressure. The residue was dissolved in ethyl acetate (80 mL) and water (20 mL). The organic layer was washed with brine (10 mL) and dried over Na$_2$SO$_4$, filtered and concentrated in vacuo to give the title compound as colorless solid. LC/MS 407.0 (M+1).

Step B: N-(2-chloroethyl)-2-(4-chlorophenyl)-2-(4-(methylsulfonamido)-1H-indol-1-yl)butanamide

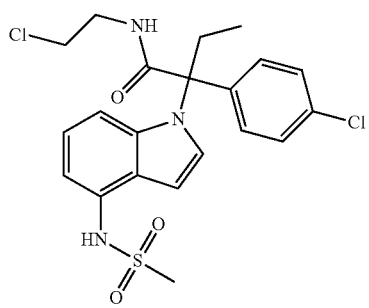 [SMILES: CCC(C(=O)NCCCl)(c1ccc(Cl)cc1)n1ccc2c(NS(C)(=O)=O)cccc21]

A mixture of the product of Step A (40 mg, 0.1 mmol), HATU (57 mg, 0.15 mmol), N,N-diisopropylethylamine (26 mg, 0.2 mmol) and 2-chloroethanamine (16 mg, 0.2 mmol) in N,N-dimethylformamide (2 mL) was stirred at room temperature overnight. The crude product was purified by CombiFlash (Mobile phase: acetonitrile/water (0.03% TFA)) to afford the title compound as a white amorphous solid. LC/MS m/z=467.9[M+H]$^+$.

Following the same procedure for the preparation of EXAMPLE 30 step B, but using 2-aminoacetonitrile instead of 2-chloroethanamine, compound 149 of Table 27 was obtained.

TABLE 27

| Compound Number | IP Rating | Structure | IUPAC Name | LCMS m/z [M + H]$^+$ |
|---|---|---|---|---|
| 148 | B | 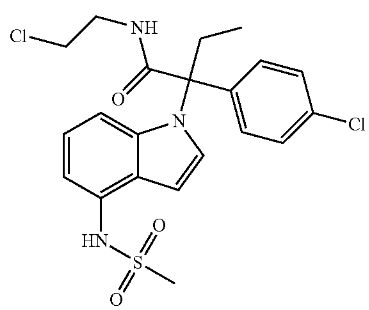 [SMILES: CCC(C(=O)NCCCl)(c1ccc(Cl)cc1)n1ccc2c(NS(C)(=O)=O)cccc21] | N-(2-chloroethyl)-2-(4-chlorophenyl)-2-(4-(methylsulfonamido)-1H-indol-1-yl)butanamide (enantiomer) | 456.1 |
| 149 | A | 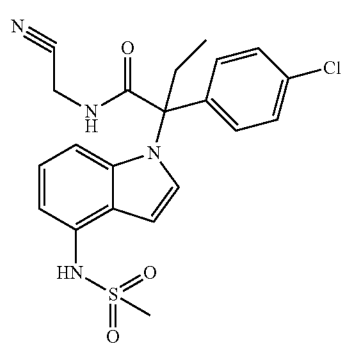 [SMILES: CCC(C(=O)NCC#N)(c1ccc(Cl)cc1)n1ccc2c(NS(C)(=O)=O)cccc21] | 2-(4-chlorophenyl)-N-(cyanomethyl)-2-(4-(methylsulfonamido)-1H-indol-1-yl)butanamide | 445.1 |

Example 31

N-(1-(1-(4-chlorophenyl)-1-(3-methyl-1,2,4-oxadiazol-5-yl)propyl)-1H-indol-4-yl)methanesulfonamide (Compound 150)

Step A: 2-(4-chlorophenyl)-N-(1-(hydroxyimino)ethyl)-2-(4-(methylsulfonamido)-1H-indol-1-yl)butanamide

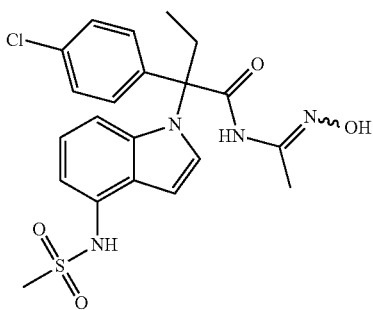 [SMILES: CCC(C(=O)NC(C)=NO)(c1ccc(Cl)cc1)n1ccc2c(NS(C)(=O)=O)cccc21]

To a solution of 2-(4-chlorophenyl)-2-[4-(methylsulfonamido)-1H-indol-1-yl]butanoiacid (200 mg, 0.49 mmol), as described in Example 30 Step A, in THF (5 mL), was added EDCI (141 mg, 0.74 mmol), triethylamine (75 mg, 0.74 mmol) and HOBT (13 mg, 0.098 mmol) at RT. The mixture was stirred for 15 minutes and then N-hydroxyacetimidamide (73 mg, 1.47 mmol) was added. After 4 hours, the resulting mixture was diluted with saturated aqueous ammonium chloride (10 mL) and extracted with EA (20 mL). The combined organic layers were washed with brine (10 mL), dried over anhydrous sodium sulfate, filtered, and the solvent was removed in vacuo. The residue was used to next step without further purification.

Step B: N-(1-(1-(4-chlorophenyl)-1-(3-methyl-1,2,4-oxadiazol-5-yl)propyl)-1H-indol-4-yl)methanesulfonamide A solution of 2-(4-chlorophenyl)-N-(1-(hydroxyimino)ethyl)-2-(4-(methylsulfonamido)-1H-indol-1-yl)butanamide (148 mg, 0.32 mmol) in THF (5 mL) was heated at 70° C. for 2 days. Then the solvent was removed in vacuo to afford the crude product. The product was purified by column chromatography (50% EtOAc/hexanes), then by chiral separation following the conditions below provided the title compound as a single enantiomer.

Using the same procedure described for the preparation of Example 31, but replacing the N'-hydroxyacetimidamide in step A with N'-hydroxypropionimidamide gave the title compound 151.

Compound 150 was obtained by the below chiral separation conditions:
Column: OJ-H
Mobile phase: A: n-Hexane, B: EtOH (0.1% DEA), A:B=70:30 at 1.0 mL/min
Column Temp: 40° C.

Compound 151 was obtained by the below chiral separation conditions:
Column: AS-H
Mobile phase: A: $CO_2$, B: MeOH (0.1% DEA), A:B=70:30 at 3.0 mL/min
Column Temp: 39.8° C.

TABLE 28

| Compound Number | IP Rating | Structure | IUPAC Name | LCMS m/z $[M + H]^+$ |
|---|---|---|---|---|
| 150 | A | 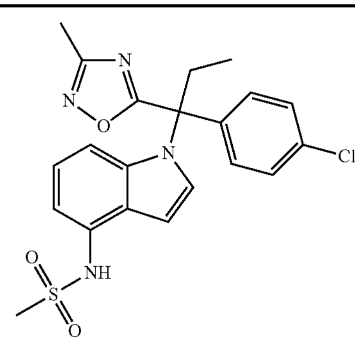 | N-(1-(1-(4-chlorophenyl)-1-(3-methyl-1,2,4-oxadiazol-5-yl)propyl)-1H-indol-4-yl)methanesulfonamide (enantiomer A, r.t. = 13.95 min) | 445.1 |
| 151 | A | 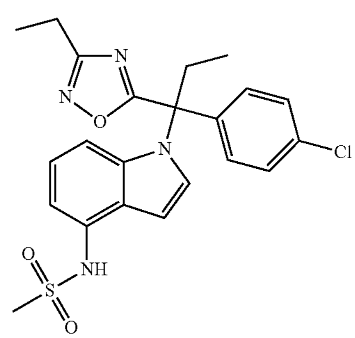 [SMILES: CCc1noc(C(CC)(c2ccc(Cl)cc2)n2ccc3c(NS(C)(=O)=O)cccc32)n1] | N-(1-(1-(4-chlorophenyl)-1-(3-ethyl-1,2,4-oxadiazol-5-yl)propyl)-1H-indol-4-yl)methanesulfonamide (enantiomer A, r.t. = 2.84 min) | 458.9 |

Example 32

N-(1-(1-(4-chlorophenyl)-1-(2-ethyl-2H-1,2,3-triazol-4-yl)propyl)-1H-indol-4-yl)methane sulfonamide (Compound 152)

Step A: tert-butyl 1-(3-(4-chlorophenyl)pent-1-yn-3-yl)-1H-indol-4-ylcarbamate

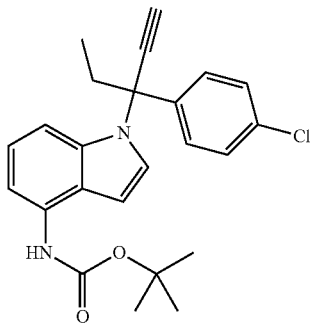 [SMILES: C#CC(CC)(c1ccc(Cl)cc1)n1ccc2c(NC(=O)OC(C)(C)C)cccc21]

A mixture of tert-butyl 1-(2-(4-chlorophenyl)-1-oxobutan-2-yl)-1H-indol-4-ylcarbamate (500 mg, 1.21 mmol), as described in Example 21 Step B, and dimethyl 1-diazo-2-oxopropylphosphonate (244 mg, 1.27 mmol) in MeOH (10 mL) was stirred at rt for 4 hours. After removing the solvent in vacuo, the residue was purified via column chromatography (0-30% EtOAc/hexanes) to provide the title compound.

Step B: tert-butyl 1-(1-(4-chlorophenyl)-1-(2H-1,2,3-triazol-4-yl)propyl)-1H-indol-4-ylcarbamate

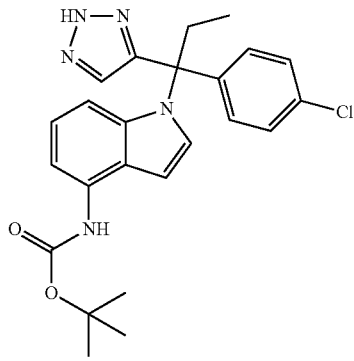 [SMILES: CCC(c1ccc(Cl)cc1)(c1cn[nH]n1)n1ccc2c(NC(=O)OC(C)(C)C)cccc21]

A solution of tert-butyl 1-(3-(4-chlorophenyl)pent-1-yn-3-yl)-1H-indol-4-ylcarbamate (200 mg, 0.5 mmol) in trimethylsilyl azide (3 mL) was heated at 100° C. under microwave for 3 h. The resulting mixture was diluted with brine (10 mL) and extracted with EA. The combined organic layers were dried over anhydrous sodium sulfate, filtered, and the solvent was removed in vacuo to afford the crude product. The product was purified via column chromatography (75% EtOAc/hexanes) to provide the title product.

Step C: tert-butyl 1-(1-(4-chlorophenyl)-1-(2-ethyl-2H-1,2,3-triazol-4-yl)propyl)-1H-indol-4-ylcarbamate

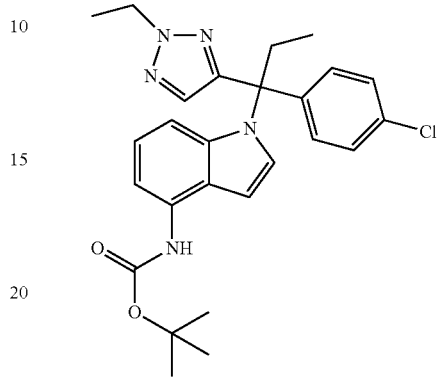

A solution of tert-butyl 1-(1-(4-chlorophenyl)-1-(2H-1,2,3-triazol-4-yl)propyl)-1H-indol-4-ylcarbamate (150 mg, 0.33 mmol) in DMF (5 mL), was added potassium carbonate (91 mg, 0.66 mmol) and iodoethane (62 mg, 0.40 mmol). After stirring for 2 hours, the mixture was diluted with saturated aqueous ammonium chloride (10 mL) and extracted with EA. The combined organic layers were washed with brine (10 mL), dried over anhydrous sodium sulfate, filtered, and the solvent was removed in vacuo to afford the crude product. The product was purified via column chromatography (50% EtOAc/hexanes) to provide the title product.

Step D: 1-(1-(4-chlorophenyl)-1-(2-ethyl-2H-1,2,3-triazol-4-yl)propyl)-1H-indol-4-amine

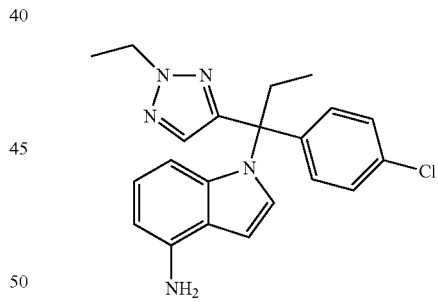

Using the same procedure described for the preparation of Example 14, step G but replacing the 2-(4-(tert-butoxycarbonylamino)-6-fluoro-1H-indol-1-yl)-2-(4-chlorophenyl)acetic acid with tert-butyl 1-(1-(4-chlorophenyl)-1-(2-ethyl-2H-1,2,3-triazol-4-yl)propyl)-1H-indol-4-ylcarbamate gave the title compound.

Step E: N-(1-(1-(4-chlorophenyl)-1-(2-ethyl-2H-1,2,3-triazol-4-yl)propyl)-1H-indol-4-yl)methanesulfonamide (Compound 152)

Using the same procedure described for the preparation of Example 14, step K but replacing the methyl 2-(4-amino-6-fluoro-1H-indol-1-yl)-2-(4-chlorophenyl)butanoate with 1-(1-(4-chlorophenyl)-1-(2-ethyl-2H-1,2,3-triazol-4-yl)propyl)-1H-indol-4-amine gave the title compound.

TABLE 29

| Compound Number | IP Rating | Structure | IUPAC Name | LCMS m/z [M + H]+ |
|---|---|---|---|---|
| 152 | A | 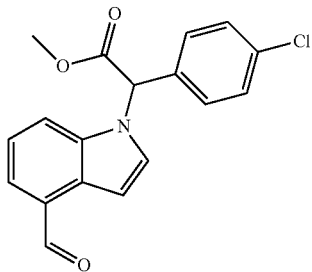 [SMILES: COC(=O)C(c1ccc(Cl)cc1)n1ccc2c(C=O)cccc21] | N-(1-(1-(4-chlorophenyl)-1-(2-ethyl-2H-1,2,3-triazol-4-yl)propyl)-1H-indol-4-yl)methanesulfonamide | 480.1 |

Example 33

Methyl 2-(4-chlorophenyl)-2-(4-(2-(methylsulfonyl)ethyl)-1H-indol-1-yl)butanoate (Compound 153)

Step A: methyl 2-(4-chlorophenyl)-2-(4-formyl-1H-indol-1-yl)acetate

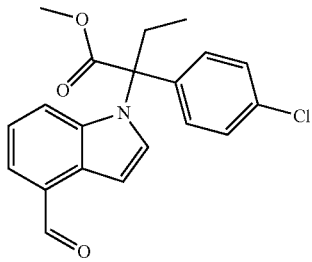 [SMILES: CCC(C(=O)OC)(c1ccc(Cl)cc1)n1ccc2c(C=O)cccc21]

To a solution of 1H-indole-4-carbaldehyde (2.0 g, 13.79 mmol) in DMF (50 mL) was added NaH (0.66 g, 16.55 mmol) at 0° C. After stirring for 30 min at 0° C., a solution of methyl 2-bromo-2-(4-chlorophenyl)-acetate (4.67 g, 17.92 mmol) in DMF (20 mL) was added dropwise. The reaction was allowed to warm to rt and stirred for an additional 1 hr. Then it was diluted with EtOAc (200 mL) and quenched with water. The organic layer was separated and washed with brine (50 mL), dried over $Na_2SO_4$, filtered and the solvent was removed in vacuo. The residue was purified via column chromatography (0-20% EtOAc/hexanes) to provide the title compound.

Step B: methyl 2-(4-chlorophenyl)-2-(4-formyl-1H-indol-1-yl)butanoate

To a solution of methyl 2-(4-chlorophenyl)-2-(4-formyl-1H-indol-1-yl)acetate (2.34 g, 7.17 mmol) in THF (60 mL) and HMPA (15 mL) was added LiHMDS (1 M in THF, 11.0 mL, 11 mmol) dropwise at 0° C. The mixture was stirred at 0° C. for 30 min before adding iodoethane (1.23 g, 7.88 mmol). After stirring for another 30 min at 0° C., the mixture was diluted with EtOAc (120 mL) and then quenched with water (20 mL). The organic layer was separated and washed with brine (20 mL), dried over $Na_2SO_4$, filtered and the solvent was removed in vacuo. The residue was purified via column chromatography (0-15% EtOAc/hexanes) to provide the title compound.

Step C: (E)-methyl 2-(4-chlorophenyl)-2-(4-(2-(methylsulfonyl)vinyl)-1H-indol-1-yl)butanoate

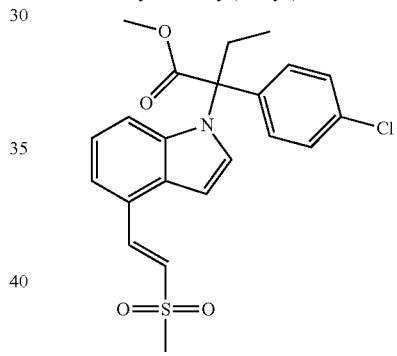

To a solution of diethyl methylsulfonylmethylphosphonate (1.05 g, 4.56 mmol) in $CH_3CN$ (30 mL) at RT was added LiCl (0.16 g, 3.80 mmol) and DBU (2.40 g, 9.56 mmol). After 5 min, a solution of methyl 2-(4-chlorophenyl)-2-(4-formyl-1H-indol-1-yl)butanoate (1.35 g, 3.80 mmol) in $CH_3CN$ (10 mL) was added dropwise. The resulting mixture was stirred for 4 hours at RT. Then it was diluted with DCM (50 mL) and the organic layer was washed with water (30 mL), dried over $Na_2SO_4$, filtered. After removal of the solvent, the residue was purified via column chromatography (0-30% EtOAc/hexanes) to provide the title compound. LC/MS m/z=432.0 [M+H]+.

Step D: methyl 2-(4-chlorophenyl)-2-(4-(2-(methylsulfonyl)ethyl)-1H-indol-1-yl butanoate To a solution of (E)-methyl 2-(4-chlorophenyl)-2-(4-(2-(methylsulfonyl)vinyl)-1H-indol-1-yl)butanoate (1.18 g, 2.73 mmol) in EtOAc (50 mL) was added Pd/C (10% on carbon, 0.2 g). The mixture was stirred under $H_2$ atmosphere for 30 min. Then the reaction mixture was filtered through a celite pad, and the filtrate was concentrated in vacuo. The residue was purified via column chromatography (0-30% EtOAc/hexanes) to provide the title compound. LC/MS m/z=434.1[M+H]+.

TABLE 30

| Compound Number | IP Rating | Structure | IUPAC Name | LCMS m/z [M + H]+ |
|---|---|---|---|---|
| 153 | A | 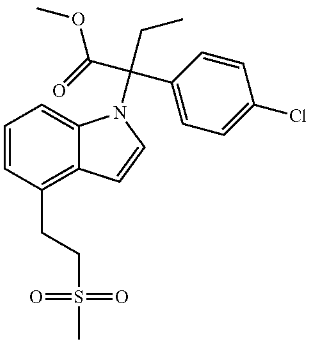 [SMILES: CCC(C(=O)OC)(c1ccc(Cl)cc1)n1ccc2c(CCS(C)(=O)=O)cccc21] | Methyl 2-(4-chlorophenyl)-2-(4-(2-(methylsulfonyl)ethyl)-1H-indol-1-yl)butanoate | 434.1 |

Example 34

N-(1-(1-(4-chlorophenyl)-1-(1-hydroxycyclopropyl)propyl)-1H-indol-4-yl)methanesulfonamide (Compound 154)

Step A: tert-butyl 1-(1-(4-chlorophenyl)-1-(1-hydroxycyclopropyl)propyl)-1H-indol-4-ylcarbamate

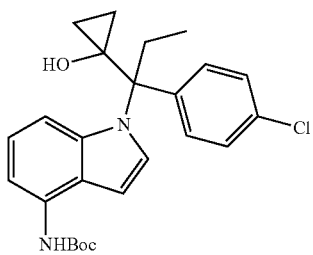 [SMILES: CCC(c1ccc(Cl)cc1)(n1ccc2c(NC(=O)OC(C)(C)C)cccc21)C1(O)CC1]

To a solution of methyl 2-{4-[(tert-butoxycarbonyl)amino]-1H-indol-1-yl}-2-(4-chlorophenyl)butanoate (0.44 g, 1 mmol), as described in Example 3 step A, in THF (20 mL) was added titanium (IV) isopropoxide (0.3 g, 1 mmol) and the solution was cooled to 0° C. Ethylmagnesium bromide 3 N in ether (1.8 mL, 5 mmol) was then added via syringe pump over 1 hr period and the reaction was stirred for an additional 30 min at this temperature. The mixture was warmed into RT and stirred over night. The final mixture was diluted with EA, treated with saturated sodium bicarbonate solution, extracted with EA and DCM, dried over sodium sulfate and concentrated. The residue was purified by flash-chromatography over silica gel (eluted with hexanes/EA 95:5 to EA) to give the title compound. LC/MS m/z=441.0[M+H]+.

Step B: 1-(1-(4-amino-1H-indol-1-yl)-1-(4-chlorophenyl)propyl)cyclopropanol

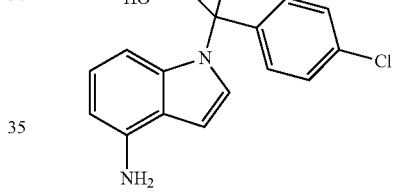

Compound from step A (96 mg, 0.22 mmol) was treated with 10 mL 4N HCl/MeOH solution over night. The solvents were removed by reduced pressure to give white product. LC/MS m/z=341.0[M+H]+.

Step C: N-(1-(1-(4-chlorophenyl)-1-(1-hydroxycyclopropyl)propyl)-1H-indol-4-yl) methane sulfonamide To a mixture of compound from step B (83 mg, 0.22 mmol) and NMM (44 mg, 0.44 mmol) in DCM (5 mL) was added methylsulfonyl chloride (37 mg, 0.3 mmol) dropwise. Then the mixture was stirred at room temperature overnight. The reaction was quenched with saturated ammonium chloride solution, and extracted with ethyl acetate (20 mL). The organic layer was washed with brine, dried over sodium sulfate, filtered and evaporated. The residue was purified by Pre-HPLC to afford the title compound as a white solid. LC/MS m/z=419.1[M+H]+.

Compound 154 was obtained by the below chiral separation conditions:

Column: OD-H

Mobile phase: A: $CO_2$, B: MeOH, A:B=70:30 at 3.0 mL/min

Column Temp: 40.2° C.

TABLE 31

| Compound Number | IP Rating | Structure | IUPAC Name | LCMS m/z [M + H]+ |
|---|---|---|---|---|
| 154 | A | 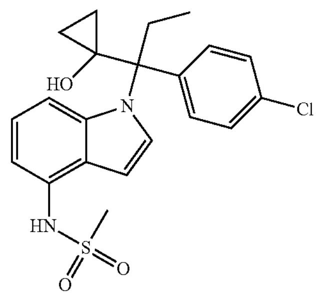 [SMILES: CCC(c1ccc(Cl)cc1)(n1ccc2c(NS(C)(=O)=O)cccc21)C1(O)CC1] | N-(1-(1-(4-chlorophenyl)-1-(1-hydroxycyclopropyl)propyl)-1H-indol-4-yl)methanesulfonamide (enantiomer A, r.t. = 3.32 min) | 419.1 |

Example 35

N-(1-(3-(4-chlorophenyl)-1-cyanopent-1-yn-3-yl)-1H-indol-4-yl)methanesulfonamide Step A: methyl 4-(4-chlorophenyl)-4-(4-(N-((2-(trimethylsilyl)ethoxy)methyl) methyl sulfonamido)-1H-indol-1-yl)hex-2-ynoate

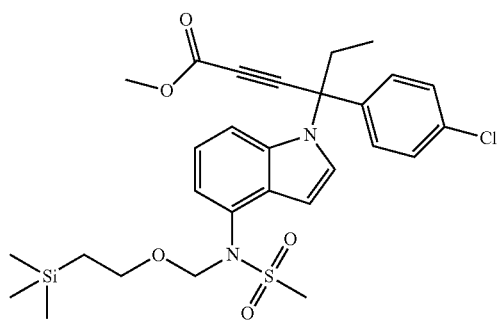 [SMILES: CCC(C#CC(=O)OC)(c1ccc(Cl)cc1)n1ccc2c(N(COCC[Si](C)(C)C)S(C)(=O)=O)cccc21]

To a solution of compound N-(1-(3-(4-chlorophenyl)pent-1-yn-3-yl)-1H-indol-4-yl)-N-((2-(trimethylsilyl)ethoxy)methyl)methanesulfonamide (2.9 g, 5.6 mmol, enantiomer A), as described in Example 55 Step A, in dry THF (10 mL) was added BuLi (4.5 mL, 11.2 mmol, 2.5 M in hexane) at −78° C. After stirring for 30 min, methyl carbonchloridate (0.88 mL, 6.2 mmol) was added to the mixture at −78° C. The resulting mixture was stirred for another 2 h and then quenched with saturated NH$_4$Cl (10 mL), extracted with ethyl acetate, washed with brine (50 mL), dried over sodium sulfate, then filtered. After removing the organic solvent, the residue was purified by column chromatography (EA/PE=1:10) to obtain the title compound. LC/MS m/z=597.0 [M+Na]+.

Step B: 4-(4-chlorophenyl)-4-(4-(N-((2-(trimethylsilyl)ethoxy)methyl)methylsulfonamido)-1H-indol-1-yl)hex-2-ynoic acid

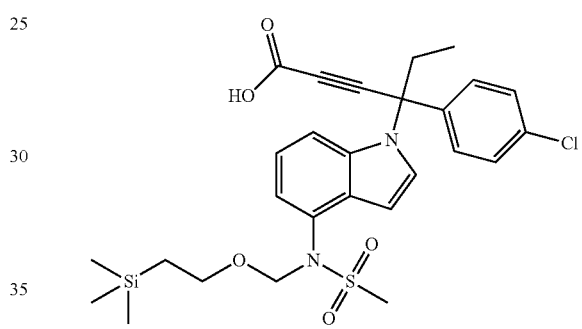

To a solution of the compound from step A (100 mg, 0.17 mmol, enantiomer A) in MeOH (5 mL) was added H$_2$O (1 mL), LiOH (72 mg, 1.7 mmol). The mixture was stirred at RT overnight. After removing the organic solvent, the residue was dissolved with H$_2$O (5 mL) and adjusted to pH=4 with 1M HCl, then extracted with ethyl acetate, and washed with brine (20 mL), dried over dry sodium sulfate, then filtered. The solvent was evaporated to give the title compound. LC/MS m/z=583.0 [M+Na]+.

Step C: 4-(4-chlorophenyl)-4-(4-(N-((2-(trimethylsilyl)ethoxy)methyl)methylsulfonamido)-1H-indol-1-yl)hex-2-ynamide

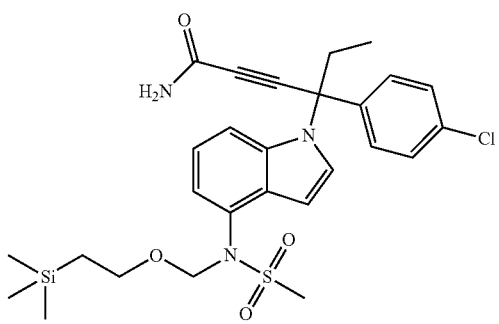 [SMILES: CCC(C#CC(N)=O)(c1ccc(Cl)cc1)n1ccc2c(N(COCC[Si](C)(C)C)S(C)(=O)=O)cccc21]

To a solution of the product from step B (40 mg, 0.071 mmol, enantiomer A) in DMF (5 mL) was added DIPEA (18 mg, 0.142 mmol), HATU (40 mg, 0.11 mmol), NH$_4$Cl (38 mg, 0.71 mmol). The mixture was stirred at RT overnight. After removing the organic solvent, the residue was dissolved with H$_2$O (20 mL), extracted with ethyl acetate, and washed with brine, dried over sodium sulfate, then filtered. The solvent was evaporated and the residue was purified by Prep-TLC (EA/PE=2:1) to obtain the title compound. LC/MS m/z=582.0 [M+Na]$^+$.

mL). The mixture was stirred at 50° C. overnight. The volatile was removed under reduced pressure and the residue was purified by Combiflash (Mobile phase: MeOH/H$_2$O (0.08% of NH$_4$HCO$_3$) to obtain the title compound. LC/MS m/z=412.1 [M+H]$^+$. $^1$H NMR (400 MHz, CDC$_{13}$) δ••7.53 (d, J=3.6 Hz, 1H), 7.33 (d, J=8.8 Hz, 2H), 7.17 (d, J=8.0 Hz, 1H), 7.12 (d, J=8.4 Hz, 2H), 7.01 (t, J=8.0 Hz, 1H), 6.73 (d, J=8.4 Hz, 1H), 6.70 (d, J=3.6 Hz, 1H), 6.62 (br, 1H), 3.04 (s, 3H), 2.80-2.76 (m, 1H), 2.52-2.48 (m, 1H), 1.05 (t, J=7.2 Hz, 3H).

TABLE 53

| Compound Number | IP Rating | Structure | IUPAC Name | LCMS m/z [M + H]$^+$ |
|---|---|---|---|---|
| 155 | A | 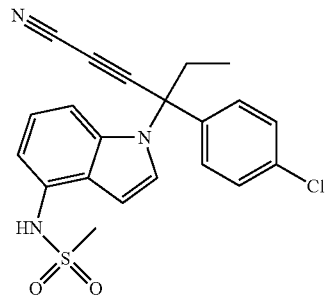 [SMILES: CCC(C#CC#N)(c1ccc(Cl)cc1)n1ccc2c(NS(C)(=O)=O)cccc21] | N-(1-(3-(4-chlorophenyl)-1-cyanopent-1-yn-3-yl)-1H-indol-4-yl)methanesulfonamide (enantiomer) | 412.1 |

Step D: N-(1-(3-(4-chlorophenyl)-1-cyanopent-1-yn-3-yl)-1H-indol-4-yl)-N-((2-(trimethyl silyl)ethoxy)methyl)methanesulfonamide To a solution of the product from step C (20 mg, 0.036 mmol, enantiomer A) in pyridine (5 mL) was added POCl$_3$ (0.05 mL). The mixture was stirred at RT for 2 h. The residue was purified by Combiflash (Mobile phase: MeOH/H$_2$O (0.08% of NH$_4$HCO$_3$) to obtain the title compound. LC/MS m/z=564.0 [M+Na]$^+$.

Step E: N-(1-(3-(4-chlorophenyl)-1-cyanopent-1-yn-3-yl)-1H-indol-4-yl)methanesulfonamide To a solution of the product from step D (15 mg, 0.028 mmol, enantiomer A) in EtOH (2 mL) was added 2N HCl (0.5

Example 36

Methyl 2-(4-chlorophenyl)-4-fluoro-2-(4-(methylsulfonamido)-1H-indol-1-yl)butanoate (Compound 156)

Step A: methyl 2-(4-(tert-butoxycarbonylamino)-1H-indol-1-yl)-2-(4-chlorophenyl)-4-fluorobutanoate

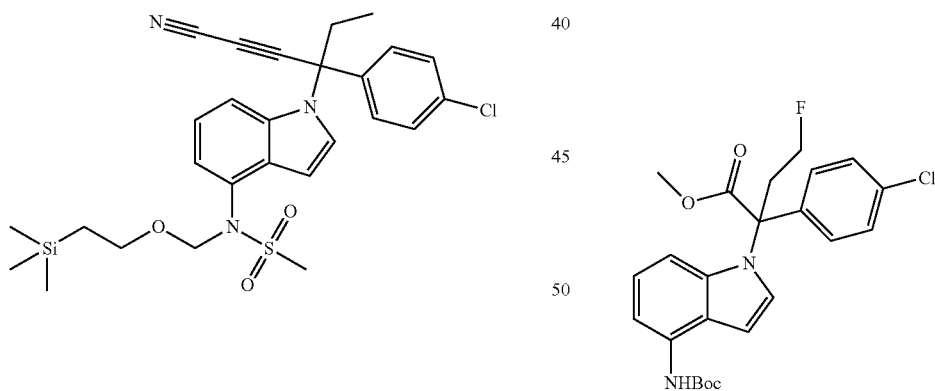

To a suspension of NaH (60% dispersion in mineral oil) (22 mg, 0.55 mmol) in anhydrous DMF (3 mL) under nitrogen atmosphere was added methyl 2-(4-(tert-butoxycarbonylamino)-1H-indol-1-yl)-2-(4-chlorophenyl)acetate (207 mg, 0.5 mmol), as described in Example 2 step B, in anhydrous DMF (2 mL) and the mixture was then stirred at 0° C. for 1 h. To this mixture was added 1-fluoro-2-iodoethane (17.4 mg, 1 mmol), and the mixture was then stirred at room temperature for 4 h. The volatile was evaporated. The residue was purified by silica gel chromatography eluting with PE/EA (10/1 to 3/1, v/v) to afford the title compound as a white solid. LC/MS m/z=405.1[M+H]⁺.

Step B: methyl 2-(4-amino-1H-indol-1-yl)-2-(4-chlorophenyl)-4-fluorobutanoate

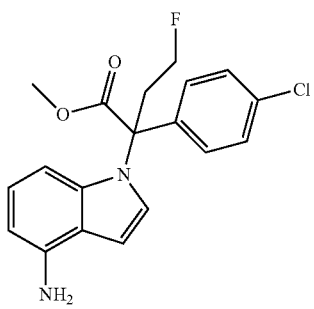 [SMILES: COC(=O)C(CCF)(c1ccc(Cl)cc1)n1ccc2c(N)cccc21]

A mixture of the product from Step A (100 mg, 0.217 mmol) and 4 N HCl/MeOH (10 mL) was stirred at room temperature for 2 h. After removing the solvent, the residue was dried in vacuo to afford the title compound as brown oil. LC/MS m/z=361.1[M+H]⁺.

Step C: methyl 2-(4-chlorophenyl)-4-fluoro-2-(4-(methylsulfonamido)-1H-indol-1-yl)butanoate To a mixture of compound from step B (68 mg, 0.189 mmol) and NMM (38 mg, 0.37 mmol) in DCM (7 mL) was added methylsulfonyl chloride (32 mg, 0.283 mmol) dropwise. Then the mixture was stirred at room temperature for 4 h. The reaction was quenched with saturated ammonium chloride solution, extracted with ethyl acetate (50 mL). The organic layer was washed with brine, dried over sodium sulfate, filtered and evaporated. The residue was purified by silica gel chromatography eluting with PE/EA (10/1 to 3/1, v/v) to afford the title compound as a white solid. LC/MS m/z=439.0[M+H]⁺.

Example 37

5-(1-(4-chlorophenyl)-1-(4-(methylsulfonamido)-1H-indazol-1-yl)propyl)-1,2,4-oxadiazole-3-carboxamide

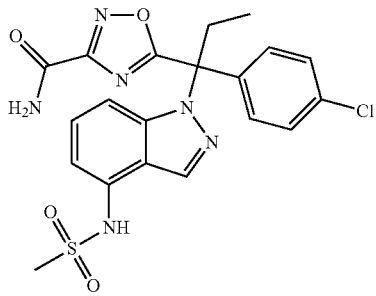 [SMILES: CCC(c1ccc(Cl)cc1)(c1nc(C(N)=O)no1)n1ncc2c(NS(C)(=O)=O)cccc21]

Step A: 2-(4-((tert-butoxycarbonyl)amino)-1H-indazol-1-yl)-2-(4-chlorophenyl)butanoic acid

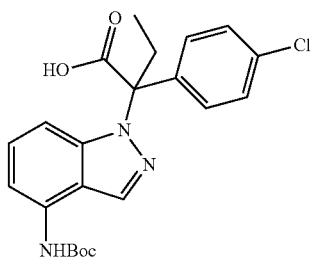 [SMILES: CCC(C(=O)O)(c1ccc(Cl)cc1)n1ncc2c(NC(=O)OC(C)(C)C)cccc21]

Methyl 2-(4-((tert-butoxycarbonyl)amino)-1H-indazol-1-yl)-2-(4-chlorophenyl) butanoate (0.5 g, 1.13 mmol) (enantiomer A intermediate), as described in example 18 step D, as described in Example 18 step D, was dissolved in a mixture of 1,4-dioxane (1.0 mL) and water (0.25 mL) followed by addition of LiOH (0.27 g, 11.26 mmol). The mixture was stirred at 70° C. for 5 hours, then concentrated to remove solvent. The residue was dissolved in water (20 mL) and acidified with 1 N

TABLE 33

| Compound Number | IP Rating | Structure | IUPAC Name | LCMS m/z [M + H]⁺ |
|---|---|---|---|---|
| 156 | A | | methyl 2-(4-chlorophenyl)-4-fluoro-2-(4-(methylsulfonamido)-1H-indol-1-yl)butanoate | 439.0 | aq. HCl solution (11.3 mL) to give white precipitate. The solid was filtered, washed with water, and dried under vacuum to give title compound. LC/MS m/z=430.1[M+H]$^+$.

Step B: ethyl 2-amino-2-(((2-(4-((tert-butoxycarbonyl)amino)-1H-indazol-1-yl)-2-(4-chlorophenyl)butanoyl)oxy)imino)acetate

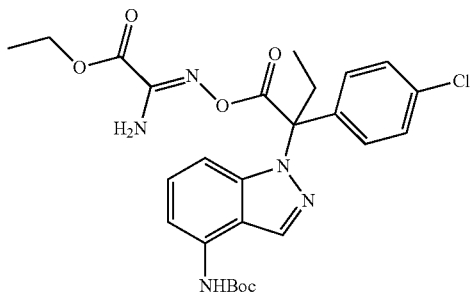 [SMILES: CCOC(=O)/C(N)=N/OC(=O)C(CC)(c1ccc(Cl)cc1)n1ncc2c(NC(=O)OC(C)(C)C)cccc21]

To a suspension of 2-(4-((tert-butoxycarbonyl)amino)-1H-indazol-1-yl)-2-(4-chlorophenyl)butanoic acid from Step A above (0.16 g, 0.37 mmol) in DCM (1.5 mL) was added 1,1'-carbonyldiimdazole (0.13 g, 0.78 mmol) to give a clear solution. The mixture was stirred for 7.5 hours at RT followed by addition of ethyl 2-oximinooxamate (0.13 g, 0.93 mmol). After stirring at RT overnight, the resulting mixture was diluted with EtOAc, washed with saturated NaHCO$_3$ solution, water and brine. The organic layer was separated, and concentrated. The resulting crude product was re-dissolved in a mixture of acetonitrile and water and dried in a lyophilized to give the title compound as light yellow solid. LC/MS m/z=544.1[M+H]$^+$.

Step C: ethyl 5-(1-(4-((tert-butoxycarbonyl)amino)-1H-indazol-1-yl)-1-(4-chlorophenyl)propyl)-1,2,4-oxadiazole-3-carboxylate

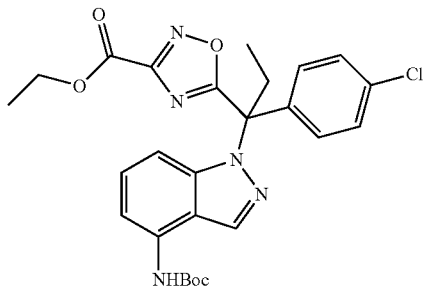 [SMILES: CCOC(=O)c1noc(C(CC)(c2ccc(Cl)cc2)n2ncc3c(NC(=O)OC(C)(C)C)cccc32)n1]

To a solution of the product from Step B above (0.18 g, 0.33 mmol) in pyridine (9.0 mL) was added phosphorus oxychloride (0.25 g, 1.65 mmol). The mixture was heated at 70° C. for 7 hours, and stirred at 35° C. overnight, then concentrated to dryness under reduced pressure. The residue was dissolved in EtOAc and washed with saturated NaHCO$_3$, water and brine. The organic layer was separated and dried over Na$_2$SO$_4$. The crude product was purified on a silica gel column using a gradient of 0-50% ethyl acetate in hexanes to give the title compound as light brown solid. LC/MS m/z=526.1[M+H]$^+$.

Step D: ethyl 5-(1-(4-amino-1H-indazol-1-yl)-1-(4-chlorophenyl)propyl)-1,2,4-oxadiazole-3-carboxylate

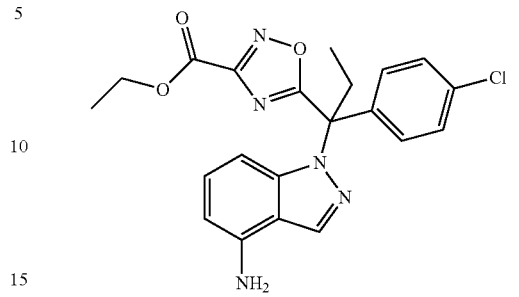

To a solution of the product from Step C above (0.083 g, 0.16 mmol) and anisole (0.068 g, 0.63 mmol) in DCM (1.0 mL) was added TFA (0.18 g, 1.58 mmol). After stirred overnight at RT, the reaction mixture was concentrated to dryness under reduced pressure. The resulting residue was re-dissolved in a mixture of acetonitrile and water followed by addition of 1 N HCl aqueous solution (0.16 mL). The solution was dried in a lyophilized to give crude title compound. LC/MS m/z=426.1[M+H]$^+$.

Step E: ethyl 5-(1-(4-chlorophenyl)-1-(4-(methylsulfonamido)-1H-indazol-1-yl)propyl)-1,2,4-oxadiazole-3-carboxylate

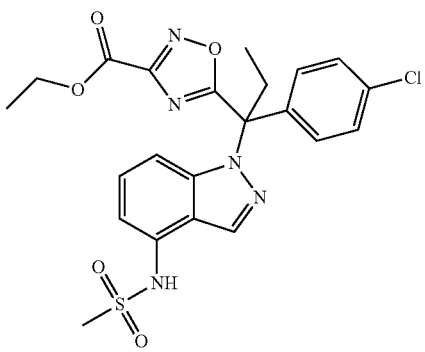 [SMILES: CCOC(=O)c1noc(C(CC)(c2ccc(Cl)cc2)n2ncc3c(NS(C)(=O)=O)cccc32)n1]

To a solution of the product from Step D above (0.080 g, 0.17 mmol) and N-methylmorpholine (0.035 g, 0.35 mmol) in DCM (1.0 mL) was added methanesulfonyl chloride (0.019 g, 0.17 mmol) at 0° C. After stirring at RT for 30 min, the reaction mixture was concentrated under reduced pressure. The resulting residue was diluted with dioxane/water, acidified with TFA, and purified directly on RP-HPLC to give the title compound. LC/MS m/z=504.1[M+H]$^+$.

Step F: 5-(1-(4-chlorophenyl)-1-(4-(methylsulfonamido)-1H-indazol-1-yl)propyl)-1,2,4-oxadiazole-3-carboxamide The product from Step E above (0.015 g, 0.030 mmol) was dissolved in a 7 N solution of ammonia in methanol (2.6 mL). After stirring at RT for 45 min, the resulting mixture was concentrated under reduced pressure. The residue was dissolved in dioxane/water, acidified with TFA, and purified directly on RP-HPLC to give the title compound. LC/MS m/z=475.0[M+H]$^+$. $^1$H NMR (500 MHz, CD$_3$OD): δ (ppm) 8.34 (s, 1H), 7.43 (d, J=8.8 Hz, 2H), 7.37 (d, J=8.8 Hz, 2H), 7.16-7.14 (m, 2H); 6.48-6.45 (m, 1H), 3.20-3.12 (m, 1H), 3.14-3.05 (m, 1H), 3.04 (s, 3H), 0.89 (t, J=7.4 Hz, 3H).

TABLE 34

| Compound Number | IP Rating | Structure | IUPAC Name | LCMS m/z [M + H]+ |
|---|---|---|---|---|
| 157 | B | 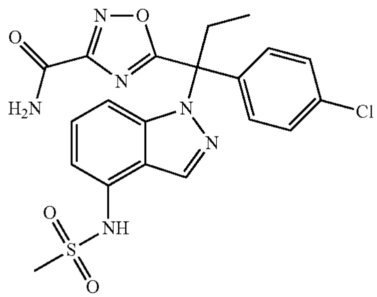 [SMILES: CCC(c1ccc(Cl)cc1)(c1nc(C(N)=O)no1)n1ncc2c(NS(C)(=O)=O)cccc21] | 5-(1-(4-chlorophenyl)-1-(4-(methylsulfonamido)-1H-indazol-1-yl)propyl)-1,2,4-oxadiazole-3-carboxamide (enantiomer) | 475.0 |

Example 38
N-(1-(1-(4-chlorophenyl)-1-(3-cyano-1,2,4-oxadiazol-5-yl)propyl)-1H-indazol-4-yl)methane sulfonamide To a solution of the product from Example 37 step F above (6.8 mg, 0.014 mmol) in pyridine (1.0 mL) was added POCl$_3$ (32.8 mg, 0.28 mmol) at 0° C. After stirring at RT overnight, the reaction mixture was concentrated under reduced pressure. The resulting residue was diluted with dioxane/water, acidified with TFA, and purified directly on RP-HPLC to give the title compound. LC/MS m/z=457.1[M+H]+.

A bottle flask was charged with NaH (580 mg, 14.4 mmol, 60% in oil) and then a solution of methyl 2-(4-(tert-butoxycarbonylamino)-1H-indazol-1-yl)-2-(4-chlorophenyl)acetate (3 g, 7.22 mmol), as described in Example 18 Step C, and 2,2,2-trifluoroethyl trifluoromethanesulfonate (3.35 g, 14.4 mmol) in THF (40 mL) at 0° C. The mixture was stirred for 30 min, quenched with saturated NH$_4$Cl solution (10 mL), extracted with ethyl acetate. The organic layers were washed with brine (15 mL), dried over sodium sulfate, filtered and evaporated. The residue was purified by silica gel chromatography (PE/EA=3:1) to afford the title compound as colorless oil. LC/MS m/z=498.1[M+H]+.

TABLE 35

| Compound Number | IP Rating | Structure | IUPAC Name | LCMS m/z [M + H]+ |
|---|---|---|---|---|
| 158 | A | 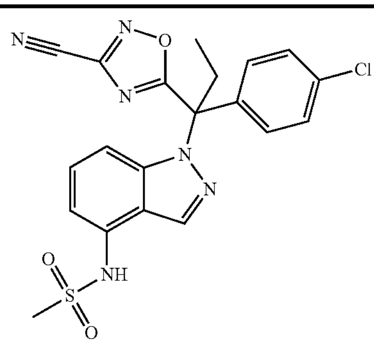 | N-(1-(1-(4-chlorophenyl)-1-(3-cyano-1,2,4-oxadiazol-5-yl)propyl)-1H-indazol-4-yl)methanesulfonamide (enantiomer) | 457.1 |

Example 39
N-(1-(3-(4-chlorophenyl)-1,1,1-trifluoropentan-3-yl)-1H-indazol-4-yl)methanesulfonamide (Compound 159)

Step A: methyl 2-(4-(tert-butoxycarbonylamino)-1H-indazol-1-yl)-2-(4-chlorophenyl)-4,4,4-trifluorobutanoate

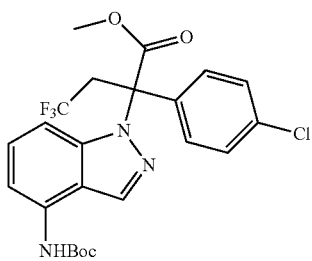 [SMILES: COC(=O)C(CC(F)(F)F)(c1ccc(Cl)cc1)n1ncc2c(NC(=O)OC(C)(C)C)cccc21]

Step B: tert-butyl 1-(2-(4-chlorophenyl)-4,4,4-trifluoro-1-hydroxybutan-2-yl)-1H-indazol-4-ylcarbamate

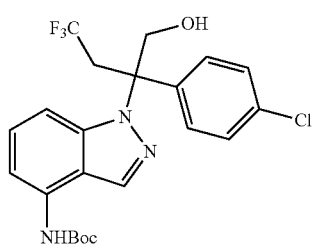 [SMILES: CC(C)(C)OC(=O)Nc1cccc2c1cnn2C(CO)(CC(F)(F)F)c1ccc(Cl)cc1]

To a solution of the product of Step A (300 mg, 0.6 mmol) in THF (5 mL) was added LiAlH₄ (38 mg, 0.96 mmol) at 0° C. The mixture was stirred at RT for 1 h and quenched with H₂O (5 mL), extracted with ethyl acetate, and washed with brine (10 mL), dried over sodium sulfate, then filtered. After the solvent was removed, the residue was purified by silica gel chromatography (EA/PE=1:3) to afford the title compound. LC/MS m/z=470.1[M+H]⁺.

Step C: tert-butyl 1-(2-(4-chlorophenyl)-4,4,4-trifluoro-1-oxobutan-2-yl)-1H-indazol-4-ylcarbamate

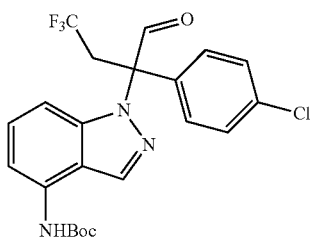 [SMILES: CC(C)(C)OC(=O)Nc1cccc2c1cnn2C(C=O)(CC(F)(F)F)c1ccc(Cl)cc1]

To a solution of the product of Step B (200 mg, 0.42 mmol) in DCM (5 mL) was added Dess-Martin periodinane (350 mg, 0.84 mmol) in portion at room temperature. The mixture was stirred at for 0.5 h, and then diluted with water (5 mL), extracted with ethyl acetate. The organic layers were washed with brine (5 mL), dried over sodium sulfate, filtered and evaporated. The residue was purified by silica gel chromatography (EA/PE=1:8) to afford the title compound. LC/MS m/z=468.2[M+H]⁺.

Step D: tert-butyl 1-(3-(4-chlorophenyl)-5,5,5-trifluoropent-1-yn-3-yl)-1H-indazol-4-ylcarbamate

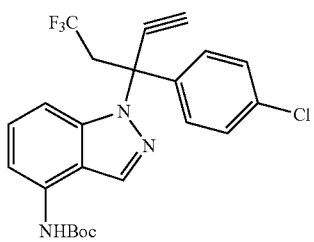 [SMILES: C#CC(CC(F)(F)F)(c1ccc(Cl)cc1)n1ncc2c(NC(=O)OC(C)(C)C)cccc21]

To a solution of the product of Step C (120 mg, 0.25 mmol) in methanol (5 mL) was added K₂CO₃ (69 mg, 0.5 mmol), dimethyl 1-diazo-2-oxopropylphosphonate (96 mg, 0.5 mmol). The mixture was stirred at room temperature for 2 h. After removing the organic solvent, the residue was added H₂O (10 mL), extracted with ethyl acetate, and washed with brine (10 mL), dried over sodium sulfate, then filtered. The organic solvent was evaporated, and the residue was purified by silica gel chromatography (EA/PE=1:8) to obtain the title compound as colorless oil. LC/MS m/z=464.1[M+H]⁺.

Step E: tert-butyl 1-(3-(4-chlorophenyl)-1,1,1-trifluoropentan-3-yl)-1H-indazol-4-ylcarbamate

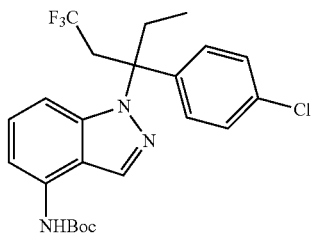 [SMILES: CCC(CC(F)(F)F)(c1ccc(Cl)cc1)n1ncc2c(NC(=O)OC(C)(C)C)cccc21]

To a solution of the product of Step D (100 mg, 0.21 mmol) in ethanol (3 mL) was added PtO₂ (10 mg, 0.044 mmol) at room temperature under H₂ atmosphere for 2 h. The solid was filtered off and filtrate was concentrated in vacuo to obtain the title compound as colorless oil. LC/MS m/z=468.1[M+H]⁺.

Step F: 1-(3-(4-chlorophenyl)-1,1,1-trifluoropentan-3-yl)-1H-indazol-4-amine

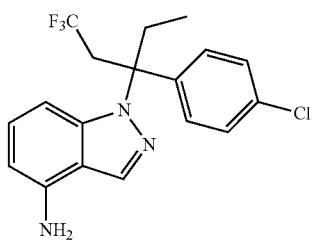 [SMILES: CCC(CC(F)(F)F)(c1ccc(Cl)cc1)n1ncc2c(N)cccc21]

A mixture of the product of Step E (80 mg, 0.17 mmol) and 4 N HCl/MeOH (2 mL) was stirred at room temperature for 2 h. After removing the solvent, the residue was dried in vacuo to give the title compound as colorless oil. LC/MS m/z=368.1 [M+H]⁺.

Step G: N-(1-(3-(4-chlorophenyl)-1,1,1-trifluoropentan-3-yl)-1H-indazol-4-yl)methane sulfonamide To a mixture of the product of Step F (50 mg, 0.13 mmol) and NMM (31 mg, 0.3 mmol) in DCM (3 mL) was added methanesulfonyl chloride (20 mg, 0.21 mmol). The mixture was stirred at room temperature for 3 h, then quenched with saturated ammonium chloride solution (10 mL), and extracted with ethyl acetate. The organic layers were washed with brine (10 mL), dried over sodium sulfate, filtered and evaporated. The residue was purified by Pre-HPLC (Mobile phase: acetonitrile/water (0.03% TFA)) to afford the title compound. LC/MS m/z=446.1[M+H]⁺.

TABLE 36

| Compound Number | IP Rating | Structure | IUPAC Name | LCMS m/z [M + H]+ |
|---|---|---|---|---|
| 159 | A | (structure shown) | N-(1-(3-(4-chlorophenyl)-1,1,1-trifluoropentan-3-yl)-1H-indazol-4-yl)methanesulfonamide | 446.1 |

Example 40

N-(1-(3-(4-Chlorophenyl)-1-hydroxypentan-3-yl)-1H-indol-4-yl)methanesulfonamide

Step A: 4-tert-butyl 1-methyl 2-(4-(tert-butoxycarbonylamino)-1H-indol-1-yl)-2-(4-chlorophenyl)succinate

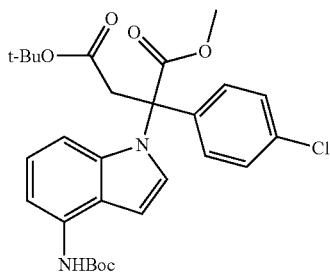 [SMILES: COC(=O)C(CC(=O)OC(C)(C)C)(c1ccc(Cl)cc1)n1ccc2c(NC(=O)OC(C)(C)C)cccc21]

A solution of methyl 2-(4-(tert-butoxycarbonylamino)-1H-indazol-1-yl)-2-(4-chlorophenyl)acetate (2 g, 4.83 mmol), as described in Example 2 Step B, and tert-butyl 2-bromoacetate (1.4 g, 7.25 mmol) in THF (10 mL) was added to NaH (290 mg, 7.25 mmol, 60% in oil) dropwise at 0° C. and stirred for 30 min. The mixture was quenched with saturated NH$_4$Cl solution, and extracted with ethyl acetate. The organic layer was washed with brine (20 mL), dried over sodium sulfate, filtered and evaporated. The residue was purified by silica gel chromatography (PE:EA=3:1) to afford the title compound. LC/MS m/z=529.2[M+H]+.

Step B: 4-tert-butoxy-2-(4-(tert-butoxycarbonylamino)-1H-indol-1-yl)-2-(4-chlorophenyl)-4-oxobutanoic acid

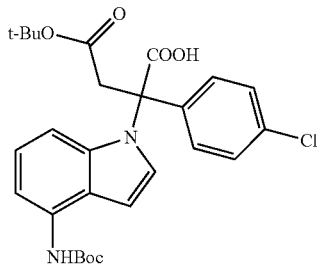 [SMILES: CC(C)(C)OC(=O)CC(C(=O)O)(c1ccc(Cl)cc1)n1ccc2c(NC(=O)OC(C)(C)C)cccc21]

A mixture of the product of step A (1.8 g, 3.4 mmol) and 3 N LiOH (410 mg, 17 mmol) was stirred at room temperature for 3 h. After the solvent was evaporated, the residue was dissolved in ethyl acetate (20 mL), and pH value adjusted to 6-7 with 1 M HCl. The organic layer was washed with brine, dried over sodium sulfate, filtered and concentrated in vacuo to give the title compound as colorless oil. LC/MS m/z=515.2 [M+H]+.

Step C: tert-Butyl 3-(4-(tert-butoxycarbonylamino)-1H-indol-1-yl)-3-(4-chlorophenyl)-4-hydroxybutanoate

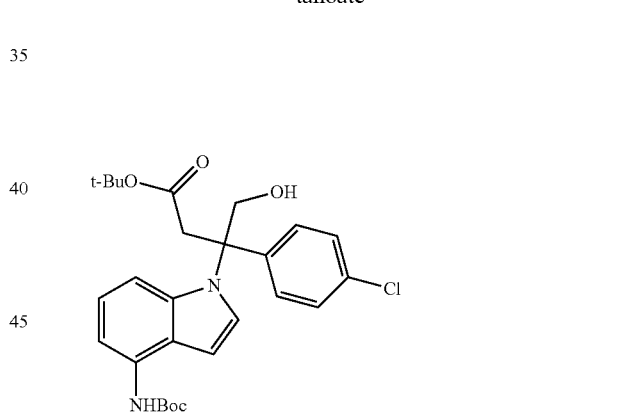

To a mixture of the product of step B (1.5 g, 2.9 mmol) and NMM (590 mg, 5.83 mmol) in DME (15 mL) was added isobutyl carbonochloridate (793 mg, 5.83 mmol) dropwise at 0° C. After stirring for 30 min. NaBH$_4$ was added to the mixture at 0° C. The resulting mixture was stirred at room temperature for another 1 h, and then quenched with saturated ammonium chloride solution (10 mL), extracted with ethyl acetate. The organic layers were washed with brine (10 mL), dried over sodium sulfate, filtered and evaporated. The residue was purified by silica gel chromatography (PE:EA=3:1) to afford the title compound as colorless oil. LC/MS m/z=501.2[M+H]+.

Step D: tert-butyl 3-(4-(tert-butoxycarbonylamino)-1H-indol-1-yl)-3-(4-chlorophenyl)-4-oxobutanoate

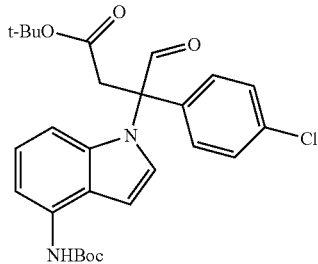 [SMILES: CC(C)(C)OC(=O)CC(C=O)(c1ccc(Cl)cc1)n1ccc2c(NC(=O)OC(C)(C)C)cccc21]

To a solution of the product of Step C (1.2 g, 2.4 mmol) in DCM (10 mL) was added Dess-Martin periodinane (2.03 g, 4.8 mmol) in portion at room temperature. After stirring for 0.5 h, the mixture was diluted with water (15 mL), extracted with ethyl acetate. The organic layers were washed with brine (10 mL), dried over sodium sulfate, filtered and evaporated. The residue was purified by silica gel chromatography (EA/PE=1:8) to afford the title compound. LC/MS m/z=499.2[M+H]$^+$.

Step E: tert-Butyl 3-(4-(tert-Butoxycarbonylamino)-1H-indol-1-yl)-3-(4-chlorophenyl)pent-4-ynoate

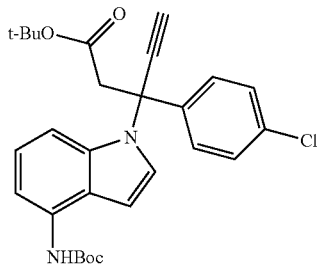 [SMILES: C#CC(CC(=O)OC(C)(C)C)(c1ccc(Cl)cc1)n1ccc2c(NC(=O)OC(C)(C)C)cccc21]

To a solution of the product of Step D (750 mg, 1.5 mmol) in MeOH (10 mL) was added K$_2$CO$_3$ (414 mg, 3 mmol) and dimethyl 1-diazo-2-oxopropylphosphonate (576 mg, 3 mmol). The mixture was stirred at room temperature for 2 h. After removing the organic solvent, the residue was added H$_2$O (10 mL), extracted with ethyl acetate, and washed with brine (10 mL), dried over sodium sulfate, then filtered. The solvent was evaporated in vacuo, and the residue was purified by silica gel chromatography (EA/PE=1:8) to obtain the title compound as colorless solid. LC/MS m/z=495.2[M+H]$^+$.

Step F: tert-Butyl 3-(4-(tert-butoxycarbonylamino)-1H-indol-1-yl)-3-(4-chlorophenyl)pentanoate

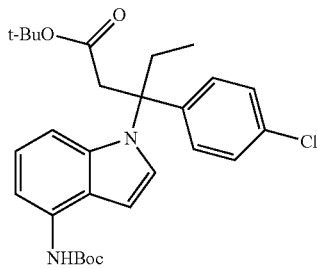 [SMILES: CCC(CC(=O)OC(C)(C)C)(c1ccc(Cl)cc1)n1ccc2c(NC(=O)OC(C)(C)C)cccc21]

To a solution of the product of Step E (150 mg, 0.3 mmol) in ethanol (3 mL) was added PtO$_2$ (6.8 mg, 0.03 mmol) at room temperature under H$_2$ atmosphere for 2 h. The solid was filtered off and the filtrate was concentrated in vacuo to give the title compound as colorless oil. LC/MS m/z=499.2[M+H]$^+$.

Step G: Methyl 3-(4-amino-1H-indol-1-yl)-3-(4-chlorophenyl)pentanoate

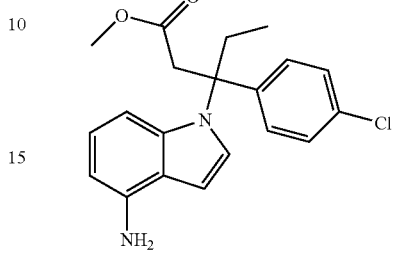

A mixture of the product of Step F (120 mg, 0.24 mmol) and 4 N HCl/MeOH (2 mL) was stirred at room temperature for 2 h. The volatile was removed in vacuo to give the title compound as colorless oil. LC/MS m/z=357.1[M+H]$^+$.

Step H: Methyl 3-(4-chlorophenyl)-3-(4-(methylsulfonamido)-1H-indol-1-yl)pentanoate

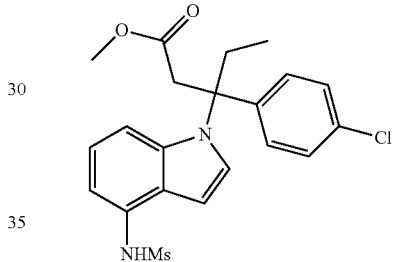

To a mixture of the product of Step G (75 mg, 0.21 mmol) and NMM (42 mg, 0.42 mmol) in DCM (3 mL) was added methanesulfonyl chloride (36 mg, 0.38 mmol). Then the mixture was stirred at room temperature for 3 h, quenched with saturated ammonium chloride solution, and extracted with ethyl acetate. The organic layers were washed with brine (10 mL), dried over sodium sulfate, filtered and evaporated. The residue was purified by silica gel chromatography (PE/EA=3/1) to afford the title compound as colorless oil. LC/MS m/z=435.1[M+H]$^+$.

Step I: N-(1-(3-(4-Chlorophenyl)-1-hydroxypentan-3-yl)-1H-indol-4-yl)methanesulfonamide To a solution of the product of Step H (60 mg, 0.138 mmol) in THF (5 mL) was added LiAlH$_4$ (10.4 mg, 0.276 mmol) at 0° C. The mixture was stirred for 1 h and quenched with H$_2$O (2 mL), extracted with ethyl acetate, and washed with brine (5 mL), dried over sodium sulfate, then filtered. After removing the organic solvent, the residue was purified by silica gel chromatography (EA/PE=1:3) to afford the title racemic compound. The racemic compound was submitted to chiral SFC separation using AS-H column (50% EtOH/CO$_2$, 4.6× 250 mm, 39.3° C.) to give two separated enantiomers. LC/MS m/z=406.9[M+H]$^+$.

Compound 160 and compound 161 were obtained by the below chiral separation conditions:
Column: AS-H
Mobile phase: A: CO$_2$, B: MeOH (0.1% DEA), A:B=55:45 at 3.0 mL/min
Column Temp: 40.2° C.

TABLE 37

| Compound Number | IP Rating | Structure | IUPAC Name | LCMS m/z [M + H]+ |
|---|---|---|---|---|
| 160 | A | 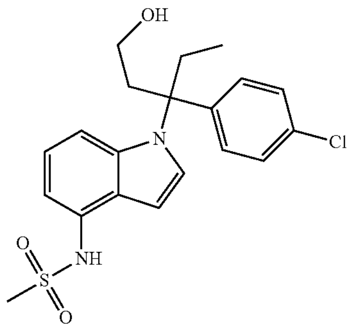 [SMILES: CCC(CCO)(c1ccc(Cl)cc1)n1ccc2c(NS(C)(=O)=O)cccc21] | N-(1-(3-(4-Chlorophenyl)-1-hydroxypentan-3-yl)-1H-indol-4-yl)methanesulfonamide (Enantiomer A, r.t. = 2.67 min) | 406.9 |
| 161 | A | 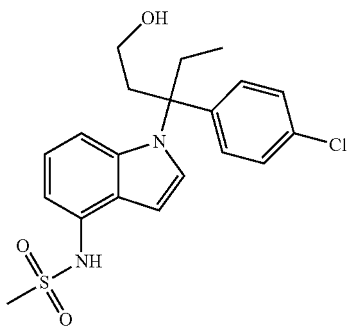 [SMILES: CCC(CCO)(c1ccc(Cl)cc1)n1ccc2c(NS(C)(=O)=O)cccc21] | N-(1-(3-(4-Chlorophenyl)-1-hydroxypentan-3-yl)-1H-indol-4-yl)methanesulfonamide (Enantiomer B, r.t. = 3.22 min) | 406.9 |

Example 41

N-(1-(3-(4-chlorophenyl)-1-fluoropentan-3-yl)-1H-indol-4-yl)methanesulfonamide

Step A: N-(1-(3-(4-Chlorophenyl)-1-fluoropentan-3-yl)-1H-indol-4-yl)methanesulfonamide To a solution of N-(1-(3-(4-chlorophenyl)-1-hydroxypentan-3-yl)-1H-indol-4-yl)methanesulfonamide (20 mg, 0.05 mmol), as described in Example 40 Step I, in DCM (5 mL) was added DAST (16 mg, 0.1 mmol) at 0° C. The mixture was stirred for 1 h, then quenched with saturated aqueous ammonium chloride (5 mL) and extracted with ethyl acetate. The combined organics were washed with water (5 mL) and brine (5 mL), dried over MgSO$_4$, filtered and concentrated. The resulting crude product was purified by Pre-HPLC (Mobile phase: acetonitrile/water (0.03% TFA)) to afford the title racemic compound as a white solid. The racemic compound was submitted to chiral SFC separation using IC (30% MeOH (0.1% DEA)/CO$_2$, 4.6×250 mm, 41° C.) to give two separated enantiomers. LC/MS m/z=409.1 [M+H]+.

Compound 162 and compound 163 were obtained by following the below chiral separation conditions:
Column: IC
Mobile phase: A: CO$_2$, B: MeOH (0.1% EDA), A:B=70:30 at 3.0 mL/min
Column Temp: 39.1° C.

TABLE 38

| Compound Number | IP Rating | Structure | IUPAC Name | LCMS m/z [M + H]+ |
|---|---|---|---|---|
| 162 | A | 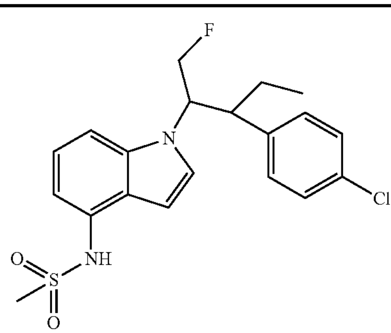 | N-(1-(3-(4-Chlorophenyl)-1-fluoropentan-3-yl)-1H-indol-4-yl)methanesulfonamide (Enantiomer A, r.t. = 3.5 min) | 409.1 |

TABLE 38-continued

| Compound Number | IP Rating | Structure | IUPAC Name | LCMS m/z [M + H]+ |
|---|---|---|---|---|
| 163 | A | 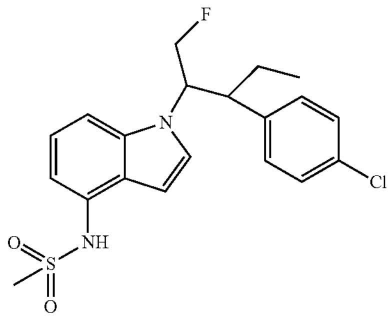 [SMILES: CCC(c1ccc(Cl)cc1)C(CF)n1ccc2c(NS(C)(=O)=O)cccc21] | N-(1-(3-(4-Chlorophenyl)-1-fluoropentan-3-yl)-1H-indol-4-yl)methanesulfonamide (Enantiomer B, r.t. = 4.16 min) | 409.1 |

Example 42

3-(4-Chlorophenyl)-3-(4-(methylsulfonamido)-1H-indol-1-yl)pentyl methanesulfonate (Compound 164)

Step A: 3-(4-Chlorophenyl)-3-(4-(methylsulfonamido)-1H-indol-1-yl)pentyl methanesulfonate To a mixture of N-(1-(3-(4-chlorophenyl)-1-hydroxypentan-3-yl)-1H-indol-4-yl)methanesulfonamide (20 mg, 0.05 mmol), as described in Example 40 Step I, and NMM (10 mg, 0.1 mmol) in DCM (3 mL) was added methanesulfonyl chloride (7 mg, 0.06 mmol). Then the mixture was stirred at room temperature for 1 h, quenched with saturated ammonium chloride solution (5 mL), and extracted with ethyl acetate. The organic layers were washed with brine (5 mL), dried over sodium sulfate, filtered and evaporated. The residue was purified by Prep-TLC (PE/EA=4/1) to afford the title compound as colorless oil. LC/MS m/z=485.1[M+H]+.

Example 43

N-(1-(3-(4-Chlorophenyl)-1-methoxypentan-3-yl)-1H-indol-4-yl)methanesulfonamide (Compound 165)

Step A: N-(1-(3-(4-Chlorophenyl)-1-methoxypentan-3-yl)-1H-indol-4-yl)methanesulfonamide To a mixture of 3-(4-chlorophenyl)-3-(4-(methylsulfonamido)-1H-indol-1-yl)pentyl methanesulfonate (10 mg, 0.02 mmol), as described in Example 40 Step I, in methanol (2 mL) was added $CH_3ONa$ (21 mg, 0.4 mmol) at room temperature. Then the mixture was heated to 40° C. for 2 h. The solution was quenched with saturated ammonium chloride solution (10 mL), and extracted with ethyl acetate. The organic layers were washed with brine, dried over sodium sulfate, filtered and evaporated. The residue was purified by Prep-HPLC (Mobile phase: acetonitrile/water (0.03% TFA)) to afford the title compound as a white solid. LC/MS m/z=421.1[M+H]+.

Following the same procedure for the preparation of EXAMPLE 43, but using sodium methanethiolate, Compound 166 of Table 40 was obtained.

TABLE 39

| Compound Number | IP Rating | Structure | IUPAC Name | LCMS m/z [M + H]+ |
|---|---|---|---|---|
| 164 | A | 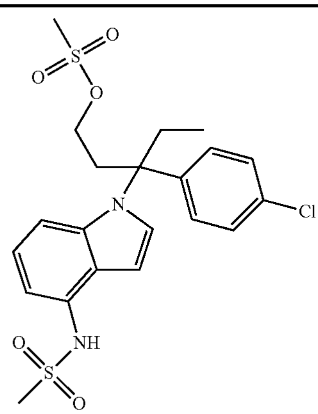 | 3-(4-Chlorophenyl)-3-(4-(methylsulfonamido)-1H-indol-1-yl)pentyl methanesulfonate | 485.1 |

TABLE 40

| Compound Number | IP Rating | Structure | IUPAC Name | LCMS m/z [M + H]+ |
|---|---|---|---|---|
| 165 | A | 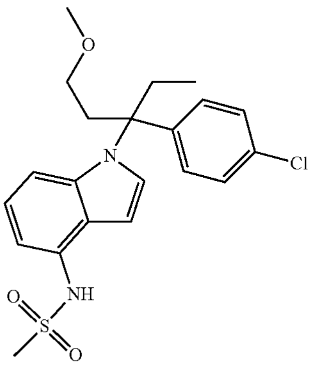 [SMILES: CCC(CCOC)(c1ccc(Cl)cc1)n1ccc2c(NS(C)(=O)=O)cccc21] | N-(1-(3-(4-Chlorophenyl)-1-methoxypentan-3-yl)-1H-indol-4-yl)methanesulfonamide | 421.1 |
| 166 | A | 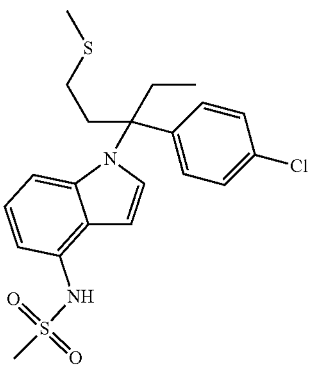 [SMILES: CCC(CCSC)(c1ccc(Cl)cc1)n1ccc2c(NS(C)(=O)=O)cccc21] | N-(1-(3-(4-chlorophenyl)-1-(methylthio)pentan-3-yl)-1H-indol-4-yl)methanesulfonamide | 437.1 |

Example 44

Methyl 4-(4-chlorophenyl)-4-(4-(methylsulfonamido)-1H-indol-1-yl)hexanoate (Compound 167)

Step A: tert-butyl 1-(3-(4-chlorophenyl)pent-1-yn-3-yl)-1H-indol-4-ylcarbamate

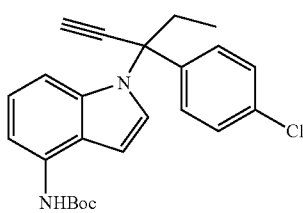 [SMILES: C#CC(CC)(c1ccc(Cl)cc1)n1ccc2c(NC(=O)OC(C)(C)C)cccc21]

To a mixture of tert-butyl (1-(2-(4-chlorophenyl)-1-oxobutan-2-yl)-1H-indol-4-yl)carbamate (412 mg, 1 mmol), as described in Example 21 Step B, and K$_2$CO$_3$ (276 mg, 2 mmol) in methanol (10 mL) was added dimethyl 1-diazo-2-oxopropylphosphonate (230 mg, 1.2 mmol) at room temperature. The mixture was stirred for 2 h and the solid was filtered off and the filtrate was concentrated under reduced pressure. The crude product was purified by silica gel chromatography eluting with PE/EA (20/1 to 10/1, v/v) to give the title compound as colorless amorphous solid. LC/MS m/z= 352.9[M-$^t$Bu+H]$^+$.

Step B: methyl 4-(4-(tert-butoxycarbonylamino)-1H-indol-1-yl)-4-(4-chlorophenyl)hex-2-ynoate

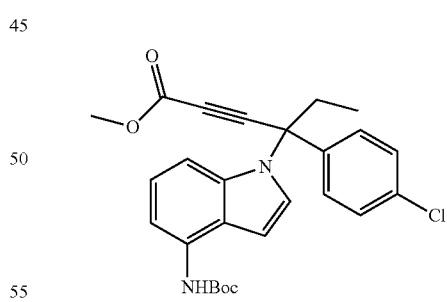

To a solution of the product of Step A (436.5 mg, 1.07 mmol) in tetrahydrofuran (10 mL) was added BuLi (0.9 mL, 2.25 mmol, 2.5 M in hexane) at −78° C. After stirring at −78° C. for 30 min, methyl carbonchloridate (121 mg, 1.28 mmol) was added to the mixture. The resulting mixture was stirred for another 1 h, then quenched with aqueous NH$_4$Cl (10 mL) and extracted with ethyl acetate. The combined organic layers were washed with brine (15 mL), dried over Na$_2$SO$_4$, filtered and concentrated. The crude product was purified by silica gel chromatography eluting with PE/EA (20/1 to 10/1, v/v) to give the title compound as a colorless amorphous solid. LC/MS m/z=410.9[M-$^t$Bu+H]$^+$.

Step C: methyl 4-(4-(tert-butoxycarbonylamino)-1H-indol-1-yl)-4-(4-chlorophenyl)hexanoate

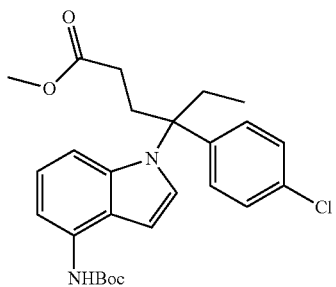 [SMILES: CCC(CCC(=O)OC)(c1ccc(Cl)cc1)n1ccc2c(NC(=O)OC(C)(C)C)cccc21]

A mixture of the product of Step B (200 mg, 0.43 mmol), PtO$_2$ (10 mg, 0.043 mmol) and methanol (2 mL) was degassed three times and backfilled with hydrogen. The mixture was stirred at room temperature for 2 h under hydrogen atmosphere. The solid was filtered off and the filtrate was concentrated in vacuo to give the title compound as colorless oil. LC/MS m/z=414.9[M-$^t$Bu+H]$^+$.

Step D: methyl 4-(4-amino-1H-indol-1-yl)-4-(4-chlorophenyl)hexanoate

A mixture of the product of Step C (190 mg, 0.4 mmol) and MeOH/HCl (2 mL, 4 M) was stirred at room temperature for 2 h. The volatile was removed in vacuo to give the title compound as colorless oil. LC/MS m/z=371.1[M+H]$^+$.

Step E: methyl 4-(4-amino-1H-indol-1-yl)-4-(4-chlorophenyl)hexanoate

To a solution of the product of Step D (100 mg, 0.27 mmol) and N-methylmorpholine (41 mg, 0.4 mmol) in dichloromethane (3 mL) was added methanesulfonyl chloride (40 mg, 0.35 mmol) at room temperature. The mixture was stirred for 2 h, then diluted with water (15 mL) and extracted with ethyl acetate. The combined organic layers were washed with brine (10 mL), dried over Na$_2$SO$_4$, filtered and concentrated. The crude product was purified by PREP-TLC eluting with PE/EA (4/1, v/v) to give the title compound as a colorless amorphous solid. LC/MS m/z=471.0[M+Na]$^+$.

Following the same procedure for the preparation of EXAMPLE 44, but in step A, using tert-butyl (1-(2-(4-chlorophenyl)-1-oxobutan-2-yl)-1H-indazol-4-yl)carbamate, compound 168 of Table 41 was obtained.

TABLE 41

| Compound Number | IP Rating | Structure | IUPAC Name | LCMS m/z [M + H]$^+$ |
|---|---|---|---|---|
| 167 | A | 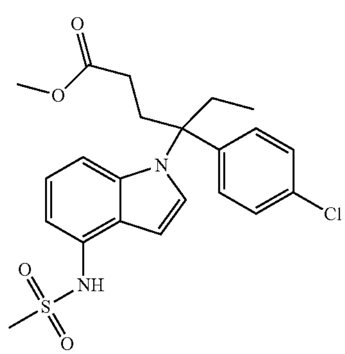 | methyl 4-(4-amino-1H-indol-1-yl)-4-(4-chlorophenyl)hexanoate | 449.1 |

TABLE 41-continued

| Compound Number | IP Rating | Structure | IUPAC Name | LCMS m/z [M + H]+ |
|---|---|---|---|---|
| 168 | A | 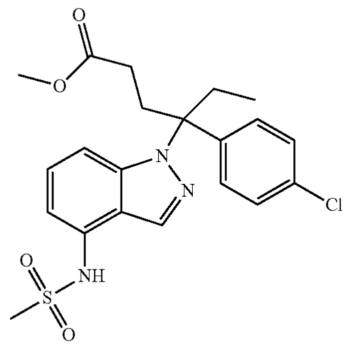 [SMILES: CCC(CCC(=O)OC)(c1ccc(Cl)cc1)n1ncc2c(NS(C)(=O)=O)cccc21] | methyl 4-(4-chlorophenyl)-4-(4-(methylsulfonamido)-1H-indazol-1-yl)hexanoate | 450.1 |

Example 45

N-(1-(3-(4-chlorophenyl)-6-hydroxyhexan-3-yl)-1H-indol-4-yl)methanesulfonamide

Step A: N-(1-(3-(4-chlorophenyl)-6-hydroxyhexan-3-yl)-1H-indol-4-yl)methanesulfonamide To a solution of methyl 4-(4-chlorophenyl)-4-(4-(methylsulfonamido)-1H-indol-1-yl)hexanoate (20 mg, 0.045 mmol), as described in Example 44 Step E, in tetrahydrofuran (2 mL) was added lithium aluminium hydride (2.5 mg, 0.0675 mmol) at 0° C. The mixture was gradually warmed to room temperature and stirred for 4 h. Water (1 mL) was carefully added to the reaction mixture, and extracted with ethyl acetate. The combined organic layers were washed with brine (30 mL), dried over anhydrous sodium sulfate, filtered and concentrated. The crude product was purified by PREP-TLC eluting with PE/EA (2/1, v/v) to give the title compound as colorless oil. LC/MS m/z=421.0[M+H]+.

Compound 169 was obtained by the below chiral separation conditions:

Column: OD-H

Mobile phase: A: $CO_2$, B: MeOH, A:B=70:30 at 3.0 mL/min

Column Temp: 39.9° C.

TABLE 42

| Compound Number | IP Rating | Structure | IUPAC Name | LCMS m/z [M + H]+ |
|---|---|---|---|---|
| 169 | A | 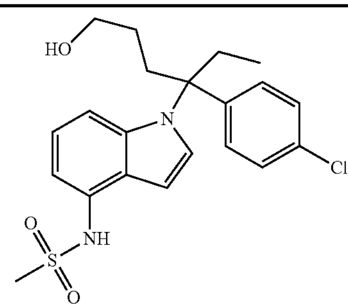 | N-(1-(3-(4-chlorophenyl)-6-hydroxyhexan-3-yl)-1H-indol-4-yl)methanesulfonamide (enantiomer A, r.t. = 3.49 min) | 421.0 |

Example 46

N-(1-(3-(4-chlorophenyl)-6-fluorohexan-3-yl)-1H-indol-4-yl)methanesulfonamide (Compound 170)

Step A: N-(1-(3-(4-chlorophenyl)-6-fluorohexan-3-yl)-1H-indol-4-yl)methanesulfonamide To a solution of N-(1-(3-(4-chlorophenyl)-6-hydroxyhexan-3-yl)-1H-indol-4-yl)methanesulfonamide (21 mg, 0.05 mmol), as described in Example 45 Step A, in dichloromethane (2 mL) was added DAST (16 mg, 0.1 mmol) at −78° C. The mixture was gradually warmed to room temperature and stirred for 3 h, then quenched with methanol (0.5 mL). The crude product was purified by PREP-TLC eluting with PE/EA (2/1, v/v) to obtain the title compound as colorless oil. LC/MS m/z=444.7[M+Na]+.

TABLE 43

| Compound Number | IP Rating | Structure | IUPAC Name | LCMS m/z [M + Na]+ |
|---|---|---|---|---|
| 170 | A | 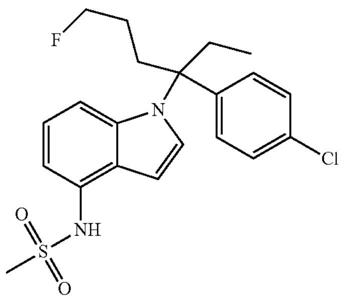 [SMILES: CCC(CCCF)(c1ccc(Cl)cc1)n1ccc2c(NS(C)(=O)=O)cccc21] | N-(1-(3-(4-chlorophenyl)-6-fluorohexan-3-yl)-1H-indol-4-yl)methanesulfonamide | 444.7 |

Example 47

(E)-methyl 4-(4-chlorophenyl)-4-(4-(methylsulfonamido)-1H-indazol-1-yl)hex-2-enoate (Compound 171)

Step A: (E)-methyl 4-(4-amino-1H-indazol-1-yl)-4-(4-chlorophenyl)hex-2-enoate

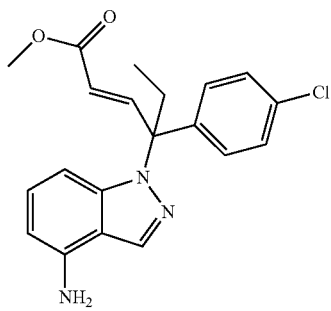 [SMILES: CCC(/C=C/C(=O)OC)(c1ccc(Cl)cc1)n1ncc2c(N)cccc21]

A mixture of methyl (E)-tert-butyl 1-(3-(4-chlorophenyl)-1-cyanopent-1-en-3-yl)-1H-indazol-4-ylcarbamate (500 mg), as described in Example 22 Step A, in 15 mL of 4 N HCl/MeOH was stirred at room temperature for 1 h. Then the solvent was removed. The residue was dissolved in EA (30 mL) and pH value was adjusted to 9~10 with saturated aq. NaHCO$_3$. The organic layer was washed with water (10 mL), brine, dried (Na$_2$SO$_4$) and concentrated. The residue was purified on revered—phase HPLC (0.05% NH$_4$HCO$_3$ in H$_2$O-MeCN) to give the title product as a pale brown solid. LC/MS m/z=370.2[M+H]+.

Step B: (E)-methyl 4-(4-chlorophenyl)-4-(4-(methylsulfonamido)-1H-indazol-1-yl)hex-2-enoate To a mixture of (E)-methyl 4-(4-amino-1H-indazol-1-yl)-4-(4-chlorophenyl)hex-2-enoate (120 mg) and NMM (98 mg) in DCM (5 mL) was added MsCl (45 mg). Then the mixture was stirred at room temperature for 2 h. The solution was quenched with saturated NH$_4$Cl solution, and extracted with ethyl acetate (30 mL). The organic layer was washed with brine, dried over dry sodium sulfate, filtered and evaporated. The residue was purified by silica gel chromatography (PE/EA=5/1) to afford the title compound as a pale yellow solid. LC/MS m/z=448.2[M+H]+.

TABLE 44

| Compound Number | IP Rating | Structure | IUPAC Name | LCMS m/z [M + H]+ |
|---|---|---|---|---|
| 171 | B | 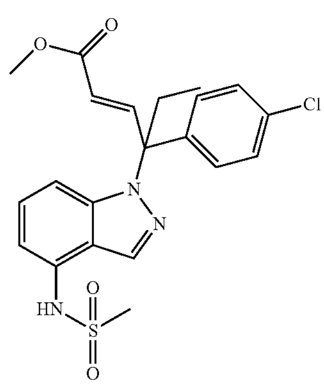 [SMILES: CCC(/C=C/C(=O)OC)(c1ccc(Cl)cc1)n1ncc2c(NS(C)(=O)=O)cccc21] | (E)-methyl 4-(4-chlorophenyl)-4-(4-(methylsulfonamido)-1H-indazol-1-yl)hex-2-enoate | 448.2 |

Example 48

N-(1-(3-(4-chlorophenyl)-6-oxoheptan-3-yl)-1H-indazol-4-yl)methanesulfonamide (Compound 172)

Step A: N-(1-(3-(4-chlorophenyl)-6-oxoheptan-3-yl)-1H-indazol-4-yl)methanesulfonamide A mixture of methyl 4-(4-chlorophenyl)-4-(4-(methylsulfonamido)-1H-indazol-1-yl)hexanoate (50 mg), as described in Example 44 Step E, in 2 mL of anhydrous THF was added CH$_3$Li (1.5 M in ether, 0.2 mL) dropwise at 0° C. and stirred for 30 min. The solution was quenched with saturated NH$_4$Cl solution, and extracted with ethyl acetate (20 mL). The organic layer was washed with brine, dried over dry sodium sulfate, filtered and evaporated. The residue was purified on revered—phase HPLC (0.05% TFA in H$_2$O-MeCN) to give the title product as a white solid. LC/MS m/z=434.1 [M+H]$^+$.

washed with brine (15 mL), dried over sodium sulfate, filtered and evaporated. The residue was purified by silica gel chromatography with PE/EA (10/1 to 3/1, v/v) to afford the title compound as a colorless solid. LC/MS m/z=448.9[M+Na]$^+$.

Step B: 3-(4-amino-1H-indol-1-yl)-3-(4-chlorophenyl)-1-methoxypentan-2-ol

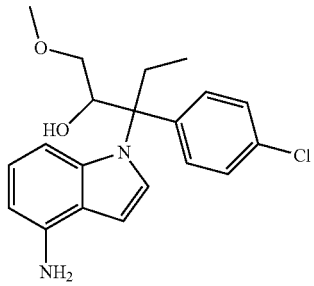

TABLE 45

| Compound Number | IP Rating | Structure | IUPAC Name | LCMS m/z [M + H]$^+$ |
|---|---|---|---|---|
| 172 | A | 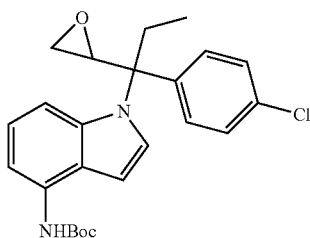 [SMILES: CCC(c1ccc(Cl)cc1)(C1CO1)n1ccc2c(NC(=O)OC(C)(C)C)cccc21] | N-(1-(3-(4-chlorophenyl)-6-oxoheptan-3-yl)-1H-indazol-4-yl)methanesulfonamide | 434.1 |

Example 49

N-(1-(3-(4-chlorophenyl)-2-hydroxy-1-methoxypentan-3-yl)-1H-indol-4-yl)methanesulfonamide (Compound 173)

Step A: tert-butyl (1-(1-(4-chlorophenyl)-1-(oxiran-2-yl)propyl)-1H-indol-4-yl)carbamate To a solution of NaH (41 mg, 0.764 mmol, 60% in oil) in DMSO (15 mL) at 0° C. was added trimethylsulfoxonium iodide (235 mg, 1.07 mmol) divided into several portions. The mixture was stirred at room temperature until the mixture became clear. To the solution of tert-butyl 1-(2-(4-chlorophenyl)-1-oxobutan-2-yl)-1H-indol-4-ylcarbamate (210 mg, 0.509 mmol), as described in Example 21 Step B, in THF (15 mL) was added the upper solution dropwise at 0° C. Then the mixture was stirred at room temperature for 2 h. The reaction was quenched with saturated ammonium chloride solution, and extracted with ethyl acetate. The organic layer was To a solution of the product from Step A (60 mg, 0.140 mmol) in MeOH (3 mL) was added MeONa (15 mg, 0.281 mmol). The mixture was stirred at 120° C. under microwave for 0.5 h. The solution was removed and the residue was purified by PREP-TLC eluting with PE/EA (1/1, v/v) to give the title compound as a colorless amorphous solid. LC/MS m/z=359.1[M+H]$^+$.

Step C: N-(1-(3-(4-chlorophenyl)-2-hydroxy-1-methoxypentan-3-yl)-1H-indol-4-yl)methane sulfonamide To the mixture of the product from Step B (39 mg, 0.108 mmol) and NMM (22 mg, 0.216 mmol) in DCM (8 mL) was added methylsulfonyl chloride (18 mg, 0.163 mmol) dropwise. Then the mixture was stirred at room temperature overnight. The reaction was quenched with saturated ammonium chloride solution, and extracted with ethyl acetate (10 mL). The organic layer was washed with brine, dried over sodium sulfate, filtered and evaporated. The residue was purified by PREP-TLC eluting with PE/EA (1/1, v/v) to get the title compound as a colorless amorphous solid. LC/MS m/z=437.1[M+H]$^+$.

TABLE 46

| Compound Number | IP Rating | Structure | IUPAC Name | LCMS m/z [M + H]+ |
|---|---|---|---|---|
| 173 | B | 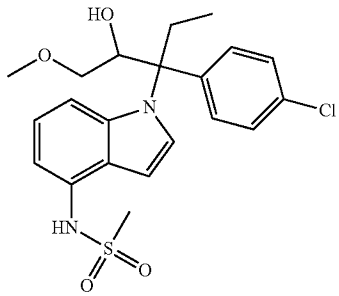 [SMILES: CCC(c1ccc(Cl)cc1)(C(O)COC)n1ccc2c(NS(C)(=O)=O)cccc21] | N-(1-(3-(4-chlorophenyl)-2-hydroxy-1-methoxypentan-3-yl)-1H-indol-4-yl)methanesulfonamide | 437.1 |

Example 50

N-(1-(3-(4-chlorophenyl)pentan-3-yl)-1H-indol-4-yl)methanesulfonamide (Compound 174)

Step A: tert-butyl 1-(3-(4-chlorophenyl)pentan-3-yl)-1H-indol-4-ylcarbamate

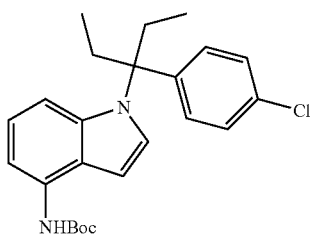 [SMILES: CCC(CC)(c1ccc(Cl)cc1)n1ccc2c(NC(=O)OC(C)(C)C)cccc21]

A mixture of tert-butyl 1-(3-(4-chlorophenyl)pent-1-yn-3-yl)-1H-indol-4-ylcarbamate (100 mg, 0.245 mmol), as described in Example 44 Step A, PtO$_2$ (5.5 mg, 0.0245 mmol) and methanol (2 mL) was degassed three times and backfilled with dihydrogen. The mixture was stirred at room temperature for 2 h under dihydrogen atmosphere. The solid was filtered off and the filtrate was concentrated in vacuo to give the title compound as colorless oil. LC/MS m/z= 357.0[M-$^t$Bu+H]$^+$.

Step B: 1-(3-(4-chlorophenyl)pentan-3-yl)-1H-indol-4-amine

A mixture of the product of Step A (90 mg, 0.218 mmol) and MeOH/HCl (2 mL, 4 M) was stirred at room temperature for 2 h. The volatile was removed in vacuo to give the title compound as colorless oil. LC/MS m/z=313.1[M+H]$^+$.

Step C: N-(1-(3-(4-chlorophenyl)pentan-3-yl)-1H-indol-4-yl)methanesulfonamide

To a solution of the product of Step B (50 mg, 0.16 mmol) and N-methylmorpholine (32 mg, 0.32 mmol) in dichloromethane (2 mL) was added methanesulfonyl chloride (23 mg, 0.24 mmol) at room temperature. The mixture was stirred for 2 h, then diluted with water (15 mL) and extracted with ethyl acetate. The combined organic layers were washed with brine (10 mL), dried over Na$_2$SO$_4$, filtered and concentrated. The crude product was purified by PREP-TLC eluting with PE/EA (2/1, v/v) to give the title compound as a colorless solid. LC/MS m/z=391.0[M+H]$^+$.

TABLE 47

| Compound Number | IP Rating | Structure | IUPAC Name | LCMS m/z [M + H]+ |
|---|---|---|---|---|
| 174 | B | 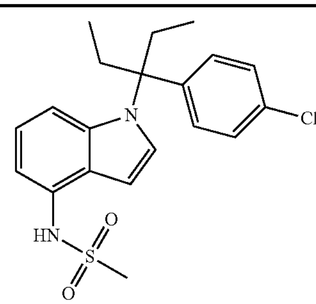 | N-(1-(3-(4-chlorophenyl)pentan-3-yl)-1H-indol-4-yl)methanesulfonamide | 391.0 |

Example 51

N-(1-(3-(4-chlorophenyl)pent-1-en-3-yl)-1H-indol-4-yl)methanesulfonamide (Compound 175)

Step A: tert-butyl 1-(3-(4-chlorophenyl)pent-1-en-3-yl)-1H-indol-4-ylcarbamate

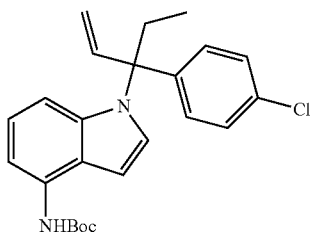 [SMILES: C=CC(CC)(c1ccc(Cl)cc1)n1ccc2c(NC(=O)OC(C)(C)C)cccc21]

A mixture of tert-butyl 1-(3-(4-chlorophenyl)pent-1-en-3-yl)-1H-indol-4-ylcarbamate (100 mg, 0.245 mmol), as described in Example 44 Step A, Lindlar's catalyst (10 mg) and methanol (2 mL) was degassed three times and backfilled with hydrogen. The mixture was stirred at room temperature for 2 h under hydrogen atmosphere. The solid was filtered off and the filtrate was concentrated in vacuo to give the title compound as colorless oil. LC/MS m/z=355.0[M-$^t$Bu+H]$^+$.

Step B: 1-(3-(4-chlorophenyl)pent-1-en-3-yl)-1H-indol-4-amine

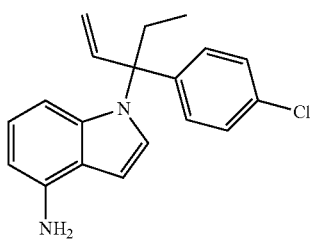 [SMILES: C=CC(CC)(c1ccc(Cl)cc1)n1ccc2c(N)cccc21]

A mixture of the product of Step A (95 mg, 0.232 mmol) and MeOH/HCl (4 mL, 2M) was stirred at 0° C. for 2 h. The volatile was removed in vacuo to give the title compound as colorless oil. LC/MS m/z=311.1 [M+H]$^+$.

Step C: N-(1-(3-(4-chlorophenyl)pent-1-en-3-yl)-1H-indol-4-yl)methanesulfonamide To a solution of the product of Step B (40 mg, 0.128 mmol) and N-methylmorpholine (26 mg, 0.256 mmol) in dichloromethane (2 mL) was added methanesulfonyl chloride (18 mg, 0.192 mmol) at room temperature. The mixture was stirred for 2 h, then diluted with water (10 mL) and extracted with ethyl acetate. The combined organic layers were washed with brine (10 mL), dried over Na$_2$SO$_4$, filtered and concentrated. The crude product was purified by PREP-TLC eluting with PE/EA (3/1, v/v) to give the title compound as a colorless solid. LC/MS m/z=388.9 [M+H]$^+$.

Compound 175 was obtained by the below chiral separation conditions:

Column: AD-H

Mobile phase: A: CO$_2$, B: MeOH, A:B=70:30 at 3.0 mL/min

Column Temp: 38.6° C.

TABLE 48

| Compound Number | IP Rating | Structure | IUPAC Name | LCMS m/z [M + H]$^+$ |
|---|---|---|---|---|
| 175 | B | 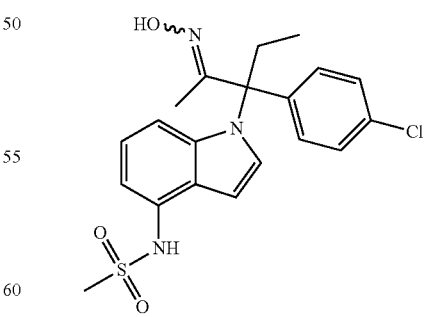 | N-(1-(3-(4-chlorophenyl)pent-1-en-3-yl)-1H-indol-4-yl)methanesulfonamide (enantiomer B, r.t. = 4.33 min) | 388.9 |

Example 52

N-(1-(2-amino-3-(4-chlorophenyl)pentan-3-yl)-1H-indol-4-yl)methanesulfonamide (Compound 176)

Step A: N-(1-(3-(4-chlorophenyl)-2-(hydroxyimino)pentan-3-yl)-1H-indol-4-yl)methane sulfonamide To a solution of N-(1-(3-(4-chlorophenyl)-2-oxopentan-3-yl)-1H-indol-4-yl)methanesulfonamide (200 mg, 0.49 mmol), as described in Example 23 Step A, in EtOH (5 mL) was added hydroxylamine hydrochloride (68 mg, 0.99 mmol) and K$_2$CO$_3$ (137 mg, 0.99 mmol). The mixture was stirred at 130° C. under microwave for 2 h. After removing the solvent, the residue was dissolved in ethyl acetate (30 mL). The organic layer was washed with saturated sodium bicarbonate solution (10 mL) and brine (10 mL), dried over sodium sulfate, and then filtered. After removing the organic solvent, the residue was purified by silica gel chromatography eluting with PE/EA (10/1 to 5/1, v/v) to afford the title compound as a white solid. LC/MS m/z=441.9 [M+Na]$^+$.

Step B: N-(1-(2-amino-3-(4-chlorophenyl)pentan-3-yl)-1H-indol-4-yl)methanesulfonamide A mixture of the product from Step A (68 mg, 0.162 mmol) and Raney-Ni (1 mg) in MeOH (10 mL) was purged air three times and then backfilled with $H_2$. The mixture was stirred at ambient temperature overnight. The suspension was filtered off and the filtrate was concentrated to afford the title compound as a colorless solid. LC/MS m/z=406.0 [M+H]$^+$. Compound 176 was obtained by the below chiral separation conditions:
Column: AS-H
Mobile phase: A: $CO_2$, B: MeOH, A:B=70:30 at 3.0 mL/min
Column Temp: 39.8° C.

Using the procedure described in Example 39, but in step A replacing N-(1-(3-(4-chlorophenyl)-2-oxopentan-3-yl)-1H-indol-4-yl)methanesulfonamide with N-(1-(2-(4-chlorophenyl)-1-oxobutan-2-yl)-1H-indol-4-yl)methanesulfonamide, compound 177 of Table 49 was prepared.

Example 53

N-(1-(1-(4-chlorophenyl)-1-cyanopropyl)-1H-indol-4-yl)ethanesulfonamide (Compound 178)

Step A: methyl 2-(4-chlorophenyl)-2-(4-(ethylsulfonamido)-1H-indol-1-yl)butanoate

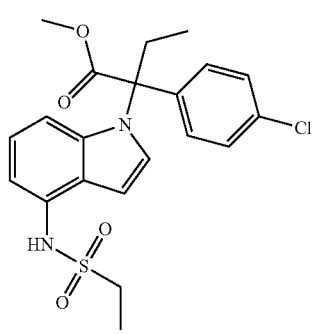

TABLE 49

| Compound Number | IP Rating | Structure | IUPAC Name | LCMS m/z [M + H]$^+$ |
|---|---|---|---|---|
| 176 | A | 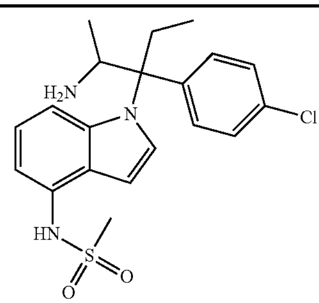 | N-(1-(2-amino-3-(4-chlorophenyl)pentan-3-yl)-1H-indol-4-yl)methanesulfonamide (diastereoisomer B, r.t. = 4.67 min) | 406.0 |
| 177 | B | 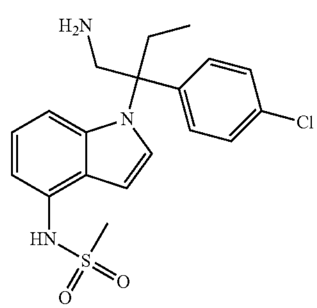 [SMILES: CCC(CN)(c1ccc(Cl)cc1)n1ccc2c(NS(C)(=O)=O)cccc21] | N-(1-(1-amino-2-(4-chlorophenyl)butan-2-yl)-1H-indol-4-yl)methanesulfonamide | 392.2 |

Ethanesulfonyl chloride (0.26 g, 2 mmol) was added to a stirred solution of methyl 2-(4-amino-1H-indol-1-yl)-2-(4-chlorophenyl)butanoate (0.58 g, 1.7 mmol), as described in Example 3 Step B, and 4-methylmorpholine (0.25 g, 2.5 mmol) in DCM (8 mL) at 0° C. After 30 min, an additional portion of ethanesulfonyl chloride (0.1 g, 1 mmol) was added. After 1 h, the reaction mixture was partitioned between DCM and saturated aqueous ammonium chloride. The layers were separated and the aqueous layer was extracted with DCM. The combined organic layers were washed with brine, dried sodium sulfate, filtered and concentrated in vacuo. The residue was purified by silica gel flash chromatography (PE:EA=2:1) to afford the title compound. LC/MS m/z=435.1 [M+H]$^+$.

1.0 mL/min
Column Temp: 39.6° C.
enantiomer A, r.t.=2.1 min, enantiomer B, r.t.=3.54 min

Step C: N-(1-(1-(4-chlorophenyl)-1-cyanopropyl)-1H-indol-4-yl)ethanesulfonamide Cyanuric chloride (92 mg, 0.5 mmol) was added to a stirred solution of the product enantiomer A from step B (210 mg, 0.5 mmol) in DMF (3 mL), and the reaction mixture was allowed to stir at RT for 3 h. The reaction mixture was poured into brine and the resulting mixture was extracted with ethyl acetate. dried over sodium sulfate and concentrated in vacuo. The residue was purified by silica gel flash chromatography (PE:EA=2:1) to afford the title compound. LC/MS m/z=402.0 [M+H]$^+$.

TABLE 50

| Compound Number | IP Rating | Structure | IUPAC Name | LCMS m/z [M + H]$^+$ |
|---|---|---|---|---|
| 178 | B | 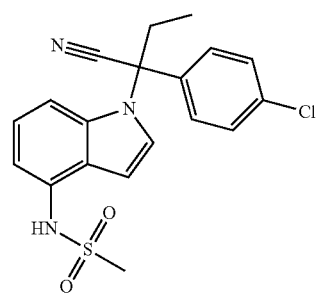 | N-(1-(1-(4-chlorophenyl)-1-cyanopropyl)-1H-indol-4-yl)ethanesulfonamide (enantiomer) | 402.0 |

Step B: 2-(4-chlorophenyl)-2-(4-(ethylsulfonamido)-1H-indol-1-yl)butanamide

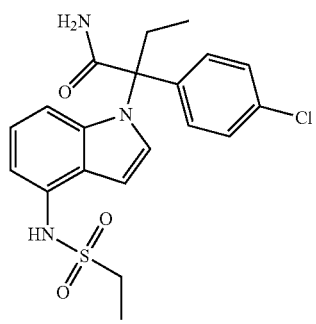 [SMILES: CCC(C(N)=O)(c1ccc(Cl)cc1)n1ccc2c(NS(=O)(=O)CC)cccc21]

The product from Step A above (0.43 g, 1.0 mmol) was dissolved in a 7 N solution of ammonia in methanol (25 mL). After stirring at RT for 10 h, the resulting mixture was concentrated under reduced pressure. The residue was dissolved in dioxane/water, acidified with TFA, and purified directly on RP-HPLC to give the title compound. LC/MS m/z=420.1 [M+H]$^+$. The two enantiomers were separated by SFC chiral separation.
Enantiomer A and enantiomer B were obtained by the below chiral separation conditions:
Column: IA
Mobile phase: A: CO$_2$, B: MeOH (0.1% DEA), A:B=60:40 at

Example 54

N-(1-(1-(4-chlorophenyl)-1-(2-ethyl-2H-tetrazol-5-yl)propyl)-1H-indol-4-yl)methane sulfonamide

Step A: N-(1-(1-(4-chlorophenyl)-1-cyanopropyl)-1H-indol-4-yl)methanesulfonamide The title compound was prepared according to the procedure described in Example 53.

Step B: N-(1-(1-(4-chlorophenyl)-1-(2H-tetrazol-5-yl)propyl)-1H-indol-4-yl)methane sulfonamide

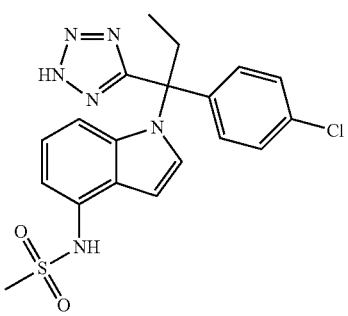 [SMILES: CCC(c1ccc(Cl)cc1)(c1nn[nH]n1)n1ccc2c(NS(C)(=O)=O)cccc21]

Sodium azide (117.6m g, 1.809 mmol) was added to a stirred solution of N-(1-(1-(4-chlorophenyl)-1-cyanopropyl)-1H-indol-4-yl)methanesulfonamide (100 mg, 0.258 mmol) and ammonium chloride (110.6 g, 2.067 mmol) in DMF (2 mL) was heated at 130° C. for 3 h in microwave reactor. The reaction was quenched with water, and extracted with ethyl acetate (100 mL). The organic layer was washed with brine, dried over sodium sulfate, filtered and evaporated. The residue was purified by silica gel chromatography eluting with PE/EA (5/1 to 1/1, v/v) to afford the title compound as a yellow solid. LC/MS m/z=431.0 [M+H]$^+$.

Step C: N-(1-(1-(4-chlorophenyl)-1-(2-ethyl-2H-tetrazol-5-yl)propyl)-1H-indol-4-yl)methane sulfonamide A mixture of the product from Step B (65 mg, 0.151 mmol), K$_2$CO$_3$ (41.7 mg, 0.302 mmol) and iodoethane (30.8 mg 0.181 mmol) in DMF (1 mL) was stirred at 80° C. overnight. The volatile was evaporated. The residue was extracted with ethyl acetate (50 mL). The organic layer was washed with water and brine, dried over sodium sulfate, filtered and evaporated. The residue was purified by silica gel chromatography eluting with PE/EA (5/1 to 1/1, v/v) to afford the title compound as a yellow solid. LC/MS m/z=459.0 [M+H]$^+$.
Compound 179 was obtained by the below chiral separation conditions:
Column: AS-H
Mobile phase: A: CO$_2$, B: MeOH, A:B=70:30 at 3.0 mL/min
Column Temp: 38.2° C.

Example 55

N-(1-(3-(4-chlorophenyl)-6,6,6-trifluorohexan-3-yl)-1H-indol-4-yl)methane sulfonamide (Compound 180)

Step A: N-(1-(3-(4-chlorophenyl)pent-1-yn-3-yl)-1H-indol-4-yl)-N-((2-(trimethylsilyl)ethoxy)methyl)methanesulfonamide

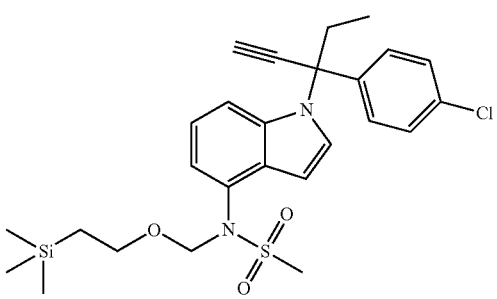 [SMILES: C#CC(CC)(c1ccc(Cl)cc1)n1ccc2c(N(COCC[Si](C)(C)C)S(C)(=O)=O)cccc21]

The title compound was prepared according to the procedure in Example 32 Step A using N-(1-(2-(4-chlorophenyl)-1-oxobutan-2-yl)-1H-indazol-4-yl)-N-((2-(trimethylsilyl)ethoxy)methyl) methane sulfonamide(enantiomer A), as described in Example 20 Step E, as starting material.

Step B: N-(1-(3-(4-chlorophenyl)-6,6,6-trifluorohex-4-yn-3-yl)-1H-indol-4-yl)-N-((2-(trimethylsilyl)ethoxy)methyl)methanesulfonamide

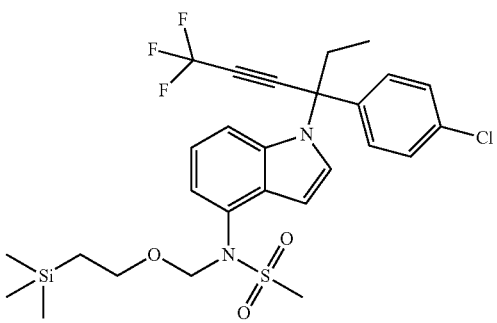 [SMILES: CCC(C#CC(F)(F)F)(c1ccc(Cl)cc1)n1ccc2c(N(COCC[Si](C)(C)C)S(C)(=O)=O)cccc21]

TABLE 51

| Compound Number | IP Rating | Structure | IUPAC Name | LCMS m/z [M + H]$^+$ |
|---|---|---|---|---|
| 179 | A | 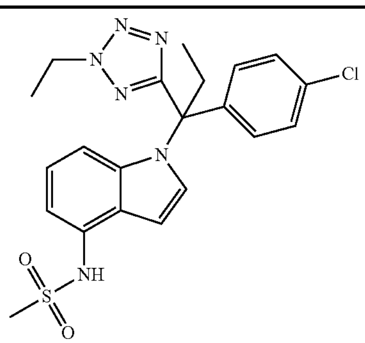 | N-(1-(1-(4-chlorophenyl)-1-(2-ethyl-2H-tetrazol-5-yl)propyl)-1H-indol-4-yl)methane sulfonamide (enantiomer A, r.t. = 3.4 min) | 459.0 |

A three-neck round-bottom flask was charged with CuI (38 mg, 0.2 mmol), Phen.H$_2$O (40 mg, 0.2 mmol), KF (58 mg, 1.0 mmol) and stirring bar. The flask was dried at 130° C. in vacuo for 3 h. After cooling to RT, the flask was backfilled with air and TMSCF$_3$ (142 mg, 1.0 mmol), DMF (2 mL) was added. Then the flask was heated to 130° C. for 30 min. A solution of N-(1-(3-(4-chlorophenyl)pent-1-yn-3-yl)-1H-indol-4-yl)-N-((2-(trimethylsilyl)ethoxy)methyl) methanesulfonamide (102 mg, 0.2 mmol, enantiomer A) in DMF (1 mL) was slowly added to the mixture at 130° C. over 1 h. The resulting mixture was stirred for another 1 h at 130° C. The crude product was purified by Combiflash (mobile phase: CH$_3$CN/ water (0.08% of NH$_4$HCO$_3$)) to give the title compound. LC/MS m/z=606.7 [M+Na]$^+$.

Step C: N-(1-(3-(4-chlorophenyl)-6,6,6-trifluoro-hexan-3-yl)-1H-indol-4-yl)-N-((2-(trimethylsilyl)ethoxy)methyl)methanesulfonamide

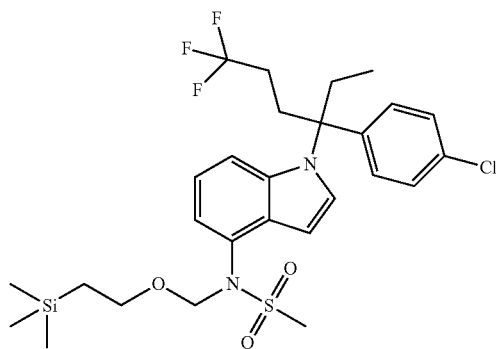 [SMILES: CCC(CCC(F)(F)F)(c1ccc(Cl)cc1)n1ccc2c(N(COCC[Si](C)(C)C)S(C)(=O)=O)cccc21]

A mixture of the product from Step B (63 mg, 0.108 mmol, enantiomer A) and PtO$_2$ (2.4 mg, 0.0108 mmol) in MeOH (3 mL) was purged air three times and then backfilled with H$_2$. The mixture was stirred at RT overnight. The suspension was filtered off and filtrate was concentrated to give the title compound which was used for next step without purification. LC/MS m/z=610.7 [M+Na]$^+$.

Step D: N-(1-(3-(4-chlorophenyl)-6,6,6-trifluoro-hexan-3-yl)-1H-indol-4-yl)methanesulfonamide A mixture of the product from step C (20 mg, 0.034 mmol, enantiomer A), 2 M HCl (1 mL) and EtOH (2 mL) was heated to 50° C. for 3 h. The volatile was removed under reduced pressure. The residue was purified by Combiflash (mobile phase: MeOH/water (0.08% of NH$_4$HCO$_3$)) to give the title compound. LC/MS m/z=458.7 [M+H]$^+$. $^1$H NMR (400 MHz, CDCl$_3$) δ 7.50 (d, J=3.6 Hz, 1H), 7.29 (d, J=8.4 Hz, 2H), 7.10 (d, J=7.6 Hz, 1H), 7.05 (d, J=8.8 Hz, 2H), 6.86 (t, J=8.1 Hz, 1H), 6.59-6.58 (m, 2H), 6.40 (d, J=8.4 Hz, 1H), 3.03 (s, 3H), 2.74-2.67 (m, 1H), 2.55-2.45 (m, 2H), 2.26-2.16 (m, 1H), 1.89-1.86 (m, 1H), 1.45-1.38 (m, 1H), 0.67 (t, J=7.2 Hz, 3H).

TABLE 52

| Compound Number | IP Rating | Structure | IUPAC Name | LCMS m/z [M + H]$^+$ |
|---|---|---|---|---|
| 180 | A | (structure shown) | N-(1-(3-(4-chlorophenyl)-6,6,6-trifluorohexan-3-yl)-1H-indol-4-yl)methanesulfonamide (enantiomer) | 458.7 |

Biological Assay

The activity of the compounds of the present invention regarding mineralocorticoid receptor antagonism can be evaluated using the following assay.

Assessment of MR Potency in HMR NH Pro Assay

The human MR NH Pro assay is a commercially available PathHunter™ Protein:Protein interaction assay (DiscoveRx; http://www.discoverx.com/nhrs/prod-nhrs.php) that measures the ability of compounds to antagonize full-length human Mineralocorticoid Receptor (MR) binding to a coactivator peptide. PathHunter™ CHO-K1 cells that overexpress human MR (Cat #93-0456C2, Lot No: 09B0913) were cultured in growth media (F12K w/Glutamine and phenol red (Gibco 11765-047) supplemented with 10% HI FBS (Gibco 16000); 0.25 mg/ml Hygromycin in PBS (Invitrogen 10687-010, 50 mg/ml); 100 I.U./mL and 100 µg/mL Pen/Strep (Gibco 15140-122); 0.6 mg/mL Geneticin).

Compounds were assessed for MR antagonist activity by incubating the cells with a titrating dose of compound in F12K w/Glutamine and phenol red culture media (Invitrogen 11765-047) supplemented with 1% Charcoal/Dextran Treated FBS (Hyclone #SH30068.01) and aldosterone (0.3 nM) for 6 hours at 37° C. Cells were then treated with DiscoveRx detection reagent for 1 hour at room temperature and read using an Envision luminescence plate reader. % activity was measured relative to cells treated with aldosterone alone and IC$_{50}$ values were calculated using ADA software.

1. Growth Media:
F12K w/Glutamine and phenol red (Gibco 11765-047)
10% HI FBS (Gibco 16000)
0.25 mg/ml Hygromycin in PBS (Invitrogen 10687-010, 50 mg/ml)

100 I.U./mL and 100 µg/mL Pen/Strep (Gibco 15140-122)
0.6 mg/mL Geneticin (Gibco 10131, 50 mg/ml)
2. Assay media:
F12K w/Glutamine and phenol red (Invitrogen 11765-047)
1% Charcoal/Dextran Treated FBS (Hyclone #SH30068.01)
3. 3× PathHunter Detection Reagents (Cat#93-0001) (need ~6 ml/plate). Do not freeze and thaw the reagents more than 3 times.
19× PathHunter Cell Assay Buffer
5× Emerald II
1× Galacton Star
4. Control Agonist: Aldosterone: Sigma cat#A9477
Prepare stock solution—10 µM in DMSO kept at −20° C.
for assay, dilute in assay media to 1.8 or 6 nM (6× of final concentration=about 0.3 nM to about 1.0 nM)
5. Cell line: PathHunter CHO-K1 MR cells Cat #93-0456C2, Lot No: 09B0913, from operation liquid nitrogen stock.
6. Control Antagonist: Spironolactone: Sigma #S-3378 and Eplerenone Sigma #107724-20-9 (10 mM stock concentration also prepared in DMSO and stored at −20° C.).
Methods:
Assay Set up and Calculations:
1. Cells are grown in F12+FBS+Hygromycin+pen/strep+Genetin
2. Cells are collected with 0.05% trypsin and the cell suspension is spun and resuspended in a volume of F12+1.5% CD-FBS and counted.
3. The cells are resuspended to $4\times10^5$ cells/mL.
4. Cells are (25 µL/well) added to the wells of a 384 well plate.
5. The plate is then incubated at 37° C. over night in a humidified incubator with 5% $CO_2$.
6. Test compounds are titrated starting at 4.4 mM, 10-point titration in 1:3 dilution.
7. Aldosterone is diluted in assay media to 1.8 nM or 6 nM from 10 µM stock (final concentration to be about 0.3 nM to about 1.0 nM)
Protocol for 384 well plate format: 6 hr treatment:
1. Plate 10K exponentially growing cells/well (25 µL) resuspended in assay media to each well using the Multidrop (Thermo Electron) (use white wall, clear bottom assay plates (Costar #3570) and incubate overnight at 37° C., 5% $CO_2$.
2. Add 0.25 µL 120× test compound (final DMSO concentration should be <1%) to each well n=2, 10 point titrations starting at 36.7 µM final concentration.
3. Add 5 µL 6× agonist (final aldosterone concentration should be about 0.3 nM to about 1.0 nM) to all wells (using the PlateMate Plus.)
(ThermoFisher) (except those wells in columns 23 and 24)
4. Add 5 uL of assay media to all wells in column 23 and 24.
5. Incubate 6 hrs at 37° C., 5% $CO_2$.
6. Add 15 uL 3× DiscoveRx detection reagent to each well.
7. Incubate 1 hour at room temperature (keep plates stored in the dark).
8. Read plates on Envision (PerkinElmer) luminesence plate reader and analyze using ADA.
LC/MS method: (LC2M_Low/Med_Positive mode).
LC Conditions: 5-98% $CH_3CN/H_2O$+v 0.1% TFA over 1.25 min; Flow Rate=1.5 mL/min, UV wavelength 254 nm; Column: Waters XTerra® MS C18 3.5 µm 2.1×20 mm IS™

As seen in the Examples above, compounds of the instant invention that were tested and had an IP value greater than 0 nM but less than 100 nM were given an "A" rating. Compounds of the instant invention that were tested and had an IP value equal to, or greater than, 100 nM, but less than 500 nM, were given a "B" rating. Compounds of the instant invention that were tested and had an IP value equal to, or greater than 500 nM, but less than 5,000 nM, were given a "C" rating.

The invention claimed is:

1. A compound selected from

| IUPAC Name |
| --- |
| N-(1-(2-(4-chlorophenyl)-1-hydroxybutan-2-yl)-1H-indazol-4-yl)methanesulfonamide; |
| N-(1-(1-hydroxy-2-(4-(trifluoromethyl)phenyl)butan-2-yl)-1H-indazol-y4-l)methanesulfonamide; |
| N-(1-(3-(4-chlorophenyl)-2-hydroxy-2-methylpentan-3-yl)-1H-indazol-4-yl)methanesulfonamide; |
| N-(1-(2-hydroxy-2-methyl-3-(4-(trifluoromethyl)phenyl)pentan-3-yl)-1H-indazol-4-yl)methanesulfonamide; |
| N-(1-(2-(4-chlorophenyl)-1-methoxybutan-2-yl)-1H-indazol-4-yl)methanesulfonamide; |
| N-{1-[3-(4-chlorophenyl)-2-hydroxypentan-3-yl]-1H-indazol-4-ylmethanesulfonamide; |
| N-{1-[3-(4-chlorophenyl)-2-hydroxypentan-3-yl]-1H-indazol-4-ylmethanesulfonamide |
| N-(6-fluoro-1-(2-hydroxy-3-(4-(trifluoromethyl)phenyl)pentan-3-yl)-1H-indazol-4-yl)methanesulfonamide; |
| N-(1-(2-hydroxy-3-(4-(trifluoromethyl)phenyl)pentan-3-yl)-1H-indazol-4-yl)methanesulfonamide |
| N-(3-(3-(4-chlorophenyl)-2-hydroxypentan-3-yl)-1H-indazol-7-yl)methanesulfonamide; |
| N-(1-(2-(4-chlorophenyl)-1-cyanobutan-2-yl)-1H-indazol-4-yl)methanesulfonamide; |
| N-(1-(3-(4-chlorophenyl)-1-cyanopentan-3-yl)-1H-indazol-4-yl)methanesulfonamide; |
| N-(1-(1-cyano-3-(4-(trifluoromethyl)phenyl)pentan-3-yl)-1H-indazol-4-yl)methanesulfonamide |
| N-(1-(1-cyano-3-phenylpentan-3-yl)-6-fluoro-1H-indazol-4-yl)methanesulfonamide; |
| N-(1-(3-(4-chlorophenyl)-1-cyanopentan-3-yl)-6-fluoro-1H-indazol-4-yl)methanesulfonamide; |
| N-(l-(3-(4-Chlorophenyl)-1-cyano-2-oxopentan-3-yl)-1H-indol-4-yl)methanesulfonamide; |
| N-(1-(3-(4-chlorophenyl)-1,1,1-trifluoropentan-3-yl)-1H-indazol-4-yl)methanesulfonamide; |
| methyl 4-(4-chlorophenyl)-4-(4-(methylsulfonamido)-1H-indazol-1-yl)hexanoate; | or a pharmaceutically acceptable salt thereof.

2. The compound of claim 1 which is

N-(1-(2-(4-chlorophenyl)-1-hydroxybutan-2-yl)-1H-indazol-4-yl)methanesulfonamide;

N-{1-[3-(4-chlorophenyl)-2-hydroxypentan-3-yl]-1H-indazol-4-ylmethanesulfonamide;

N-(1-(3-(4-chlorophenyl)-2-hydroxy-2-methylpentan-3-yl)-1H-indazol-4-yl)methanesulfonamide;

N-(1-(2-hydroxy-2-methyl-3-(4-(trifluoromethyl)phenyl)pentan-3-yl)-1H-indazol-4-yl)methanesulfonamide;

N-(1-(2-hydroxy-3-(4-(trifluoromethyl)phenyl)pentan-3-yl)-1H-indazol-4-yl)methanesulfonamide;

N-(1-(3-(4-chlorophenyl)-1-cyanopentan-3-yl)-1H-indazol-4-yl)methanesulfonamide;

N-(1-(1-cyano-3-(4-(trifluoromethyl)phenyl)pentan-3-yl)-1H-indazol-4-yl)methanesulfonamide;

N-(1-(1-cyano-3-phenylpentan-3-yl)-6-fluoro-1H-indazol-4-yl)methanesulfonamide;

or a pharmaceutically acceptable salt thereof.

3. The compound of claim 2 which is:

N-(1-(2-(4-chlorophenyl)-1-hydroxybutan-2-yl)-1H-indazol-4-yl)methanesulfonamide;

N-{1-[3-(4-chlorophenyl)-2-hydroxypentan-3-yl]-1H-indazol-4-ylmethanesulfonamide;

1-(1-(3-(4-chlorophenyl)-2-hydroxy-2-methylpentan-3-yl)-1H-indazol-4-yl)-3-methyl-sulfonylurea;

or a pharmaceutically acceptable salt thereof.

4. A compound of Formula I:

[Structure of Formula I: indazole-like bicyclic ring with substituents R¹, R², R³ on a carbon attached to N, (Rˣ)ₓ on the benzene ring, R⁴, and Rʸ, with Y]

or pharmaceutically acceptable salts thereof, wherein
Y is N;
Ry is independently H or $C_1$-$C_6$ alkyl, said alkyl is optionally substituted with halo or OH;
Each $R^x$ is independently H, halo, OR, $C_1$-$C_6$ alkyl, $(CR_2)_{0-1}CN$, $C_3$-$C_{10}$ cycloalkyl, or $NH_2$, said alkyl is optionally substituted with 1 to 3 substituents selected from halo, OR and $C_1$-$C_6$ alkyl;
Each R is independently H, $C_1$-$C_6$ alkyl or aryl, said alkyl and aryl are optionally substituted with 1 to 3 substituents selected from halo, aryl and $C_1$-$C_6$ alkyl;
$R^1$ is:
  1) $C_1$-$C_6$ alkyl, said alkyl is optionally substituted with one to three $C_1$-$C_6$ alkyl, OR, $NR_2$, $CF_3$, SR, $OS(O)_2R^8$, CN or halo substituents, or
  2) —$(CR^a{}_2)_nC(O)NRR^7$;
$R^2$ is $C_1$-$C_6$ alkyl, which is optionally substituted with one to three groups selected from $R^{12}$;
$R^3$ is phenyl, wherein said phenyl is optionally substituted with one to three $R^9$;
$R^4$ is —$N(R^6)S(O)_2R^8$;
$R^6$ is H or $(C_1$-$C_6)$alkyl;
Each $R^7$ is independently H or $(C_1$-$C_6)$alkyl;
Each $R^8$ is independently $C_1$-$C_6$ alkyl, which is optionally substituted with one to three halo, CN, OR or $NH_2$ substituent, or —$NRR^7$;
Each $R^9$ is independently halo, CN, $C_1$-$C_6$ alkyl, OR, or $NH_2$, said alkyl is optionally substituted with one to three halo, CN, OR, $C_1$-$C_6$ alkyl, $NH_2$ substituents
Each $R^{11}$ is independently H, $C_1$-$C_6$ alkyl, or aryl;
Each $R^{12}$ is independently halo, CN, $C(O)OR^{11}$, $C_1$-$C_6$ alkyl, OR, or $NH_2$, where said alkyl is optionally substituted with one to three halo, CN, OR, $C_1$-$C_6$ alkyl or $NH_2$ substituents;
Each $R^a$ is independently H or $C_1$-$C_6$ alkyl, said alkyl is optionally substituted with one to three halo substituents;
n is 0, 1, 2, 3 or 4; and
x is 0, 1, 2 or 3.

5. A pharmaceutical composition comprised of an effective amount the compound of claim 4 and a pharmaceutically acceptable carrier.

6. A pharmaceutical composition of claim 5 which further comprises an effective amount one or more additional pharmaceutically active agents.

7. A method for treating aldosterone-mediated disorders in a human patient in need thereof, comprising administering a therapeutically effective amount of a compound of claim 4, or a pharmaceutically acceptable salt thereof.

8. A method of treating cardiovascular disease, heart failure, hypertension, atherosclerosis, primary hyperaldosteronism or a related condition in a human patient in need thereof, comprising administering a therapeutically effective amount of a compound of claim 4, or a pharmaceutically acceptable salt thereof.

9. A method of treating metabolic syndrome in a mammal in need of such treatment, comprising administering a therapeutically effective amount of a compound of claim 4 or a pharmaceutically acceptable salt thereof.

10. A method of treating a physiological or pathologic disease, selected from including Conn's Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Butter's Syndrome, and disorders associated with excess catecholamine levels in a human patient in need of, comprising administering to the patient a therapeutically effective amount of a compound of claim 4 or a pharmaceutically acceptable salt thereof.

11. A method of treating renal failure in a human patient in need of such treatment comprising administering a therapeutically effective amount of a compound of claim 4 or a pharmaceutically acceptable salt thereof.

12. The A compound of claim 4 or a pharmaceutically acceptable salt thereof, which has the formula

[Chemical structure: indazole with 4-methanesulfonamido group, 1-position substituted with a pentan-3-yl group bearing 2-hydroxy and a 4-(trifluoromethyl)phenyl group]

13. The compound of claim 12, which is:
N-(1-(2-hydroxy-3-(4-(trifluoromethyl)phenyl)pentan-3-yl)-1H-indazol-4-yl)methanesulfonamide, diastereoisomer A;
N-(1-(2-hydroxy-3-(4-(trifluoromethyl)phenyl)pentan-3-yl)-1H-indazol-4-yl)methanesulfonamide, diastereoisomer C; or
N-(1-(2-hydroxy-3-(4-(trifluoromethyl)phenyl)pentan-3-yl)-1H-indazol-4-yl)methanesulfonamide, diastereoisomer D.

14. The compound of claim 4 wherein $R^y$ is H.

15. the compound of claim 4, as illustrated by Formula III:

[Structure of Formula III: indazole with R⁴ at 4-position and N1 bearing C(R¹)(R²)(R³)]

or a pharmaceutically acceptable salt thereof, wherein:
$R^2$ is $C_1$-$C_6$ alkyl, said alkyl is optionally substituted with one to three OR, CN or halo substituents;
$R^3$ is phenyl, wherein said phenyl is optionally substituted with one to three $R^9$;
$R^4$ is —$NR^6S(O)_2R^8$;
Each $R^9$ is independently halo or OR.

16. The compound of claim 4, as illustrated by Formula IV:

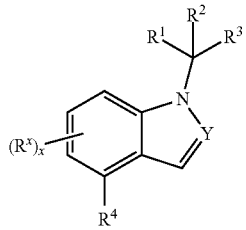

IV or a pharmaceutically acceptable salt thereof, wherein:
Y is N;
Each $R^x$ is independently H, halo, OR, or $C_1$-$C_6$ alkyl, said alkyl is optionally substituted with 1 to 3 substituents selected from halo, OR and $C_1$-$C_6$ alkyl;
Each R is independently H, $C_1$-$C_6$ alkyl or aryl, said alkyl and aryl are optionally substituted with 1 to 3 substituents selected from halo, aryl and $C_1$-$C_6$ alkyl;
$R^1$ is $C_1$-$C_6$ alkyl, said alkyl is optionally substituted with one to three $C_1$-$C_6$ alkyl, OR, $NR_2$, $CF_3$, SR, $OS(O)_2R^8$, CN or halo substituents,
$R^2$ is $C_1$-$C_6$ alkyl, which is optionally substituted with one to three groups selected from $R^{12}$;
$R^3$ is phenyl, wherein said phenyl is optionally substituted with one to three $R^9$;
Each $R^9$ is independently halo, CN, $C_1$-$C_6$ alkyl, OR, or $NH_2$, where said alkyl may be optionally substituted with one to three halo, CN, OR, $C_1$-$C_6$ alkyl or $NH_2$ substituents;
Each $R^{11}$ is independently H or $C_1$-$C_6$ alkyl;
Each $R^{12}$ is independently halo, CN, $C(O)OR^{11}$, $C_1$-$C_6$ alkyl, OR, $NH_2$, where said alkyl may be optionally substituted with one to three halo, CN, OR, $C_1$-$C_6$ alkyl or $NH_2$ substituents; and
x is 0 or 1.

17. A compound of claim 4 which is:

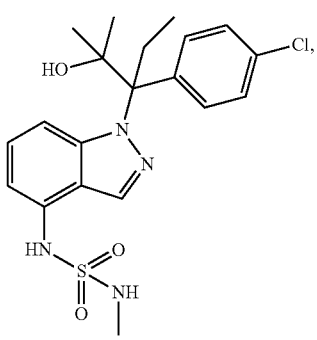

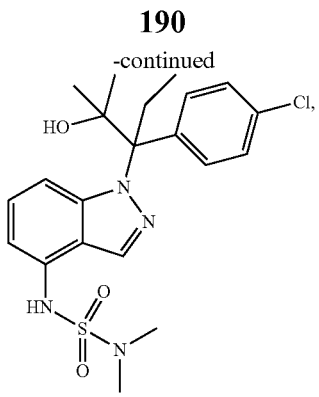

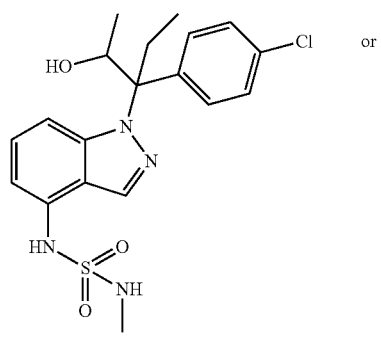

or

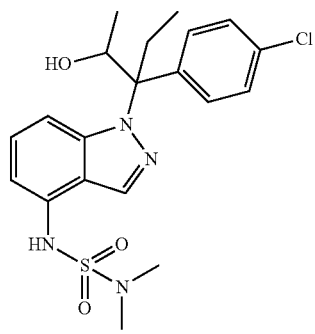

or a pharmaceutically acceptable salt thereof.

* * * * *